US006485960B1

(12) United States Patent
Harris et al.

(10) Patent No.: US 6,485,960 B1
(45) Date of Patent: Nov. 26, 2002

(54) POLYCYSTIC KIDNEY DISEASE 1 GENE AND USES THEREOF

(75) Inventors: Peter Charles Harris; Belen Peral; Christopher J. Ward; James Hughes, all of Oxford (GB); Martin Hendrik Breuning, Zaandam (NL); Dorothea Johanna Maria Peters; Jeroen Hendrik Roelfsema, both of Leiden (NL); Julian Sampson, Cardiff (GB); Dirkje Jorijntje Johanna Halley; Mark David Nellist, both of Rotterdam (NL); Lambertus Antonius Jacobus Janssen, Barendrecht; Ajenne Lique Wilhelma Hesseling, Spijkenisse, both of (NL)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 08/422,582

(22) Filed: Apr. 14, 1995

Related U.S. Application Data

(63) Continuation-in-part of application No. PCT/GB94/02822, filed on Dec. 23, 1994.

(30) Foreign Application Priority Data

Dec. 24, 1993 (GB) .............................. 9326470
Jun. 14, 1994 (GB) .............................. 9411900

(51) Int. Cl.[7] .......................... C12N 1/21; C12N 15/00; C12N 15/09; C07H 21/04
(52) U.S. Cl. ............................... 435/252.3; 435/320.1; 536/23.5; 536/24.31; 536/23.1
(58) Field of Search ......................... 435/252.3, 320.1, 435/325; 536/23.5, 24.31, 23.1

(56) References Cited

U.S. PATENT DOCUMENTS 5,654,170 A * 8/1997 Klinger et al. ............. 435/69.1

FOREIGN PATENT DOCUMENTS

WO    WO 9316178    8/1993

OTHER PUBLICATIONS

Watnick et al. Molecular Basis of Autosomal Dominant Polycystic Kidney Disease. Sem. Nephrol. 19(4): 327–343, 1999.*
Gabow, P.A. "Cystic disease of the kidney." in: Wyngaarden, J.B. and Smith, Jr., L.H. (Eds), Cecil Textbook of Medicine (Philadelphia, W.B. Saunders Company, 1988), pp. 644–647.*

EMBL Database, Accession n. T09245, EST07138, clone HIBBR18, Aug. 3, 1993; Adams, M.D. et al., "Rapid cDNA sequencing (espressed sequence tags) from a directionally cloned human infant brain cDNA library" Nature Genetics (1993), vol. 4, pp. 373–380.*
Engelman, et al., "Identifying nonpolar transbilayer helices in amino acid sequences of membrane proteins," Ann. Rev. Biophys. Chem., 15:321–53 (1986).
Aksentijevich, et al., Refined Mapping of the Gene Causing Familial Mediterranean Fever, by Linkage and Homozygosity Studies, Am. J. Hum. Genet., 53:451–461 (1993).
Altschul, et al., "Basic Local Alignment Search Tool", J. Mol. Biol., 215, 403–410 (1990).
Bevilacqua, et al., "Endothelial Leukocyte Adhesion Molecule 1: An Inducible Receptor for Neutrophils Related to Complement Regulatory Proteins and Lectins", Science, vol. 243, 1160–1187 (1989).
Breuning, et al., "Improved early diagnosis of adult polycystic kidney disease with flanking DNA markers", The Lancet, 1359–1361, Dec. 12, 1987.
Peters, et al., "Genetic Heterogeneity of Polycystic Kidney Disease in Europe", Contrib. Nephrol., vol. 97, pp. 128–139 (1992).
Breuning, et al., Map of 16 polymorphic loci on the short arm of chromosome 16 close to the polycystic kidney disease gene (PKD1), F. Med Genet, vol. 27:603–613 (1990).
Brook–Carter, et al., "Deletion of the TSC2 and PKD1 genes associated with severe infantile polycystic kidney disease—a contiguous gene syndrome", Nature Genetics, vol. 8: 328–332, (1994).
Brown, et al., "X chromosome inactivation of the human TIMP gene," Nucleic Acids Research, vol. 18, No. 14 (1990).
Brümmendorf, et al., "Protein Profile", vol. 1, 1994, pp. 951–962.
Buckle, et al., "Fluorescent in situ hybridization", Human Genetic Disease, pp. 59–82.
Carone, et al., "Biology of Polycystic Kidney Disease", Laboratory Investigation, vol. 70, No. 4, p. 437 (1994).
Carone, et al., "Impaired tubulogenesis of cyst–derived cells from autosomal dominant polycystic kidneys," Kidney International, vol. 47 (1995) pp. 861–868.
Calvet, et al., "Polycystic kidney disease: Primary extracellular matrix abnormality or defective cellular differentiation?", Kidney International, vol. 43 (1993) pp. 101–108.

(List continued on next page.)

Primary Examiner—Christopher S. F. Low
Assistant Examiner—Holly Schnizer
(74) Attorney, Agent, or Firm—Kathleen M Williams; Elizabeth N Spar; Palmer & Dodge,LLP

(57) ABSTRACT

The present invention relates to the polycystic kidney disease 1 (PKD1) gene and its nucleic acid sequence, mutations thereof in patients having PKD1-associated disorders, the protein encoded by the PKD1 gene or its mutants, and their uses in disease diagnosis and therapy.

10 Claims, 88 Drawing Sheets

OTHER PUBLICATIONS

Chapman, et al., "Intracranial aneurysms in autosomal dominant polycystic kidney disease", The New England Journal of Medicine, vol. 504, (1992).

Chao, "Neurotrophin Receptors: A Window into Neuronal Differentiation", Neuron, vol. 9, 583–593, Oct. (1992).

Chomczynski, et al., "Single–Step Method of RNA Isolation by Acid Guanidinium Thiocyanate–Phenol–Chloroform Extraction", Analytical Biochemistry, 162, 156–159 (1987).

Curtis, et al., "Sequence and expression of a membrane–associated C–type lectin that exhibits CD4–independent binding of human immunodeficiency virus envelope glycoprotein gp120", *Proc. Natl. Acad. Sci. USA*, vol. 89, pp. 8356–8360 (1992).

Dalgaard, "Bilateral Polycystic Disease of the Kidneys", Copenhagen:Bianco Lunos Bogtrykkeri A/S (1957).

Daoust, et al., "Evidence for a Third Genetic Locus for Autosomal Dominant Polycystic Kidney Disease", Genomics 25, 733–736 (1995).

Davies, et al., Polycystic Kidney Disease Re–evaluated: A Population–based Study, Quarterly Journal of Medicine, New Series 79, No. 290, pp. 477–485 (1991).

Deisseroth, et al., "Activation of phenotypic expression of human globin genes from nonerythroid cells by chromosome–dependent transfer to tetraploid mouse erythroleukemia cells", Proc. Natl. Acad. Sci. USA vol. 76, No. 5, pp. 2185–2189 (1979).

Dodé, et al., "Locus assignment of human α globin mutations by selective amplification and direct sequencing", British Journal of Haematology, vol. 76, 275–281 (1990).

Drickamer, et al., "Membrane receptors that mediate glycoprotein endocytosis: Structure and biosynthesis", Kidney International, vol. 32, Suppl. 23, pp. S–167–S–180, (1987).

Drickamer, "Two Distinct Classes of Carbohydrate–recognition Domains in Animal Lectins", The Journal of Biological Chemistry, vol. 263, No. 20, pp. 9557–9560 (1988).

Ekblom, "Developmentally regulated conversion of mesenchyme to epithelium", The FASEB Journal, vol. 3, (1989).

European Polycystic Kidney Disease Consortium, "The Polycystic Kidney Disease 1 Gene Encodes a 14 kb Transcript and Lies within a Duplicated Region on Chromosome 16", Cell. vol. 77, 881–894, (1994).

The European Chromosome 16 Tuberous Sclerosis Consortium, "Identification and Characterization of the Tuberous Sclerosis Gene on Chromosome 16", Cell. vol. 75, 1305–1315 (1993).

Fick, et al., "Characteristics of Very Early Onset Autosomal Dominant Polycystic Kidney Disease", Journal of the American Society of Nephrology, vol. 3 1863–1870 (1989).

Fick, et al., "Is there evidence for anticipation in autosomal–dominant polycystic kidney disease?", Kidney International, vol. 45, pp. 1153–1162 (1994).

Gabow, "Polycystic kidney disease: Clues to pathogenesis", Kidney International, vol. 40, pp. 989–996 (1991).

Gabow, "Autosomal Dominant Polycystic Kidney Disease", The New England Journal of Medicine, vol. 5 332–342 (1993).

Gabow, "Autosomal Dominant Polycystic Kidney Disease—More Than a Renal Disease", American Journal Kidney Diseases, vol. XVI, No. 5 403–413 (1990).

Germino, et al., "Identification of a Locus Which Shows No Genetic Recombination with the Autosomal Dominant Polycystic Kidney Disease Gene on Chromosome 16", Am. J. Hum. Genet. 46:925–933 (1990).

Gower, et al., "Alternative Splicing Generates a Secreted Form of N–CAM in Muscle and Brain", Cell. vol. 55, 955–964 (1988).

Harpaz, et al., "Many of the Immunoglobulin Superfamily Domains in Cell Adhesion Molecules and Surface Receptors Belong to a New Structural Set Which is Close to That Containing Variable Domains", J. Mol. Biol., vol. 238, 529–539 (1994).

Harris, et al., "A Long–Range Restriction Map between the α–Globin Complex and a Marker Closely Linked to the Polycystic Kidney Disease 1 (PKD1) Locus", Genomics, vol. 7, 195–206 (1990).

Harris, et al., "Rapid genetic analysis of families with polycystic kidney disease 1 by means of a microsatellite marker", Lancet vol. 338 1484–1487 (1991).

Hartmann, et al., "Predicting the orientation of eukaryotic membrane–spanning proteins", Proc. Natl. Acad. Sci. USA, vol. 86, pp. 5786–5790 (1989).

Henikoff, "Unidirectional digestion with exonuclease III creates targeted breakpoints for DNA sequencing", Gene 28 351–359 (1984).

Heijne, "A new method for predicting signal sequence cleavage sites", Nucleic Acids Research, vol. 14 4683–4690 (1986).

Himmelbauer, et al., "Saturating the Region of the Polycystic Kidney Disease Gene with NotI Linking Clones", Am. J. Hum. Genet. 48:325–334 (1991).

Hossack, et al., "Echocardiographic Findings In Autosomal Dominant Polycystic Kidney Disease", The New England Journal of Medicine, vol. 319, No. 14 907–912 (1988).

Huston, III, et al., "Value of Magnetic Resonance Angiography for the Detection of Intracranial Aneurysms in Autosomal Dominant Polycystic Kidney Disease", Journal of the American Society of Nephrology, vol. 3, No. 12 1871–1877 (1993).

Hyland, et al., "Probe, VK5B, is located in the same interval as the autosomal dominant adult polycystic kidney disease locus, PKD1", Hum. Genet 84:286–288 (1990).

Jia, et al., "The Proto–oncogene of v–eyk (v–ryk) Is a Novel Receptor–type Protein Tyrosine Kinase with Extracellular Ig/FN–III Domains", The Journal of Biological Chemistry, vol. 269, No. 3, pp. 1839–1844 (1993).

Jones, et al., "Crystal structure of an integrin–binding fragment of vascular cell adhesion molecule–1 at 1.8 Å resolution", Nature, vol. 373 539–544 (1995).

Keen, et al., "Rapid detection of single base mismatches as heteroduplexes on Hydrolink gels", TIG, vol. 7, No. 1, 5 (1991).

Kimberling, et al., Autosomal Dominant Polycystic Kidney Disease: Localization of the Second Gene to Chromosome 4q13–q23, Genomics, vol. 18, 467–472 (1993).

Kimberling, et al., "Linkage Heterogeneity of Autosomal Dominant Polycystic Kidney Disease", The New England Journal of Medicine, vol. 319, No. 14 913–918 (1988).

Kobe, et al., "The leucine–rich repeat: a versatile binding motif," TIBS, vol. 19, (1994).

Kornblihtt, et al., "Primary structure of human fibronectin: differential splicing may generate at least 10 polypeptides from a single gene", The EMBO Journal, vol. 4, No. 7, pp. 1755–1759 (1985).

Kozak, An analysis of 5'–noncoding sequences from 699 vertebrate messenger RNAs, Nuclear Acids Research, vol. 15, No. 20 8125–8144 (1987).

Kuma, et al., Motifs of Cadherin– and Fibronectin Type III–related Sequences and Evolution of the Receptor–Type–Protein Tyrosine Kinases: Sequence Similarity between Proto–Oncogene ret and Cadherin Family, Mol. Biol. Evol., 10(3):539–551 (1993).

Kwon, et al., "A melanocyte–specific gene, Pmel 17, maps near the silver coat color locus on mouse chromosome 10 and is in a syntenic region on human chromosome 12", Proc. Natl. Acad. Sci. USA vol. 88, pp. 9288–9232 (1991).

Lamballe, et al., trkC, a New Member of the trk Family of Tyrosine Protein Kinases, Is a Receptor for Neurotropin–3, Cell, vol. 66, 967–979 (1991).

Legius, et al., "Somatic deletion of the neurofibromatosis type 1 gene in a neurofibrosarcoma supports a tumour suppressor gene hypothesis", Nature Genetics, vol. 3 122–125 (1993).

Love, et al., "An autosomal transcript in skeletal muscle with homology to dystrophin", Nature, vol. 339, No. 6219, pp. 55–58 (1989).

Mandel, "Question of expansion", Nature Genetics, vol. 4 8–9 (1989).

Matsushita, et al., "Purification and Characterization of a *Clostridium perfringens* 120–Kilodalton Collagenase and Nucleotide Sequence of the Corresponding Gene", Journal of Bacteriology, vol. 176, No. 1, pp. 149–156 (Jan. 1994).

McFarland, et al., "Lutropin–Choriogonadotropin Receptor: An Unusual Member of the G Protein–Coupled Receptor Family", Science, vol. 245, 494–499, (1989).

Melton, et al., "Efficient in vitro synthesis of biologically active RNA and RNA hybridization probes from plasmids containing a bacteriophage SP6 promoter", vol. 12, No. 18, 7035–7056 (1984).

Milutinovic, et al., "Liver Cysts in Patients with Autosomal Dominant Polycystic Kidney Disease", The American Journal of Medicine, vol. 68 741–744 (1980).

Milutinovic, et al., "Autosomal Dominant Polycystic Kidney Disease—Early Diagnosis and Consideration of Pathogenesis", vol. 73, No. 6 740–747 (1980).

Nakashima, et al., "The amino acid composition is different between the cytoplasmic and extracellular sides in membrane proteins", vol. 303, No. 2, 3, 141–146 (1992).

Oldberg, et al., "A collagen–binding 59–kd protein (fibromodulin) is structurally related to the small interstitial proteoglycans PG–S1 and PG–S2 (decorin)", The EMBO Journal, vol. 8, No. 9, pp. 2601–2604 (1989).

Oldberg, et al., "The partial amino acid sequence of bovine cartilage proteoglycan, deduced from a cDNA clone, contains numerous Ser–Gly sequences arranged in homologous repeats", Biochem. J., vol. 243, 255–259 (1987).

Parfrey, et al., "The Diagnosis And Prognosis of Autosomal Dominant Polycystic Kidney Disease", The New England Journal of Medicine, vol. 323, No. 16 1085–1090 (1990).

Pearson, et al., "Improved tools for biological sequence comparison", Proc. Natl. Acad. Sci. USA, vol. 85, pp. 2444–2448 (1988).

Peral, et al., "Evidence of Linkage Disequilibrium in the Spanish Polycystic Kidney Disease I Population", Am. J. Hum. Genet. 54:899–908 (1994).

Peral, et al., "Splicing mutations of the polycystic kidney disease 1 (PKD1) gene induced by intronic deletion", Human Molecular Genetics, vol. 4, No. 4 569–574 (1995).

Peters, et al., "Chromosome 4 localization of a second gene for autosomal dominant polycystic kidney disease", Nature Genetics, vol. 5, 359–362 (1993).

Pound, et al., "Evidence of linkage disequilibrium between D16S94 and the adult onset polycystic kidney disease (PKD1) gene", Med. Genet, 29:247–248 (1992).

Ravine, et al., "Treatable complications in undiagnosed cases of autosomal dominant polycystic kidney disease", The Lancet, vol. 337, No. 8734 127–129 (1991).

Ravine, et al., "Phenotype and genotype heterogeneity in autosomal dominant polycystic kidney disease", The Lancet, vol. 340 1330–1333 (1992).

Reeders, "Multilocus polycystic disease", Nature Genetics, vol. 1 235–237 (1992).

Royle et al., "A hypervariable locus D16S309 located at the distal end of 16p", Nucleic Acids Research, vol. 20, No. 5.

Reeders, et al., "A highly polymorphic DNA marker linked to adult polycystic kidney disease on chromosome 16", Nature, vol. 317 542–544 (1985).

Reeders, et al., "Regional Localization of the Autosomal Dominant Polycystic Kidney Disease Locus", Genomics 3, 150–155 (1988).

Romeo, et al., "A Second Genetic Locus For Autosomal Dominant Polycystic Kidney Disease", The Lancet (Jul. 2, 1988), pp. 8–10.

Roth, "Developing Relationships: Arterial Platelet Adhesion, Glycoprotein Ib, and Leucine–Rich Glycoproteins", Blood, vol. 77, No. 1 (1991).

Rothberg, et al., "slit: an extracellular protein necessary for development of midline glia and commissural axon pathways contains both EGF and LRR domains", Genes & Development, 4:2169–2187 (1990).

Ryynanen, et al., "Localisation of a mutation producing autosomal dominant polycystic kidney disease without renal failure", Journal of Medical Genetics 24, 462–465 (1987).

Schafer, et al., "Characterization for the Han: SPRD rat model for hereditary polycystic kidney disease", Kidney International, vol. 46, pp. 134–152 (1994).

Scheff, et al., "Diverticular Disease in Patients with Chronic Renal Failure Due to Polycystic Kidney Disease", Annals of Internal Medicine, 92(Part 1):202–204 (1980).

Sipos, et al., "Predicting the topology of eukaryotic membrane proteins", Eur. J. Biochem. 213 1333–1340 (1993).

Snarey, et al., "Linkage Disequilibrium in the Regional of the Autosomal Dominant Polycystic Kidney Disease Gene (PKDI)", Am. J. Hum. Genet. 55:365–371 (1994).

Somlo, et al., "Fine Genetic Localization of the Gene for Autosomal Dominant Polycystic Kidney Disease (PKD1) with Respect to Physically Mapped Markers", Genomics 13, 152–158 (1992).

Somlo, et al., "A Kindred Exhibiting Cosegregation of an Overlap Connective Tissue Disorders and the Chromo–some 16 Linked Form of Autosomal Dominant Polycystic Kidney Disease", Journal of the American Society of Nephrology, vol. 4 1371–1378 (1993).

Streuli, et al., "A New Member Of The Immunoglobulin Superfamily That Has A Cytoplasmic Region Homologous To The Leukocyte Common Antigen", J. Exp. Med. vol. 168 1553–1562 (1988).

Takagi, et al., Primary Structure of the Target of Calcium Vector Protein of Amphioxus, Journal of Biological Chemistry, vol. 265, pp. 19721–19727 (1990).

Taylor, et al., Primary Structure of the Mannose Receptor Contains Multiple Motif Resembling Carbohydrate–recognition Domains, The Journal of Biological Chemistry, vol. 265, pp. 12156–12162 (1990).

Thompson, et al., "Isolation and Characterization of (AC)$_n$ Microsatellite Genetic Markers from Human Chromo–some 16", Genomics 13, 402–406 (1992).

Volkmer, et al., "Structure of the Axonal Surface Recognition Molecule Neurofascin and Its Relationship to a Neural Subgroup of the Immunoglobulin Superfamily", The Journal of Cell Biology, vol. 118, 149–161 (1992).

Weis, et al., "Structure of a C–type mannose–binding protein complexed with an oligosaccharide", Nature, vol. 360 127–134 (1992).

Wieringa, et al., "A Minimal Intron Length but No Specific Internal Sequence is Required for Splicing the Large Rabbit B–Globin Intron", Cell, vol. 37, 915–925 (1984).

Williams, et al., "The Immunoglobulin Superfamily—Domains for Cell Surface Recognition", Ann. Rev. Immunol. 6:381–405 (1988).

Wilson, et al., "Tubulocystic epithelium", International Society of Nephrology, vol. 39, pp. 450–563 (1991).

Wright, et al., "Sample Preparation From Paraffin–Embedded Tissues", PCR Protocols: A Guide to Methods and Applications San Diego:Academic Press, pp. 153–158 (1990).

Zerres, et al., "Childhood onset autosomal dominant polycystic kidney disease in sibs: clinical picture and recurrence risk", J Med Genet, 30:583–588 (1993).

Bork, et al., "Fibronectin type III modules in the receptor phosphatase CD45 and tapeworm antigens", Protein Science, 2: 1185–1187, (1993).

Frohman et al., "Rapid production of full–length cDNAs from rare transcripts: Amplification using a single gene–specific oligonucleotide primer", Proc. Natl. Acad. Sci. USA, vol. 85: 8998–9002, (Dec. 1988).

Germino et al., "A novel approach to the identification of the PKD1 gene," J. Am. Soc. Nephrol. 4:814 (1993).

Germino et al., "The gene for autosomal dominant polycystic kidney disease Lies in a 750–kb CpG–Rich Region," Genomics, 13:144–151 (1992).

Adams et al., "Rapid cDNA sequencing (expressed sequence tags) from a directionally cloned human infant brain cDNA library," Nature Genetics 4:373–380 (1993).

Adams et al., "Expressed sequence tags identify diversity of transcripts from human brain," EMBL Database, 4:256–267 (1993).

Ward et al., "The polycystic kidney disease 1 gene encoded a 14kb transcript and lies within a duplicated region on chromosome 16," Cell, 77:881–894 (1994).

Kandt et al., "Linkage of an important gene locus for tuberous sclerosis to a chromosome 16 marker for polycystic kidney disease," Nature Genetics, 2:37–41 (1992).

Kwiatkowski et al., "Report on the second international workshop on human chromosome 9," Cytogenet. Cell Genet., 64:94–106 (1993).

Green et al., "Loss of heterozygosity on chromosome 16p in hamartomas from patients with tuberous sclerosis," American Journal of Human Genetics, 53 Suppl. (1993) Abstr. #244.

Smith et al., "Loss of heterozygosity for chromosome 16p13.3 markers in renal hamartomas from tuberous sclerosis patients," American Journal Of Human Genetics, 53 Suppl. (1993) Abstr #366.

Green et al., Loss of heterozygosity on chromosome 16p13.3 in hamartomas from tuberous sclerosis patients, Nature Genetics, 6:193–196 (1994).

Viskochil et al., "Deletions and translocation interrupt a cloned gene at the neurofibromatosis type 1 locus," Cell, 62:187–192 (1990).

Rouleau et al., "Alteration in a new gene encoding a putative membrane–organizing protein causes neuro–fibromatosis type 2," Nature, 363:515–521 (1993).

Nellist et al., "Identification and characterization of the tuberous sclerosis gene on chromosome 16," Cell, 75:1305–1315 (1993).

EMBL Database, Accession No. T05931, sequence ref. HS9312, Sep. 2 1993; Adams et al., "Expressed sequence tags identify diversity of transcripts from human brain," & Nature Genetics, 4:256–267 (1991).

EMBL Database, Accession No. T04943, sequence ref. HS9431, Aug. 30, 1993, Adams et al., "Expressed tags identify diversity of transcripts from human brain," & Nature Genetics, 4:256–267 (1993).

EMBL Database, Accession No. T09303, sequence reference T09303, Aug. 7, 1993; Adams et al., "Rapid cDNA sequencing (expressed sequence tags) from a directionally cloned human infant brain cDNA library," & Nature Genetics, 4:373–380 (1993).

EMBL Database, Accession No. Z24945, sequence reference HSB74B072, Jul. 30, 1993 Genexpress: "The Genexpress cDNA program,".

Search Report for priority document PCT/GB94/02822.

Search Report for priority document PCT/GB94/02823.

Adams et al., File Medicine Abstract No. 93364420, Nature Genetics 4:256–267 (1993).

Adams et al., File Medicine Abstract No. 94004965, Nature Genetics 4:373–380 (1993).

Burn et al., Analysis of the genomic sequence for the autosomal dominant polycystic kidney disease (PKD1) gene predicts the presence of a leucine–rich repeat, Human Molecular Genetics 4(4):575–582 (1995).

Germino et al., Positional cloning approach to the dominant polycystic kidney disease gene, PKD1, Kidney International, vol. 43, Supp. 39, S–20–S–25 (1993).

An Introduction to Genetic Analysis; W.H. Freeman and Company, Fifth Ed., pp. 427, 453–461 (Dec. 1993).

Mulley et al., Integrating maps of chromosome 16; Current Opinion in Genetics and Development 3:425–431 (1993).

* cited by examiner

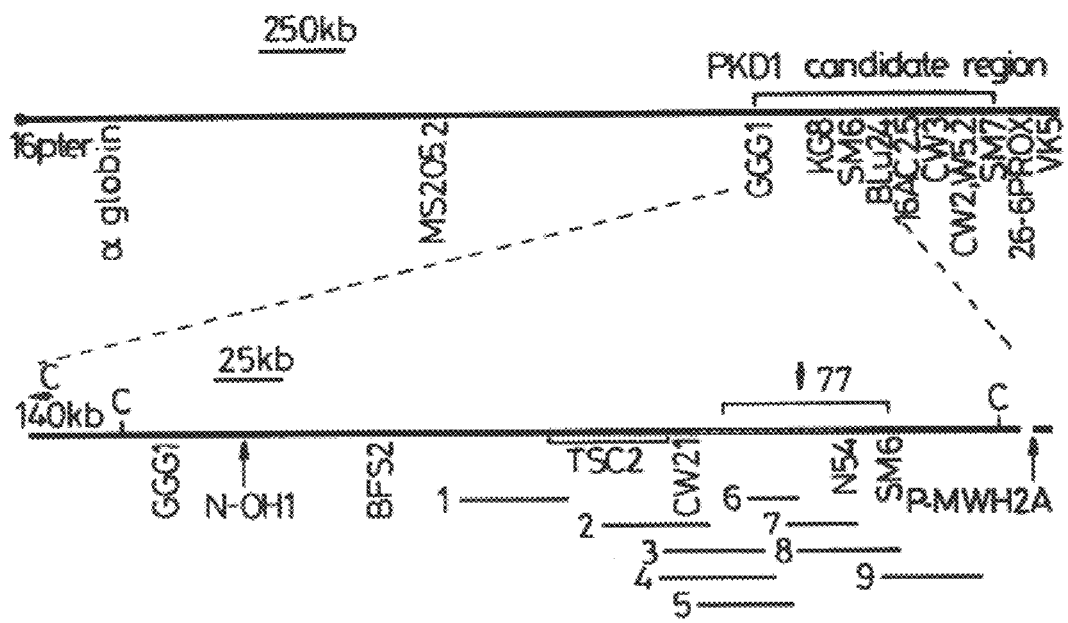
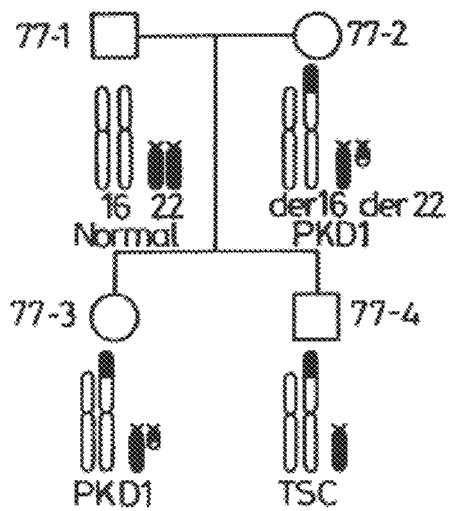 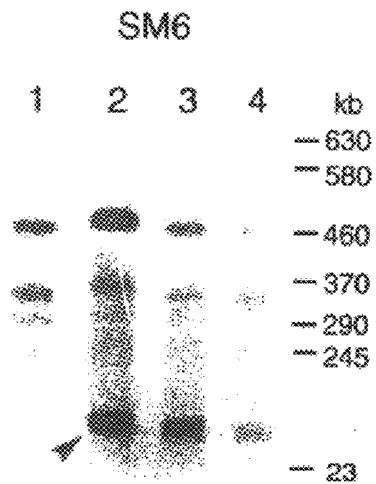
FIG. 1A
FIG. 1B  FIG. 1C

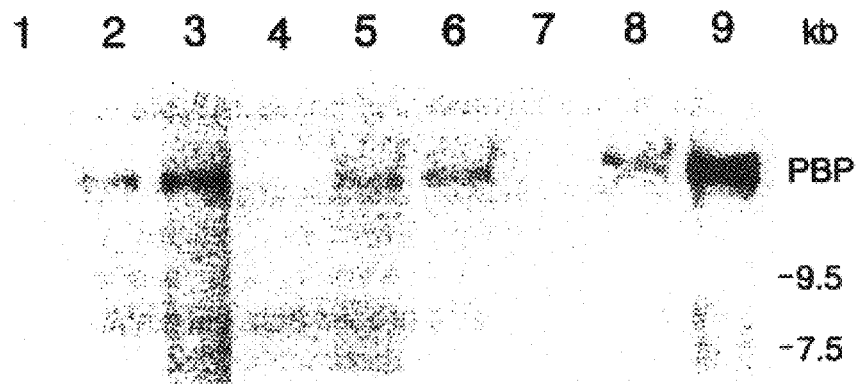
FIG. 4A
FIG. 4B
FIG. 4C

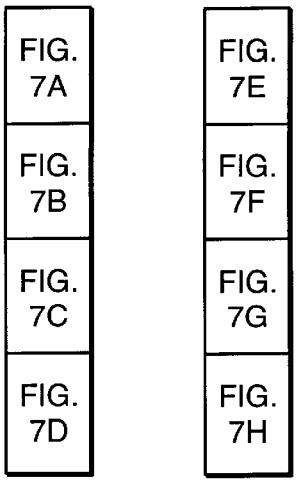

FIG. 7

```
  1  CTCAACGAGGAGCCCCTGACGCTGGCGGGCGAGGAGATCGTGGCCCAGGGCAAGCGCTCG    60
  1  L  N  E  E  P  L  T  L  A  G  E  E  I  V  A  Q  G  K  R  S     20

61  GACCCGCGGAGCCTGCTGTGCTATGGCGGCGCCCCAGGGCCTGGCTGCCACTTCTCCATC   120
 21  D  P  R  S  L  L  C  Y  G  G  A  P  G  P  G  C  H  F  S  I    40

121  CCCGAGGCTTTCAGCGGGGCCCTGGCCAACCTCAGTGACGTGGTGCAGCTCATCTTTCTG   180
 41  P  E  A  F  S  G  A  L  A  N  L  S  D  V  V  Q  L  I  F  L    60

181  GTGGACTCCAATCCCTTTCCCTTTGGCTATATCAGCAACTACACCGTCTCCACCAAGGTG   240
 61  V  D  S  N  P  F  P  F  G  Y  I  S  N  Y  T  V  S  T  K  V    80

241  GCCTCGATGGCATTCCAGACACAGGCCGCCGCCCAGATCCCCATCGAGCGGCTGGCCTCA   300
 81  A  S  M  A  F  Q  T  Q  A  G  A  Q  I  P  I  E  R  L  A  S   100

301  GAGCGCGCCATCACCGTGAAGGTGCCCAACAACTCGGACTGGGCTGCCCGGGGCCACCGC   360
101  E  R  A  I  T  V  K  V  P  N  N  S  D  W  A  A  R  G  H  R   120

361  AGCTCCGCCAACTCCGCCAACTCCGTTGTGGTCCAGCCCCAGGCCTCCGTCGGTGCTGTG   420
121  S  S  A  N  S  A  N  S  V  V  V  Q  P  Q  A  S  V  G  A  V   140

421  GTCACCCTGGACAGCAGCAACCCTGCGGCCGGGCTGCATCTGCAGCTCAACTATACGCTG   480
141  V  T  L  D  S  S  N  P  A  A  G  L  H  L  Q  L  N  Y  T  L   160

481  CTGGACGGCCACTACCTGTCTGAGGAACCTGAGCCCTACCTGGCAGTCTACCTACACTCG   540
161  L  D  G  H  Y  L  S  E  E  P  E  P  Y  L  A  V  Y  L  H  S   180

541  GAGCCCCGGCCCAATGAGCACAACTGCTCGGCTAGCAGGAGGATCCGCCCAGAGTCACTC   600
181  E  P  R  P  N  E  H  N  C  S  A  S  R  R  I  R  P  E  S  L   200
```

FIG. 7A

```
601   CAGGGTGCTGACCACCGGCCCTACACCTTCTTCATTTCCCCGGGGAGCAGAGACCCAGCG   660
201   Q  G  A  D  H  R  P  Y  T  F  F  I  S  P  G  S  R  D  P  A     220

661   GGGAGTTACCATCTGAACCTCTCCAGCCACTTCCGCTGGTCGGCGCTGCAGGTGTCCGTG   720
221   G  S  Y  H  L  N  L  S  S  H  F  R  W  S  A  L  Q  V  S  W     240

721   GGCCTGTACACGTCCCTGTGCCAGTACTTCAGCGAGGAGGACATGGTGTGGCGGACAGAG   780
241   G  L  Y  T  S  L  C  Q  Y  F  S  E  E  D  M  V  W  R  T  E     260

781   GGGCTGCTGCCCCTGGAGGAGACCTCGCCCCGCCAGGCCGTCTGCCTCACCCGCCACCTC   840
261   G  L  L  P  L  E  E  T  S  P  R  Q  A  V  C  L  T  R  H  L     280

841   ACCGCCTTCGGCGCCAGCCTCTTCGTGCCCCCAAGCCATGTCCGCTTTGTGTTTCCTGAG   900
281   T  A  F  G  A  S  L  F  V  P  P  S  H  V  R  F  V  F  P  E     300

901   CCGACAGCGGATGTAAACTACATCGTCATGCTGACATGTGCTGTGTGCCTGGTGACCTAC   960
301   P  T  A  D  V  N  Y  I  V  M  L  T  C  A  V  C  L  V  T  Y     320

961   ATGGTCATGGCCGCCATCCTGCACAAGCTGGACCAGTTGGATGCCAGCCGGGGCCGCGCC   1020
321   M  V  M  A  A  I  L  H  K  L  D  Q  L  D  A  S  R  G  R  A     340

1021  ATCCCTTTCTGTGGGCAGCGGGGCCGCTTCAAGTACGAGATCCTCGTCAAGACAGGCTGG   1080
341   I  P  F  C  G  Q  R  G  R  F  K  Y  E  I  L  V  K  T  G  W     360

1081  GGCCGGGGCTCAGGTACCACGGCCCACGTGGGCATCATGCTGTATGGGGTGGACAGCCGG   1140
361   G  R  G  S  G  T  T  A  H  V  G  I  M  L  Y  G  V  D  S  R     380

1141  AGCGGCCACCGGCACCTGGACGGCGACAGAGCCTTCCACCGCAACAGCCTGGACATCTTC   1200
381   S  G  H  R  H  L  D  G  D  R  A  F  H  R  N  S  L  D  I  F     400

1201  CGGATCGCCACCCCGCACAGCCTGGGTAGCGTGTGGAAGATCCGAGTGTGGCACGACAAC   1260
401   R  I  A  T  P  H  S  L  G  S  V  W  K  I  R  V  W  H  D  N     420
```

FIG. 7B

```
1261  AAAGGGCTCAGCCCTGCCTGGTTCCTGCAGCACGTCATCGTCAGGGACCTGCAGACGGCA  1320
 421   K  G  L  S  P  A  W  F  L  Q  H  V  I  V  R  D  L  Q  T  A   440

1321  CGCAGCGCCTTCTTCCTGGTCAATGACTGGCTTTCGGTGGAGACGGAGGCCAACGGGGGC  1380
 441   R  S  A  F  F  L  V  N  D  W  L  S  V  E  T  E  A  N  G  G   460

1381  CTGGTGGAGAAGGAGGTGCTGGCCGCGAGCGACGCAGCCCTTTTGCGCTTCCGGCGCCTG   140
 461   L  V  E  K  E  V  L  A  A  S  D  A  A  L  L  R  F  R  R  L   480

1441  CTGGTGGCTGAGCTGCAGCGTGGCTTCTTTGACAAGCACATCTGGCTCTCCATATGGGAC  1500
 481   L  V  A  E  L  Q  R  G  F  F  D  K  H  I  W  L  S  I  W  D   500

1501  CGGCCGCCTCGTAGCCGTTTCACTCGCATCCAGAGGGCCACCTGCTGCGTTCTCCTCATC  1560
 501   R  P  P  R  S  R  F  T  R  I  Q  R  A  T  C  C  V  L  L  I   520

1561  TGCCTCTTCCTGGGCGCCAACGCCGTGTGGTACGGGCTGTTGGCGACTCTGCCTACAGC   1620
 521   C  L  F  L  G  A  N  A  V  W  Y  G  A  V  G  D  S  A  Y  S   540

1621  ACGGGGCATGTGTCCAGGCTGAGCCCGCTGAGCGTCGACACAGTCGCTGTTGGCCTCGTG  1680
 541   T  G  H  V  S  R  L  S  P  L  S  V  D  T  V  A  V  G  L  V   560

1681  TCCAGCGTGGTTGTCTATCCCGTCTACCTGGCCATCCTTTTTCTCTTCCGGATGTCCCGG  1740
 561   S  S  V  V  V  Y  P  V  Y  L  A  I  L  F  L  F  R  M  S  R   580

1741  AGCAAGGTGGCTGGGAGCCCGAGCCCCCACACTGCCGGGCAGCAGGTGCTGGACATCGAC  1800
 581   S  K  V  A  G  S  P  S  P  T  P  A  G  Q  Q  V  L  D  I  D   600

1801  AGCTGCCTGGACTCGTCCGTGCTGGACAGCTCCTTCCTCACGTTCTCAGGCCTCCACGCT  1860
 601   S  C  L  D  S  S  V  L  D  S  S  F  L  T  F  S  G  L  H  A   620

1861  GAGGCCTTTGTTGGACAGATGAAGAGTGACTTGTTTCTGGATGATTCTAAGAGTCTGGTG  1920
 621   E  A  F  V  G  Q  M  K  S  D  L  F  L  D  D  S  K  S  L  V   640
```

FIG. 7C

```
1921  TGCTGGCCCTCCGGCGAGGGAACGCTCAGTTGGCCGCACCTGCTCAGTGACCCGTCCATT  1980
641    C   W   P   S   G   E   G   T   L   S   W   P   D   L   L   S   D   P   S   I    660

1981  GTGGGTAGCAATCTGCGGCAGCTGGCACGGGGCCAGGCGGGCCATGGGCTGGGCCCAGAG  2040
661    V   G   S   N   L   R   Q   L   A   R   G   Q   A   G   H   G   L   G   P   E    680

2041  GAGGACGGCTTCTCCCTGGCCAGCCCCTCCTCGCCTGCCAAATCCTTCTCAGCATCAGAT  2100
681    E   D   G   F   S   L   A   S   P   Y   S   P   A   K   S   F   S   A   S   D    700

2101  GAAGACCTGATCCAGGAGGTCCTTGCCGAGGGGGTCAGCAGCCCAGCCCCTACCCAAGAC  2160
701    E   D   L   I   Q   Q   V   L   A   E   G   V   S   S   P   A   P   T   Q   D    720

2161  ACCCACATGGAAACGGACCTGCTCAGCAGCCTGTCCAGCACTCCTGGGGAGAAGACAGAG  2220
721    T   H   M   E   T   D   L   L   S   S   L   S   S   T   P   G   E   K   T   E    740

2221  ACGCTGGCGCTGCAGAGGCTGGGGGAGCTGGGGCCACCCAGCCCAGGCCTGAACTGGGAA  2280
741    T   L   A   L   Q   R   L   G   E   L   G   P   P   S   P   G   L   N   W   E    760

2281  CAGCCCCAGGCAGCGAGGCTGTCCAGGACAGGACTGGTGGAGGGTCTGCGGAAGCGCCTG  2340
761    Q   P   Q   A   A   R   L   S   R   T   G   L   V   E   G   L   R   K   R   L    780

2341  CTGCCGGCCTGGTGTGCCTCCCTGGCCCACGGGCTCAGCCTGCTCCTGGTGGCTGTGGCT  2400
781    L   P   A   W   C   A   S   L   A   H   G   L   S   L   L   L   V   A   V   A    800

2401  GTGGCTGTCTCAGGGTGGGTGGGTGCGAGCTTCCCCCCGGGCCTGAGTGTTGCGTGGCTC  2460
801    V   A   V   S   G   W   V   G   A   S   F   P   P   G   V   S   V   A   W   L    820

2461  CTGTCCAGCAGCGCCAGCTTCCTGGCCTCATTCCTCGGCTGGGAGCCACTGAAGGTCTTG  2520
821    L   S   S   S   A   S   F   L   A   S   F   L   G   W   E   P   L   K   V   L    840
```

FIG. 7D

| | | |
|---|---|---|
| 2521 | CTGGAAGCCCTGTACTTCTCACTGGTGGCCAAGCGGCTGCACCCGGATGAAGATGACACC | 2580 |
| 841 | L E A L Y F S L V A K R L H P D E D D T | 860 |

| | | |
|---|---|---|
| 2581 | CTGGTAGAGAGCCCGGCTGTGACGCCTGTGAGCGCACGTGTGCCCCGCGTACGGCCACCC | 2640 |
| 861 | L V E S P A V T P V S A R V P R V P P | 880 |

| | | |
|---|---|---|
| 2641 | CACGGCTTTGCACTCTTCCTGGCCAAGGAAGAAGCCCGCAAGGTCAAGAGGCTACATGGC | 2700 |
| 881 | H G F A L F L A K E E A R K V K R L H G | 900 |

| | | |
|---|---|---|
| 2701 | ATGCTGCGGAGCCTCCTGGTGTACATGCTTTTTCTGCTGGTGACCCTGCTGGCCAGCTAT | 2760 |
| 901 | M L R S L L V Y M L F L L V T L L A S Y | 920 |

| | | |
|---|---|---|
| 2761 | GGGGATGCCTCATGCCATGGGCACGCCTACCGTCTGCAAAGCGCCATCAAGCAGGAGCTG | 2820 |
| 921 | G D A S C H G H A Y R L Q S A I K Q E L | 940 |

| | | |
|---|---|---|
| 2821 | CACAGCCGGGCCTTCCTGGCCATCACGCGGTCTGAGGAGCTCTGGCCATGGATGGCCCAC | 2880 |
| 941 | H S R A F L A I T R S E E L W P W M A H | 960 |

| | | |
|---|---|---|
| 2881 | GTGCTGCTGCCCTACGTCCACGGGAACCAGTCCAGCCCAGAGCTGGGGCCCCCACGGCTG | 2940 |
| 961 | V L L P Y V H G N Q S S P E L G P P R L | 980 |

| | | |
|---|---|---|
| 2941 | CGGCAGGTGCGGCTGCAGGAAGCACTCTACCCAGACCCTCCCGGCCCCAGGGTCCACACG | 3000 |
| 981 | R Q V R L Q E A L Y P D P P G P R V H T | 1000 |

| | | |
|---|---|---|
| 3001 | TGCTCGGCCGCAGGAGGCTTCAGCACCAGCGATTACGACGTTGGCTGGGAGAGTCCTCAC | 3060 |
| 1001 | C S A A G G F S T S D Y D V G W E S P H | 1020 |

| | | |
|---|---|---|
| 3061 | AATGGCTCGGGGACGTGGGCCTATTCAGCGCCGGATCTGCTGGGGGCATGGTCCTGGGGC | 3120 |
| 1021 | N G S G T W A Y S A P D L L G A W S W G | 1040 |

FIG. 7E

| | | |
|---|---|---|
| 3121 | TCCTGTGCCGTGTATGACAGCGGGGGCTACGTGCAGGAGCTGGGCCTGAGCCTGGAGGAG | 3180 |
| 1041 | S  C  A  V  Y  D  S  G  G  Y  V  Q  E  L  G  L  S  L  E  E | 1060 |
| 3181 | AGCCGCGACCGGCTGCGCTTCCTGCAGCTGCACAACTGGCTGGACAACAGGAGCCGCGCT | 3240 |
| 1061 | S  R  D  R  L  R  F  L  Q  L  H  N  W  L  D  N  R  S  R  A | 1080 |
| 3241 | GTGTTCCTGGAGCTCACGCGCTACAGCCCGGCCGTGGGGCTGCACGCCGCCGTCACGCTG | 3300 |
| 1081 | V  F  L  E  L  T  R  Y  S  P  A  V  G  L  H  A  A  V  T  L | 1100 |
| 3301 | CGCCTCGAGTTCCCGGCGGCCGGCCGCGCCCTGGCCGCCCTCAGCGTCCGCCCCTTTGCG | 3360 |
| 1101 | R  L  E  F  P  A  A  G  R  A  L  A  A  L  S  V  R  P  F  A | 1120 |
| 3361 | CTGCGCCGCCTCAGCGCGGGCCTCTCGCTGCCTCTGCTCACCTCGGTGTGCCTGCTGCTG | 3420 |
| 1121 | L  R  R  L  S  A  G  L  S  L  P  L  L  T  S  V  C  L  L  L | 1140 |
| 3421 | TTCGCCGTGCACTTCGCCGTGGCCGAGGCCCGTACTTGGCACAGGGAAGGGCGCTGGCGC | 3480 |
| 1141 | F  A  V  H  F  A  V  A  E  A  R  T  W  H  R  E  G  R  W  R | 1160 |
| 3481 | GTGCTGCGGCTCGGAGCCTGGGCGCGGTGGCTGCTGGTGGCGCTGACGGCGGCCACGGCA | 3540 |
| 1161 | V  L  R  L  G  A  W  A  R  W  L  L  V  A  L  T  A  A  T  A | 1180 |
| 3541 | CTGGTACGCCTCGCCCAGCTGGGTGCCGCTGACCGCCAGTGGACCCGTTTCGTGCGCGGC | 3600 |
| 1181 | L  V  R  L  A  Q  L  G  A  A  D  R  Q  W  T  R  F  V  R  G | 1200 |
| 3601 | CGCCCGCGCCGCTTCACTAGCTTCGACCAGGTGGCGCACGTGAGCTCCGCAGCCCGTGGC | 3660 |
| 1201 | R  P  R  R  F  T  S  F  D  Q  V  A  H  V  S  S  A  A  R  G | 1220 |
| 3661 | CTGGCGGCCTCGCTGCTCTTCCTGCTTTTGGTCAAGGCTGCCCAGCACGTACGCTTCGTG | 3720 |
| 1221 | L  A  A  S  L  L  F  L  L  L  V  K  A  A  Q  H  V  R  F  V | 1240 |
| 3721 | CGCCAGTGGTCCGTCTTTGGCAAGACATTATGCCGAGCTCTGCCAGAGCTCCTGGGGGTC | 3780 |
| 1241 | R  Q  W  S  V  F  G  K  T  L  C  R  A  L  P  E  L  L  G  V | 1260 |

FIG. 7F

```
3781  ACCTTGGGCCTGGTGGTGCTCGGGGTAGCCTACGCCCAGCTGGCCATCCTGCTCGTGTCT  3840
1261   T  L  G  L  V  V  L  G  V  A  Y  A  Q  L  A  I  L  L  V  S   1280

3841  TCCTGTGTGGACTCCCTCTGGAGCGTGGCCCAGGCCCTGTTGGTGCTGTGCCCTGGGACT  3900
1281   S  C  V  D  S  L  W  S  V  A  Q  A  L  L  V  L  C  P  G  T   1300

3901  GGGCTCTCTACCCTGTGTCCTGCCGAGTCCTGGCACCTGTCACCCCTGCTGTGTGTGGGG  3960
1301   G  L  S  T  L  C  P  A  E  S  W  H  L  S  P  L  L  C  V  G   1320

3961  CTCTGGGCACTGCGGCTGTGGGGCGCCCTACGGCTGGGGGCTGTTATTCTCCGCTGGCGC  4020
1321   L  W  A  L  R  L  W  G  A  L  R  L  G  A  V  I  L  R  W  R   1340

4021  TACCACGCCTTGCGTGGAGAGCTGTACCGGCCGGCCTGGGAGCCCCAGGACTACGAGATG  4080
1341   Y  H  A  L  R  G  E  L  Y  R  P  A  W  E  P  Q  D  Y  E  M   1360

4081  GTGGAGTTGTTCCTGCGCAGGCTGCGCCTCTGGATGGGCCTCAGCAAGGTCAAGGAGTTC  4140
1361   V  E  L  F  L  R  R  L  R  L  W  M  G  L  S  K  V  K  E  F   1380

4141  CGCCACAAAGTCCGCTTTGAAGGGATGGAGCCGCTGCCCTCTCGCTCCTCCAGGGGCTCC  4200
1381   R  H  K  V  R  F  E  G  M  E  P  L  P  S  R  S  S  R  G  S   1400

4201  AAGGTATCCCCGGATGTGCCCCCACCCAGCGCTGGCTCCGATGCCTCGCACCCCTCCACC  4260
1401   K  V  S  P  D  V  P  P  P  S  A  G  S  D  A  S  H  P  S  T   1420

4261  TCCTCCAGCCAGCTGGATGGGCTGAGCGTGAGCCTGGGCCGGCTGGGGACAAGGTGTGAG  4320
1421   S  S  S  Q  L  D  G  L  S  V  S  L  G  R  L  G  T  R  C  E   1440

4321  CCTGAGCCCTCCCGCCTCCAAGCCGTGTTCGAGGCCCTGCTCACCCAGTTTGACCGACTC  4380
1441   P  E  P  S  R  L  Q  A  V  F  E  A  L  L  T  Q  F  D  R  L   1460
```

FIG. 7G

| | | |
|---|---|---|
| 4381 | AACCAGGCCACAGAGGACGTCTACCAGCTGGAGCAGCAGCTGCACAGCCTGCAAGGCCGC | 4440 |
| 1461 | N Q A T E D V Y Q L E Q Q L H S L Q G R | 1480 |
| 4441 | AGGAGCAGCCGGGCGCCCGCCGGATCTTCCCGTGGCCCATCCCCGGGCCTGCGGCCAGCA | 4500 |
| 1481 | R S S R A P A G S S R G P S P G L R P A | 1500 |
| 4501 | CTGCCCAGCCGCCTTGCCCGGGCCAGTCGGGGTGTGGACCTGGCCACTGGCCCCAGCAGG | 4560 |
| 1501 | L P S R L A R A S R G V D L A T G P S R | 1520 |
| 4561 | ACACCTTCGGGCCAAGAACAAGGTCCACCCCAGCAGCACTTAGTCCTCCTTCCTGGCGGG | 4620 |
| 1521 | T P S G Q E Q G P P Q Q H L V L L P G G | 1540 |
| 4621 | GGTGGGCCGTGGAGTCGGAGTGGACACCGCTCAGTATTACTTTCTGCCGCTGTCAAGGCC | 46890 |
| 1541 | G G P W S R S G H R S V L L S A A V K A | 1560 |
| 4681 | GAGGGCCAGGCAGAATGGCTGCACGTAGGTTCCCCAGAGAGCAGGCAGGGGCATCTGTCT | 4740 |
| 1561 | E G Q A E W L H V G S P E S R Q G H L S | 1580 |
| 4741 | GTCTGTGGGCTTCAGCACTTTAAAGAGGCTGTGTGGCCAACCAGGACCCAGGGTCCCCTC | 4800 |
| 1581 | V C G L Q H F K E A V W P T R T Q G P L | 1600 |
| 4801 | CCCAGCTCCCTTGGGAAGGACACAGCAGTATTGGACGGTTTCTAGCCTCTGAGATGCTAA | 4860 |
| 1601 | P S S L G K D T A V L D G F | 1620 |
| 4861 | TTTATTTCCCCGAGTCCTCAGGTACAGCCGGGCTGTGCCCGGCCCCACCCCCTGGGCAGAT | 4920 |
| 4921 | GTCCCCCACTGCTAAGGCTGCTGGCTTCAGGGAGGGTTAGCCTGCACCGCCGCCACCCTG | 4980 |
| 4981 | CCCCTAAGTTATTACCTCTCCAGTTCCTACCGTACTCCCTGCACCGTCTCACTGTGTGTC | 5040 |
| 5041 | TCGTCTCAGTAATTTATATGGTGTTAAAATGTGTATATTTTTGTATGTCACTATTTTCAC | 5100 |
| 5101 | TAGGGCTGAGGGGCCTGCGCCCAGAGCTGGCCTCCCCCAACACCTGCTGCGCTTGGTAGG | 5160 |
| 5161 | TGTGGTGGCGTTATGGCAGCCCGGCTGCTGCTTGGATGCGAGCTTGGCCTTGGGCCGGTG | 5220 |
| 5221 | CTGGGGGCACAGCTGTCTGCCAGGCACTCTCATCACCCCAGAGGCCTTGTCATCCTCCCT | 5280 |
| 5281 | TGCCCCAGGCCAGGTAGCAAGAGAGCAGCGCCCAGGCCTGCTGGCATCAGGTCTGGGCAA | 5340 |
| 5341 | CTAGCAGGACTAGGCATGTCAGAGGACCCCAGGGTGGTTAGAGGAAAAGACTCCTCCTGG | 5400 |
| 5401 | GGGCTGGCTCCCAGGGTGGAGGAAGGTGACTGTGTGTGTGTGTGTGCGCGCGCGACGC | 5460 |
| 5461 | GCGACTGTGCTGTATGGCCCAGGCACGCTCAAGGCCCTCGGAGCTGGCTGTGCCTGCTTC | 5520 |
| 5521 | TGTGTACCACTTCTGTGGGCATGGCCGCTTCTAGAGCCTCGACACCCCCCCAACCCCCGC | 5580 |
| 5581 | ACCAAGCAGACAAAGTCAATAAAAGAGCTGTCTGACTGCAAAAAAAAAAAA | 5631 |

FIG. 7H

```
AGCTTGGCAC CATCAAGGGC CAGTTCAACT TTGTCCACGT GATCGTCACC CCGCTGGACT    60
ACGAGTGCAA CCTGGTGTCC CTGCAGTGCA GGAAAGACAT GGAGGGCCTT GTGGACACCA   120
GCGTGGCCAA GATCGTGTCT GACCGCAACC TGCCCTTCGT GGCCCGCCAG ATGGCCCTGC   180
ACGCAAATAT GGCCTCACAG GTGCATCATA GCCGCTCCAA CCCCACCGAT ATCTACCCCT   240
CCAAGTGGAT TGCCCGGCTC CGCCACATCA GCGGCTCCG CCAGCGGATC TGCGAGGAAG    300
CCGCCTACTC CAACCCCAGC CTACCTCTGG TGCACCCTCC GTCCCATAGC AAAGCCCCTG   360
CACAGACTCC AGCCGAGCCC ACACCTGGCT ATGAGGTGGG CCAGCGGAAG CGCCTCATCT   420
CCTGGTGGA GGACTTCACC GAGTTTGTGT GAGGCCGGGG CCCTCCCTCC TGCACTGGCC    480
TTGGACGGTA TTGCCTGTCA GTGAAATAAA TAAAGTCCTG ACCCCAGTGC ACAGACATAG   540
AGGCACAGAT TGC                                                      553
```
(1A1HO.6)

FIG. 8

```
CTGGTGTGTG TGAGACGTGC GGGGCTGGGA AGTGTTGGCA GAGCCGCGAG TACCGTCCTC    60
ACTCCTTTTG TTCTTTTGAC GTAAGCTGGC GAGTGGCACT GCCTGAGTTC CGCTCAGTGC   120
CCGCCCTGAT GTGCGGACCC CGCTGCATTC TTGCTGTTAG GTGGTGGCGG TGTGCGCTGT   180
CGCTGGTGGG CACCGAGAGT CTTTGGGAGC TTTGGGGAGG TTGTGCCAAG CCTGAGCCTC   240
GACGTCCCCC TTCCCGGCTT TCTGTTGGCT CTTCTGAGGC CAGGGCATCT CTATGAGGGC   300
CTCCTGCTGG AGCCGTCTCT GTGGATCTCC TCTGCCATCC TGGCCCATGA GTGGGTGATG   360
CGCTGGCCAC CATCTGGTGA CAGTGGCCGG GCACCGCTGC CAAATGTGGG TCCCGCATCT   420
GCAAGCCCCT CCCTGGGTCC CCTAGGGTAT GGGGTGGTTC TGCCACTGCC CTCGCTCCCC   480
CACCTTGGGG TGCCTCTCCC CCTGCTCGTG GGGAGA                             517
```
(CW10L)

FIG. 9A

```
1    AGGCAGGTCT CCCCCACGAG CAGGGGAGAG GCACCCAAGG T
```
(CW10R)

FIG. 9B

```
  C GGC GCC GCC TGC CGC GTC AAC TGC TCG GGC CGC GGG CTG CGG ACG           46
    Gly Ala Ala Cys Arg Val Asn Cys Ser Gly Arg Gly Leu Arg Thr
     1               5                  10                  15

CTC GGT CCC GCG CTG CGC ATC CCC GCG GAC GCC ACA GCG CTA GAC GTC          94
  Leu Gly Pro Ala Leu Arg Ile Pro Ala Asp Ala Thr Ala Leu Asp Val
                  20                  25                  30

TCC CAC AAC CTG CTC CGG GCG CTG GAC GTT GGG CTC CTG GCG AAC CTC         142
  Ser His Asn Leu Leu Arg Ala Leu Asp Val Gly Leu Leu Ala Asn Leu
                  35                  40                  45

TCG GCG CTG GCA GAG CTG GAT ATA AGC AAC AAC AAG ATT TCT ACG TTA         190
  Ser Ala Leu Ala Glu Leu Asp Ile Ser Asn Asn Lys Ile Ser Thr Leu
                  50                  55                  60

GAA GAA GGA ATA TTT GCT AAT TTA TTT AAT TTA AGT GAA ATA AAC CTG         238
  Glu Glu Gly Ile Phe Ala Asn Leu Phe Asn Leu Ser Glu Ile Asn Leu
                  65                  70                  75

AGT GGG AAC CCG TTT GAG TGT GAC TGT GGC CTG GCG TGG CTG CCG CGA         286
  Ser Gly Asn Pro Phe Glu Cys Asp Cys Gly Leu Ala Trp Leu Pro Arg
       80                  85                  90                  95

TGG GCG GAG GAG CAG CAG GTG CGG GTG GTG CAG CCC GAG GCA GCC ACG         334
  Trp Ala Glu Glu Gln Gln Val Arg Val Val Gln Pro Glu Ala Ala Thr
                 100                 105                 110

TGT GCT GGG CCT GGC TCC CTG GCT GGC CAG CCT CTG CTT GGC ATC CCC         382
  Cys Ala Gly Pro Gly Ser Leu Ala Gly Gln Pro Leu Leu Gly Ile Pro
             115                 120                 125
```

FIG. 10A-1

```
TTG CTG GAC AGT GGC TGT GGT GAG GAG TAT GTC GCC TGC CTC CCT GAC       430
Leu Leu Asp Ser Gly Cys Gly Glu Glu Tyr Val Ala Cys Leu Pro Asp
    130              135                 140

AAC AGC TCA GGC ACC GTG GCA GCA GTG TCC TTT TCA GCT GCC CAC GAA       478
Asn Ser Ser Gly Thr Val Ala Ala Val Ser Phe Ser Ala Ala His Glu
145                 150                 155

GGC CTG CTT CAG CCA GAG GCC TGC AGC GCC TTC TGC TTC TCC ACC GGC       526
Gly Leu Leu Gln Pro Glu Ala Cys Ser Ala Phe Cys Phe Ser Thr Gly
160             165                 170                 175

CAG GGC CTC GCA GCC CTC TCG GAG CAG GGC TGG TGC CTG TGT GGG GCG       574
Gln Gly Leu Ala Ala Leu Ser Glu Gln Gly Trp Cys Leu Cys Gly Ala
                180                 185                 190

GCC CAG CCC TCC AGT GCC TCC TTT GCC TGC CTG TCC CTC TGC TCC GGC       622
Ala Gln Pro Ser Ser Ala Ser Phe Ala Cys Leu Ser Leu Cys Ser Gly
            195                 200                 205

CCC CCG CCA CCT CCT GCC CCC ACC TGT AGG GGC CCC ACC CTC CTC CAG       670
Pro Pro Pro Pro Pro Ala Pro Thr Cys Arg Gly Pro Thr Leu Leu Gln
        210                 215                 220

CAC GTC TTC CCT GCC TCC CCA GGG GCC ACC CTG GTG GGG CCC CAC GGA       718
His Val Phe Pro Ala Ser Pro Gly Ala Thr Leu Val Gly Pro His Gly
    225                 230                 235
```

FIG. 10A-2

```
CCT CTG GCC TCT GGC CAG CTA GCA GCC TTC CAC ATC GCT GCC CCG CTC        766
Pro Leu Ala Ser Gly Gln Leu Ala Ala Phe His Ile Ala Ala Pro Leu
240             245                 250                 255

CCT GTC ACT GCC ACA CGC TGG GAC TTC GGA GAC GGC TCC GCC GAG GTG        814
Pro Val Thr Ala Thr Arg Trp Asp Phe Gly Asp Gly Ser Ala Glu Val
                260                 265                 270

GAT GCC GCT GGG CCG GCT GCC TCG CAT CGC TAT GTG CTG CCT GGG CGC        862
Asp Ala Ala Gly Pro Ala Ala Ser His Arg Tyr Val Leu Pro Gly Arg
        275                 280                 285

TAT CAC GTG ACG GCC GTG CTG GCC CTG GGG GCC GGC TCA GCC CTG CTG        910
Tyr His Val Thr Ala Val Leu Ala Leu Gly Ala Gly Ser Ala Leu Leu
            290                 295                 300

GGG ACA GAC GTG CAG GTG GAA GCG GCA CCT GCC GCC CTG GAG CTC GTG        958
Gly Thr Asp Val Gln Val Glu Ala Ala Pro Ala Ala Leu Glu Leu Val
305                 310                 315

TGC CCG TCC TCG GTG CAG AGT GAC GAG AGC CTT GAC CTC AGC ATC CAG       1006
Cys Pro Ser Ser Val Gln Ser Asp Glu Ser Leu Asp Leu Ser Ile Gln
320             325                 330                 335

AAC CGC GGT GGT TCA GGC CTG GAG GCC GCC TAC AGC ATC GTG GCC CTG       1054
Asn Arg Gly Gly Ser Gly Leu Glu Ala Ala Tyr Ser Ile Val Ala Leu
                340                 345                 350

GGC GAG GAG CCG GCC CGA GCG GTG CAC CCG CTC TGC CCC TCG GAC ACG       1102
Gly Glu Glu Pro Ala Arg Ala Val His Pro Leu Cys Pro Ser Asp Thr
        355                 360                 365
```

FIG. 10A-3

```
GAG ATC TTC CCT GGC AAC GGG CAC TGC TAC CGC CTG GTG GTG GAG AAG        1150
Glu Ile Phe Pro Gly Asn Gly His Cys Tyr Arg Leu Val Val Glu Lys
    370                 375                 380

GCG GCC TGG CTG CAG GCG CAG GAG CAG TGT CAG GCC TGG GCC GGG GCC        1198
Ala Ala Trp Leu Gln Ala Gln Glu Gln Cys Gln Ala Trp Ala Gly Ala
    385                 390                 395

GCC CTG GCA ATG GTG GAC AGT CCC GCC GTG CAG CGC TTC CTG GTC TCC        1246
Ala Leu Ala Met Val Asp Ser Pro Ala Val Gln Arg Phe Leu Val Ser
400                 405                 410                 415

CGG GTC ACC AGG AGC CTA GAC GTG TGG ATC GGC TTC TCG ACT GTG CAG        1294
Arg Val Thr Arg Ser Leu Asp Val Trp Ile Gly Phe Ser Thr Val Gln
                420                 425                 430

GGG GTG GAG GTG GGC CCA GCG CCG CAG GGC GAG GCC TTC AGC CTG GAG        1342
Gly Val Glu Val Gly Pro Ala Pro Gln Gly Glu Ala Phe Ser Leu Glu
                435                 440                 445

AGC TGC CAG AAC TGG CTG CCC GGG GAG CCA CAC CCA GCC ACA GCC GAG        1390
Ser Cys Gln Asn Trp Leu Pro Gly Glu Pro His Pro Ala Thr Ala Glu
            450                 455                 460

CAC TGC GTC CGG CTC GGG CCC ACC GGG TGG TGT AAC ACC GAC CTG TGC        1438
His Cys Val Arg Leu Gly Pro Thr Gly Trp Cys Asn Thr Asp Leu Cys
            465                 470                 475
```

FIG. 10A-4

```
TCA GCG CCG CAC AGC TAC GTC TGC GAG CTG CAG CCC GGA GGC CCA GTG          1486
Ser Ala Pro His Ser Tyr Val Cys Glu Leu Gln Pro Gly Gly Pro Val
480             485                 490                 495

CAG GAT GCC GAG AAC CTC CTC GTG GGA GCG CCC AGT GGG GAC CTG CAG          1534
Gln Asp Ala Glu Asn Leu Leu Val Gly Ala Pro Ser Gly Asp Leu Gln
                500                 505                 510

GGA CCC CTG ACG CCT CTG GCA CAG CAG GAC GGC CTC TCA GCC CCG CAC          1582
Gly Pro Leu Thr Pro Leu Ala Gln Gln Asp Gly Leu Ser Ala Pro His
            515                 520                 525

GAG CCC GTG GAG GTC ATG GTA TTC CCG GGC CTG CGT CTG AGC CGT GAA          1630
Glu Pro Val Glu Val Met Val Phe Pro Gly Leu Arg Leu Ser Arg Glu
            530                 535                 540

GCC TTC CTC ACC ACG GCC GAA TTT GGG ACC CAG GAG CTC CGG CGG CCC          1678
Ala Phe Leu Thr Thr Ala Glu Phe Gly Thr Gln Glu Leu Arg Arg Pro
545                 550                 555

GCC CAG CTG CGG CTG CAG GTG TAC CGG CTC CTC AGC ACA GCA GGG ACC          1726
Ala Gln Leu Arg Leu Gln Val Tyr Arg Leu Leu Ser Thr Ala Gly Thr
560                 565                 570                 575

CCG GAG AAC GGC AGC GAG CCT GAG AGC AGG TCC CCG GAC AAC AGG ACC          1774
Pro Glu Asn Gly Ser Glu Pro Glu Ser Arg Ser Pro Asp Asn Arg Thr
                580                 585                 590

CAG CTG GCC CCC GCG TGC ATG CCA GGG GGA CGC TGG TGC CCT GGA GCC          1822
Gln Leu Ala Pro Ala Cys Met Pro Gly Gly Arg Trp Cys Pro Gly Ala
            595                 600                 605
```

FIG. 10A-5

```
AAC ATC TGC TTG CCG CTG GAC GCC TCT TGC CAC CCC CAG GCC TGC GCC        1870
Asn Ile Cys Leu Pro Leu Asp Ala Ser Cys His Pro Gln Ala Cys Ala
        610             615                 620

AAT GGC TGC ACG TCA GGG CCA GGG CTA CCC GGG GCC CCC TAT GCG CTA        1918
Asn Gly Cys Thr Ser Gly Pro Gly Leu Pro Gly Ala Pro Tyr Ala Leu
        625             630                 635

TGG AGA GAG TTC CTC TTC TCC GTT GCC GCG GGG CCC CCC GCG CAG TAC        1966
Trp Arg Glu Phe Leu Phe Ser Val Ala Ala Gly Pro Pro Ala Gln Tyr
640             645                 650                 655

TCG GTC ACC CTC CAC GGC CAG GAT GTC CTC ATG CTC CCT GGT GAC CTC        2014
Ser Val Thr Leu His Gly Gln Asp Val Leu Met Leu Pro Gly Asp Leu
                660                 665                 670

GTT GGC TTG CAG CAC GAC GCT GGC CCT GGC GCC CTC CTG CAC TGC TCG        2062
Val Gly Leu Gln His Asp Ala Gly Pro Gly Ala Leu Leu His Cys Ser
            675                 680                 685

CCG GCT CCC GGC CAC CCT GGT CCC CAG GCC CCG TAC CTC TCC GCC AAC        2110
Pro Ala Pro Gly His Pro Gly Pro Gln Ala Pro Tyr Leu Ser Ala Asn
        690                 695                 700

GCC TCG TCA TGG CTG CCC CAC TTG CCA GCC CAG CTG GAG GGC ACT TGG        2158
Ala Ser Ser Trp Leu Pro His Leu Pro Ala Gln Leu Glu Gly Thr Trp
    705                 710                 715
```

FIG. 10A-6

```
GCC TGC CCT GCC TGT GCC CTG CGG CTG CTT GCA GCC ACG GAA CAG CTC        2206
Ala Cys Pro Ala Cys Ala Leu Arg Leu Leu Ala Ala Thr Glu Gln Leu
720             725             730             735

ACC GTG CTG CTG GGC TTG AGG CCC AAC CCT GGA CTG CGG ATG CCT GGG        2254
Thr Val Leu Leu Gly Leu Arg Pro Asn Pro Gly Leu Arg Met Pro Gly
            740             745             750

CGC TAT GAG GTC CGG GCA GAG GTG GGC AAT GGC GTG TCC AGG CAC AAC        2302
Arg Tyr Glu Val Arg Ala Glu Val Gly Asn Gly Val Ser Arg His Asn
            755             760             765

CTC TCC TGC AGC TTT GAC GTG GTC TCC CCA GTG GCT GGG CTG CGG GTC        2350
Leu Ser Cys Ser Phe Asp Val Val Ser Pro Val Ala Gly Leu Arg Val
            770             775             780

ATC TAC CCT GCC CCC CGC GAC GGC CGC CTC TAC GTG CCC ACC AAC GGC        2398
Ile Tyr Pro Ala Pro Arg Asp Gly Arg Leu Tyr Val Pro Thr Asn Gly
785             790             795

TCA GCC TTG GTG CTC CAG GTG GAC TCT GGT GCC AAC GCC ACG GCC ACG        2446
Ser Ala Leu Val Leu Gln Val Asp Ser Gly Ala Asn Ala Thr Ala Thr
800             805             810             815

GCT CGC TGG CCT GGG GGC AGT GTC AGC GCC CGC TTT GAG AAT GTC TGC        2494
Ala Arg Trp Pro Gly Gly Ser Val Ser Ala Arg Phe Glu Asn Val Cys
            820             825             830

CCT GCC CTG GTG GCC ACC TTC GTG CCC GGC TGC CCC TGG GAG ACC AAC        2542
Pro Ala Leu Val Ala Thr Phe Val Pro Gly Cys Pro Trp Glu Thr Asn
            835             840             845
```

FIG. 10A-7

```
GAT ACC CTG TTC TCA GTG GTA GCA CTG CCG TGG CTC AGT GAG GGG GAG         2590
Asp Thr Leu Phe Ser Val Val Ala Leu Pro Trp Leu Ser Glu Gly Glu
        850                 855                 860

CAC GTG GTG GAC GTG GTG GTG GAA AAC AGC GCC AGC CGG GCC AAC CTC         2638
His Val Val Asp Val Val Val Glu Asn Ser Ala Ser Arg Ala Asn Leu
        865                 870                 875

AGC CTG CGG GTG ACG GCG GAG GAG CCC ATC TGT GGC CTC CGC GCC ACG         2686
Ser Leu Arg Val Thr Ala Glu Glu Pro Ile Cys Gly Leu Arg Ala Thr
    880                 885                 890                 895

CCC AGC CCC GAG GCC CGT GTA CTG CAG GGA GTC CTA GTG AGG TAC AGC         2734
Pro Ser Pro Glu Ala Arg Val Leu Gln Gly Val Leu Val Arg Tyr Ser
                900                 905                 910

CCC GTG GTG GAG GCC GGC TCG GAC ATG GTC TTC CGG TGG ACC ATC AAC         2782
Pro Val Val Glu Ala Gly Ser Asp Met Val Phe Arg Trp Thr Ile Asn
            915                 920                 925

GAC AAG CAG TCC CTG ACC TTC CAG AAC GTG GTC TTC AAT GTC ATT TAT         2830
Asp Lys Gln Ser Leu Thr Phe Gln Asn Val Val Phe Asn Val Ile Tyr
        930                 935                 940

CAG AGC GCG GCG GTC TTC AAG CTC TCA CTG ACG GCC TCC AAC CAC GTG         2878
Gln Ser Ala Ala Val Phe Lys Leu Ser Leu Thr Ala Ser Asn His Val
        945                 950                 955
```

FIG. 10A-8

```
AGC AAC GTC ACC GTG AAC TAC AAC GTA ACC GTG GAG CGG ATG AAC AGG         2926
Ser Asn Val Thr Val Asn Tyr Asn Val Thr Val Glu Arg Met Asn Arg
960             965                 970                 975

ATG CAG GGT CTG CAG GTC TCC ACA GTG CCG GCC GTG CTG TCC CCC AAT         2974
Met Gln Gly Leu Gln Val Ser Thr Val Pro Ala Val Leu Ser Pro Asn
                980                 985                 990

GCC ACA CTG GTA CTG ACG GGT GGT GTG CTG GTG GAC TCA GCT GTG GAG         3022
Ala Thr Leu Val Leu Thr Gly Gly Val Leu Val Asp Ser Ala Val Glu
                    995                 1000                1005

GTG GCC TTC CTG TGG AAC TTT GGG GAT GGG GAG CAG GCC CTC CAC CAG         3070
Val Ala Phe Leu Trp Asn Phe Gly Asp Gly Glu Gln Ala Leu His Gln
    1010                1015                1020

TTC CAG CCT CCG TAC AAC GAG TCC TTC CCG GTT CCA GAC CCC TCG GTG         3118
Phe Gln Pro Pro Tyr Asn Glu Ser Phe Pro Val Pro Asp Pro Ser Val
    1025                1030                1035

GCC CAG GTG CTG GTG GAG CAC AAT GTC ATG CAC ACC TAC GCT GCC CCA         3166
Ala Gln Val Leu Val Glu His Asn Val Met His Thr Tyr Ala Ala Pro
1040                1045                1050                1055

GGT GAG TAC CTC CTG ACC GTG CTG GCA TCT AAT GCC TTC GAG AAC CTG         3214
Gly Glu Tyr Leu Leu Thr Val Leu Ala Ser Asn Ala Phe Glu Asn Leu
                    1060                1065                1070

ACG CAG CAG GTG CCT GTG AGC GTG CGC GCC TCC CTG CCC TCC GTG GCT         3262
Thr Gln Gln Val Pro Val Ser Val Arg Ala Ser Leu Pro Ser Val Ala
                    1075                1080                1085
```

FIG. 10A-9

```
GTG GGT GTG AGT GAC GGC GTC CTG GTG GCC GGC CGG CCC GTC ACC TTC      3310
Val Gly Val Ser Asp Gly Val Leu Val Ala Gly Arg Pro Val Thr Phe
    1090            1095            1100

TAC CCG CAC CCG CTG CCC TCG CCT GGG GGT GTT CTT TAC ACG TGG GAC      3358
Tyr Pro His Pro Leu Pro Ser Pro Gly Gly Val Leu Tyr Thr Trp Asp
    1105            1110            1115

TTC GGG GAC GGC TCC CCT GTC CTG ACC CAG AGC CAG CCG GCT GCC AAC      3406
Phe Gly Asp Gly Ser Pro Val Leu Thr Gln Ser Gln Pro Ala Ala Asn
1120            1125            1130            1135

CAC ACC TAT GCC TCG AGG GGC ACC TAC CAC GTG CGC CTG GAG GTC AAC      3454
His Thr Tyr Ala Ser Arg Gly Thr Tyr His Val Arg Leu Glu Val Asn
            1140            1145            1150

AAC ACG GTG AGC GGT GCG GCG GCC CAG GCG GAT GTG CGC GTC TTT GAG      3502
Asn Thr Val Ser Gly Ala Ala Ala Gln Ala Asp Val Arg Val Phe Glu
        1155            1160            1165

GAG CTC CGC GGA CTC AGC GTG GAC ATG AGC CTG GCC GTG GAG CAG GGC      3550
Glu Leu Arg Gly Leu Ser Val Asp Met Ser Leu Ala Val Glu Gln Gly
    1170            1175            1180

GCC CCC GTG GTG GTC AGC GCC GCG GTG CAG ACG GGC GAC AAC ATC ACG      3598
Ala Pro Val Val Val Ser Ala Ala Val Gln Thr Gly Asp Asn Ile Thr
    1185            1190            1195
```

FIG. 10A-10

```
TGG ACC TTC GAC ATG GGG GAC GGC ACC GTG CTG TCG GGC CCG GAG GCA    3646
Trp Thr Phe Asp Met Gly Asp Gly Thr Val Leu Ser Gly Pro Glu Ala
1200            1205            1210            1215

ACA GTG GAG CAT GTG TAC CTG CGG GCA CAG AAC TGC ACA GTG ACC GTG    3694
Thr Val Glu His Val Tyr Leu Arg Ala Gln Asn Cys Thr Val Thr Val
                1220            1225            1230

GGT GCG GCC AGC CCC GCC GGC CAC CTG GCC CGG AGC CTG CAC GTG CTG    3742
Gly Ala Ala Ser Pro Ala Gly His Leu Ala Arg Ser Leu His Val Leu
            1235            1240            1245

GTC TTC GTC CTG GAG GTG CTG CGC GTT GAA CCC GCC GCC TGC ATC CCC    3790
Val Phe Val Leu Glu Val Leu Arg Val Glu Pro Ala Ala Cys Ile Pro
1250            1255            1260

ACG CAG CCT GAC GCG CGG CTC ACG GCC TAC GTC ACC GGG AAC CCG GCC    3838
Thr Gln Pro Asp Ala Arg Leu Thr Ala Tyr Val Thr Gly Asn Pro Ala
1265            1270            1275

CAC TAC CTC TTC GAC TGG ACC TTC GGG GAT GGC TCC TCC AAC ACG ACC    3886
His Tyr Leu Phe Asp Trp Thr Phe Gly Asp Gly Ser Ser Asn Thr Thr
1280            1285            1290            1295

GTG CGG GGG TGC CCG ACG GTG ACA CAC AAC TTC ACG CGG AGC GGC ACG    3934
Val Arg Gly Cys Pro Thr Val Thr His Asn Phe Thr Arg Ser Gly Thr
            1300            1305            1310

TTC CCC CTG GCG CTG GTG CTG TCC AGC CGC GTG AAC AGG GCG CAT TAC    3982
Phe Pro Leu Ala Leu Val Leu Ser Ser Arg Val Asn Arg Ala His Tyr
            1315            1320            1325

TTC ACC AGC ATC TGC GTG GAG CCA GAG GTG GGC AAC GTC ACC CTG CAG    4030
Phe Thr Ser Ile Cys Val Glu Pro Glu Val Gly Asn Val Thr Leu Gln
            1330            1335            1340
```

FIG. 10A-11

```
TTC ACC AGC ATC TGC GTG GAG CCA GAG GTG GGC AAC GTC ACC CTG CAG           4030
Phe Thr Ser Ile Cys Val Glu Pro Glu Val Gly Asn Val Thr Leu Gln
    1330                1335                1340

CCA GAG AGG CAG TTT GTG CAG CTC GGG GAC GAG GCC TGG CTG GTG GCA           4078
Pro Glu Arg Gln Phe Val Gln Leu Gly Asp Glu Ala Trp Leu Val Ala
    1345                1350                1355

TGT GCC TGG CCC CCG TTC CCC TAC CGC TAC ACC TGG GAC TTT GGC ACC           4126
Cys Ala Trp Pro Pro Phe Pro Tyr Arg Tyr Thr Trp Asp Phe Gly Thr
1360                1365                1370                1375

GAG GAA GCC GCC CCC ACC CGT GCC AGG GGC CCT GAG GTG ACG TTC ATC           4174
Glu Glu Ala Ala Pro Thr Arg Ala Arg Gly Pro Glu Val Thr Phe Ile
            1380                1385                1390

TAC CGA GAC CCA GGC TCC TAT CTT GTG ACA GTC ACC GCG TCC AAC AAC           4222
Tyr Arg Asp Pro Gly Ser Tyr Leu Val Thr Val Thr Ala Ser Asn Asn
        1395                1400                1405

ATC TCT GCT GCC AAT GAC TCA GCC CTG GTG GAG GTG CAG GAG CCC GTG           4270
Ile Ser Ala Ala Asn Asp Ser Ala Leu Val Glu Val Gln Glu Pro Val
    1410                1415                1420

CTG GTC ACC AGC ATC AAG GTC AAT GGC TCC CTT GGG CTG GAG CTG CAG           4318
Leu Val Thr Ser Ile Lys Val Asn Gly Ser Leu Gly Leu Glu Leu Gln
    1425                1430                1435
```

FIG. 10A-12

```
CAG CCG TAC CTG TTC TCT GCT GTG GGC CGT GGG CGC CCC GCC AGC TAC        4366
Gln Pro Tyr Leu Phe Ser Ala Val Gly Arg Gly Arg Pro Ala Ser Tyr
1440            1445            1450            1455

CTG TGG GAT CTG GGG GAC GGT GGG TGG CTC GAG GGT CCG GAG GTC ACC        4414
Leu Trp Asp Leu Gly Asp Gly Gly Trp Leu Glu Gly Pro Glu Val Thr
        1460            1465            1470

CAC GCT TAC AAC AGC ACA GGT GAC TTC ACC GTT AGG GTG GCC GGC TGG        4462
His Ala Tyr Asn Ser Thr Gly Asp Phe Thr Val Arg Val Ala Gly Trp
    1475            1480            1485

AAT GAG GTG AGC CGC AGC GAG GCC TGG CTC AAT GTG ACG GTG AAG CGG        4510
Asn Glu Val Ser Arg Ser Glu Ala Trp Leu Asn Val Thr Val Lys Arg
        1490            1495            1500

CGC GTG CGG GGG CTC GTC GTC AAT GCA AGC CGC ACG GTG GTG CCC CTG        4558
Arg Val Arg Gly Leu Val Val Asn Ala Ser Arg Thr Val Val Pro Leu
    1505            1510            1515

AAT GGG AGC GTG AGC TTC AGC ACG TCG CTG GAG GCC GGC AGT GAT GTG        4606
Asn Gly Ser Val Ser Phe Ser Thr Ser Leu Glu Ala Gly Ser Asp Val
1520            1525            1530            1535

CGC TAT TCC TGG GTG CTC TGT GAC CGC TGC ACG CCC ATC CCT GGG GGT        4654
Arg Tyr Ser Trp Val Leu Cys Asp Arg Cys Thr Pro Ile Pro Gly Gly
        1540            1545            1550

CCT ACC ATC TCT TAC ACC TTC CGC TCC GTG GGC ACC TTC AAT ATC ATC        4702
Pro Thr Ile Ser Tyr Thr Phe Arg Ser Val Gly Thr Phe Asn Ile Ile
    1555            1560            1565
```

FIG. 10A-13

```
GTC ACG GCT GAG AAC GAG GTG GGC TCC GCC CAG GAC AGC ATC TTC GTC        4750
Val Thr Ala Glu Asn Glu Val Gly Ser Ala Gln Asp Ser Ile Phe Val
        1570            1575            1580

TAT GTC CTG CAG CTC ATA GAG GGG CTG CAG GTG GTG GGC GGT GGC CGC        4798
Tyr Val Leu Gln Leu Ile Glu Gly Leu Gln Val Val Gly Gly Gly Arg
        1585            1590            1595

TAC TTC CCC ACC AAC CAC ACG GTA CAG CTG CAG GCC GTG GTT AGG GAT        4846
Tyr Phe Pro Thr Asn His Thr Val Gln Leu Gln Ala Val Val Arg Asp
    1600            1605            1610            1615

GGC ACC AAC GTC TCC TAC AGC TGG ACT GCC TGG AGG GAC AGG GGC CCG        4894
Gly Thr Asn Val Ser Tyr Ser Trp Thr Ala Trp Arg Asp Arg Gly Pro
        1620            1625            1630

GCC CTG GCC GGC AGC GGC AAA GGC TTC TCG CTC ACC GTG CTC GAG GCC        4942
Ala Leu Ala Gly Ser Gly Lys Gly Phe Ser Leu Thr Val Leu Glu Ala
        1635            1640            1645

GGC ACC TAC CAT GTG CAG CTG CGG GCC ACC AAC ATG CTG GGC AGC GCC        4990
Gly Thr Tyr His Val Gln Leu Arg Ala Thr Asn Met Leu Gly Ser Ala
        1650            1655            1660

TGG GCC GAC TGC ACC ATG GAC TTC GTG GAG CCT GTG GGG TGG CTG ATG        5038
Trp Ala Asp Cys Thr Met Asp Phe Val Glu Pro Val Gly Trp Leu Met
        1665            1670            1675
```

FIG. 10A-14

```
GTG ACC GCC TCC CCG AAC CCA GCT GCC GTC AAC ACA AGC GTC ACC CTC      5086
Val Thr Ala Ser Pro Asn Pro Ala Ala Val Asn Thr Ser Val Thr Leu
1680            1685            1690            1695

AGT GCC GAG CTG GCT GGT GGC AGT GGT GTC GTA TAC ACT TGG TCC TTG      5134
Ser Ala Glu Leu Ala Gly Gly Ser Gly Val Val Tyr Thr Trp Ser Leu
       1700            1705            1710

GAG GAG GGG CTG AGC TGG GAG ACC TCC GAG CCA TTT ACC ACC CAT AGC      5182
Glu Glu Gly Leu Ser Trp Glu Thr Ser Glu Pro Phe Thr Thr His Ser
           1715            1720            1725

TTC CCC ACA CCC GGC CTG CAC TTG GTC ACC ATG ACG GCA GGG AAC CCG      5230
Phe Pro Thr Pro Gly Leu His Leu Val Thr Met Thr Ala Gly Asn Pro
       1730            1735            1740

CTG GGC TCA GCC AAC GCC ACC GTG GAA GTG GAT GTG CAG GTG CCT GTG      5278
Leu Gly Ser Ala Asn Ala Thr Val Glu Val Asp Val Gln Val Pro Val
       1745            1750            1755

AGT GGC CTC AGC ATC AGG GCC AGC GAG CCC GGA GGC AGC TTC GTG GCG      5326
Ser Gly Leu Ser Ile Arg Ala Ser Glu Pro Gly Gly Ser Phe Val Ala
1760            1765            1770            1775

GCC GGG TCC TCT GTG CCC TTT TGG GGG CAG CTG GCC ACG GGC ACC AAT      5374
Ala Gly Ser Ser Val Pro Phe Trp Gly Gln Leu Ala Thr Gly Thr Asn
           1780            1785            1790

GTG AGC TGG TGC TGG GCT GTG CCC GGC GGC AGC AGC AAG CGT GGC CCT      5422
Val Ser Trp Cys Trp Ala Val Pro Gly Gly Ser Ser Lys Arg Gly Pro
       1795            1800            1805
```

FIG. 10A-15

```
CAT GTC ACC ATG GTC TTC CCG GAT GCT GGC ACC TTC TCC ATC CGG CTC        5470
His Val Thr Met Val Phe Pro Asp Ala Gly Thr Phe Ser Ile Arg Leu
    1810                1815                1820

AAT GCC TCC AAC GCA GTC AGC TGG GTC TCA GCC ACG TAC AAC CTC ACG        5518
Asn Ala Ser Asn Ala Val Ser Trp Val Ser Ala Thr Tyr Asn Leu Thr
    1825                1830                1835

GCG GAG GAG CCC ATC GTG GGC CTG GTG CTG TGG GCC AGC AGC AAG GTG        5566
Ala Glu Glu Pro Ile Val Gly Leu Val Leu Trp Ala Ser Ser Lys Val
    1840                1845                1850                1855

GTG GCG CCC GGG CAG CTG GTC CAT TTT CAG ATC CTG CTG GCT GCC GGC        5614
Val Ala Pro Gly Gln Leu Val His Phe Gln Ile Leu Leu Ala Ala Gly
                1860                1865                1870

TCA GCT GTC ACC TTC CGC CTG CAG GTC GGC GGG GCC AAC CCC GAG GTG        5662
Ser Ala Val Thr Phe Arg Leu Gln Val Gly Gly Ala Asn Pro Glu Val
            1875                1880                1885

CTC CCC GGG CCC CGT TTC TCC CAC AGC TTC CCC CGC GTC GGA GAC CAC        5710
Leu Pro Gly Pro Arg Phe Ser His Ser Phe Pro Arg Val Gly Asp His
            1890                1895                1900

GTG GTG AGC GTG CGG GGC AAA AAC CAC GTG AGC TGG GCC CAG GCG CAG        5758
Val Val Ser Val Arg Gly Lys Asn His Val Ser Trp Ala Gln Ala Gln
    1905                1910                1915
```

FIG. 10A-16

```
GTG CGC ATC GTG GTG CTG GAG GCC GTG AGT GGG CTG CAG ATG CCC AAC         5806
Val Arg Ile Val Val Leu Glu Ala Val Ser Gly Leu Gln Met Pro Asn
1920                1925                1930                1935

TGC TGC GAG CCT GGC ATC GCC ACG GGC ACT GAG AGG AAC TTC ACA GCC         5854
Cys Cys Glu Pro Gly Ile Ala Thr Gly Thr Glu Arg Asn Phe Thr Ala
                1940                1945                1950

CGC GTG CAG CGC GGC TCT CGG GTC GCC TAC GCC TGG TAC TTC TCG CTG         5902
Arg Val Gln Arg Gly Ser Arg Val Ala Tyr Ala Trp Tyr Phe Ser Leu
                1955                1960                1965

CAG AAG GTC CAG GGC GAC TCG CTG GTC ATC CTG TCG GGC CGC GAC GTC         5950
Gln Lys Val Gln Gly Asp Ser Leu Val Ile Leu Ser Gly Arg Asp Val
                1970                1975                1980

ACC TAC ACG CCC GTG GCC GCG GGG CTG TTG GAG ATC CAG GTG CGC GCC         5998
Thr Tyr Thr Pro Val Ala Ala Gly Leu Leu Glu Ile Gln Val Arg Ala
1985                1990                1995

TTC AAC GCC CTG GGC AGT GAG AAC CGC ACG CTG GTG CTG GAG GTT CAG         6046
Phe Asn Ala Leu Gly Ser Glu Asn Arg Thr Leu Val Leu Glu Val Gln
2000                2005                2010                2015

GAC GCC GTC CAG TAT GTG GCC CTG CAG AGC GGC CCC TGC TTC ACC AAC         6094
Asp Ala Val Gln Tyr Val Ala Leu Gln Ser Gly Pro Cys Phe Thr Asn
                2020                2025                2030

CGC TCG GCG CAG TTT GAG GCC GCC ACC AGC CCC AGC CCC CGG CGT GTG         6142
Arg Ser Ala Gln Phe Glu Ala Ala Thr Ser Pro Ser Pro Arg Arg Val
                2035                2040                2045
```

FIG. 10A-17

```
GCC TAC CAC TGG GAC TTT GGG GAT GGG TCG CCA GGG CAG GAC ACA GAT        6190
Ala Tyr His Trp Asp Phe Gly Asp Gly Ser Pro Gly Gln Asp Thr Asp
    2050                2055                2060

GAG CCC AGG GCC GAG CAC TCC TAC CTG AGG CCT GGG GAC TAC CGC GTG        6238
Glu Pro Arg Ala Glu His Ser Tyr Leu Arg Pro Gly Asp Tyr Arg Val
    2065                2070                2075

CAG GTG AAC GCC TCC AAC CTG GTG AGC TTC TTC GTG GCG CAG GCC ACG        6286
Gln Val Asn Ala Ser Asn Leu Val Ser Phe Phe Val Ala Gln Ala Thr
2080                2085                2090                2095

GTG ACC GTC CAG GTG CTG GCC TGC CGG GAG CCG GAG GTG GAC GTG GTC        6334
Val Thr Val Gln Val Leu Ala Cys Arg Glu Pro Glu Val Asp Val Val
                2100                2105                2110

CTG CCC CTG CAG GTG CTG ATG CGG CGA TCA CAG CGC AAC TAC TTG GAG        6382
Leu Pro Leu Gln Val Leu Met Arg Arg Ser Gln Arg Asn Tyr Leu Glu
        2115                2120                2125

GCC CAC GTT GAC CTG CGC GAC TGC GTC ACC TAC CAG ACT GAG TAC CGC        6430
Ala His Val Asp Leu Arg Asp Cys Val Thr Tyr Gln Thr Glu Tyr Arg
    2130                2135                2140

TGG GAG GTG TAT CGC ACC GCC AGC TGC CAG CGG CCG GGG CGC CCA GCG        6478
Trp Glu Val Tyr Arg Thr Ala Ser Cys Gln Arg Pro Gly Arg Pro Ala
    2145                2150                2155
```

FIG. 10A-18

```
CGT GTG GCC CTG CCC GGC GTG GAC GTG AGC CGG CCT CGG CTG GTG CTG      6526
Arg Val Ala Leu Pro Gly Val Asp Val Ser Arg Pro Arg Leu Val Leu
2160          2165              2170             2175

CCG CGG CTG GCG CTG CCT GTG GGG CAC TAC TGC TTT GTG TTT GTC GTG      6574
Pro Arg Leu Ala Leu Pro Val Gly His Tyr Cys Phe Val Phe Val Val
        2180             2185              2190

TCA TTT GGG GAC ACG CCA CTG ACA CAG AGC ATC CAG GCC AAT GTG ACG      6622
Ser Phe Gly Asp Thr Pro Leu Thr Gln Ser Ile Gln Ala Asn Val Thr
        2195             2200              2205

GTG GCC CCC GAG CGC CTG GTG CCC ATC ATT GAG GGT GGC TCA TAC CGC      6670
Val Ala Pro Glu Arg Leu Val Pro Ile Ile Glu Gly Gly Ser Tyr Arg
        2210             2215              2220

GTG TGG TCA GAC ACA CGG GAC CTG GTG CTG GAT GGG AGC GAG TCC TAC      6718
Val Trp Ser Asp Thr Arg Asp Leu Val Leu Asp Gly Ser Glu Ser Tyr
        2225             2230              2235

GAC CCC AAC CTG GAG GAC GGC GAC CAG ACG CCG CTC AGT TTC CAC TGG      6766
Asp Pro Asn Leu Glu Asp Gly Asp Gln Thr Pro Leu Ser Phe His Trp
2240          2245              2250             2255

GCC TGT GTG GCT TCG ACA CAG AGG GAG GCT GGC GGG TGT GCG CTG AAC      6814
Ala Cys Val Ala Ser Thr Gln Arg Glu Ala Gly Gly Cys Ala Leu Asn
        2260             2265              2270

TTT GGG CCC CGC GGG AGC AGC ACG GTC ACC ATT CCA CGG GAG CGG CTG      6862
Phe Gly Pro Arg Gly Ser Ser Thr Val Thr Ile Pro Arg Glu Arg Leu
        2275             2280              2285
```

FIG. 10A-19

```
GCG GCT GGC GTG GAG TAC ACC TTC AGC CTG ACC GTG TGG AAG GCC GGC      6910
Ala Ala Gly Val Glu Tyr Thr Phe Ser Leu Thr Val Trp Lys Ala Gly
         2290                2295                2300

CGC AAG GAG GAG GCC ACC AAC CAG ACG GTG CTG ATC CGG AGT GGC CGG      6958
Arg Lys Glu Glu Ala Thr Asn Gln Thr Val Leu Ile Arg Ser Gly Arg
         2305                2310                2315

GTG CCC ATT GTG TCC TTG GAG TGT GTG TCC TGC AAG GCA CAG GCC GTG      7006
Val Pro Ile Val Ser Leu Glu Cys Val Ser Cys Lys Ala Gln Ala Val
         2320                2325                2330                2335

TAC GAA GTG AGC CGC AGC TCC TAC GTG TAC TTG GAG GGC CGC TGC CTC      7054
Tyr Glu Val Ser Arg Ser Ser Tyr Val Tyr Leu Glu Gly Arg Cys Leu
                     2340                2345                2350

AAT TGC AGC AGC GGC TCC AAG CGA GGG CGG TGG GCT GCA CGT ACG TTC      7102
Asn Cys Ser Ser Gly Ser Lys Arg Gly Arg Trp Ala Ala Arg Thr Phe
         2355                2360                2365

AGC AAC AAG ACG CTG GTG CTG GAT GAG ACC ACC ACA TCC ACG GGC AGT      7150
Ser Asn Lys Thr Leu Val Leu Asp Glu Thr Thr Thr Ser Thr Gly Ser
         2370                2375                2380

GCA GGC ATG CGA CTG GTG CTG CGG CGG GGC GTG CTG CGG GAC GGC GAG      7198
Ala Gly Met Arg Leu Val Leu Arg Arg Gly Val Leu Arg Asp Gly Glu
         2385                2390                2395
```

FIG. 10A-20

```
GGA TAC ACC TTC ACG CTC ACG GTG CTG GGC CGC TCT GGC GAG GAG GAG      7246
Gly Tyr Thr Phe Thr Leu Thr Val Leu Gly Arg Ser Gly Glu Glu Glu
2400            2405            2410            2415

GGC TGC GCC TCC ATC CGC CTG TCC CCC AAC CGC CCG CCG CTG GGG GGC      7294
Gly Cys Ala Ser Ile Arg Leu Ser Pro Asn Arg Pro Pro Leu Gly Gly
        2420            2425            2430

TCT TGC CGC CTC TTC CCA CTG GGC GCT GTG CAC GCC CTC ACC ACC AAG      7342
Ser Cys Arg Leu Phe Pro Leu Gly Ala Val His Ala Leu Thr Thr Lys
    2435            2440            2445

GTG CAC TTC GAA TGC ACG GGC TGG CAT GAC GCG GAG GAT GCT GGC GCC      7390
Val His Phe Glu Cys Thr Gly Trp His Asp Ala Glu Asp Ala Gly Ala
        2450            2455            2460

CCG CTG GTG TAC GCC CTG CTG CTG CGG CGC TGT CGC CAG GGC CAC TGC      7438
Pro Leu Val Tyr Ala Leu Leu Leu Arg Arg Cys Arg Gln Gly His Cys
2465            2470            2475

GAG GAG TTC TGT GTC TAC AAG GGC AGC CTC TCC AGC TAC GGA GCC GTG      7486
Glu Glu Phe Cys Val Tyr Lys Gly Ser Leu Ser Ser Tyr Gly Ala Val
2480            2485            2490            2495

CTG CCC CCG GGT TTC AGG CCA CAC TTC GAG GTG GGC CTG GCC GTG GTG      7534
Leu Pro Pro Gly Phe Arg Pro His Phe Glu Val Gly Leu Ala Val Val
            2500            2505            2510

GTG CAG GAC CAG CTG GGA GCC GCT GTG GTC GCC CTC AAC AGG TCT TTG      7582
Val Gln Asp Gln Leu Gly Ala Ala Val Val Ala Leu Asn Arg Ser Leu
        2515            2520            2525
```

FIG. 10A-21

```
GCC ATC ACC CTC CCA GAG CCC AAC GGC AGC GCA ACG GGG CTC ACA GTC         7630
Ala Ile Thr Leu Pro Glu Pro Asn Gly Ser Ala Thr Gly Leu Thr Val
        2530            2535            2540

TGG CTG CAC GGG CTC ACC GCT AGT GTG CTC CCA GGG CTG CTG CGG CAG         7678
Trp Leu His Gly Leu Thr Ala Ser Val Leu Pro Gly Leu Leu Arg Gln
        2545            2550            2555

GCC GAT CCC CAG CAC GTC ATC GAG TAC TCG TTG GCC CTG GTC ACC GTG         7726
Ala Asp Pro Gln His Val Ile Glu Tyr Ser Leu Ala Leu Val Thr Val
    2560            2565            2570            2575

CTG AAC GAG TAC GAG CGG GCC CTG GAC GTG GCG GCA GAG CCC AAG CAC         7774
Leu Asn Glu Tyr Glu Arg Ala Leu Asp Val Ala Ala Glu Pro Lys His
                2580            2585            2590

GAG CGG CAG CAC CGA GCC CAG ATA CGC AAG AAC ATC ACG GAG ACT CTG         7822
Glu Arg Gln His Arg Ala Gln Ile Arg Lys Asn Ile Thr Glu Thr Leu
        2595            2600            2605

GTG TCC CTG AGG GTC CAC ACT GTG GAT GAC ATC CAG CAG ATC GCT GCT         7870
Val Ser Leu Arg Val His Thr Val Asp Asp Ile Gln Gln Ile Ala Ala
        2610            2615            2620

GCG CTG GCC CAG TGC ATG GGG CCC AGC AGG GAG CTC GTA TGC CGC TCG         7918
Ala Leu Ala Gln Cys Met Gly Pro Ser Arg Glu Leu Val Cys Arg Ser
        2625            2630            2635
```

FIG. 10A-22

```
TGC CTG AAG CAG ACG CTG CAC AAG CTG GAG GCC ATG ATG CTC ATC CTG        7966
Cys Leu Lys Gln Thr Leu His Lys Leu Glu Ala Met Met Leu Ile Leu
2640            2645            2650            2655

CAG GCA GAG ACC ACC GCG GGC ACC GTG ACG CCC ACC GCC ATC GGA GAC        8014
Gln Ala Glu Thr Thr Ala Gly Thr Val Thr Pro Thr Ala Ile Gly Asp
            2660            2665            2670

AGC ATC CTC AAC ATC ACA GGA GAC CTC ATC CAC CTG GCC AGC TCG GAC        8062
Ser Ile Leu Asn Ile Thr Gly Asp Leu Ile His Leu Ala Ser Ser Asp
        2675            2680            2685

GTG CGG GCA CCA CAG CCC TCA GAG CTG GGA GCC GAG TCA CCA TCT CGG        8110
Val Arg Ala Pro Gln Pro Ser Glu Leu Gly Ala Glu Ser Pro Ser Arg
    2690            2695            2700

ATG GTG GCG TCC CAG GCC TAC AAC CTG ACC TCT GCC CTC ATG CGC ATC        8158
Met Val Ala Ser Gln Ala Tyr Asn Leu Thr Ser Ala Leu Met Arg Ile
2705            2710            2715

CTC ATG CGC TCC CGC GTG CTC AAC GAG GAG CCC CTG ACG CTG GCG GGC        8206
Leu Met Arg Ser Arg Val Leu Asn Glu Glu Pro Leu Thr Leu Ala Gly
2720            2725            2730            2735

GAG GAG ATC GTG GCC CAG GGC AAG CGC TCG GAC CCG CGG AGC CTG CTG        8254
Glu Glu Ile Val Ala Gln Gly Lys Arg Ser Asp Pro Arg Ser Leu Leu
            2740            2745            2750

TGC TAT GGC GGC GCC CCA GGG CCT GGC TGC CAC TTC TCC ATC CCC GAG        8302
Cys Tyr Gly Gly Ala Pro Gly Pro Gly Cys His Phe Ser Ile Pro Glu
        2755            2760            2765
```

FIG. 10A-23

```
GCT TTC AGC GGG GCC CTG GCC AAC CTC AGT GAC GTG GTG CAG CTC ATC         8350
Ala Phe Ser Gly Ala Leu Ala Asn Leu Ser Asp Val Val Gln Leu Ile
    2770            2775            2780

TTT CTG GTG GAC TCC AAT CCC TTT CCC TTT GGC TAT ATC AGC AAC TAC         8398
Phe Leu Val Asp Ser Asn Pro Phe Pro Phe Gly Tyr Ile Ser Asn Tyr
    2785            2790            2795

ACC GTC TCC ACC AAG GTG GCC TCG ATG GCA TTC CAG ACA CAG GCC GGC         8446
Thr Val Ser Thr Lys Val Ala Ser Met Ala Phe Gln Thr Gln Ala Gly
2800            2805            2810            2815

GCC CAG ATC CCC ATC GAG CGG CTG GCC TCA GAG CGC GCC ATC ACC GTG         8494
Ala Gln Ile Pro Ile Glu Arg Leu Ala Ser Glu Arg Ala Ile Thr Val
        2820            2825            2830

AAG GTG CCC AAC AAC TCG GAC TGG GCT GCC CGG GGC CAC CGC AGC TCC         8542
Lys Val Pro Asn Asn Ser Asp Trp Ala Ala Arg Gly His Arg Ser Ser
        2835            2840            2845

GCC AAC TCC GCC AAC TCC GTT GTG GTC CAG CCC CAG GCC TCC GTC GGT         8590
Ala Asn Ser Ala Asn Ser Val Val Val Gln Pro Gln Ala Ser Val Gly
        2850            2855            2860

GCT GTG GTC ACC CTG GAC AGC AGC AAC CCT GCG GCC GGG CTG CAT CTG         8638
Ala Val Val Thr Leu Asp Ser Ser Asn Pro Ala Ala Gly Leu His Leu
    2865            2870            2875
```

FIG. 10A-24

```
CAG CTC AAC TAT ACG CTG CTG GAC GGC CAC TAC CTG TCT GAG GAA CCT        8686
Gln Leu Asn Tyr Thr Leu Leu Asp Gly His Tyr Leu Ser Glu Glu Pro
2880            2885            2890            2895

GAG CCC TAC CTG GCA GTC TAC CTA CAC TCG GAG CCC CGG CCC AAT GAG        8734
Glu Pro Tyr Leu Ala Val Tyr Leu His Ser Glu Pro Arg Pro Asn Glu
        2900            2905            2910

CAC AAC TGC TCG GCT AGC AGG AGG ATC CGC CCA GAG TCA CTC CAG GGT        8782
His Asn Cys Ser Ala Ser Arg Arg Ile Arg Pro Glu Ser Leu Gln Gly
            2915            2920            2925

GCT GAC CAC CGG CCC TAC ACC TTC TTC ATT TCC CCG GGG AGC AGA GAC        8830
Ala Asp His Arg Pro Tyr Thr Phe Phe Ile Ser Pro Gly Ser Arg Asp
                2930            2935            2940

CCA GCG GGG AGT TAC CAT CTG AAC CTC TCC AGC CAC TTC CGC TGG TCG        8878
Pro Ala Gly Ser Tyr His Leu Asn Leu Ser Ser His Phe Arg Trp Ser
2945            2950            2955

GCG CTG CAG GTG TCC GTG GGC CTG TAC ACG TCC CTG TGC CAG TAC TTC        8926
Ala Leu Gln Val Ser Val Gly Leu Tyr Thr Ser Leu Cys Gln Tyr Phe
2960            2965            2970            2975

AGC GAG GAG GAC ATG GTG TGG CGG ACA GAG GGG CTG CTG CCC CTG GAG        8974
Ser Glu Glu Asp Met Val Trp Arg Thr Glu Gly Leu Leu Pro Leu Glu
        2980            2985            2990

GAG ACC TCG CCC CGC CAG GCC GTC TGC CTC ACC CGC CAC CTC ACC GCC        9022
Glu Thr Ser Pro Arg Gln Ala Val Cys Leu Thr Arg His Leu Thr Ala
            2995            3000            3005
```

FIG. 10A-25

```
TTC GGC GCC AGC CTC TTC GTG CCC CCA AGC CAT GTC CGC TTT GTG TTT       9070
Phe Gly Ala Ser Leu Phe Val Pro Pro Ser His Val Arg Phe Val Phe
       3010            3015            3020

CCT GAG CCG ACA GCG GAT GTA AAC TAC ATC GTC ATG CTG ACA TGT GCT       9118
Pro Glu Pro Thr Ala Asp Val Asn Tyr Ile Val Met Leu Thr Cys Ala
       3025            3030            3035

GTG TGC CTG GTG ACC TAC ATG GTC ATG GCC GCC ATC CTG CAC AAG CTG       9166
Val Cys Leu Val Thr Tyr Met Val Met Ala Ala Ile Leu His Lys Leu
       3040            3045            3050            3055

GAC CAG TTG GAT GCC AGC CGG GGC CGC GCC ATC CCT TTC TGT GGG CAG       9214
Asp Gln Leu Asp Ala Ser Arg Gly Arg Ala Ile Pro Phe Cys Gly Gln
               3060            3065            3070

CGG GGC CGC TTC AAG TAC GAG ATC CTC GTC AAG ACA GGC TGG GGC CGG       9262
Arg Gly Arg Phe Lys Tyr Glu Ile Leu Val Lys Thr Gly Trp Gly Arg
       3075            3080            3085

GGC TCA GGT ACC ACG GCC CAC GTG GGC ATC ATG CTG TAT GGG GTG GAC       9310
Gly Ser Gly Thr Thr Ala His Val Gly Ile Met Leu Tyr Gly Val Asp
       3090            3095            3100

AGC CGG AGC GGC CAC CGG CAC CTG GAC GGC GAC AGA GCC TTC CAC CGC       9358
Ser Arg Ser Gly His Arg His Leu Asp Gly Asp Arg Ala Phe His Arg
       3105            3110            3115
```

FIG. 10A-26

```
AAC AGC CTG GAC ATC TTC CGG ATC GCC ACC CCG CAC AGC CTG GGT AGC        9406
Asn Ser Leu Asp Ile Phe Arg Ile Ala Thr Pro His Ser Leu Gly Ser
3120          3125              3130              3135

GTG TGG AAG ATC CGA GTG TGG CAC GAC AAC AAA GGG CTC AGC CCT GCC        9454
Val Trp Lys Ile Arg Val Trp His Asp Asn Lys Gly Leu Ser Pro Ala
            3140              3145              3150

TGG TTC CTG CAG CAC GTC ATC GTC AGG GAC CTG CAG ACG GCA CGC AGC        9502
Trp Phe Leu Gln His Val Ile Val Arg Asp Leu Gln Thr Ala Arg Ser
            3155              3160              3165

GCC TTC TTC CTG GTC AAT GAC TGG CTT TCG GTG GAG ACG GAG GCC AAC        9550
Ala Phe Phe Leu Val Asn Asp Trp Leu Ser Val Glu Thr Glu Ala Asn
            3170              3175              3180

GGG GGC CTG GTG GAG AAG GAG GTG CTG GCC GCG AGC GAC GCA GCC CTT        9598
Gly Gly Leu Val Glu Lys Glu Val Leu Ala Ala Ser Asp Ala Ala Leu
            3185              3190              3195

TTG CGC TTC CGG CGC CTG CTG GTG GCT GAG CTG CAG CGT GGC TTC TTT        9646
Leu Arg Phe Arg Arg Leu Leu Val Ala Glu Leu Gln Arg Gly Phe Phe
3200          3205              3210              3215

GAC AAG CAC ATC TGG CTC TCC ATA TGG GAC CGG CCG CCT CGT AGC CGT        9694
Asp Lys His Ile Trp Leu Ser Ile Trp Asp Arg Pro Pro Arg Ser Arg
              3220              3225              3230

TTC ACT CGC ATC CAG AGG GCC ACC TGC TGC GTT CTC CTC ATC TGC CTC        9742
Phe Thr Arg Ile Gln Arg Ala Thr Cys Cys Val Leu Leu Ile Cys Leu
              3235              3240              3245
```

FIG. 10A-27

```
TTC CTG GGC GCC AAC GCC GTG TGG TAC GGG GCT GTT GGC GAC TCT GCC      9790
Phe Leu Gly Ala Asn Ala Val Trp Tyr Gly Ala Val Gly Asp Ser Ala
        3250            3255            3260

TAC AGC ACG GGG CAT GTG TCC AGG CTG AGC CCG CTG AGC GTC GAC ACA      9838
Tyr Ser Thr Gly His Val Ser Arg Leu Ser Pro Leu Ser Val Asp Thr
        3265            3270            3275

GTC GCT GTT GGC CTG GTG TCC AGC GTG GTT GTC TAT CCC GTC TAC CTG      9886
Val Ala Val Gly Leu Val Ser Ser Val Val Val Tyr Pro Val Tyr Leu
    3280            3285            3290            3295

GCC ATC CTT TTT CTC TTC CGG ATG TCC CGG AGC AAG GTG GCT GGG AGC      9934
Ala Ile Leu Phe Leu Phe Arg Met Ser Arg Ser Lys Val Ala Gly Ser
            3300            3305            3310

CCG AGC CCC ACA CCT GCC GGG CAG CAG GTG CTG GAC ATC GAC AGC TGC      9982
Pro Ser Pro Thr Pro Ala Gly Gln Gln Val Leu Asp Ile Asp Ser Cys
        3315            3320            3325

CTG GAC TCG TCC GTG CTG GAC AGC TCC TTC CTC ACG TTC TCA GGC CTC      10030
Leu Asp Ser Ser Val Leu Asp Ser Ser Phe Leu Thr Phe Ser Gly Leu
        3330            3335            3340

CAC GCT GAG GCC TTT GTT GGA CAG ATG AAG AGT GAC TTG TTT CTG GAT      10078
His Ala Glu Ala Phe Val Gly Gln Met Lys Ser Asp Leu Phe Leu Asp
        3345            3350            3355
```

FIG. 10A-28

```
GAT TCT AAG AGT CTG GTG TGC TGG CCC TCC GGC GAG GGA ACG CTC AGT       10126
Asp Ser Lys Ser Leu Val Cys Trp Pro Ser Gly Glu Gly Thr Leu Ser
3360          3365              3370              3375

TGG CCG GAC CTG CTC AGT GAC CCG TCC ATT GTG GGT AGC AAT CTG CGG       10174
Trp Pro Asp Leu Leu Ser Asp Pro Ser Ile Val Gly Ser Asn Leu Arg
         3380              3385              3390

CAG CTG GCA CGG GGC CAG GCG GGC CAT GGG CTG GGC CCA GAG GAG GAC       10222
Gln Leu Ala Arg Gly Gln Ala Gly His Gly Leu Gly Pro Glu Glu Asp
             3395              3400              3405

GGC TTC TCC CTG GCC AGC CCC TAC TCG CCT GCC AAA TCC TTC TCA GCA       10270
Gly Phe Ser Leu Ala Ser Pro Tyr Ser Pro Ala Lys Ser Phe Ser Ala
         3410              3415              3420

TCA GAT GAA GAC CTG ATC CAG CAG GTC CTT GCC GAG GGG GTC AGC AGC       10318
Ser Asp Glu Asp Leu Ile Gln Gln Val Leu Ala Glu Gly Val Ser Ser
         3425              3430              3435

CCA GCC CCT ACC CAA GAC ACC CAC ATG GAA ACG GAC CTG CTC AGC AGC       10366
Pro Ala Pro Thr Gln Asp Thr His Met Glu Thr Asp Leu Leu Ser Ser
3440              3445              3450              3455

CTG TCC AGC ACT CCT GGG GAG AAG ACA GAG ACG CTG GCG CTG CAG AGG       10414
Leu Ser Ser Thr Pro Gly Glu Lys Thr Glu Thr Leu Ala Leu Gln Arg
             3460              3465              3470

CTG GGG GAG CTG GGG CCA CCC AGC CCA GGC CTG AAC TGG GAA CAG CCC       10462
Leu Gly Glu Leu Gly Pro Pro Ser Pro Gly Leu Asn Trp Glu Gln Pro
             3475              3480              3485
```

FIG. 10A-29

```
CAG GCA GCG AGG CTG TCC AGG ACA GGA CTG GTG GAG GGT CTG CGG AAG      10510
Gln Ala Ala Arg Leu Ser Arg Thr Gly Leu Val Glu Gly Leu Arg Lys
    3490            3495             3500

CGC CTG CTG CCG GCC TGG TGT GCC TCC CTG GCC CAC GGG CTC AGC CTG       10558
Arg Leu Leu Pro Ala Trp Cys Ala Ser Leu Ala His Gly Leu Ser Leu
 3505            3510             3515

CTC CTG GTG GCT GTG GCT GTG GCT GTC TCA GGG TGG GTG GGT GCG AGC       10606
Leu Leu Val Ala Val Ala Val Ala Val Ser Gly Trp Val Gly Ala Ser
3520             3525            3530             3535

TTC CCC CCG GGC GTG AGT GTT GCG TGG CTC CTG TCC AGC AGC GCC AGC       10654
Phe Pro Pro Gly Val Ser Val Ala Trp Leu Leu Ser Ser Ser Ala Ser
             3540             3545             3550

TTC CTG GCC TCA TTC CTC GGC TGG GAG CCA CTG AAG GTC TTG CTG GAA       10702
Phe Leu Ala Ser Phe Leu Gly Trp Glu Pro Leu Lys Val Leu Leu Glu
             3555             3560             3565

GCC CTG TAC TTC TCA CTG GTG GCC AAG CGG CTG CAC CCG GAT GAA GAT       10750
Ala Leu Tyr Phe Ser Leu Val Ala Lys Arg Leu His Pro Asp Glu Asp
             3570             3575             3580

GAC ACC CTG GTA GAG AGC CCG GCT GTG ACG CCT GTG AGC GCA CGT GTG       10798
Asp Thr Leu Val Glu Ser Pro Ala Val Thr Pro Val Ser Ala Arg Val
             3585             3590             3595
```

FIG. 10A-30

```
CCC CGC GTA CGG CCA CCC CAC GGC TTT GCA CTC TTC CTG GCC AAG GAA    10846
Pro Arg Val Arg Pro Pro His Gly Phe Ala Leu Phe Leu Ala Lys Glu
3600            3605            3610            3615

GAA GCC CGC AAG GTC AAG AGG CTA CAT GGC ATG CTG CGG AGC CTC CTG    10894
Glu Ala Arg Lys Val Lys Arg Leu His Gly Met Leu Arg Ser Leu Leu
        3620            3625            3630

GTG TAC ATG CTT TTT CTG CTG GTG ACC CTG CTG GCC AGC TAT GGG GAT    10942
Val Tyr Met Leu Phe Leu Leu Val Thr Leu Leu Ala Ser Tyr Gly Asp
            3635            3640            3645

GCC TCA TGC CAT GGG CAC GCC TAC CGT CTG CAA AGC GCC ATC AAG CAG    10990
Ala Ser Cys His Gly His Ala Tyr Arg Leu Gln Ser Ala Ile Lys Gln
        3650            3655            3660

GAG CTG CAC AGC CGG GCC TTC CTG GCC ATC ACG CGG TCT GAG GAG CTC    11038
Glu Leu His Ser Arg Ala Phe Leu Ala Ile Thr Arg Ser Glu Glu Leu
            3665            3670            3675

TGG CCA TGG ATG GCC CAC GTG CTG CTG CCC TAC GTC CAC GGG AAC CAG    11086
Trp Pro Trp Met Ala His Val Leu Leu Pro Tyr Val His Gly Asn Gln
3680            3685            3690            3695

TCC AGC CCA GAG CTG GGG CCC CCA CGG CTG CGG CAG GTG CGG CTG CAG    11134
Ser Ser Pro Glu Leu Gly Pro Pro Arg Leu Arg Gln Val Arg Leu Gln
        3700            3705            3710

GAA GCA CTC TAC CCA GAC CCT CCC GGC CCC AGG GTC CAC ACG TGC TCG    11182
Glu Ala Leu Tyr Pro Asp Pro Pro Gly Pro Arg Val His Thr Cys Ser
            3715            3720            3725
```

FIG. 10A-31

```
GCC GCA GGA GGC TTC AGC ACC AGC GAT TAC GAC GTT GGC TGG GAG AGT     11230
Ala Ala Gly Gly Phe Ser Thr Ser Asp Tyr Asp Val Gly Trp Glu Ser
        3730            3735            3740

CCT CAC AAT GGC TCG GGG ACG TGG GCC TAT TCA GCG CCG GAT CTG CTG     11278
Pro His Asn Gly Ser Gly Thr Trp Ala Tyr Ser Ala Pro Asp Leu Leu
        3745            3750            3755

GGG GCA TGG TCC TGG GGC TCC TGT GCC GTG TAT GAC AGC GGG GGC TAC     11326
Gly Ala Trp Ser Trp Gly Ser Cys Ala Val Tyr Asp Ser Gly Gly Tyr
        3760            3765            3770            3775

GTG CAG GAG CTG GGC CTG AGC CTG GAG GAG AGC CGC GAC CGG CTG CGC     11374
Val Gln Glu Leu Gly Leu Ser Leu Glu Glu Ser Arg Asp Arg Leu Arg
        3780            3785            3790

TTC CTG CAG CTG CAC AAC TGG CTG GAC AAC AGG AGC CGC GCT GTG TTC     11422
Phe Leu Gln Leu His Asn Trp Leu Asp Asn Arg Ser Arg Ala Val Phe
        3795            3800            3805

CTG GAG CTC ACG CGC TAC AGC CCG GCC GTG GGG CTG CAC GCC GCC GTC     11470
Leu Glu Leu Thr Arg Tyr Ser Pro Ala Val Gly Leu His Ala Ala Val
        3810            3815            3820

ACG CTG CGC CTC GAG TTC CCG GCG GCC GGC CGC GCC CTG GCC GCC CTC     11518
Thr Leu Arg Leu Glu Phe Pro Ala Ala Gly Arg Ala Leu Ala Ala Leu
        3825            3830            3835
```

FIG. 10A-32

```
AGC GTC CGC CCC TTT GCG CTG CGC CGC CTC AGC GCG GGC CTC TCG CTG         11566
Ser Val Arg Pro Phe Ala Leu Arg Arg Leu Ser Ala Gly Leu Ser Leu
3840            3845                3850                3855

CCT CTG CTC ACC TCG GTG TGC CTG CTG CTG TTC GCC GTG CAC TTC GCC         11614
Pro Leu Leu Thr Ser Val Cys Leu Leu Leu Phe Ala Val His Phe Ala
                3860                3865                3870

GTG GCC GAG GCC CGT ACT TGG CAC AGG GAA GGG CGC TGG CGC GTG CTG         11662
Val Ala Glu Ala Arg Thr Trp His Arg Glu Gly Arg Trp Arg Val Leu
            3875                3880                3885

CGG CTC GGA GCC TGG GCG CGG TGG CTG CTG GTG GCG CTG ACG GCG GCC         11710
Arg Leu Gly Ala Trp Ala Arg Trp Leu Leu Val Ala Leu Thr Ala Ala
        3890                3895                3900

ACG GCA CTG GTA CGC CTC GCC CAG CTG GGT GCC GCT GAC CGC CAG TGG         11758
Thr Ala Leu Val Arg Leu Ala Gln Leu Gly Ala Ala Asp Arg Gln Trp
    3905                3910                3915

ACC CGT TTC GTG CGC GGC CGC CCG CGC CGC TTC ACT AGC TTC GAC CAG         11806
Thr Arg Phe Val Arg Gly Arg Pro Arg Arg Phe Thr Ser Phe Asp Gln
3920            3925                3930                3935

GTG GCG CAC GTG AGC TCC GCA GCC CGT GGC CTG GCG GCC TCG CTG CTC         11854
Val Ala His Val Ser Ser Ala Ala Arg Gly Leu Ala Ala Ser Leu Leu
                3940                3945                3950

TTC CTG CTT TTG GTC AAG GCT GCC CAG CAC GTA CGC TTC GTG CGC CAG         11902
Phe Leu Leu Leu Val Lys Ala Ala Gln His Val Arg Phe Val Arg Gln
                3955                3960                3965
```

FIG. 10A-33

```
TGG TCC GTC TTT GGC AAG ACA TTA TGC CGA GCT CTG CCA GAG CTC CTG      11950
Trp Ser Val Phe Gly Lys Thr Leu Cys Arg Ala Leu Pro Glu Leu Leu
     3970            3975            3980

GGG GTC ACC TTG GCC CTG GTG GTG CTC GGG GTA GCC TAC GCC CAG CTG      11998
Gly Val Thr Leu Gly Leu Val Val Leu Gly Val Ala Tyr Ala Gln Leu
     3985            3990            3995

GCC ATC CTG CTC GTG TCT TCC TGT GTG GAC TCC CTC TGG AGC GTG GCC      12046
Ala Ile Leu Leu Val Ser Ser Cys Val Asp Ser Leu Trp Ser Val Ala
4000            4005            4010            4015

CAG GCC CTG TTG GTG CTG TGC CCT GGG ACT GGG CTC TCT ACC CTG TGT      12094
Gln Ala Leu Leu Val Leu Cys Pro Gly Thr Gly Leu Ser Thr Leu Cys
         4020            4025            4030

CCT GCC GAG TCC TGG CAC CTG TCA CCC CTG CTG TGT GTG GGG CTC TGG      12142
Pro Ala Glu Ser Trp His Leu Ser Pro Leu Leu Cys Val Gly Leu Trp
         4035            4040            4045

GCA CTG CGG CTG TGG GGC GCC CTA CGG CTG GGG GCT GTT ATT CTC CGC      12190
Ala Leu Arg Leu Trp Gly Ala Leu Arg Leu Gly Ala Val Ile Leu Arg
         4050            4055            4060

TGG CGC TAC CAC GCC TTG CGT GGA GAG CTG TAC CGG CCG GCC TGG GAG      12238
Trp Arg Tyr His Ala Leu Arg Gly Glu Leu Tyr Arg Pro Ala Trp Glu
         4065            4070            4075
```

FIG. 10A-34

```
CCC CAG GAC TAC GAG ATG GTG GAG TTG TTC CTG CGC AGG CTG CGC CTC      12286
Pro Gln Asp Tyr Glu Met Val Glu Leu Phe Leu Arg Arg Leu Arg Leu
4080            4085            4090            4095

TGG ATG GGC CTC AGC AAG GTC AAG GAG TTC CGC CAC AAA GTC CGC TTT      12334
Trp Met Gly Leu Ser Lys Val Lys Glu Phe Arg His Lys Val Arg Phe
        4100            4105            4110

GAA GGG ATG GAG CCG CTG CCC TCT CGC TCC TCC AGG GGC TCC AAG GTA      12382
Glu Gly Met Glu Pro Leu Pro Ser Arg Ser Ser Arg Gly Ser Lys Val
    4115            4120            4125

TCC CCG GAT GTG CCC CCA CCC AGC GCT GGC TCC GAT GCC TCG CAC CCC      12430
Ser Pro Asp Val Pro Pro Pro Ser Ala Gly Ser Asp Ala Ser His Pro
4130            4135            4140

TCC ACC TCC TCC AGC CAG CTG GAT GGG CTG AGC GTG AGC CTG GGC CGG      12478
Ser Thr Ser Ser Ser Gln Leu Asp Gly Leu Ser Val Ser Leu Gly Arg
    4145            4150            4155

CTG GGG ACA AGG TGT GAG CCT GAG CCC TCC CGC CTC CAA GCC GTG TTC      12526
Leu Gly Thr Arg Cys Glu Pro Glu Pro Ser Arg Leu Gln Ala Val Phe
4160            4165            4170            4175

GAG GCC CTG CTC ACC CAG TTT GAC CGA CTC AAC CAG GCC ACA GAG GAC      12574
Glu Ala Leu Leu Thr Gln Phe Asp Arg Leu Asn Gln Ala Thr Glu Asp
        4180            4185            4190

GTC TAC CAG CTG GAG CAG CAG CTG CAC AGC CTG CAA GGC CGC AGG AGC      12622
Val Tyr Gln Leu Glu Gln Gln Leu His Ser Leu Gln Gly Arg Arg Ser
    4195            4200            4205
```

FIG. 10A-35

```
AGC CGG GCG CCC GCC GGA TCT TCC CGT GGC CCA TCC CCG GGC CTG CGG         12670
Ser Arg Ala Pro Ala Gly Ser Ser Arg Gly Pro Ser Pro Gly Leu Arg
        4210            4215            4220

CCA GCA CTG CCC AGC CGC CTT GCC CGG GCC AGT CGG GGT GTG GAC CTG         12718
Pro Ala Leu Pro Ser Arg Leu Ala Arg Ala Ser Arg Gly Val Asp Leu
        4225            4230            4235

GCC ACT GGC CCC AGC AGG ACA CCT TCG GGC CAA GAA CAA GGT CCA CCC         12766
Ala Thr Gly Pro Ser Arg Thr Pro Ser Gly Gln Glu Gln Gly Pro Pro
4240            4245            4250            4255

CAG CAG CAC TTA GTC CTC CTT CCT GGC GGG GGT GGG CCG TGG AGT CGG         12814
Gln Gln His Leu Val Leu Leu Pro Gly Gly Gly Gly Pro Trp Ser Arg
        4260            4265            4270

AGT GGA CAC CGC TCA GTA TTA CTT TCT GCC GCT GTC AAG GCC GAG GGC         12862
Ser Gly His Arg Ser Val Leu Leu Ser Ala Ala Val Lys Ala Glu Gly
        4275            4280            4285

CAG GCA GAA TGG CTG CAC GTA GGT TCC CCA GAG AGC AGG CAG GGG CAT         12910
Gln Ala Glu Trp Leu His Val Gly Ser Pro Glu Ser Arg Gln Gly His
        4290            4295            4300

CTG TCT GTC TGT GGG CTT CAG CAC TTT AAA GAG GCT GTG TGG CCA ACC         12958
Leu Ser Val Cys Gly Leu Gln His Phe Lys Glu Ala Val Trp Pro Thr
        4305            4310            4315
```

FIG. 10A-36

```
AGG ACC CAG GGT CCC CTC CCC AGC TCC CTT GGG AAG GAC ACA GCA GTA        13006
Arg Thr Gln Gly Pro Leu Pro Ser Ser Leu Gly Lys Asp Thr Ala Val
4320            4325            4330            4335

TTG GAC GGT TTC TAGCCTCTGA GATGCTAATT TATTTCCCCG AGTCCTCAGG            13058
Leu Asp Gly Phe

TACAGCGGGC TGTGCCCGGC CCCACCCCCT GGGCAGATGT CCCCCACTGC TAAGGCTGCT      13118

GGCTTCAGGG AGGGTTAGCC TGCACCGCCG CCACCCTGCC CCTAAGTTAT TACCTCTCCA      13178

GTTCCTACCG TACTCCCTGC ACCGTCTCAC TGTGTGTCTC GTGTCAGTAA TTTATATGGT      13238

GTTAAAATGT GTATATTTTT GTATGTCACT ATTTTCACTA GGGCTGAGGG GGCTGCCGCC      13298

AGAGCTGGCC TCCCCCAACA CCTGCTGCGC TTGGTAGGTG TGGTGGCGTT ATGGCAGCCC      13358

GGCTGCTGCT TGGATGCGAG CTTGGCCTTG GCCCGGTGCT GGGGCACAG CTGTCTGCCA       13418

GGCACTCTCA TCACCCAGA GGCCTTGTCA TCCTCCCTTG CCCCAGGCCA GGTAGCAAGA       13478

GAGCAGCGCC CAGGCCTGCT GGCATCAGGT CTGGGCAAGT AGCAGGACTA GGCATGTCAG      13538

AGGACCCCAG GGTGGTTAGA GGAAAAGACT CCTCCTGGGG GCTGGCTCCC AGGGTGGAGG     13598

AAGGTGACTG TGTGTGTGTG TGTGTGCGCG CGCGACGCGC GAGTGTCCTG TATGCCCCAG      13658

GCAGCCTCAA GGCCCTGGA GCTGGCTGTG CCTGCTTCTG TGTACCACTT CTGTGGGCAT       13718

GGCCGCTTCT AGAGCCTCGA CACCCCCCCA ACCCCCGCAC CAAGCAGACA AAGTCAATAA      13778

AAGAGCTGTC TGACTGCAAA AAAAAAAA                                        13807
```

```
  1  GCACTGCAGCGCCAGCGTCCGAGCGGGCGGCCGAGCTCCCGGAGCGGCCTGGCCCCGAGC   60

61  CCCGAGCGGGCGTCGCTCAGCAGCAGGTCGCGGCCGCGCAGCCCCATCCAGCCCCGCGCC  120

121  CGCCATGCCGTCCGCGGGCCCCGCCTGAGCTGCGGTCTCCGCGCGCGGGCGGGCCTGGGG  180

181  ACGGCGGGGCCATGCGCGCGCTGCCCTAACGATGCCGCCCGCCGCGCCCGCCCGCCTGGC  240
  1                                     M  P  P  A  A  P  A  R  L  A   10

241  GCTGGCCCTGGGCCTGGGCCTGTGGCTCGGGGCGCTGGCGGGGGGCCCCGGGCGCGGCTG  300
 11   L  A  L  G  L  G  L  W  L  G  A  L  A  G  G  P  G  R  G  C   30
                                        ▲
301  CGGGCCCTGCGAGCCCCCCTGCCTCTGCGGCCCAGCGCCCGGCGCCGCCTGCCGCGTCAA  360
 31   G  P  C  E  P  P  C  L  C  G  P  A  P  G  A  A  C  R  V  N   50
                                                                  *
361  CTGCTCGGGCCGCGGGCTGCGGACGCTCGGTCCCGCGCTGCGCATCCCCGCGGACGCCAC  420
 51   C  S  G  R  G  L  R  T  L  G  P  A  L  R  I  P  A  D  A  T   70

421  AGCGCTAGACGTCTCCCACAACCTGCTCCGGGCGCTGGACGTTGGGCTCCTGGCGAACCT  480
 71   A  L  D  V  S  H  N  L  L  R  A  L  D  V  G  L  L  A  N  L   90
                                                                  *
481  CTCGGCGCTGGCAGAGCTGGATATAAGCAACAACAAGATTTCTACGTTAGAAGAAGGAAT  540
 91   S  A  L  A  E  L  D  I  S  N  N  K  I  S  T  L  E  E  G  I  110

541  ATTTGCTAATTTATTTAATTTAAGTGAAATAAACCTGAGTGGGAACCCGTTTGAGTGTGA  600
111   F  A  N  L  F  N  L  S  E  I  N  L  S  G  N  P  F  E  C  D  130
                     *              *
```

FIG. 15A

```
601  CTGTGGCCTGGCGTGGCTGCCGCGATGGGCGGAGGAGCAGCAGGTGCGGGTGGTGCAGCC   660
131   C  G  L  A  W  L  P  R  W  A  E  E  Q  Q  V  R  V  V  Q  P    150

661  CGAGGCAGCCACGTGTGCTGGGCCTGGCTCCCTGGCTGGCCAGCCTCTGCTTGGCATCCC   720
151   E  A  A  T  C  A  G  P  G  S  L  A  G  Q  P  L  L  G  I  P    170

721  CTTGCTGGACAGTGGCTGTGGTGAGGAGTATGTCGCCTGCCTCCCTGACAACAGCTCAGG   780
171   L  L  D  S  G  C  G  E  E  Y  V  A  C  L  P  D  N  S  S  G    190
                                                      *
781  CACCGTGGCAGCAGTGTCCTTTTCAGCTGCCCACGAAGGCCTGCTTCAGCCAGAGGCCTG   840
191   T  V  A  A  V  S  F  S  A  A  H  E  G  L  L  Q  P  E  A  C    210

841  CAGCGCCTTCTGCTTCTCCACCGGCCAGGGCCTCGCAGCCCTCTCGGAGCAGGGCTGGTG   900
211   S  A  F  C  F  S  T  G  Q  G  L  A  A  L  S  E  Q  G  W  C    230

901  CCTGTGTGGGGCGGCCCAGCCCTCCAGTGCCTCCTTTGCCTGCCTGTCCCTCTGCTCCGG   960
231   L  C  G  A  A  Q  P  S  S  A  S  F  A  C  L  S  L  C  S  G    250

961  CCCCCCGCCACCTCCTGCCCCCACCTGTAGGGGCCCCACCCTCCTCCAGCACGTCTTCCC  1020
251   P  P  P  P  P  A  P  T  C  R  G  P  T  L  L  Q  H  V  F  P    270

1021 TGCCTCCCCAGGGGCCACCCTGGTGGGGCCCCACGGACCTCTGGCCTCTGGCCAGCTAGC  1080
271   A  S  P  G  A  T  L  V  G  P  H  G  P  L  A  S  G  Q  L  A    290

1081 AGCCTTCCACATCGCTGCCCCGCTCCCTGTCACTGCCACACGCTGGGACTTCGGAGACGG  1140
291   A  F  H  I  A  A  P  L  P  V  T  A  T  R  W  D  F  G  D  G    310

1141 CTCCGCCGAGGTGGATGCCGCTGGGCCGGCTGCCTCGCATCGCTATGTGCTGCCTGGGCG  1200
311   S  A  E  V  D  A  A  G  P  A  A  S  H  R  Y  V  L  P  G  R    330
```

FIG. 15B

```
1201  CTATCACGTGACGGCCGTGCTGGCCCTGGGGGCCGGCTCAGCCCTGCTGGGGACAGACGT  1260
331    Y  H  V  T  A  V  L  A  L  G  A  G  S  A  L  L  G  T  D  V   350

1261  GCAGGTGGAAGCGGCACCTGCCGCCCTGGAGCTCGTGTGCCCGTCCTCGGTGCAGAGTGA  1320
351    Q  V  E  A  A  P  A  A  L  E  L  V  C  P  S  S  V  Q  S  D   370

1321  CGAGAGCCTTGACCTCAGCATCCAGAACCGCGGTGGTTCAGGCCTGGAGGCCGCCTACAG  1380
371    E  S  L  D  L  S  I  Q  N  R  G  G  S  G  L  E  A  A  Y  S   390

1381  CATCGTGGCCCTGGGCGAGGAGCCGGCCCGAGCGGTGCACCCGCTCTGCCCCTCGGACAC  1440
391    I  V  A  L  G  E  E  P  A  R  A  V  H  P  L  C  P  S  D  T   410

1441  GGAGATCTTCCCTGGCAACGGGCACTGCTACCGCCTGGTGGTGGAGAAGGCGGCCTGGCT  1500
411    E  I  F  P  G  N  G  H  C  Y  R  L  V  V  E  K  A  A  W  L   430

1501  GCAGGCGCAGGAGCAGTGTCAGGCCTGGGCCGGGGCCGCCCTGGCAATGGTGGACAGTCC  1560
431    Q  A  Q  E  Q  C  Q  A  W  A  G  A  A  L  A  M  V  D  S  P   450

1561  CGCCGTGCAGCGCTTCCTGGTCTCCCGGGTCACCAGGAGCCTAGACGTGTGGATCGGCTT  1620
451    A  V  Q  R  F  L  V  S  R  V  T  R  S  L  D  V  W  I  G  F   470

1621  CTCGACTGTGCAGGGGGTGGAGGTGGGCCCAGCGCCGCAGGGCGAGGCCTTCAGCCTGGA  1680
471    S  T  V  Q  G  V  E  V  G  P  A  P  Q  G  E  A  F  S  L  E   490

1681  GAGCTGCCAGAACTGGCTGCCCGGGGAGCCACACCCAGCCACAGCCGAGCACTGCGTCCG  1740
491    S  C  Q  N  W  L  P  G  E  P  H  P  A  T  A  E  H  C  V  R   510

1741  GCTCGGGCCCACCGGGTGGTGTAACACCGACCTGTGCTCAGCGCCGCACAGCTACGTCTG  1800
511    L  G  P  T  G  W  C  N  T  D  L  C  S  A  P  H  S  Y  V  C   530
```

FIG. 15C

```
1801 CGAGCTGCAGCCCGGAGGCCCAGTGCAGGATGCCGAGAACCTCCTCGTGGGAGCGCCCAG 1860
531   E  L  Q  P  G  G  P  V  Q  D  A  E  N  L  L  V  G  A  P  S   550

1861 TGGGGACCTGCAGGGACCCCTGACGCCTCTGGCACAGCAGGACGGCCTCTCAGCCCCGCA 1920
551   G  D  L  Q  G  P  L  T  P  L  A  Q  Q  D  G  L  S  A  P  H   570

1921 CGAGCCCGTGGAGGTCATGGTATTCCCGGGCCTGCGTCTGAGCCGTGAAGCCTTCCTCAC 1980
571   E  P  V  E  V  M  V  F  P  G  L  R  L  S  R  E  A  F  L  T   590

1981 CACGGCCGAATTTGGGACCCAGGAGCTCCGGCGGCCCGCCCAGCTGCGGCTGCAGGTGTA 2040
591   T  A  E  F  G  T  Q  E  L  R  R  P  A  Q  L  R  L  Q  V  Y   610

2041 CCGGCTCCTCAGCACAGCAGGGACCCCGGAGAACGGCAGCGAGCCTGAGAGCAGGTCCCC 2100
611   R  L  L  S  T  A  G  T  P  E  N  G  S  E  P  E  S  R  S  P   630
                                 *
2101 GGACAACAGGACCCAGCTGGCCCCCGCGTGCATGCCAGGGGGACGCTGGTGCCCTGGAGC 2160
631   D  N  R  T  Q  L  A  P  A  C  M  P  G  G  R  W  C  P  G  A   650
      *
2161 CAACATCTGCTTGCCGCTGGACGCCTCTTGCCACCCCCAGGCCTGCGCCAATGGCTGCAC 2220
651   N  I  C  L  P  L  D  A  S  C  H  P  Q  A  C  A  N  G  C  T   670

2221 GTCAGGGCCAGGGCTACCCGGGGCCCCCTATGCGCTATGGAGAGAGTTCCTCTTCTCCGT 2280
671   S  G  P  G  L  P  G  A  P  Y  A  L  W  R  E  F  L  F  S  V   690

2281 TGCCGCGGGGCCCCCCGCGCAGTACTCGGTCACCCTCCACGGCCAGGATGTCCTCATGCT 2340
691   A  A  G  P  P  A  Q  Y  S  V  T  L  H  G  Q  D  V  L  M  L   710

2341 CCCTGGTGACCTCGTTGGCTTGCAGCACGACGCTGGCCCTGGCGCCCTCCTGCACTGCTC 2400
711   P  G  D  L  V  G  L  Q  H  D  A  G  P  G  A  L  L  H  C  S   730
```

FIG. 15D

```
2401 GCCGGCTCCCGGCCACCCTGGTCCCCAGGCCCCGTACCTCTCCGCCAACGCCTCGTCATG 2460
 731   P  A  P  G  H  P  G  P  Q  A  P  Y  L  S  A  N  A  S  S  W   750
                                                      *
2461 GCTGCCCCACTTGCCAGCCCAGCTGGAGGGCACTTGGGCCTGCCCTGCCTGTGCCCTGCG 2520
 751   L  P  H  L  P  A  Q  L  E  G  T  W  A  C  P  A  C  A  L  R   770

2521 GCTGCTTGCAGCCACGGAACAGCTCACCGTGCTGCTGGGCTTGAGGCCCAACCCTGGACT 2580
 771   L  L  A  A  T  E  Q  L  T  V  L  L  G  L  R  P  N  P  G  L   790

2581 GCGGATGCCTGGGCGCTATGAGGTCCGGGCAGAGGTGGGCAATGGCGTGTCCAGGCACAA 2640
 791   R  M  P  G  R  Y  E  V  R  A  E  V  G  N  G  V  S  R  H  N   810
                                                                  *
2641 CCTCTCCTGCAGCTTTGACGTGGTCTCCCCAGTGGCTGGGCTGCGGGTCATCTACCCTGC 2700
 811   L  S  C  S  F  D  V  V  S  P  V  A  G  L  R  V  I  Y  P  A   830

2701 CCCCCGCGACGGCCGCCTCTACGTGCCCACCAACGGCTCAGCCTTGGTGCTCCAGGTGGA 2760
 831   P  R  D  G  R  L  Y  V  P  T  N  G  S  A  L  V  L  Q  V  D   850
                                      *
2761 CTCTGGTGCCAACGCCACGGCCACGGCTCGCTGGCCTGGGGGCAGTGTCAGCGCCCGCTT 2820
 851   S  G  A  N  A  T  A  T  A  R  W  P  G  G  S  V  S  A  R  F   870
            *
2821 TGAGAATGTCTGCCCTGCCCTGGTGGCCACCTTCGTGCCCGGCTGCCCCTGGGAGACCAA 2880
 871   E  N  V  C  P  A  L  V  A  T  F  V  P  G  C  P  W  E  T  N   890
                                                                  *
2881 CGATACCCTGTTCTCAGTGGTAGCACTGCCGTGGCTCAGTGAGGGGGAGCACGTGGTGGA 2940
 891   D  T  L  F  S  V  V  A  L  P  W  L  S  E  G  E  H  V  V  D   910

2941 CGTGGTGGTGGAAAACAGCGCCAGCCGGGCCAACCTCAGCCTGCGGGTGACGGCGGAGGA 3000
 911   V  V  V  E  N  S  A  S  R  A  N  L  S  L  R  V  T  A  E  E   930
                        *
3001 GCCCATCTGTGGCCTCCGCGCCACGCCCAGCCCCGAGGCCCGTGTACTGCAGGGAGTCCT 3060
 931   P  I  C  G  L  R  A  T  P  S  P  E  A  R  V  L  Q  G  V  L   950
```

FIG. 15E

```
3061 AGTGAGGTACAGCCCCGTGGTGGAGGCCGGCTCGGACATGGTCTTCCGGTGGACCATCAA 3120
 951   V  R  Y  S  P  V  V  E  A  G  S  D  M  V  F  R  W  T  I  N   970

3121 CGACAAGCAGTCCCTGACCTTCCAGAACGTGGTCTTCAATGTCATTTATCAGAGCGCGGC 3180
 971   D  K  Q  S  L  T  F  Q  N  V  V  F  N  V  I  Y  Q  S  A  A   990

3181 GGTCTTCAAGCTCTCACTGACGGCCTCCAACCACGTGAGCAACGTCACCGTGAACTACAA 3240
 991   V  F  K  L  S  L  T  A  S  N  H  V  S  N  V  T  V  N  Y  N  1010
                                              *

3241 CGTAACCGTGGAGCGGATGAACAGGATGCAGGGTCTGCAGGTCTCCACAGTGCCGGCCGT 3300
1011   V  T  V  E  R  M  N  R  M  Q  G  L  Q  V  S  T  V  P  A  V  1030

3301 GCTGTCCCCCAATGCCACACTGGTACTGACGGGTGGTGTGCTGGTGGACTCAGCTGTGGA 3360
1031   L  S  P  N  A  T  L  V  L  T  G  G  V  L  V  D  S  A  V  E  1050
                *

3361 GGTGGCCTTCCTGTGGAACTTTGGGGATGGGGAGCAGGCCCTCCACCAGTTCCAGCCTCC 3420
1051   V  A  F  L  W  N  F  G  D  G  E  Q  A  L  H  Q  F  Q  P  P  1070

3421 GTACAACGAGTCCTTCCCGGTTCCAGACCCCTCGGTGGCCCAGGTGCTGGTGGAGCACAA 3480
1071   Y  N  E  S  F  P  V  P  D  P  S  V  A  Q  V  L  V  E  H  N  1090
             *

3481 TGTCATGCACACCTACGCTGCCCCAGGTGAGTACCTCCTGACCGTGCTGGCATCTAATGC 3540
1091   V  M  H  T  Y  A  A  P  G  E  Y  L  L  T  V  L  A  S  N  A  1110

3541 CTTCGAGAACCTGACGCAGCAGGTGCCTGTGAGCGTGCGCGCCTCCCTGCCCTCCGTGGC 3600
1111   F  E  N  L  T  Q  Q  V  P  V  S  V  R  A  S  L  P  S  V  A  1130
                *
```

FIG. 15F

```
3601  TGTGGGTGTGAGTGACGGCGTCCTGGTGGCCGGCCGGCCCGTCACCTTCTACCCGCACCC  3660
1131    V  G  V  S  D  G  V  L  V  A  G  R  P  V  T  F  Y  P  H  P    1150

3661  GCTGCCCTCGCCTGGGGGTGTTCTTTACACGTGGGACTTCGGGGACGGCTCCCCTGTCCT  3720
1151    L  P  S  P  G  G  V  L  Y  T  W  D  F  G  D  G  S  P  V  L    1170

3721  GACCCAGAGCCAGCCGGCTGCCAACCACACCTATGCCTCGAGGGGCACCTACCACGTGCG  3780
1171    T  Q  S  Q  P  A  A  N  H  T  Y  A  S  R  G  T  Y  H  V  R    1190
                              *

3781  CCTGGAGGTCAACAACACGGTGAGCGGTGCGGCGGCCCAGGCGGATGTGCGCGTCTTTGA  3840
1191    L  E  V  N  N  T  V  S  G  A  A  A  Q  A  D  V  R  V  F  E    1210
              *

3841  GGAGCTCCGCGGACTCAGCGTGGACATGAGCCTGGCCGTGGAGCAGGGCGCCCCCGTGGT  3900
1211    E  L  R  G  L  S  V  D  M  S  L  A  V  E  Q  G  A  P  V  V    1230

3901  GGTCAGCGCCGCGGTGCAGACGGGCGACAACATCACGTGGACCTTCGACATGGGGGACGG  3960
1231    V  S  A  A  V  Q  T  G  D  N  I  T  W  T  F  D  M  G  D  G    1250
                                    *

3961  CACCGTGCTGTCGGGCCCGGAGGCAACAGTGGAGCATGTGTACCTGCGGGCACAGAACTG  4020
1251    T  V  L  S  G  P  E  A  T  V  E  H  V  Y  L  R  A  Q  N  C    1270
                                                              *

4021  CACAGTGACCGTGGGTGCGGCCAGCCCCGCCGGCCACCTGGCCCGGAGCCTGCACGTGCT  4080
1271    T  V  T  V  G  A  A  S  P  A  G  H  L  A  R  S  L  H  V  L    1290

4081  GGTCTTCGTCCTGGAGGTGCTGCGCGTTGAACCCGCCGCCTGCATCCCCACGCAGCCTGA  4140
1291    V  F  V  L  E  V  L  R  V  E  P  A  A  C  I  P  T  Q  P  D    1310

4141  CGCGCGGCTCACGGCCTACGTCACCGGGAACCCGGCCCACTACCTCTTCGACTGGACCTT  4200
1311    A  R  L  T  A  Y  V  T  G  N  P  A  H  Y  L  F  D  W  T  F    1330
```

FIG. 15G

```
4201 CGGGGATGGCTCCTCCAACACGACCGTGCGGGGGTGCCCGACGGTGACACACAACTTCAC 4260
1331    G  D  G  S  S  N  T  T  V  R  G  C  P  T  V  T  H  N  F  T  1350
                     *                                   *
4261 GCGGAGCGGCACGTTCCCCCTGGCGCTGGTGCTGTCCAGCCGCGTGAACAGGGCGCATTA 4320
1351    R  S  G  T  F  P  L  A  L  V  L  S  S  R  V  N  R  A  H  Y  1370

4321 CTTCACCAGCATCTGCGTGGAGCCAGAGGTGGGCAACGTCACCCTGCAGCCAGAGAGGCA 4380
1371    F  T  S  I  C  V  E  P  E  V  G  N  V  T  L  Q  P  E  R  Q  1390
                                       *

4381 GTTTGTGCAGCTCGGGGACGAGGCCTGGCTGGTGGCATGTGCCTGGCCCCCGTTCCCCTA 4440
1391    F  V  Q  L  G  D  E  A  W  L  V  A  C  A  W  P  P  F  P  Y  1410

4441 CCGCTACACCTGGGACTTTGGCACCGAGGAAGCCGCCCCCACCCGTGCCAGGGGCCCTGA 4500
1411    R  Y  T  W  D  F  G  T  E  E  A  A  P  T  R  A  R  G  P  E  1430

4501 GGTGACGTTCATCTACCGAGACCCAGGCTCCTATCTTGTGACAGTCACCGCGTCCAACAA 4560
1431    V  T  F  I  Y  R  D  P  G  S  Y  L  V  T  V  T  A  S  N  N  1450
                                                                  *
4561 CATCTCTGCTGCCAATGACTCAGCCCTGGTGGAGGTGCAGGAGCCCGTGCTGGTCACCAG 4620
1451    I  S  A  A  N  D  S  A  L  V  E  V  Q  E  P  V  L  V  T  S  1470
                  *

4621 CATCAAGGTCAATGGCTCCCTTGGGCTGGAGCTGCAGCAGCCGTACCTGTTCTCTGCTGT 4680
1471    I  K  V  N  G  S  L  G  L  E  L  Q  Q  P  Y  L  F  S  A  V  1490
               *

4681 GGGCCGTGGGCGCCCCGCCAGCTACCTGTGGGATCTGGGGGACGGTGGGTGGCTCGAGGG 4740
1491    G  R  G  R  P  A  S  Y  L  W  D  L  G  D  G  G  W  L  E  G  1510

4741 TCCGGAGGTCACCCACGCTTACAACAGCACAGGTGACTTCACCGTTAGGGTGGCCGGCTG 4800
1511    P  E  V  T  H  A  Y  N  S  T  G  D  F  T  V  R  V  A  G  W  1530
                              *
```

FIG. 15H

```
4801 GAATGAGGTGAGCCGCAGCGAGGCCTGGCTCAATGTGACGGTGAAGCGGCGCGTGCGGGG 4860
1531  N  E  V  S  R  S  E  A  W  L  N  V  T  V  K  R  R  V  R  G  1550
                                    *
4861 GCTCGTCGTCAATGCAAGCCGCACGGTGGTGCCCCTGAATGGGAGCGTGAGCTTCAGCAC 4920
1551  L  V  V  N  A  S  R  T  V  V  P  L  N  G  S  V  S  F  S  T  1570
              *                       *
4921 GTCGCTGGAGGCCGGCAGTGATGTGCGCTATTCCTGGGTGCTCTGTGACCGCTGCACGCC 4980
1571  S  L  E  A  G  S  D  V  R  Y  S  W  V  L  C  D  R  C  T  P  1590

4981 CATCCCTGGGGGTCCTACCATCTCTTACACCTTCCGCTCCGTGGGCACCTTCAATATCAT 5040
1591  I  P  G  G  P  T  I  S  Y  T  F  R  S  V  G  T  F  N  I  I  1610

5041 CGTCACGGCTGAGAACGAGGTGGGCTCCGCCCAGGACAGCATCTTCGTCTATGTCCTGCA 5100
1611  V  T  A  E  N  E  V  G  S  A  Q  D  S  I  F  V  Y  V  L  Q  1630

5101 GCTCATAGAGGGGCTGCAGGTGGTGGGCGGTGGCCGCTACTTCCCCACCAACCACACGGT 5160
1631  L  I  E  G  L  Q  V  V  G  G  G  R  Y  F  P  T  N  H  T  V  1650
                                              *
5161 ACAGCTGCAGGCCGTGGTTAGGGATGGCACCAACGTCTCCTACAGCTGGACTGCCTGGAG 5220
1651  Q  L  Q  A  V  V  R  D  G  T  N  V  S  Y  S  W  T  A  W  R  1670
                              *
5221 GGACAGGGGCCCCGGCCCTGGCCGGCAGCGGCAAAGGCTTCTCGCTCACCGTGCTCGAGGC 5280
1671  D  R  G  P  A  L  A  G  S  G  K  G  F  S  L  T  V  L  E  A  1690

5281 CGGCACCTACCATGTGCAGCTGCGGGCCACCAACATGCTGGGCAGCGCCTGGGCCGACTG 5340
1691  G  T  Y  H  V  Q  L  R  A  T  N  M  L  G  S  A  W  A  D  C  1710

5341 CACCATGGACTTCGTGGAGCCTGTGGGGTGGCTGATGGTGACCGCCTCCCCGAACCCAGC 5400
1711  T  M  D  F  V  E  P  V  G  W  L  M  V  T  A  S  P  N  P  A  1730
```

FIG. 15I

```
5341 CACCATGGACTTCGTGGAGCCTGTGGGGTGGCTGATGGTGACCGCCTCCCCGAACCCAGC  5400
1711  T  M  D  F  V  E  P  V  G  W  L  M  V  T  A  S  P  N  P  A   1730

5401 TGCCGTCAACACAAGCGTCACCCTCAGTGCCGAGCTGGCTGGTGGCAGTGGTGTCGTATA  5460
1731  A  V  N  T  S  V  T  L  S  A  E  L  A  G  G  S  G  V  V  Y   1750
         *
5461 CACTTGGTCCTTGGAGGAGGGGCTGAGCTGGGAGACCTCCGAGCCATTTACCACCCATAG  5520
1751  T  W  S  L  E  E  G  L  S  W  E  T  S  E  P  F  T  T  H  S   1770

5521 CTTCCCCACACCCGGCCTGCACTTGGTCACCATGACGGCAGGGAACCCGCTGGGCTCAGC  5580
1771  F  P  T  P  G  L  H  L  V  T  M  T  A  G  N  P  L  G  S  A   1790

5581 CAACGCCACCGTGGAAGTGGATGTGCAGGTGCCTGTGAGTGGCCTCAGCATCAGGGCCAG  5640
1791  N  A  T  V  E  V  D  V  Q  V  P  V  S  G  L  S  I  R  A  S   1810
      *
5641 CGAGCCCGGAGGCAGCTTCGTGGCGGCCGGGTCCTCTGTGCCCTTTTGGGGGCAGCTGGC  5700
1811  E  P  G  G  S  F  V  A  A  G  S  S  V  P  F  W  G  Q  L  A   1830

5701 CACGGGCACCAATGTGAGCTGGTGCTGGGCTGTGCCCGGCGGCAGCAGCAAGCGTGGCCC  5760
1831  T  G  T  N  V  S  W  C  W  A  V  P  G  G  S  S  K  R  G  P   1850
                  *
5761 TCATGTCACCATGGTCTTCCCGGATGCTGGCACCTTCTCCATCCGGCTCAATGCCTCCAA  5820
1851  H  V  T  M  V  F  P  D  A  G  T  F  S  I  R  L  N  A  S  N   1870
                                                          *
5821 CGCAGTCAGCTGGGTCTCAGCCACGTACAACCTCACGGCGGAGGAGCCCATCGTGGGCCT  5880
1871  A  V  S  W  V  S  A  T  Y  N  L  T  A  E  E  P  I  V  G  L   1890
                            *
5881 GGTGCTGTGGGCCAGCAGCAAGGTGGTGGCGCCCGGGCAGCTGGTCCATTTTCAGATCCT  5940
1891  V  L  W  A  S  S  K  V  V  A  P  G  Q  L  V  H  F  Q  I  L   1910

5941 GCTGGCTGCCGGCTCAGCTGTCACCTTCCGCCTGCAGGTCGGCGGGGCCAACCCCGAGGT  6000
1911  L  A  A  G  S  A  V  T  F  R  L  Q  V  G  G  A  N  P  E  V   1930
```

FIG. 15J

```
6001 GCTCCCCGGGCCCCGTTTCTCCCACAGCTTCCCCCGCGTCGGAGACCACGTGGTGAGCGT 6060
1931  L  P  G  P  R  F  S  H  S  F  P  R  V  G  D  H  V  V  S  V  1950

6061 GCGGGGCAAAAACCACGTGAGCTGGGCCCAGGCGCAGGTGCGCATCGTGGTGCTGGAGGC 6120
1951  R  G  K  N  H  V  S  W  A  Q  A  Q  V  R  I  V  V  L  E  A  1970

6121 CGTGAGTGGGCTGCAGATGCCCAACTGCTGCGAGCCTGGCATCGCCACGGGCACTGAGAG 6180
1971  V  S  G  L  Q  M  P  N  C  C  E  P  G  I  A  T  G  T  E  R  1990

6181 GAACTTCACAGCCCGCGTGCAGCGCGGCTCTCGGGTCGCCTACGCCTGGTACTTCTCGCT 6240
1991  N  F  T  A  R  V  Q  R  G  S  R  V  A  Y  A  W  Y  F  S  L  2010
         *

6241 GCAGAAGGTCCAGGGCGACTCGCTGGTCATCCTGTCGGGCCGCGACGTCACCTACACGCC 6300
2011  Q  K  V  Q  G  D  S  L  V  I  L  S  G  R  D  V  T  Y  T  P  2030

6301 CGTGGCCGCGGGGCTGTTGGAGATCCAGGTGCGCGCCTTCAACGCCCTGGGCAGTGAGAA 6360
2031  V  A  A  G  L  L  E  I  Q  V  R  A  F  N  A  L  G  S  E  N  2050
                                                             *

6361 CCGCACGCTGGTGCTGGAGGTTCAGGACGCCGTCCAGTATGTGGCCCTGCAGAGCGGCCC 6420
2051  R  T  L  V  L  E  V  Q  D  A  V  Q  Y  V  A  L  Q  S  G  P  2070

6421 CTGCTTCACCAACCGCTCGGCGCAGTTTGAGGCCGCCACCAGCCCCAGCCCCCGGCGTGT 6480
2071  C  F  T  N  R  S  A  Q  F  E  A  A  T  S  P  S  P  R  R  V  2090
              *

6481 GGCCTACCACTGGGACTTTGGGGATGGGTCGCCAGGGCAGGACACAGATGAGCCCAGGGC 6540
2091  A  Y  H  W  D  F  G  D  G  S  P  G  Q  D  T  D  E  P  R  A  2110

6541 CGAGCACTCCTACCTGAGGCCTGGGGACTACCGCGTGCAGGTGAACGCCTCCAACCTGGT 6600
2111  E  H  S  Y  L  R  P  G  D  Y  R  V  Q  V  N  A  S  N  L  V  2130
                                                    *
```

FIG. 15K

```
6601  GAGCTTCTTCGTGGCGCAGGCCACGGTGACCGTCCAGGTGCTGGCCTGCCGGGAGCCGGA  6660
2131   S  F  F  V  A  Q  A  T  V  T  V  Q  V  L  A  C  R  E  P  E    2150

6661  GGTGGACGTGGTCCTGCCCCTGCAGGTGCTGATGCGGCGATCACAGCGCAACTACTTGGA  6720
2151   V  D  V  V  L  P  L  Q  V  L  M  R  R  S  Q  R  N  Y  L  E    2170

6721  GGCCCACGTTGACCTGCGCGACTGCGTCACCTACCAGACTGAGTACCGCTGGGAGGTGTA  6780
2171   A  H  V  D  L  R  D  C  V  T  Y  Q  T  E  Y  R  W  E  V  Y    2190

6781  TCGCACCGCCAGCTGCCAGCGGCCGGGGCGCCCAGCGCGTGTGGCCCTGCCCGGCGTGGA  6840
2191   R  T  A  S  C  Q  R  P  G  R  P  A  R  V  A  L  P  G  V  D    2210

6841  CGTGAGCCGGCCTCGGCTGGTGCTGCCGCGGCTGGCGCTGCCTGTGGGGCACTACTGCTT  6900
2211   V  S  R  P  R  L  V  L  P  R  L  A  L  P  V  G  H  Y  C  F    2230

6901  TGTGTTTGTCGTGTCATTTGGGGACACGCCACTGACACAGAGCATCCAGGCCAATGTGAC  6960
2231   V  F  V  V  S  F  G  D  T  P  L  T  Q  S  I  Q  A  N  V  T    2250
                                                               *

6961  GGTGGCCCCCGAGCGCCTGGTGCCCATCATTGAGGGTGGCTCATACCGCGTGTGGTCAGA  7020
2251   V  A  P  E  R  L  V  P  I  I  E  G  G  S  Y  R  V  W  S  D    2270

7021  CACACGGGACCTGGTGCTGGATGGGAGCGAGTCCTACGACCCCAACCTGGAGGACGGCGA  7080
2271   T  R  D  L  V  L  D  G  S  E  S  Y  D  P  N  L  E  D  G  D    2290

7081  CCAGACGCCGCTCAGTTTCCACTGGGCCTGTGTGGCTTCGACACAGAGGGAGGCTGGCGG  7140
2291   Q  T  P  L  S  F  H  W  A  C  V  A  S  T  Q  R  E  A  G  G    2310

7141  GTGTGCGCTGAACTTTGGGCCCCGCGGGAGCAGCACGGTCACCATTCCACGGGAGCGGCT  7200
2311   C  A  L  N  F  G  P  R  G  S  S  T  V  T  I  P  R  E  R  L    2330
```

FIG. 15L

```
7201 GGCGGCTGGCGTGGAGTACACCTTCAGCCTGACCGTGTGGAAGGCCGGCCGCAAGGAGGA 7260
2331  A  A  G  V  E  Y  T  F  S  L  T  V  W  K  A  G  R  K  E  E  2350

7261 GGCCACCAACCAGACGGTGCTGATCCGGAGTGGCCGGGTGCCCATTGTGTCCTTGGAGTG 7320
2351  A  T  N  Q  T  V  L  I  R  S  G  R  V  P  I  V  S  L  E  C  2370
            *

7321 TGTGTCCTGCAAGGCACAGGCCGTGTACGAAGTGAGCCGCAGCTCCTACGTGTACTTGGA 7380
2371  V  S  C  K  A  Q  A  V  Y  E  V  S  R  S  S  Y  V  Y  L  E  2390

7381 GGGCCGCTGCCTCAATTGCAGCAGCGGCTCCAAGCGAGGGCGGTGGGCTGCACGTACGTT 7440
2391  G  R  C  L  N  C  S  S  G  S  K  R  G  R  W  A  A  R  T  F  2410
               *

7441 CAGCAACAAGACGCTGGTGCTGGATGAGACCACCACATCCACGGGCAGTGCAGGCATGCG 7500
2411  S  N  K  T  L  V  L  D  E  T  T  T  S  T  G  S  A  G  M  R  2430
         *

7501 ACTGGTGCTGCGGCGGGGCGTGCTGCGGGACGGCGAGGGATACACCTTCACGCTCACGGT 7560
2431  L  V  L  R  R  G  V  L  R  D  G  E  G  Y  T  F  T  L  T  V  2450

7561 GCTGGGCCGCTCTGGCGAGGAGGAGGGCTGCGCCTCCATCCGCCTGTCCCCCAACCGCCC 7620
2451  L  G  R  S  G  E  E  E  G  C  A  S  I  R  L  S  P  N  R  P  2470

7621 GCCGCTGGGGGGCTCTTGCCGCCTCTTCCCACTGGGCGCTGTGCACGCCCTCACCACCAA 7680
2471  P  L  G  G  S  C  R  L  F  P  L  G  A  V  H  A  L  T  T  K  2490

7681 GGTGCACTTCGAATGCACGGGCTGGCATGACGCGGAGGATGCTGGCGCCCCGCTGGTGTA 7740
2491  V  H  F  E  C  T  G  W  H  D  A  E  D  A  G  A  P  L  V  Y  2510

7741 CGCCCTGCTGCTGCGGCGCTGTCGCCAGGGCCACTGCGAGGAGTTCTGTGTCTACAAGGG 7800
2511  A  L  L  L  R  R  C  R  Q  G  H  C  E  E  F  C  V  Y  K  G  2530
```

FIG. 15M

```
7801 CAGCCTCTCCAGCTACGGAGCCGTGCTGCCCCCGGGTTTCAGGCCACACTTCGAGGTGGG 7860
2531  S   L   S   S   Y   G   A   V   L   P   P   G   F   R   P   H   F   E   V   G  2550

7861 CCTGGCCGTGGTGGTGCAGGACCAGCTGGGAGCCGCTGTGGTCGCCCTCAACAGGTCTTT 7920
2551  L   A   V   V   V   Q   D   Q   L   G   A   A   V   V   A   L   N   R   S   L  2570
                                                                      *

7921 GGCCATCACCCTCCCAGAGCCCAACGGCAGCGCAACGGGGCTCACAGTCTGGCTGCACGG 7980
2571  A   I   T   L   P   E   P   N   G   S   A   T   G   L   T   V   W   L   H   G  2590
                      *              ─────────────────────────────────
                                                    TM1

7981 GCTCACCGCTAGTGTGCTCCCAGGGCTGCTGCGGCAGGCCGATCCCCAGCACGTCATCGA 8040
2591  L   T   A   S   V   L   P   G   L   L   R   Q   A   D   P   Q   H   V   I   E  2610
     ─────────────────────────────

8041 GTACTCGTTGGCCCTGGTCACCGTGCTGAACGAGTACGAGCGGGCCCTGGACGTGGCGGC 8100
2611  Y   S   L   A   L   V   T   V   L   N   E   Y   E   R   A   L   D   V   A   A  2630

8101 AGAGCCCAAGCACGAGCGGCAGCACCGAGCCCAGATACGCAAGAACATCACGGAGACTCT 8160
2631  E   P   K   H   E   R   Q   H   R   A   Q   I   R   K   N   I   T   E   T   L  2650
                                                              *

8161 GGTGTCCCTGAGGGTCCACACTGTGGATGACATCCAGCAGATCGCTGCTGCGCTGGCCCA 8220
2651  V   S   L   R   V   H   T   V   D   D   I   Q   Q   I   A   A   A   L   A   Q  2670

8221 GTGCATGGGGCCCAGCAGGGAGCTCGTATGCCGCTCGTGCCTGAAGCAGACGCTGCACAA 8280
2671  C   M   G   P   S   R   E   L   V   C   R   S   C   L   K   Q   T   L   H   K  2690

8281 GCTGGAGGCCATGATGCTCATCCTGCAGGCAGAGACCACCGCGGGCACCGTGACGCCCAC 8340
2691  L   E   A   M   M   L   I   L   Q   A   E   T   T   A   G   T   V   T   P   T  2710
              ──────────────────────────────────────────────────────
                                          TM2
```

FIG. 15N

```
8341 CGCCATCGGAGACAGCATCCTCAACATCACAGGAGACCTCATCCACCTGGCCAGCTCGGA   8400
2711  A  I  G  D  S  I  L  N  I  T  G  D  L  I  H  L  A  S  S  D    2730
               *
8401 CGTGCGGGCACCACAGCCCTCAGAGCTGGGAGCCGAGTCACCATCTCGGATGGTGGCGTC   8460
2731  V  R  A  P  Q  P  S  E  L  G  A  E  S  P  S  R  M  V  A  S    2750

8461 CCAGGCCTACAACCTGACCTCTGCCCTCATGCGCATCCTCATGCGCTCCCGCGTGCTCAA   8520
2751  Q  A  Y  N  L  T  S  A  L  M  R  I  L  M  R  S  R  V  L  N    2770
            *
8521 CGAGGAGCCCCTGACGCTGGCGGGCGAGGAGATCGTGGCCCAGGGCAAGCGCTCGGACCC   8580
2771  E  E  P  L  T  L  A  G  E  E  I  V  A  Q  G  K  R  S  D  P    2790

8581 GCGGAGCCTGCTGTGCTATGGCGGCGCCCCAGGGCCTGGCTGCCACTTCTCCATCCCCGA   8640
2791  R  S  L  L  C  Y  G  G  A  P  G  P  G  C  H  F  S  I  P  E    2810

8641 GGCTTTCAGCGGGGCCCTGGCCAACCTCAGTGACGTGGTGCAGCTCATCTTTCTGGTGGA   8700
2811  A  F  S  G  A  L  A  N  L  S  D  V  V  Q  L  I  F  L  V  D    2830
                     *
8701 CTCCAATCCCTTTCCCTTTGGCTATATCAGCAACTACACCGTCTCCACCAAGGTGGCCTC   8760
2831  S  N  P  F  P  F  G  Y  I  S  N  Y  T  V  S  T  K  V  A  S    2850
                           *
8761 GATGGCATTCCAGACACAGGCCGGCGCCCAGATCCCCATCGAGCGGCTGGCCTCAGAGCG   8820
2851  M  A  F  Q  T  Q  A  G  A  Q  I  P  I  E  R  L  A  S  E  R    2870

8821 CGCCATCACCGTGAAGGTGCCCAACAACTCGGACTGGGCTGCCCGGGGCCACCGCAGCTC   8880
2871  A  I  T  V  K  V  P  N  N  S  D  W  A  A  R  G  H  R  S  S    2890
                           *
8881 CGCCAACTCCGCCAACTCCGTTGTGGTCCAGCCCCAGGCCTCCGTCGGTGCTGTGGTCAC   8940
2891  A  N  S  A  N  S  V  V  V  Q  P  Q  A  S  V  G  A  V  V  T    2910
```

FIG. 15O

```
8941 CCTGGACAGCAGCAACCCTGCGGCCGGGCTGCATCTGCAGCTCAACTATACGCTGCTGGA  9000
2911   L  D  S  S  N  P  A  A  G  L  H  L  Q  L  N  Y  T  L  L  D  2930
                                                    *

9001 CGGCCACTACCTGTCTGAGGAACCTGAGCCCTACCTGGCAGTCTACCTACACTCGGAGCC  9060
2931   G  H  Y  L  S  E  E  P  E  P  Y  L  A  V  Y  L  H  S  E  P  2950

9061 CCGGCCCAATGAGCACAACTGCTCGGCTAGCAGGAGGATCCGCCCAGAGTCACTCCAGGG  9120
2951   R  P  N  E  H  N  C  S  A  S  R  R  I  R  P  E  S  L  Q  G  2970
                *

9121 TGCTGACCACCGGCCCTACACCTTCTTCATTTCCCCGGGGAGCAGAGACCCAGCGGGGAG  9180
2971   A  D  H  R  P  Y  T  F  F  I  S  P  G  S  R  D  P  A  G  S  2990

9181 TTACCATCTGAACCTCTCCAGCCACTTCCGCTGGTCGGCGCTGCAGGTGTCCGTGGGCCT  9240
2991   Y  H  L  N  L  S  S  H  F  R  W  S  A  L  Q  V  S  V  G  L  3010
             *

9241 GTACACGTCCCTGTGCCAGTACTTCAGCGAGGAGGACATGGTGTGGCGGACAGAGGGGCT  9300
3011   Y  T  S  L  C  Q  Y  F  S  E  E  D  M  V  W  R  T  E  G  L  3030

9301 GCTGCCCCTGGAGGAGACCTCGCCCCGCCAGGCCGTCTGCCTCACCCGCCACCTCACCGC  9360
3031   L  P  L  E  E  T  S  P  R  Q  A  V  C  L  T  R  H  L  T  A  3050

9361 CTTCGGCGCCAGCCTCTTCGTGCCCCCAAGCCATGTCCGCTTTGTGTTTCCTGAGCCGAC  9420
3051   F  G  A  S  L  F  V  P  P  S  H  V  R  F  V  F  P  E  P  T  3070

9421 AGCGGATGTAAACTACATCGTCATGCTGACATGTGCTGTGTGCCTGGTGACCTACATGGT  9480
3071   A  D  V  N  Y  I  V  M  L  T  C  A  V  C  L  V  T  Y  M  V  3090
                      ═══════════════════════════════════════════
                                           TM3
9481 CATGGCCGCCATCCTGCACAAGCTGGACCAGTTGGATGCCAGCCGGGGCCGCGCCATCCC  9540
3091   M  A  A  I  L  H  K  L  D  Q  L  D  A  S  R  G  R  A  I  P  3110
       ═══════════════
```

FIG. 15P

```
9541  TTTCTGTGGGCAGCGGGGCCGCTTCAAGTACGAGATCCTCGTCAAGACAGGCTGGGGCCG  9600
3111   F  C  G  Q  R  G  R  F  K  Y  E  I  L  V  K  T  G  W  G  R  3130

9601  GGGCTCAGGTACCACGGCCCACGTGGGCATCATGCTGTATGGGGTGGACAGCCGGAGCGG  9660
3131   G  S  G  T  T  A  H  V  G  I  M  L  Y  G  V  D  S  R  S  G  3150

9661  CCACCGGCACCTGGACGGCGACAGAGCCTTCCACCGCAACAGCCTGGACATCTTCCGGAT  9720
3151   H  R  H  L  D  G  D  R  A  F  H  R  N  S  L  D  I  F  R  I  3170

9721  CGCCACCCCGCACAGCCTGGGTAGCGTGTGGAAGATCCGAGTGTGGCACGACAACAAAGG  9780
3171   A  T  P  H  S  L  G  S  V  W  K  I  R  V  W  H  D  N  K  G  3190

9781  GCTCAGCCCTGCCTGGTTCCTGCAGCACGTCATCGTCAGGGACCTGCAGACGGCACGCAG  9840
3191   L  S  P  A  W  F  L  Q  H  V  I  V  R  D  L  Q  T  A  R  S  3210

9841  CGCCTTCTTCCTGGTCAATGACTGGCTTTCGGTGGAGACGGAGGCCAACGGGGGCCTGGT  9900
3211   A  F  F  L  V  N  D  W  L  S  V  E  T  E  A  N  G  G  L  V  3230

9901  GGAGAAGGAGGTGCTGGCCGCGAGCGACGCAGCCCTTTTGCGCTTCCGGCGCCTGCTGGT  9960
3231   E  K  E  V  L  A  A  S  D  A  A  L  L  R  F  R  R  L  L  V  3250

9961  GGCTGAGCTGCAGCGTGGCTTCTTTGACAAGCACATCTGGCTCTCCATATGGGACCGGCC  10020
3251   A  E  L  Q  R  G  F  F  D  K  H  I  W  L  S  I  W  D  R  P  3270

10021 GCCTCGTAGCCGTTTCACTCGCATCCAGAGGGCCACCTGCTGCGTTCTCCTCATCTGCCT  10080
3271   P  R  S  R  F  T  R  I  Q  R  A  T  C  C  V  L  L  I  C  L  3290
                                     ‾‾‾‾‾‾‾‾‾‾‾‾‾‾‾‾‾‾‾‾‾‾‾‾‾

10081 CTTCCTGGGCGCCAACGCCGTGTGGTACGGGGCTGTTGGCGACTCTGCCTACAGCACGGG  10140
3291   F  L  G  A  N  A  V  W  Y  G  A  V  G  D  S  A  Y  S  T  G  3310
      ‾‾‾‾‾‾‾‾‾‾‾‾‾‾‾‾‾‾‾‾‾‾‾‾‾‾‾‾‾
            TM4
```

FIG. 15Q

```
10141  GCATGTGTCCAGGCTGAGCCCGCTGAGCGTCGACACAGTCGCTGTTGGCCTGGTGTCCAG  10200
3311    H  V  S  R  L  S  P  L  S  V  D  T  V  A  V  G  L  V  S  S   3330

10201  CGTGGTTGTCTATCCCGTCTACCTGGCCATCCTTTTTCTCTTCCGGATGTCCCGGAGCAA  10260
3331    V  V  V  Y  P  V  Y  L  A  I  L  F  L  F  R  M  S  R  S  K   3350
                          TM5
10261  GGTGGCTGGGAGCCCGAGCCCCACACCTGCCGGGCAGCAGGTGCTGGACATCGACAGCTG  10320
3351    V  A  G  S  P  S  P  T  P  A  G  Q  Q  V  L  D  I  D  S  C   3370

10321  CCTGGACTCGTCCGTGCTGGACAGCTCCTTCCTCACGTTCTCAGGCCTCCACGCTGAGGC  10380
3371    L  D  S  S  V  L  D  S  S  F  L  T  F  S  G  L  H  A  E  A   3390

10381  CTTTGTTGGACAGATGAAGAGTGACTTGTTTCTGGATGATTCTAAGAGTCTGGTGTGCTG  10440
3391    F  V  G  Q  M  K  S  D  L  F  L  D  D  S  K  S  L  V  C  W   3410

10441  GCCCTCCGGCGAGGGAACGCTCAGTTGGCCGGACCTGCTCAGTGACCCGTCCATTGTGGG  10500
3411    P  S  G  E  G  T  L  S  W  P  D  L  L  S  D  P  S  I  V  G   3430

10501  TAGCAATCTGCGGCAGCTGGCACGGGGCCAGGCGGGCCATGGGCTGGGCCCAGAGGAGGA  10560
3431    S  N  L  R  Q  L  A  R  G  Q  A  G  H  G  L  G  P  E  E  D   3450

10561  CGGCTTCTCCCTGGCCAGCCCCTACTCGCCTGCCAAATCCTTCTCAGCATCAGATGAAGA  10620
3451    G  F  S  L  A  S  P  Y  S  P  A  K  S  F  S  A  S  D  E  D   3470

10621  CCTGATCCAGCAGGTCCTTGCCGAGGGGGTCAGCAGCCCAGCCCCTACCCAAGACACCCA  10680
3471    L  I  Q  Q  V  L  A  E  G  V  S  S  P  A  P  T  Q  D  T  H   3490

10681  CATGGAAACGGACCTGCTCAGCAGCCTGTCCAGCACTCCTGGGGAGAAGACAGAGACGCT  10740
3491    M  E  T  D  L  L  S  S  L  S  S  T  P  G  E  K  T  E  T  L   3510
```

FIG. 15R

```
10741  GGCGCTGCAGAGGCTGGGGGAGCTGGGGCCACCCAGCCCAGGCCTGAACTGGGAACAGCC  10800
 3511   A  L  Q  R  L  G  E  L  G  P  P  S  P  G  L  N  W  E  Q  P   3530

10801  CCAGGCAGCGAGGCTGTCCAGGACAGGACTGGTGGAGGGTCTGCGGAAGCGCCTGCTGCC  10860
 3531   Q  A  A  R  L  S  R  T  G  L  V  E  G  L  R  K  R  L  L  P   3550

10861  GGCCTGGTGTGCCTCCCTGGCCCACGGGCTCAGCCTGCTCCTGGTGGCTGTGGCTGTGGC  10920
 3551   A  W  C  A  S  L  A  H  G  L  S  L  L  L  V  A  V  A  V  A   3570
                                   ━━━━━━━━━━━━━━━━━━━━━━━━━━━━━
                                                TM6

10921  TGTCTCAGGGTGGGTGGGTGCGAGCTTCCCCCCGGGCGTGAGTGTTGCGTGGCTCCTGTC  10980
 3571   V  S  G  W  V  G  A  S  F  P  P  G  V  S  V  A  W  L  L  S   3590
        ━━━━━━━━━━━━━━━━━━━━━━━━━        ━━━━━━━━━━━━━━━━━━━━━━━━

10981  CAGCAGCGCCAGCTTCCTGGCCTCATTCCTCGGCTGGGAGCCACTGAAGGTCTTGCTGGA  11040
 3591   S  S  A  S  F  L  A  S  F  L  G  W  E  P  L  K  V  L  L  E   3610
        ━━━━━━━━━━━━━━━━━━━━━━━━━━━━━━━━━━
                    TM7

11041  AGCCCTGTACTTCTCACTGGTGGCCAAGCGGCTGCACCCGGATGAAGATGACACCCTGGT  11100
 3611   A  L  Y  F  S  L  V  A  K  R  L  H  P  D  E  D  D  T  L  V   3630

11101  AGAGAGCCCGGCTGTGACGCCTGTGAGCGCACGTGTGCCCCGCGTACGGCCACCCCACGG  11160
 3631   E  S  P  A  V  T  P  V  S  A  R  V  P  R  V  R  P  P  H  G   3650

11161  CTTTGCACTCTTCCTGGCCAAGGAAGAAGCCCGCAAGGTCAAGAGGCTACATGGCATGCT  11220
 3651   F  A  L  F  L  A  K  E  E  A  R  K  V  K  R  L  H  G  M  L   3670

11221  GCGGAGCCTCCTGGTGTACATGCTTTTTCTGCTGGTGACCCTGCTGGCCAGCTATGGGGA  11280
 3671   R  S  L  L  V  Y  M  L  F  L  L  V  T  L  L  A  S  Y  G  D   3690
        ━━━━━━━━━━━━━━━━━━━━━━━━━━━━━━━━━━━━━━━━━━━━━━━━━━━━━━━━
                                TM8
```

FIG. 15S

```
11281  TGCCTCATGCCATGGGCACGCCTACCGTCTGCAAAGCGCCATCAAGCAGGAGCTGCACAG  11340
3691    A  S  C  H  G  H  A  Y  R  L  Q  S  A  I  K  Q  E  L  H  S   3710

11341  CCGGGCCTTCCTGGCCATCACGCGGTCTGAGGAGCTCTGGCCATGGATGGCCCACGTGCT  11400
3711    R  A  F  L  A  I  T  R  S  E  E  L  W  P  W  M  A  H  V  L   3730

11401  GCTGCCCTACGTCCACGGGAACCAGTCCAGCCCAGAGCTGGGGCCCCCACGGCTGCGGCA  11460
3731    L  P  Y  V  H  G  N  Q  S  S  P  E  L  G  P  P  R  L  R  Q   3750
                          *

11461  GGTGCGGCTGCAGGAAGCACTCTACCCAGACCCTCCCGGCCCCAGGGTCCACACGTGCTC  11520
3751    V  R  L  Q  E  A  L  Y  P  D  P  P  G  P  R  V  H  T  C  S   3770

11521  GGCCGCAGGAGGCTTCAGCACCAGCGATTACGACGTTGGCTGGGAGAGTCCTCACAATGG  11580
3771    A  A  G  G  F  S  T  S  D  Y  D  V  G  W  E  S  P  H  N  G   3790
                                                             *

11581  CTCGGGGACGTGGGCCTATTCAGCGCCGGATCTGCTGGGGGCATGGTCCTGGGGCTCCTG  11640
3791    S  G  T  W  A  Y  S  A  P  D  L  L  G  A  W  S  W  G  S  C   3810

11641  TGCCGTGTATGACAGCGGGGGCTACGTGCAGGAGCTGGGCCTGAGCCTGGAGGAGAGCCG  11700
3811    A  V  Y  D  S  G  G  Y  V  Q  E  L  G  L  S  L  E  E  S  R   3830

11701  CGACCGGCTGCGCTTCCTGCAGCTGCACAACTGGCTGGACAACAGGAGCCGCGCTGTGTT  11760
3831    D  R  L  R  F  L  Q  L  H  N  W  L  D  N  R  S  R  A  V  F   3850
                                           *

11761  CCTGGAGCTCACGCGCTACAGCCCGGCCGTGGGGCTGCACGCCGCCGTCACGCTGCGCCT  11820
3851    L  E  L  T  R  Y  S  P  A  V  G  L  H  A  A  V  T  L  R  L   3870

11821  CGAGTTCCCGGCGGCCGGCCGCGCCCTGGCCGCCCTCAGCGTCCGCCCCTTTGCGCTGCG  11880
3871    E  F  P  A  A  G  R  A  L  A  A  L  S  V  R  P  F  A  L  R   3890
```

FIG. 15T

```
11881  CCGCCTCAGCGCGGGCCTCTCGCTGCCTCTGCTCACCTCGGTGTGCCTGCTGCTGTTCGC  11940
3891    R  L  S  A  G  L  S  L  P  L  L  T  S  V  C  L  L  L  F  A   3910
                        TM9

11941  CGTGCACTTCGCCGTGGCCGAGGCCCGTACTTGGCACAGGGAAGGGCGCTGGCGCGTGCT  12000
3911    V  H  F  A  V  A  E  A  R  T  W  H  R  E  G  R  W  R  V  L   3930

12001  GCGGCTCGGAGCCTGGGCGCGGTGGCTGCTGGTGGCGCTGACGGCGGCCACGGCACTGGT  12060
3931    R  L  G  A  W  A  R  W  L  L  V  A  L  T  A  A  T  A  L  V   3950

12061  ACGCCTCGCCCAGCTGGGTGCCGCTGACCGCCAGTGGACCCGTTTCGTGCGCGGCCGCCC  12120
3951    R  L  A  Q  L  G  A  A  D  R  Q  W  T  R  F  V  R  G  R  P   3970

12121  GCGCCGCTTCACTAGCTTCGACCAGGTGGCGCACGTGAGCTCCGCAGCCCGTGGCCTGGC  12180
3971    R  R  F  T  S  F  D  Q  V  A  H  V  S  S  A  A  R  G  L  A   3990

12181  GGCCTCGCTGCTCTTCCTGCTTTTGGTCAAGGCTGCCCAGCACGTACGCTTCGTGCGCCA  12240
3991    A  S  L  L  F  L  L  L  V  K  A  A  Q  H  V  R  F  V  R  Q   4010

12241  GTGGTCCGTCTTTGGCAAGACATTATGCCGAGCTCTGCCAGAGCTCCTGGGGGTCACCTT  12300
4011    W  S  V  F  G  K  T  L  C  R  A  L  P  E  L  L  G  V  T  L   4030

12301  GGGCCTGGTGGTGCTCGGGGTAGCCTACGCCCAGCTGGCCATCCTGCTCGTGTCTTCCTG  12360
4031    G  L  V  V  L  G  V  A  Y  A  Q  L  A  I  L  L  V  S  S  C   4050
                        TM10

12361  TGTGGACTCCCTCTGGAGCGTGGCCCAGGCCCTGTTGGTGCTGTGCCCTGGGACTGGGCT  12420
4051    V  D  S  L  W  S  V  A  Q  A  L  L  V  L  C  P  G  T  G  L   4070
                        TM11

12421  CTCTACCCTGTGTCCTGCCGAGTCCTGGCACCTGTCACCCCTGCTGTGTGTGGGGCTCTG  12480
4071    S  T  L  C  P  A  E  S  W  H  L  S  P  L  L  C  V  G  L  W   4090
```

FIG. 15U

```
12481  GGCACTGCGGCTGTGGGGCGCCCTACGGCTGGGGGCTGTTATTCTCCGCTGGCGCTACCA  12540
 4091   A  L  R  L  W  G  A  L  R  L  G  A  V  I  L  R  W  R  Y  H    4110

12541  CGCCTTGCGTGGAGAGCTGTACCGGCCGGCCTGGGAGCCCCAGGACTACGAGATGGTGGA  12600
 4111   A  L  R  G  E  L  Y  R  P  A  W  E  P  Q  D  Y  E  M  V  E    4130

12601  GTTGTTCCTGCGCAGGCTGCGCCTCTGGATGGGCCTCAGCAAGGTCAAGGAGTTCCGCCA  12660
 4131   L  F  L  R  R  L  R  L  W  M  G  L  S  K  V  K  E  F  R  H    4150

12661  CAAAGTCCGCTTTGAAGGGATGGAGCCGCTGCCCTCTCGCTCCTCCAGGGGCTCCAAGGT  12720
 4151   K  V  R  F  E  G  M  E  P  L  P  S  R  S  S  R  G  S  K  V    4170

12721  ATCCCCGGATGTGCCCCCACCCAGCGCTGGCTCCGATGCCTCGCACCCCTCCACCTCCTC  12780
 4171   S  P  D  V  P  P  P  S  A  G  S  D  A  S  H  P  S  T  S  S    4190

12781  CAGCCAGCTGGATGGGCTGAGCGTGAGCCTGGGCCGGCTGGGGACAAGGTGTGAGCCTGA  12840
 4191   S  Q  L  D  G  L  S  V  S  L  G  R  L  G  T  R  C  E  P  E    4210

12841  GCCCTCCCGCCTCCAAGCCGTGTTCGAGGCCCTGCTCACCCAGTTTGACCGACTCAACCA  12900
 4211   P  S  R  L  Q  A  V  F  E  A  L  L  T  Q  F  D  R  L  N  Q    4230

12901  GGCCACAGAGGACGTCTACCAGCTGGAGCAGCAGCTGCACAGCCTGCAAGGCCGCAGGAG  12960
 4231   A  T  E  D  V  Y  Q  L  E  Q  Q  L  H  S  L  Q  G  R  R  S    4250

12961  CAGCCGGGCGCCCGCCGGATCTTCCCGTGGCCCATCCCCGGGCCTGCGGCCAGCACTGCC  13020
 4251   S  R  A  P  A  G  S  S  R  G  P  S  P  G  L  R  P  A  L  P    4270

13021  CAGCCGCCTTGCCCGGGCCAGTCGGGGTGTGGACCTGGCCACTGGCCCCAGCAGGACACC  13080
 4271   S  R  L  A  R  A  S  R  G  V  D  L  A  T  G  P  S  R  T  P    4290
```

FIG. 15V

| | | |
|---|---|---|
| 13081 | CCTTCGGGCCAAGAACAAGGTCCACCCCAGCAGCACTTAGTCCTCCTTCCTGGCGGGGGT | 13140 |
| 4291 | L  R  A  K  N  K  V  H  P  S  S  T | 4310 |

13141 GGGCCGTGGAGTCGGAGTGGACACCGCTCAGTATTACTTTCTGCCGCTGTCAAGGCCGAG 13200

13201 GGCCAGGCAGAATGGCTGCACGTAGGTTCCCCAGAGAGCAGGCAGGGGCATCTGTCTGTC 13260

13261 TGTGGGCTTCAGCACTTTAAAGAGGCTGTGTGGCCAACCAGGACCCAGGGTCCCCTCCCC 13320

13321 AGCTCCCTTGGGAAGGACACAGCAGTATTGGACGGTTTCTAGCCTCTGAGATGCTAATTT 13380

13381 ATTTCCCCGAGTCCTCAGGTACAGCGGGCTGTGCCCGGCCCCACCCCCTGGGCAGATGTC 13440

13441 CCCCACTGCTAAGGCTGCTGGCTTCAGGGAGGGTTAGCCTGCACCGCCGCCACCCTGCCC 13500

13501 CTAAGTTATTACCTCTCCAGTTCCTACCGTACTCCCTGCACCGTCTCACTGTGTGTCTCG 13560

13561 TGTCAGTAATTTATATGGTGTTAAAATGTGTATATTTTTGTATGTCACTATTTTCACTAG 13620

13621 GGCTGAGGGGCCTGCGCCCAGAGCTGGCCTCCCCCAACACCTGCTGCGCTTGGTAGGTGT 13680

13681 GGTGGCGTTATGGCAGCCCGGCTGCTGCTTGGATGCGAGCTTGGCCTTGGGCCGGTGCTG 13740

13741 GGGGCACAGCTGTCTGCCAGGCACTCTCATCACCCCAGAGGCCTTGTCATCCTCCCTTGC 13800

13801 CCCAGGCCAGGTAGCAAGAGAGCAGCGCCCAGGCCTGCTGGCATCAGGTCTGGGCAAGTA 13860

13861 GCAGGACTAGGCATGTCAGAGGACCCCAGGGTGGTTAGAGGAAAAGACTCCTCCTGGGGG 13920

13921 CTGGCTCCCAGGGTGGAGGAAGGTGACTGTGTGTGTGTGTGTGCGCGCGCGACGCGCG 13980

13981 AGTGTGCTGTATGGCCCAGGCAGCCTCAAGGCCCTCGGAGCTGGCTGTGCCTGCTTCTGT 14040

14041 GTACCACTTCTGTGGGCATGGCCGCTTCTAGAGCCTCGACACCCCCCAACCCCCGCACC 14100

14101 AAGCAGACAAAGTCAATAAAAGAGCTGTCTGACTGCAAAAAAAAAAAAA 14148

```
PKDLRR1                          LDVSHNLTRAL
PKDLRR2      DVGILANLSALAELDISNNKISTL
PKDLRR3      EEGIFANLFNLSEINLSGN

CONCENSUS       L    L  LL  L NL  L
                F        a     a

PKD1         CE  CLCGPAPGAAC  RVNCSGR  GLR   TLGPA IRIPADATA
OMgp         CP  CICTEHR      HVDCSGR  NLS   TI    PSGLQE  NIIH
SLIT1        CP  CSCTGL       NVDCSHR  GLT   SV    PRKTSA  DVER
CHAOPTIN     CE  VMCTCSKSSTDLGIVHCKNV  PPP   AL    PRMVNQ  SKVP
GPIB BETA    CP  CSCAGT       LMDCGRR  GLTWA SL    PTAHPV  DTTE
BIGLYCAN     CP  CHCHLR       VVQCSDL  GLK   SV    PKETSP  DTTL
DECORIN      CP  CQCHLR       VVQCSDL  GLD   KV    PKDLPP  DTTL
FIBROMODULIN CP  CDCPPNFPT    AMYCDNR  NLK   YL    P FVPS  RMKY
Trk          CP  C CPHGSSG    LIRCTRD  GALDSLH HL  PGAENLT ELYI
LH-CG        CP  CDCAPDG      AIRCFGPRAGIARLSLTYL  PVKWIPS QAFR

CONCENSUS    CP  C   C         V CS      GL       L P   a     DTT
              P                 a p       h       a  h        phh
```

FIG. 16B

```
PKD1         P   DCGLA    WLPPWAEEQQVRVVQPEAA
Slit 1       P   DCHILS   WLSPFLRSATRLAPYT
Slit 2       P   NCNLR    WLADYLHKIPIETSGA
Toll-1       P   DCTIL    WFIQLVRGVHKPQYSRQFKLRTDRL
GPIX         P   DCSLTYLRLRLWLEDRTPEALLQV
GP Ib BETA   P   DCRIVPLRAWLAGRPEFAPYRDL
Trk              SCALR    WLQRWEEEGLGGVPEQKL CONCENSUS    P   DC L     WL
                 p  a     h p pp
```

FIG. 16C

```
PKD1         TCAGPGSLAGQPL  LGIPLLDSGCGEEY
Slit 1       RCQSPSQLKGQNV  ADLHDQEFKCSGLT
Slit 2       RCESPKRMHRRRI  ESLREEKFKCSWGE
Toll-1       VCSQPNVLEGTPV  RQIEPQTLICPLDF
GPIX         RCASPSLAAHGPL  RLTGYQLGSCGWQL
GP Ib BETA   RCVAPPAL       RGRLJPYLAEDELRAACAP
Trk          QCHGQGPL       AHM  PNASCGVPTLKVQV CONCENSUS    RC  P   L          h       C  C
              p  p   h      h               h
```

| | | | | | | |
|---|---|---|---|---|---|---|
| PKD1 | | HPLCPSDTEIFPGNGHCYRLVVEKAAMLQAEQCQA | WAGAAIAMVDSPAVQRFIVSRVTRSLD | VWIGLSTV |
| BRA3 | | ECTCPGNLDWQEYDGHCYWASTYQVRWNDAQLACQTVHPGAYIATHQSQLENAFESETVSNNR | | LWIGLNDI |
| Kupffer | LQLIM | QDMKYFNGKEFYFSRDKKSWHEAENFCVS | QGAHLASVTSQEEQAFIVQITNAVDH | | WIGLTDQ |
| C.S.P | QKLCE | EGMTKFQGHCYRHFPDRATWDAESQRK | QQSHISSIVTPEEQEFVNNAQDYQ | | WIGLNDK |
| ASIAL. | RTCCP | VNMVEHQSCYWFSHSGKAWAEAEKYCQL | ENAHLVINSWEEQKFIVQHTNPFNT | | WIGLTDS |
| E_Selectin | ALVFV | LLAGESTAWIYNASSELMTYDEASAYCQR | DYTHLVAIQNKEFINYINSNLKHSPSYYWIGIRKV | | |
| GP120 binding | CHPCP | WEMTFFQGNCYFMSNSQRNMHDSITACKE | GAQLMVIKSAEEQNFLQLSSRSNRFTWMGLSDL | | |

CONSENSUS          CP             W

```
PKD1A       LEAHVDLRDCVTY  QIEIRMEVYRTASCQRGRPARVAIPGVDVSRP
    B       ESYDENLEDGDQI  PLSIHWACV   ASTQREAGGCAINFGPRGSS
    C       RSSYVYLECRQLNCSSGSKRCRWAAR              TFSNKTLVLDTTTSTGSAGM
    D       CRLFPLGAVHALTTKVHFECTGWHDA  EDAGAPLVVALLLRRCRQGHCEEFCVYKGSLSS
NEUROGLIAN  DNRSPILHYTLQI  NTSFIPASWDAA            YEKYPNTD
L1          DHNAPIEKYDIEYEDKEMAPEKMYSL              GKVPGNQ
F11         DNHSPISKYTLQSK TFLSEEWKDA              KTEPSDYEGNME
TAG1        DNHSPIAKYTLQAR TPPAGKWKQV              RTNPANLEGNAE
F3          PSEAPTEVGVKVLS SSELSVHWKHV             WYDAKEANMEGHDKEAAAHRVQVTSQEY
NCAM        TGGVPILKYKAEW  KSLGEEAWHSK             WTDAKEANMEG
DOC         LSWRPPAEAKGNI  QTFIVFFSR               EGDNRERALNTTOPGSL
LAR         PSAPPQKVMCVSM  GSTTVRVSWVPP            PADSRNGVITQYSVAHEAVDGEDRGRHVVDGISREHS
HPTP        TVPSPWKDIGIST  KANSLLISWSHG            SGNVERYRLMLMDKGILVHGGVVDKHAT
RN          VSDVPI RDLEVVAATPTSLLISWDAP            AVTVRYYIBTTYGETGGNSPVQEFTVPGSKS

B strands      A              B         C         D

CONCENSUS   P  h h h       h h r     w             hph
```

FIG. 19A

| FIG. 19A |
|----------|
| FIG. 19B |

FIG. 19

POLYCYSTIC KIDNEY DISEASE 1 GENE AND USES THEREOF

This application is a CIP of international application number PCT GB94/02822, filed Dec. 23, 1994.

BACKGROUND TO THE INVENTION

In humans, one of the commonest of all genetic disorders is autosomal polycystic kidney disease (ADPKD) also termed adult polycystic kidney disease (APKD), affecting approximately 1/1000 individuals (Dalgaard, 1957). ADPKD is a progressive disease of cyst formation and enlargement typically leading to end stage renal disease (ESRD) in late middle age. The major cause of morbidity in ADPKD is progressive renal disease characterized by the formation and enlargement of fluid filled cysts, resulting in grossly enlarged kidneys. Renal function deteriorates as normal tissue is compromised by cystic growth, resulting in end stage renal disease (ESRD) in more than 50% of patients by the age of 60 years (Gabow, et al., 1992). ADPKD accounts for 8–10% of all renal transplantation and dialysis patients in Europe and the USA (Gabow, 1993).

ADPKD also causes cystic growth in other organs (reviewed in Gabow, 1990) and occasionally presents in childhood (Fink, et al., 1993; Zerres, et al., 1993). Extrarenal manifestations include liver cysts (Milutinovic, et al., 1980), and more rarely cysts of the pancreas (Gabow, 1993) and other organs. Intracranial aneurysms occur in approximately 5% of patients and are a significant cause of morbidity and mortality due to subarachnoid haemorrhage (Chapman, et al., 1992). ADPKD is associated with a higher prevalence of various connective tissue disorders. An increased prevalence of heart valve defects (Hossack, et al., 1988), hernia (Gabow, 1990) and colonic diverticulae (Scheff, et al., 1980) have been reported.

Considerable progress has been made in the last few years in understanding the pathophysiology of ADPKD (and other animal models of cystic disease). Cysts in ADPKD are known to develop from outpouchings of descending or ascending kidney tubules and the early stages are characterized by a thickening and disorganization of the basement membrane, accompanied by a de-differentiation of tubular epithelial cells. Several of the characteristics of ADPKD epithelia: altered growth responses, abnormal expression of various proteins and reversal of polarity, may be a sign of this de-differentiation and important in cyst expansion. The nature of the primary defect which triggers these changes is, however, unknown and consequently much effort has been devoted to identifying the causative agent by genetic means.

The first step towards positional cloning of an ADPKD gene was the demonstration of linkage of one locus now designated the polycystic kidney disease 1 (PKD1) locus to the α globin cluster on the short arm of chromosome 16 (Reeders, et al., 1985). Subsequently, families with ADPKD unlinked to markers one of 16p were described (Kimberling, et al., 1988; Romeo, et al., 1988) and a second ADPKD locus (PKD2) has recently been assigned to chromosome region 4q13-q23 (Kimberling, et al., 1993; Peter, et al., 1993). It is estimated that approximately 85% of ADPKD is due to PKD1 (Peters and Sankuijl, 1992) with PKD2 accounting for most of the remainder. PKD2 appears to be milder condition with a later age of onset and ESRD (Parfrey, et al., 1990; Gabow, et al., 1992; Ravine, et al., 1992).

The position of the PKD1 locus was refined to chromosome band 16p13.3 and many markers were isolated from that region (Breuning, et al., 1987; Reeders, et al., 1988; Breuning, et al., 1990; Germino, et al., 1990; Hyland, et al., 1990; Himmelbauer, et al., 1991). Their order, and the position of the PKD1 locus, has been determined by extensive linkage analysis in normal and PKD1 families and by the use of a panel of somatic cell hybrids (Reeders et al., 1988; Breuning, et al., 1990; Germino, et al., 1990). ADPKD is genetically heterogenous with loci mapped not only to 16p13.3 (PKD1), but also to chromosome 4 (PKD2). Although the phenotype of PKD1 and PKD2 are clearly similar, it is now well documented that PKD1 (which accounts for about 85% of ADPKD; (Peters, 1992) is a more severe disease with an average age at ESRD of about 56 years compared to about 71.5 years for PKD2 (Ravine, 1992). An accurate long range restriction map of the 16p13.3 region (Harris, et al., 1990; Germino, et al., 1992) has located the PKD1 locus in an interval of approximately 600 kb between the markers GGG1 and SM7 (Harris, et al., 1991; Somlo, et al., 1992) (see FIG. 1a). The density of CpG islands and identification of many mRNA transcripts indicated that this area is rich in gene sequences. Germino et al. (1992) estimated that the candidate region contains approximately 20 genes.

Identification of the PKD1 gene from within this area has thus proved difficult and other means to pinpoint the disease gene have been sought. Linkage disequilibrium has been demonstrated between PKD1 and the proximal marker VK5, in a Scottish population (Pound, et al., 1992) and between PKD1 and BLu24 (see FIG. 1a), in a Spanish population (Peral, et al., 1994). Studies with additional markers have shown evidence of a common ancestor in a proportion of each population (Peral, et al., 1994; Snarey, et al., 1994), but the association has not precisely positioned the PKD1 locus.

Disease associated genomic rearrangements, detected by cytogenetics or pulsed field gel electrophoresis (PFGE) have been instrumental in the identification of various genes associated with various genetic disorders. Hitherto, no such abnormalities related to PKD1 have been described. This situation contrasts with that for the tuberous sclerosis locus, which lies within 16p13.3 (TSC2). In that case, TSC associated deletions were detected by PFGE within the interval thought to contain the PKD1 gene and their characterisation was a significant step toward the rapid identification of the TSC2 gene (European Chromosome 16 Tuberous Sclerosis Consortium, 1993). The TSC2 gene therefore maps within the candidate region for the hitherto unidentified PKD1 gene; as polycystic kidneys are a feature common to TSC and ADPKD1 (Bernstein and Robbins, 1991) the possibility of an etiological link, as proposed by Kandt et al. (1992), was considered. A contiguous gene syndrome resulting from the disruption of PKD1 and the adjacent tuberous sclerosis 2 (TSC2) gene, which is associated with TSC and severe childhood onset polycystic kidney disease, has also been defined (Brook-Carter et al, 1994).

We have now identified a pedigree in which the two distinct phenotypes, typical ADPKD or TSC, are seen in different members. In this family, the two individuals with ADPKD are carriers of a balanced chromosome translocation with a breakpoint within 16p13.3. We have located the chromosome 16 translocation breakpoint and a gene disrupted by this rearrangement has been defined; the discovery of additional mutations of that gene in other PKD1 patients shows that we have identified the PKD1 gene. Full characterisation of the PKD1 transcript has been significantly complicated because of the unusual genomic region containing most of the gene. All but 3.5 kb at the 3' end of the transcript (which is about 14 kb in total) is encoded by a region which is reiterated several times elsewhere on the same chromosome (in 16p13.1 and termed the HG area). The structure of the duplication is complex, with some regions copied more times than others, and the HG region encoding three large transcripts. The transcripts from the HG area are: HG-A (21 kb), HG-B (17 kb) and HG-C (8.5 kb) and although these have 3' ends which differ from PKD1, over most of their length they share substantial homology to the PKD1 transcript. Consequently, cloning and characterizing a bona fide PKD1 cDNA has proven difficult. To overcome the problem caused by duplication we have cloned cDNAs covering the entire transcript from a cell line which contains the PKD1 but not the HG loci. Characterisation of these cDNAs has enabled the PKD1 protein sequence to be predicted and led to the identification of several homologies with described motifs.

SUMMARY OF THE INVENTION

Accordingly, in one aspect, this invention provides an isolated, purified or recombinant nucleic acid sequence comprising:

(a) a PKD1-encoding nucleic acid or its complementary strand, (b) a sequence substantially homologous to, or capable of hybridizing to, a substantial portion of a molecule defined in (a) above, or (c) a fragment of a molecule defined in (a) or (b) above.

In particular, there is provided a sequence wherein the PKD1 gene has the nucleic acid sequence according to FIG. 15 (SEQ ID NO. 7), or the partial sequence of FIGS. 7 (SEQ ID NO. 1) or 10 (SEQ ID NO. 5). The invention therefore includes a DNA molecule coding for a polypeptide having the amino acid sequence of FIG. 15 (SEQ ID NO. 8), or a polypeptide fragment thereof; and genomic DNA corresponding to a molecule as in (a)–(c) above.

As used herein, "substantially homologous" refers to a nucleic acid strand that is sufficiently duplicative of the PKD1 sequence presented in FIG. 15 (SEQ ID NO. 7) such that it is capable of hybridizing to that sequence under moderately stringent, and preferably stringent conditions, as defined herein below. Preferably "substantially homologous" refers to a homology of between 97 and 100%. Further, such a strand will encode or be complementary to a strand that encodes PKD1 protein having the biological activity described below. As used herein, a "substantial portion of a molecule" refers to at least 60%, preferably 80% and most preferably 90% of the molecule in terms of its linear residue length or its molecular weight. "Nucleic acid" refers to both DNA and RNA.

The PKD1 gene described herein is a gene found on human chromosome 16, and the results of studies described herein form the basis for concluding that this PKD1 gene encodes a protein called PKD1 protein which has a role in the prevention or suppression of ADPKD. The PKD1 gene therefore includes the DNA sequences shown in FIG. 15 (SEQ ID NO. 7), and all functional equivalents. By "functional equivalents", we mean nucleic acid sequences that are substantially homologous to the PKD1 nucleic acid sequence, as presented in FIG. 15 (SEQ ID NO. 7), and encoding a protein that possesses one or more of the biological functions or activities of PKD1; i.e., that is involved in cell/cell adhesion, cell/cell recognition or cell/cell communication, for example to effect adhesion of cells to other cells or components of the extracellular matrix; effect communication and/or interaction between epithelial cells and the basal membrane (whether in kidneys or otherwise); assist in development of connective tissue such as assembly and/or maintenance of the basal membrane; in signal transduction between cells or cells and components of the extracellular matrix; and/or to promote binding of cells carrying proteins such as integrins or carbohydrates to target cells. The biological function of PKD1 of course includes maintaining a healthy physiological state; that is, the native protein's aberrations or absence results in ADPKD or an associated disorder.

The PKD1 gene may furthermore include regulatory regions which control the expression of the PKD1 coding sequence, including promoter, enhancer and terminator regions. Other DNA sequences such as introns spliced from the end-product PKD1 RNA transcript are also encompassed. Although work has been carried out in relation to the human gene, the corresponding genetic and functional sequences present in lower animals are also encompassed.

The present invention therefore further provides a PKD1 gene or its complementary strand having the sequence according to FIG. 15 (SEQ ID NO. 7) which gene or strand is mutated in some ADPKD patients (more specifically, PKD1 patients). Therefore, the invention further provides a nucleic acid sequence comprising a mutant PKD1 gene as described herein, including wherein Intron 43 as defined hereinbelow has a deletion of 18 or 20 bp resulting in an intron of 55 or 57 bp.

As used herein, "PKD1 mutant" or "mutation" encompasses alterations of the native PKD1 nucleotide (SEQ ID NO. 7) or amino acid sequence (SEQ ID NO. 8), as defined by FIG. 15, i.e., substitutions, deletions or additions, and also encompasses deletion of DNA containing the entire PKD1 gene.

The invention further provides a nucleic acid sequence comprising a mutant PKD1 gene, especially one selected from a sequence comprising a partial sequence according to FIGS. 7 (SEQ ID NO. 1) and/or 10 (SEQ ID NO. 5), or the corresponding sequences disclosed in FIG. 15 (SEQ ID NO. 7), when:

(a) [OX114] base pairs 1746–2192 as defined in FIG. 7 (SEQ ID NO. 1) are deleted (446 bp);

(b) [OX32] base pairs 3696–3831 as defined in FIG. 7 (SEQ ID NO. 1) are deleted by a splicing defect;

(c) [OX875] about 5.5 kb flanked by the two XbaI sites shown in FIG. 3a are deleted and the EcoR1 site separating the CW10 (41 kb) and JH1 (18 kb) sites is thereby absent (d) [WS53] about 100 kb extending between the JH1 and CW21 and the SM6 and JH17 sites shown in FIG. 6 and the PKD1 gene is thereby absent, the deletion lying proximally between SM6 and JH17;

(e) [461] 18 bp are deleted in the 75 bp intron amplified by the primer pair 3A3C (SEQ ID NOS. 11 and 12) insert at position 3696 of the 3' sequence (SEQ ID NO. 1) as shown in FIG. 11;

(f) [OX1054] 20 bp are deleted in the 75 bp intron amplified by the primer pair 3A3C insert at position 3696 of the 3' sequence as shown in FIG. 11 (SEQ ID NO. 18);

(g) [WS212] about 75 kb are deleted between SM9-CW9 distally and the PKD1 3'UTR proximally as shown in FIG. 12;

(h) [WS-215] about 160 kb are deleted between CW20 and SM6-JH17 as shown in FIG. 12;

(i) [WS-227] about 50 kb are deleted between CW20 and JH11 as shown in FIG. 12;

(j) [WS-219] about 27 kb are deleted between JH1 and JH6 as shown in FIG. 12;

(k) [WS-250] about 160 kb are deleted between CW20 and Blu24 as shown in FIG. 12;

(l) [WS-194] about 65 kb is deleted between CW20 and CW10.

The invention therefore extends to RNA molecules comprising an RNA sequence corresponding to any of the DNA sequences set out above. Such molecule may be the transcript reference PBP and identifiable with respect to the restriction map of FIG. 3*a* and having a length of about 14 kb.

In another aspect, the invention provides a nucleic acid probe having a sequence as set out above; in particular, this invention extends to a purified nucleic acid probe which hybridizes to at least a portion of the DNA or RNA molecule of any of the preceding sequences. Preferably, the probe includes a label such as a radiolabel, for example, a $^{32}P$ label.

In another aspect, this invention provides a purified DNA or RNA coding for a protein comprising the amino acid sequence of FIG. 15 (SEQ ID NO. 8), or a protein polypeptide having homologous properties with said protein, or having at least one functional domain or active site in common with said protein.

The DNA molecule defined above may be incorporated in a recombinant cloning vector for expressing a protein having the amino acid sequence of FIG. 15 (SEQ ID NO. 8), or a protein or a polypeptide having at least one functional domain or active site in common with said protein. Such a vector may include any vector for expression in bacteria, e.g., *E. coli*; yeast, insect, or mammalian cells.

The invention also features a nucleic acid probe for detecting PKD1 nucleic acid comprising 10 consecutive nucleotides as presented in FIG. 15 (SEQ ID NO. 7). Preferably, the probe may comprise 15, 20, 50, 100, 200, or 300, etc., consecutive nucleotides (nt) presented in FIG. 13, and may fall within the size range 15 nt–13 kb, 100 nt–5 kb, 150 nt–4 kb, 300 nt–2 kb, and 500 nt–1 kb.

Probes are used according to the invention in hybridization reactions to identify PKD1 sequences, whether they be native or mutated PKD1 DNA or RNA, as disclosed herein. Such probes are useful for identifying the PKD1 gene or a mutation thereof, as defined herein.

The invention also features a synthetic polypeptide corresponding in amino acid residue sequence to at least a portion of the sequence of naturally occurring PKD1, and having a molecular weight equal to less than that of the native protein. A synthetic polypeptide of the invention is useful for inducing the production of antibodies specific for the synthetic polypeptide and that bind to naturally occurring PKD1.

Preferred embodiments of this aspect of the invention include a group of synthetic polypeptides whose members correspond to a fragment of the PKD1 protein comprising a stretch of amino acids of at least 8, and preferably 15, 30, 50, or 100 residues in length from the sequence disclosed in FIG. 15 (SEQ ID NO. 8).

In another aspect, the invention provides a polypeptide encoded by a sequence as set out above, or having the amino acid sequence according to the amino acid sequence of FIG. 15 (SEQ ID NO. 8), or a protein or polypeptide having homologous properties with said protein, or having at least one functional domain or active site in common with said protein. In particular, there is provided an isolated, purified or recombinant polypeptide comprising a PKD1 protein or a mutant or variant thereof or encoded by a sequence set out above or a variant thereof having substantially the same activity as the PKDL protein. The present invention may further comprise a polypeptide having 9 or 13 transmembrane pairs instead of 11 transmembrane domains as described hereinbelow. Further comprising this invention is a molecule which interacts with a polypeptide as herein described which molecule synergises, causes, enhances or is necessary for the functioning of the PKD1 protein as herein described.

The invention also encompasses recombinant expression vectors comprising a nucleic acid or isolated DNA encoding PKD1 and a process for preparing PKD1 polypeptide, comprising culturing a suitable host cell comprising the vector under conditions suitable for promoting expression of PKD1, and recovering said PKD1.

This invention also provides an in vitro method of determining whether an individual is likely to be affected with tuberous sclerosis, comprising assaying a biological sample from the individual to determine the presence and/or amount of PKD1 protein or polypeptide having the amino acid sequence of FIG. 15 (SEQ ID NO. 8).

As used herein, "biological sample" includes any fluid or tissue sample from a mammal, preferably a human, including but not limited to blood, urine, saliva, any body organ tissue, cells from any body tissue, including blood cells.

Additionally or alternatively, a sample may be assayed to determine the presence and/or amount of mRNA coding for the protein or polypeptide having the amino acid sequence of FIG. 15 (SEQ ID NO. 8), or to determine the fragment lengths of fragments of nucleotide sequences coding for the protein or polypeptide of FIG. 15 (SEQ ID NO. 8), or to detect inactivating mutations in DNA coding for a protein having the amino acid sequence of FIG. 15 (SEQ ID NO. 8) or a protein having homologous properties. The screening preferably includes applying a nucleic acid amplification process, as described herein in detail, to said sample to amplify a fragment of the DNA sequence. The nucleic acid amplification process advantageously utilizes at least one of the following sets of primers as identified herein: AH3 F9 (SEQ ID NO. 9):AH3 B7 (SEQ ID NO. 10); 3A3 C1 (Seq ID No: 11):3A3 C2 (Seq ID No: 12); and AH4 F2 (Seq ID No:13):JH14 B3 (Seq ID No: 14).

Alternatively, the screening method may comprise digesting the sample DNA to provide EcoRI fragments and hybridizing with a DNA probe which hybridizes to the EcoRI fragment identified (A) in FIG. 3(*a*), and the DNA probe may comprise the DNA probe CW10 (SEQ ID NO. 4) identified herein.

Another screening method may comprise digesting the sample to provide BamHI fragments and hybridizing with a DNA probe which hybridizes to the BamHI fragment identified (B) in FIG. 3(*a*), and the DNA probe may comprise the DNA probe 1A1H.6 identified herein.

A method according to the present invention may comprise detecting a PKD1-associated disorder in a patient suspected of having or having predisposition to the disorder (i.e., a carrier), the method comprising detecting the presence of and/or evaluating the characteristics of PKD1 DNA, PKD1 mRNA and.or PKD1 protein in a sample taken from the patient. Such method may comprise detecting and/or evaluating whether the PKD1 DNA is deleted, missing, mutated, aberrant or not expressing normal PKD1 protein. One way of carrying out such a method comprises: A. taking a biological, tissue or biopsy sample from the patient; B. detecting the presence of and/or evaluating the characteristics of PKD1 DNA, PKD1 mRNA and/or PKD1 protein in the sample to obtain a first set of results; C. comparing the first set of results with a second set of results obtained using the same or similar methodology for an individual that is not suspected of having the disorder; and if the first and second sets of results differ in that the PKD1 DNA is deleted, missing, aberrant, mutated or not expressing PKD1 protein then that is indicative of the presence, predisposition or tendency of the patient to develop the disorder. As used herein, a "PKD1-associated disorder" refers to adult polycystic kidney disease, as described herein, and also refers to tuberous sclerosis, as well as other disorders having symptoms such as cyst formation in common with these diseases.

A specific method according to the invention comprises extracting from a patient a sample of PKD1 DNA or DNA from the PKD1 locus purporting to be PKD1 DNA, cultivating the sample in vitro and analyzing the resulting protein, and comparing the resulting protein with normal PKD1 protein according to the well-established Protein Truncation Test. Less sensitive tests include analysis of RNA using RT PCR (reverse transcriptase polymerase chain reaction), and examination of genomic DNA.

Step C of the above method may be replaced by: comparing the first set of results with a second set of results obtained using the same or similar methodology in an individual that is known to have the or at least one of the disorder(s); and if the first and second sets of results are substantially identical, this indicates that the PKD1 DNA in the patient is deleted, mutated or not expressing normal PKD1 protein.

The invention further provides a method of characterizing a mutation in a subject suspected of having a mutation in the PKD1 gene, which method comprises: A. amplifying each of the exons in the PKD1 gene of the subject; B. denaturing the complementary strands of the amplified exons; C. diluting the denatured separate, complementary strands to allow each single-stranded DNA molecule to assume a secondary structural confirmation; D. subjecting the DNA molecule to electrophoresis under non-denaturing conditions; E. comparing the electrophoresis pattern of the single-stranded molecule with the electrophoresis pattern of a single-stranded molecule containing the same amplified exon from a control individual which has either a normal or PKD1 heterozygous genotype; and, F. sequencing any amplification product which has an electrophoretic pattern different from the pattern obtained from the DNA of the control individual.

The invention also extends to a diagnostic kit for carrying out a method as set out above, comprising nucleic acid primers for amplifying a fragment of the DNA or RNA sequences defined above, and packaging means therefore. The kit may optionally include written instructions stating that the primers are to be used for detection of disorders associated with the PKD1 gene. The nucleic acid primers may comprise at least one of the following sets: AH3 F9 (Seq ID No:9):AH3 B7 (Seq ID No:10); 3A3 C1 (Seq ID No:11):3A3 C2 (Seq ID No:12); and AH4 F2 (Seq ID No:13):JH14 B3 (Seq ID No: 14).

Another embodiment of kit may combine one or more substances for digesting a sample to provide EcoRI fragments and a DNA probe as previously defined. A further embodiment of kit may comprise one or more substances for digesting a sample to provide BamHI fragments and a DNA probe as previously defined.

A vector (such as Bluescript (available from Stratagene)) comprising a nucleic acid sequence set out above; and a host cell (such as *E. coli* strain SL-1 Blue (available from Stratagene)) transfected or transformed with the vector are also provided, together with the use of such a vector or a nucleic acid sequence set out above in gene therapy and/or in the preparation of an agent for treating or preventing a PKD1-associated disorder.

Therefore, there is further provided a method of treating or preventing a PKD1-associated disorder which method comprises administering to a patient in need thereof a functional PKD1 gene to affected cells in a manner that permits expression of PKD1 protein therein and/or a transcript produced from a mutated chromosome (such as the deleted WS-212 chromosome) which is capable of expressing functional-PKD1 protein therein.

As used herein, the term "hybridization" refers to conventional DNA/DNA or DNA/RNA hybridization conditions. For example, for a DNA or RNA probe of about 10–50 nucleotides, moderately stringent hybridization conditions are preferred and include 10×SSC, 5×Denhardts, 0.1% SDS, at 35–50 degrees for 15 hours; for a probe of about 50–300 nucleotides, "stringent" hybridization conditions are preferred and refer to hybridization in 6×SSC, 5×Denhardts, 0.1% SDS at 65 degrees for 15 hours.

The present invention further provides the use of PKD1 protein or polycystin or a mutant or variant thereof having substantially the same biological activity there as in therapy. In particular, to effect cell adhesion, recognition or communication for example to effect adhesion of cells to other cells or components of the extracellular matrix; effect communication and/or interaction between epithelial cells and the basal membrane (whether in kidneys or otherwise); assisting in development of connective tissue such as assembly and/or maintenance of the basal membrane; in signal transduction between cells or cells and components of the extracellular matrix; and/or to promote binding of cells carrying proteins such as integrins or carbohydrates to target cells.

Accordingly, where it is preferred to administer the polypeptide directly to a patient in need thereof, the invention further provides the :use of a PKD1 protein or polycystin in the preparation of a medicament. Therefore, there is also provided a pharmaceutical formulation comprising a PKD1 protein, functional PKD1 gene and/or a transcript produced from a mutated chromosome which is capable of expressing functional PKD1 protein, in association with a pharmaceutically acceptable carrier therefor.

The invention also features an immunoglobin, i.e., a polyclonal or monoclonal antibody specific for an epitope of PKD1, which epitope is found in the amino acid sequence presented in FIG. 15 (SEQ ID NO. 8).

The invention also features a method of assaying for the presence of PKD1 in a sample of mammalian, preferably human cells, comprising the steps of: (a) providing an antibody specific for said PKD1; and (b) assaying for the presence of PKD1 by admixing an aliquot from a sample of mammalian cells with antibody under conditions sufficient to allow for formation and detection of an immune complex of PKD1 and the antibody. Such method is useful for detecting disorders involving aberrant expression of the PKD1 gene or processing of the protein, as described herein.

Preferably, this method includes providing a monoclonal antibody specific for an epitope that is antigenically the same, as determined by Western blot assay, ELISA or immunocytochemical staining, and substantially corresponds in amino acid sequence to the amino acid sequence of a portion of PKD1 and having a molecular weight equal to less than that of PKD1.

The invention thus also features a kit for detecting PKD1, the kit including at least one package containing an antibody or idiotype-containing polyamide portion of an antibody raised to a synthetic polypeptide of this invention or to a conjugate of that polypeptide bound to a carrier. An indicating group or label is utilized to indicate the formation of an immune reaction between the antibody and PKD1 when the antibody is admixed with tissue or cells.

Further features will become more fully apparent in the following description of the embodiments of this invention and from the appended claims.

BRIEF DESCRIPTION OF THE DRAWINGS

Before describing preferred embodiments of the invention in detail, the drawings will briefly be described.

FIG. 1a (top): A long range map of the terminal region of the short arm of chromosome 16 showing the PKD1 candidate region defined by genetic linkage analysis. The positions of selected DNA probes and microsatellites used for haplotype, linkage or heterozygosity analyses are indicated. Markers previously described in linkage disequilibrium studies are shown in bold (from: Harris, et al., 1990; Harris, et al., 1991; Germino, et al., 1992; Somlo, et al., 1992; Peral, et al., 1994; Snarey, et al., 1994).

(bottom): A detailed map of the distal part of the PKD1 candidate region showing: the area of 16p13.3 duplicated in 16p13.1 (hatched); C, Cla I restriction sites; the breakpoints in the somatic cell hybrids, N—OH1 and P-MWH2A; DNA probes and the TSC2 gene. The limits of the position of the translocation breakpoint found in family 77 (see b), determined by evidence of heterozygosity (in 77-4) and PFGE (see c and text) is also indicated. The contig covering the 77 breakpoint region consists of the cosmids: 1, CW9D; 2, ZDS5; 3, JH2A; 4, REP59; 5, JC10.2B; 6, CW10III; 7, SM25A; 8, SMII; 9, NM17.

FIG. 1b: Pedigree of family 77 which segregates a 16;22 translocation; showing the chromosomal composition of each subject. Individuals 77-2 and 77-3 have the balanced products of the exchange—and have PKD1; 77-4 is monosomic for 16p13.3-->16pter and 22q11.21-->22pter—and has TSC.

FIG. 1c: PFGE of DNA from members of the 77 family: 77-1 (1); 77-2 (2); 77-3 (3); 77-4 (4); digested with Cla I and hybridised with SM6. In addition to the normal fragments of 340 and partially digested fragment of 480 kb a proximal breakpoint fragment of approximately 100 kb (arrowed) is seen in individuals, 77-2, 77-3 and 77-4; concordant with segregation of the der(16) chromosome.

Figure 2:
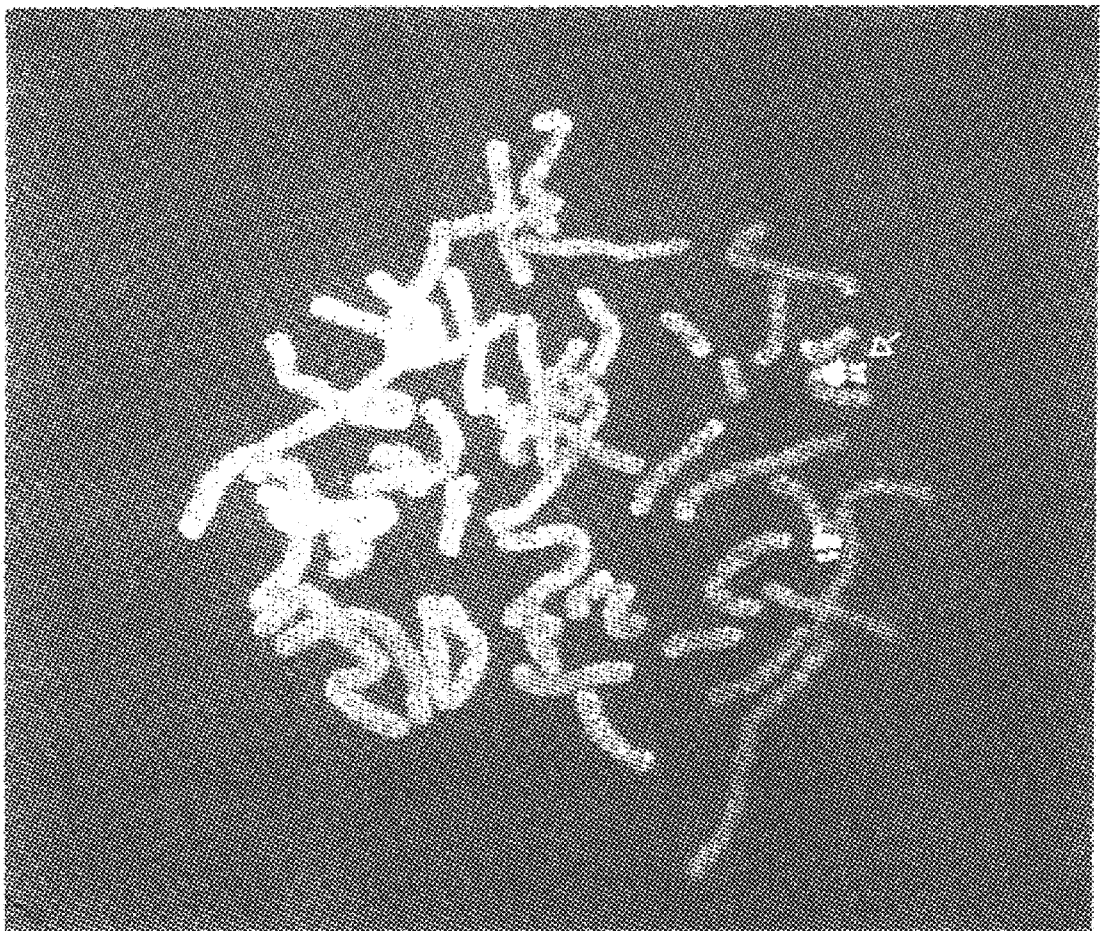

FIG. 2: FISH of the cosmid CW10III (cosmid 6; FIG. 1a) to a normal male metaphase. Duplication of this locus is illustrated with two sites of hybridisation on 16p; the distal site (the PKD1 region) is arrowed. The signal from the proximal site (16p13.1) is stronger than that from the distal, indicating that sequences homologous to CW10III are reiterated in 16p13.1.

Figure 3A:
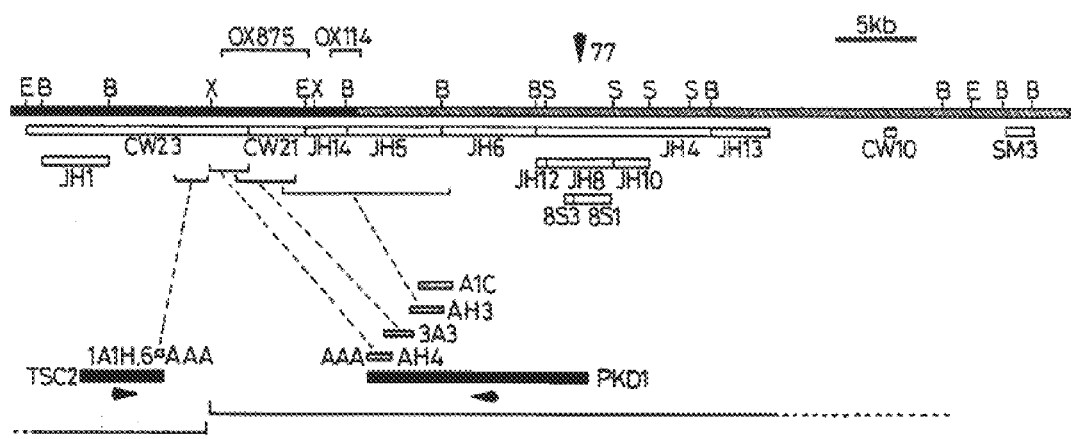

FIG. 3a: A detailed map of the 77 translocation region showing the precise localisation of the 77 breakpoint and the region that is duplicated in 16p13.1 (hatched). DNA probes (open boxes); the transcripts, PKD1 and TSC2 (filled boxes; with direction of transcription indicated by an arrow) and cDNAs (grey boxes) are shown below the genomic map. The known genomic extent of each gene is indicated at the bottom of the diagram and the approximate genomic locations of each cDNA is indicated under the genomic map. The positions of genomic deletions found in PKD1 patients, OX875 and OX114, are also indicated. Restriction sites for EcoR I (E) and incomplete maps for BamH I (B); Sac I (S) and Xba I (X) are shown. SM3 is a 2 kb BamH1 fragment shown at the 5' end of the gene.

Figure 3B:
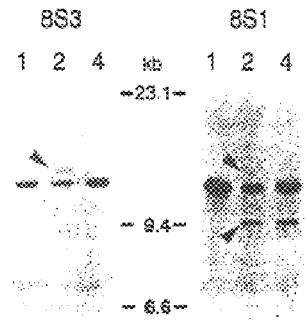

FIG. 3b: Southern blots of BamH I digested DNA from individuals: 77-1 (1); 77-2 (2); and 77-4 (4) hybridised with: left panel, 8S3 and right panel, 8S1 (see a). 8S3 detects a novel fragment on the telomeric side of the breakpoint (12 kb: arrowed) associated with the der(22) chromosome in 77-2, but not 77-4; 8S1 identifies a novel fragment on the centromeric side of the breakpoint (9 kb: arrowed)—associated with the der(16) chromosome—in 77-2 and 77-4. The telomeric breakpoint fragment is also seen weakly with 8S1 (arrowed) indicating that the breakpoint lies in the distal part of 8S1. The 8S3 and 8S1 loci are both duplicated; the normal BamH I fragment detected at the 16p13.3 site by these probes is 11 kb (see a), but a similar sized fragment is also detected at the 16p13.1 site. Consequently, the breakpoint fragments are much fainter than the normal (16p13.1 plus 16p13.3) band.

FIG. 4a: PBP cDNA, 3A3, hybridised to a Northern blot containing about 1 μg polyA selected mRNA per lane of the tissue specific cell lines: lane 1, MJ, EBV-transformed lymphocytes; lane 2, K562, erythroleukemia; lane 3, FS1, normal fibroblasts; lane 4, HeLa, cervical carcinoma; lane 5, G401, renal Wilm's tumour; lane 6, Hep3B, hepatoma; lane 7, HT29, colonic adenocarcinoma; lane 8, SW13, adrenal carcinoma; lane 9, G-CCM, astrocytoma. A single transcript of approximately 14 kb is seen; the highest level of expression is in fibroblasts and in the astrocytoma cell line, G-CCM. Although in this comparative experiment little expression is seen in lanes 1, 4 and 7, we have demonstrated at least a low level of expression in these cell lines on other Northern blots and by RT-PCR (see later).

FIG. 4b: A Northern blot containing about 20 μg of total RNA from the cell line G-CCM hybridised with cDNAs or a genomic probe which identify various parts of the PBP gene. Left panel, a single about 14 kb transcript is seen with a cDNA from the single copy area, 3A3. Right panel, a cDNA, 21P.9, that is homologous to parts of the region that is duplicated (JH12, JH8 and JH10; see FIG. 3a) hybridises to the PBP transcript and three novel transcripts; HG-A (about 21 kb), HG-B (about 17 kb) and HG-C (8.5 kb). A similar pattern of transcripts is seen with cDNAs and genomic fragments that hybridise to the area between JH5 and JH13, with the exception of the JH8 area. Middle panel, JH8 hybridises to the transcripts PBP, HG-A and HG-B but not to HG-C.

FIG. 4c: A Northern blot of 20 μg total fibroblast RNA from: normal control (N); 77-2 (2); 77-4 (4) hybridised with 8S1, which contains the 16;22 translocation breakpoint (see FIG. 3). A transcript of about 9 kb (PBP-77) is identified in the two patients with this translocation but not in the normal control. PBP-77 is a chimeric PBP transcript formed due to the translocation and is not seen in 77-2 or 77-4 RNA with probes which map distal to the breakpoint.

Figure 5A:
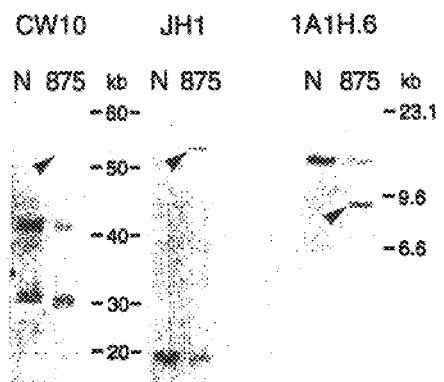

FIG. 5a: FIGE of DNA from: normal (N) and ADPKD patient OX875 (875), digested with EcoR I and hybridised with, left panel, CW10; middle panel, JH1. Normal fragments of 41 kb (plus a 31 kb fragment from the 16p13.1 site), CW10, and 18 kb, JHI, are identified with these probes; OX875 has an additional 53 kb band (arrowed). The EcoR I site separating these two fragments is removed by the deletion (see FIG. 3a). The right panel shows a Southern blot of BamH I digested DNA (as above) hybridised with 1A1H.6. A novel fragment of 9.5 kb is seen in OX875 DNA, as well as the normal 15 kb fragment. These results indicate that OX875 has a 5.5 kb deletion; its position was determined more precisely by mapping relative to two Xba I sites which flank the deletion (see FIG. 3a).

Figure 5B:
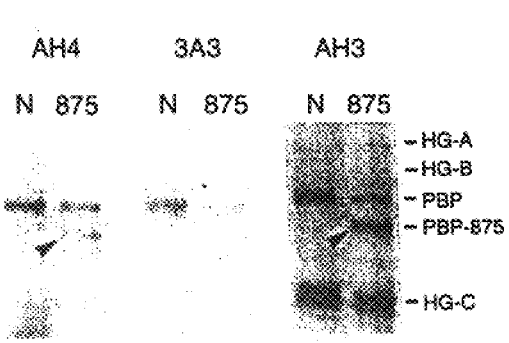

FIG. 5b: Northern blot of total fibroblast RNA, as (a), hybridised with the cDNAs, AH4, 3A3 and AH3. A novel transcript (PBP-875) of about 11 kb is seen with AH4 (the band is reduced in intensity because the probe is partly deleted) and AH3 (arrowed), which flank the deletion, but not 3A3 which is entirely deleted (see FIG. 3a). The transcripts HG-A, HG-B and HG-C, from the duplicated area, are;seen with AH3 (see FIG. 4b).

Figure 5C:
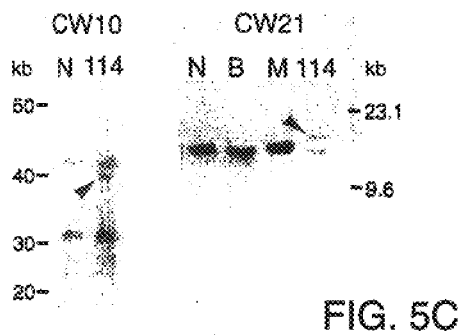

FIG. 5c: Left panel; FIGE of DNA from: normal (N) and ADPKD patient OX114 (114), digested with EcOR I and hybridised with CW10; a novel fragment of 39 kb (arrowed) is seen in OX114. Middle panel; DNA, as above, plus the normal mother (M) and brother (B) of OX114 digested with BamH I and hybridised with CW21. A larger than normal fragment of 19 kb (arrowed) was detected in OX114 but not other family members due to deletion of a BamH I site; together these results are consistent with a 2 kb deletion (see FIG. 3a). Right panel; RT-PCR of RNA, as above, with primers flanking the OX114 deletion (see Experimental Procedures). A novel fragment of 810 bp (arrowed) is seen in OX114, indicating a deletion of 446 bp in the PBP transcript.

Figure 5D:
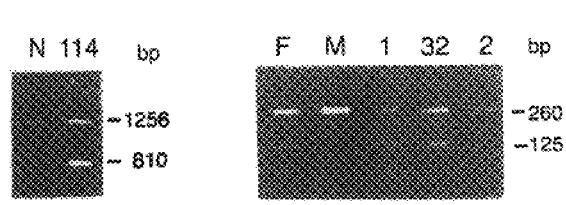

FIG. 5d: RT-PCR of RNA from: ADPKD patient OX32 (32) plus the probands, normal mother (M) and affected father (F) and sibs (1) and (2) using the C primer pair from 3A3 (SEQ ID NOS. 11 and 12) (see Experimental Procedures). A novel fragment of 125 bp is detected in each of the affected individuals.

Figure 6:
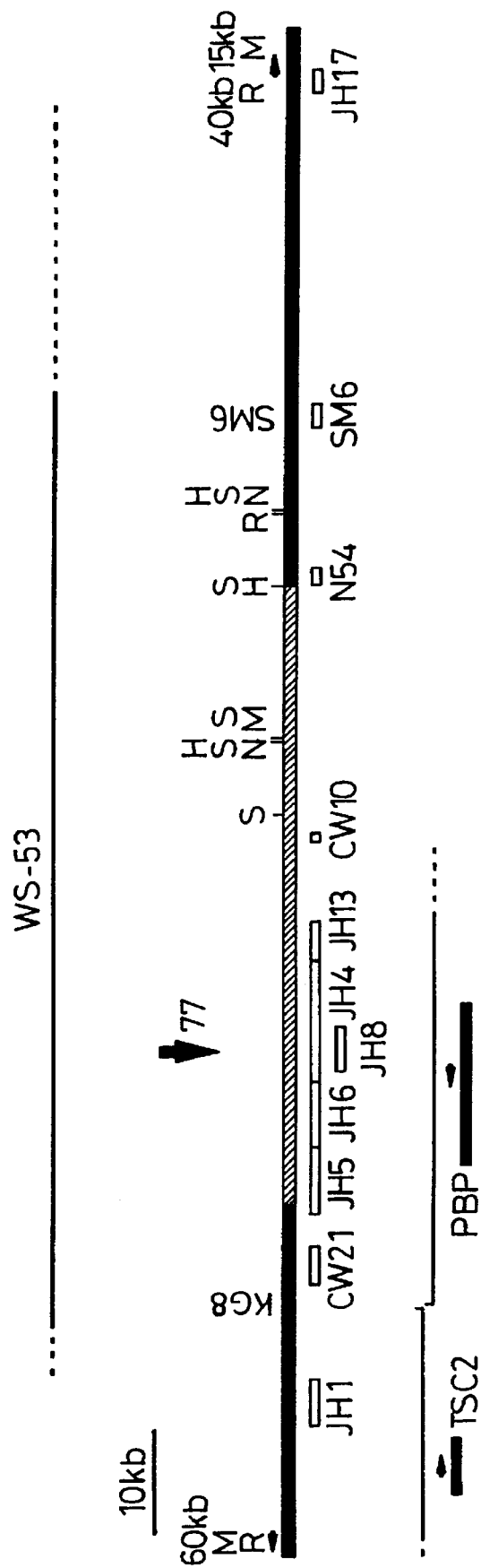

FIG. 6: Map of the region containing the TSC2 and PBP genes showing the area deleted in patient WS-53 and the position of the 77 translocation breakpoint. Localisation of the distal end of the WS-53 deletion was described (European Chromosome 16 Tuberous Sclerosis Consortium, 1993) and we have now localised the proximal end between SM6 and JH17. The size of the aberrant Mlu I fragment in WS-53, detected by JH1 and JH17, is 90 kb and these probes lie on adjacent Mlu I fragments of 120 kb and 70 kb, respectively. Therefore the WS-53 deletion is about 100 kb. Restriction sites for: Mlu I (M); Nru I (R) Not I (N); and partial maps for Sac II (S) and BssH II (H) are shown. DNA probes (open boxes) and the TSC2 and PBP transcripts (filled boxes) are indicated below the line with their known genomic extents (brackets). The locations of the microsatellites KG8 and SM6 are also indicated.

FIG. 7: The partial nucleotide sequence (cDNA) of the PKD1 transcript extending 5631 bp to the 3' end of the gene (SEQ ID NO. 1). The corresponding predicted protein (SEQ ID NO.2) is shown below the sequence and extends from the start of the nucleotide sequence. The GT-repeat, KG8, is in the 3' untranslated region between 5430–5448 bp. This sequence corresponds to GenBank Accession No. L33243. Also shown is probe 1A1H0.6 [Seq. I.D. No. 3].

FIG. 8: The sequence of the probe 1A1H.0.6 [Seq. I.D. No. 19].

FIG. 9: The sequence of the probe CW10 [Seq I.D. No. 4] which is about 0.5 kb. Also shown are the sequences of probes CW10F [Seq. I.D. No. 10] and CW10R [Seq. I.D. No. 21].

Figure 10:
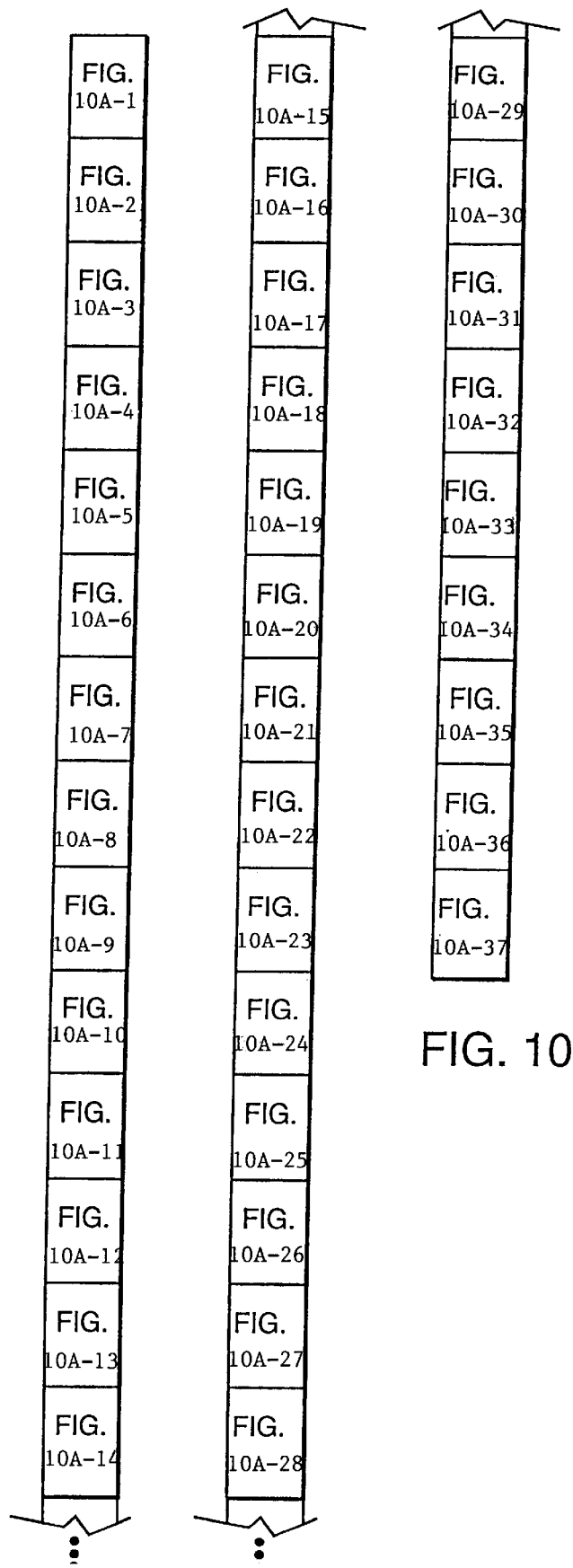

FIG. 10: Panels 10A–10A-KK show the larger partial nucleotide sequence (SEQ ID NO:1) of the PKD1 transcript (cDNA) extending from bp 2 to 13807 bp to the 3' end of the gene together with corresponding predicted protein (also shown in SEQ ID NO:2). This larger partial sequence encompasses the (smaller) partial sequence of FIG. 7 from amino acid residue 2726 in SEQ ID NO:3 and relates to the entire PKD1 gene sequence apart from its extreme 5' end.

Figure 11:
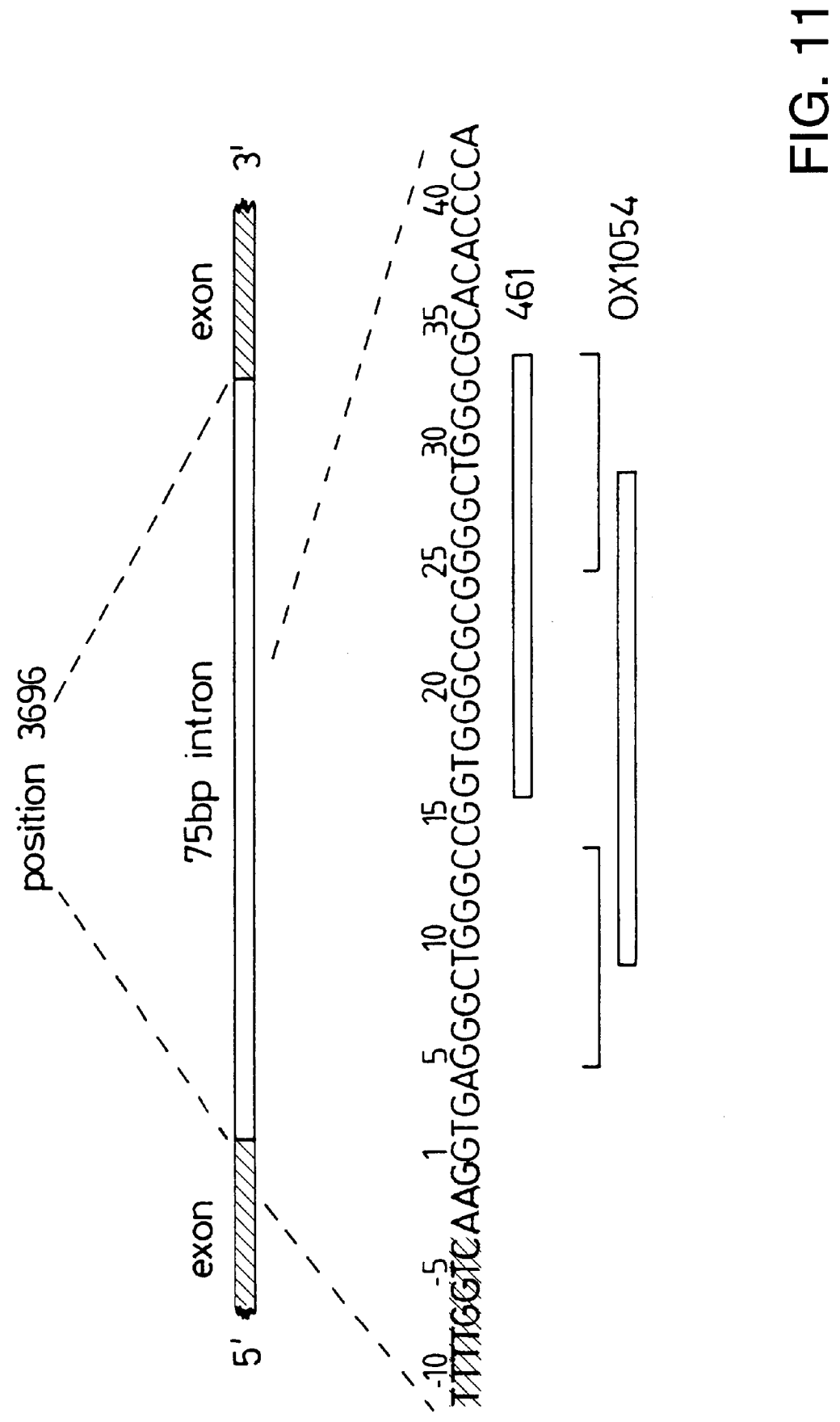

FIG. 11: A map of the 75 bp intron amplified by the primer set 3A3C [Seq. I.D. Nos. 11 and 12], insert [Seq. I.D. No. 18] at position 3696 of the 3' sequence [Seq. I.D. No. 1] showing the positions of genomic deletions found in PKD1 patients 461 and OX1054.

Figure 12:
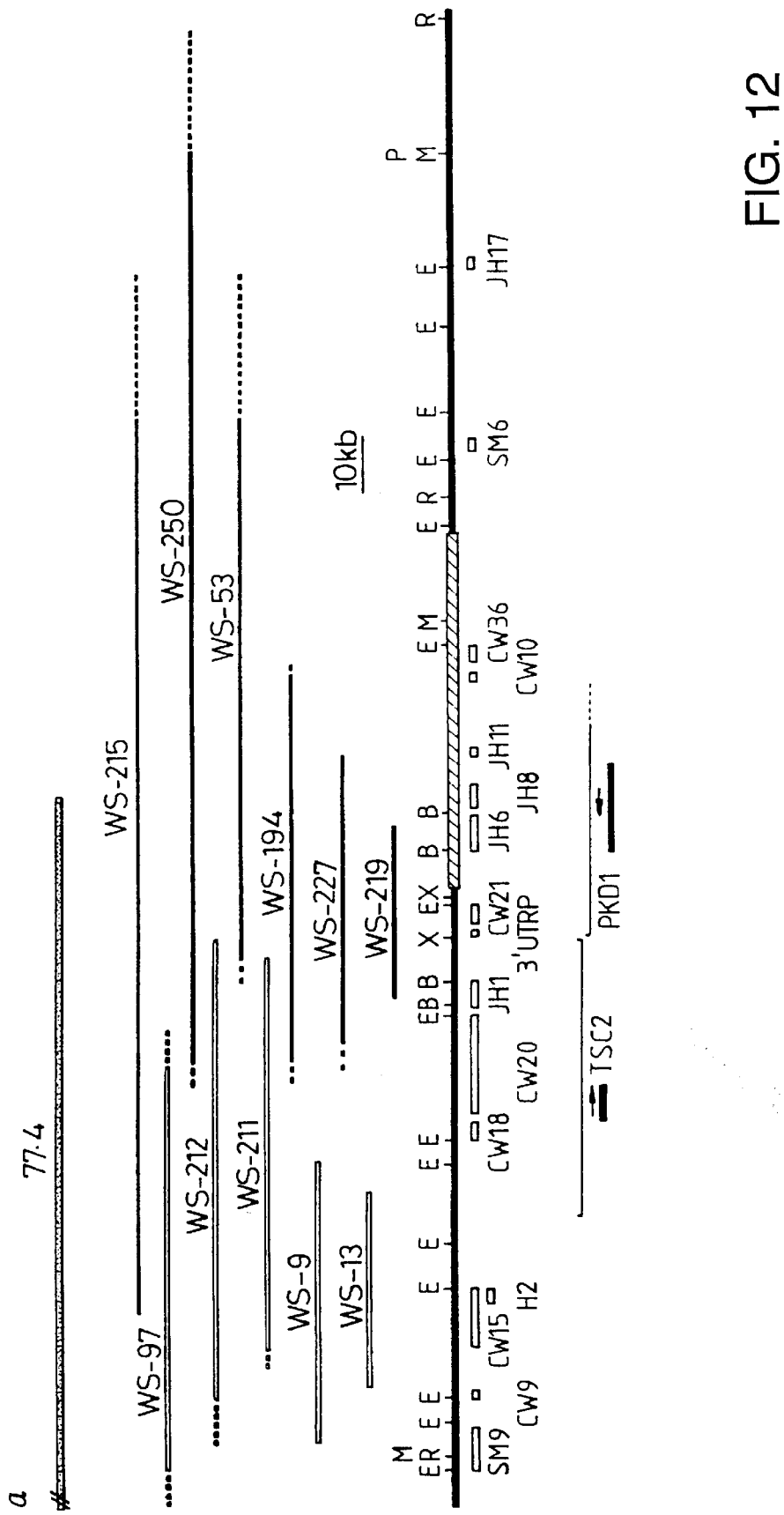

FIG. 12: A map of the region of chromosome 16 containing the TSC2 and PKD1 genes showing the areas affected in patients WS-215, WS-250, WS-212, WS-194, WS-227 and WS-219; also WS-53 (but cf. FIG. 6). Genomic sites for the enzymes Mlul (M), Clal (C), Pvul (P) and Nrul (R) are shown. Positions of single copy probes and cosmids used to screen for deletions are shown below the line which represents about 400 kb of genomic DNA. The genomic distribution of the approximately 45 kb TSC2 gene and known extent of the PKD1 gene are indicated above. The hatched area represents an about 50 kb region which is duplicated more proximally on chromosome 16p.

Figure 13:
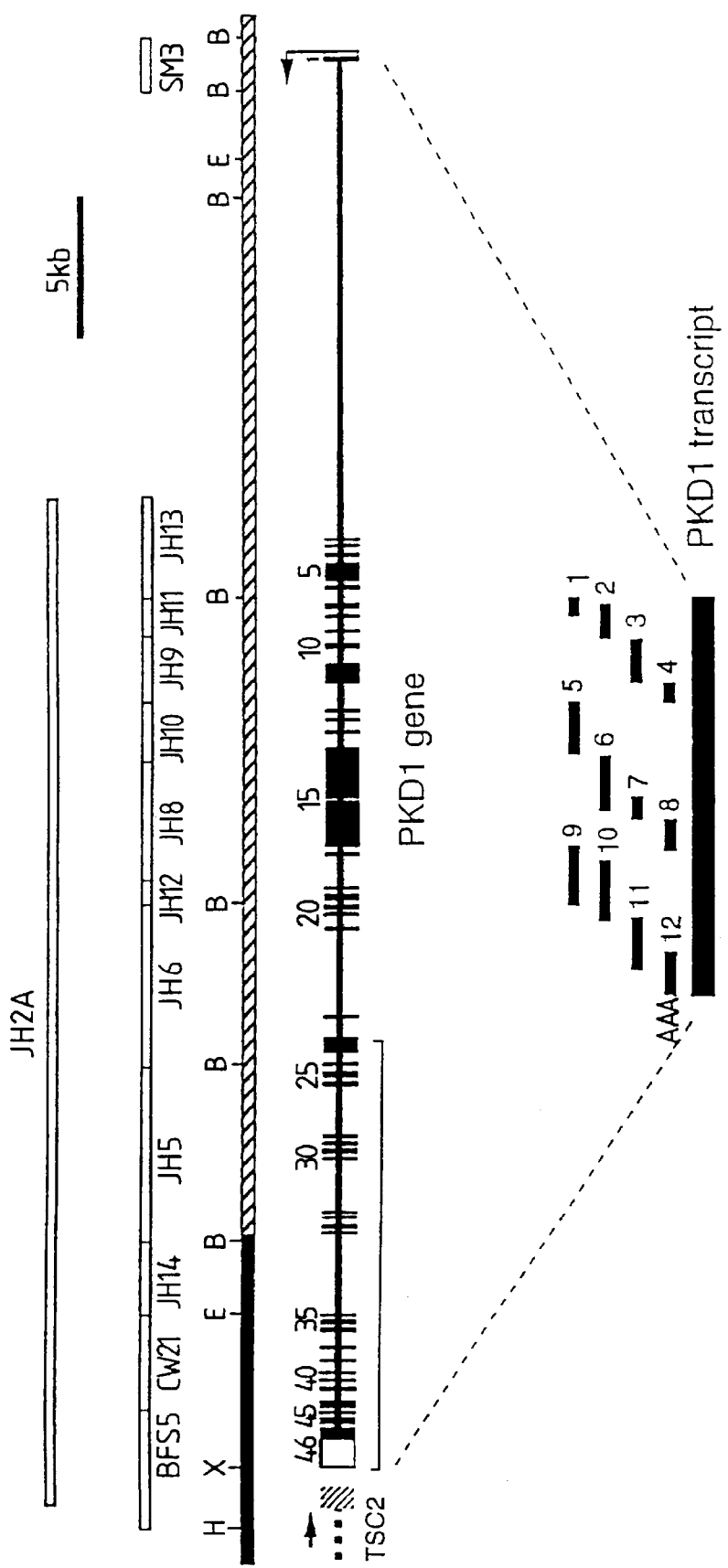

FIG. 13 is a: genomic map of the PKD1 gene. (Top) A restriction map of the genomic area containing the PKD1 gene showing sites for Bam H1(B), EcoRI(E) and partial maps for Xbal (X) and Hind III(H), and the duplicated area (hatched). The position of genomic clones and the cosmid JH2A are shown above the map (open boxes). The positions of the 46 exons of the PKD1 gene are shown below the map (solid boxes, translated areas; open boxes, untranslated regions; UTRs). Each 5th exon is numbered and the direction of transcription arrowed. The area sequenced in FIGS. 7 and 10 is bracketed and the approximate location of the 3' end of the TSC2 gene is shown on the left (dashed line and hatched box). (Bottom) The cDNA contig covering the PKD1 transcript. The cDNAs are: 1, rev1; 2, S13;3, S3/4; 4, S1/3;5, GAP e; 6, GAP d; 7, GAP g; 8, GAP a (see table 2 for details); 9, A1C; 10, AH3; 11, 3A3; 12, AH4.

Figure 14A:
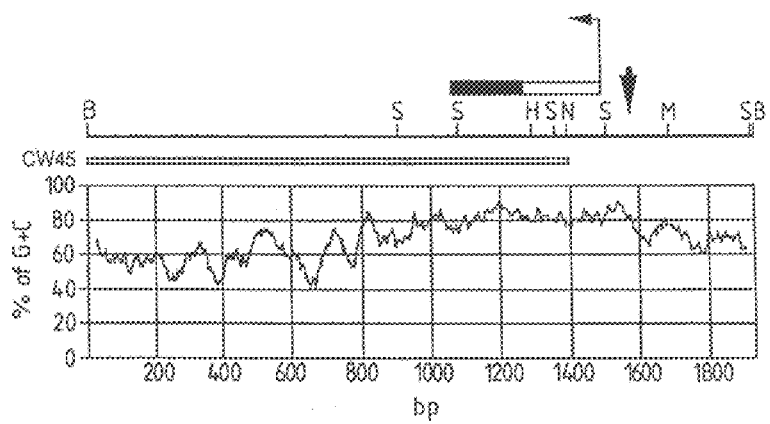

FIG. 14(a) (Top): Map of the genomic BamH I fragment, SM3 which contains the CpG island at the 5' end of the PKD1 gene, showing the probe CW45 (open box). Genomic restriction sites for the methylation sensitive enzymes: SacII (S), NotI (N), MluI (M) and BssHII (H) are illustrated. The approximate position of the DNase1 hypersensitive site is also shown (large arrow), plus the location of the first exon including the proposed transcription start site (small arrow), the 5'UTR (open box) and the translated region (solid bar). (Bottom) The GC content across the area is plotted with a window size of 50 nt. A peak of GC content of over 80% is seen in the area of the transcriptional start site and the first exon. A corresponding lack of CpG suppression was also found with an average CpG/GC ratio of 0.84 between 800–1,800 bp.

Figure 14B:
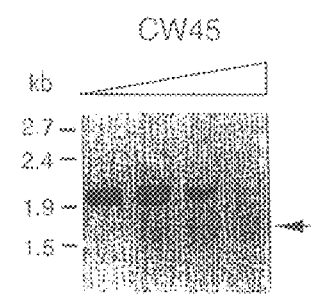

FIG. 14(b). Analysis of DNase I hypersensitivity at the PKD1 CpG island. DNA isolated from HeLa cells treated with an increasing amount of DNase I (left to right; first lane contains no DNase 1), digested with BamH I and hybridised with CW45. A fragment about 400 bp smaller than the restriction fragment is seen with increasing DNase 1, indicating a hypersensitive site as shown in (a). SM3 is within the duplicated area and so both the PKD1 and HG loci are assayed together. The degree of DNase1 digestion seen at the end of the assay indicates that cleavage occurs at the PKD1 and HG loci.

Figure 15:
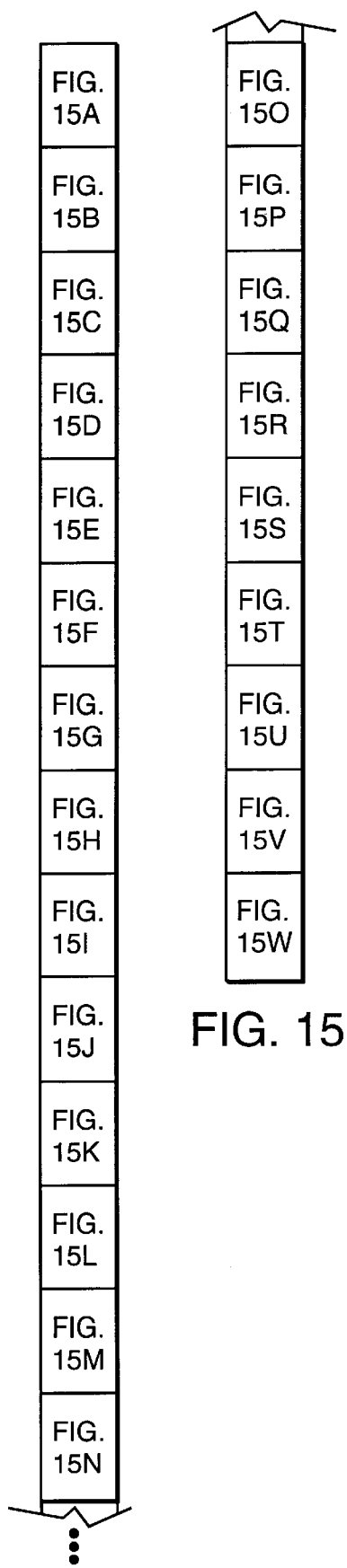

FIG. 15 provides the sequence of the PKD1 transcript [Seq. I.D. No. 7] and predicted protein [Seq. I.D. No. 8]. The full sequence of 14,148 bp from the transcription start site to the poly A tail is shown. The probable signal sequence of 23 amino acids is shown after the first methionine (underlined) plus the cleavage site (arrow). The predicted transmembrane (TM) domains (double underlined and numbered) and N-linked glycosylation sites (asterisk) are indicated. The position of a possible hinge sequence is underlined and tyrosine kinase and protein kinase C phosphorylation sites marked with a box and circle, respectively.

FIG. 16(a). The leucine rich repeats (LRRs) found in the PKD1 protein (72–125aa) are compared with each other and to the LRR consensus (Rothberg, 1990; Kobe, 1994); a, aliphatic. A total of just over 2 full repeats are present in PKD1 but they have been arranged into 3 incomplete repeats to show their similarity to those found in slit (Rothberg, 1990). The black boxes show identity to the LRR consensus and shaded boxes other regions of similarity between the repeats which have also been noted in other LRRs (Kobe, 1994).

FIG. 16(b). The amino flanking region to the LRR in the PKD1 protein (33–71aa) is compared similar regions from a variety of other proteins. Black boxes shown identity with the consensus (adapted from [Rothberg, 1990 #1126]) and shaded boxes conserved amino acids. The different types of residue indicated in the consensus are: a, as above; p, polar or turn-like; h, hydrophobic. The listed proteins, with the species and Protein Identification Resource no. (PIR) shown in brackets, are: OMgp, oligodendrocyte myelin glycoprotein (Human, A34210); Slit (Drosophila; A36665); Chaoptin (Drosophila; A29943); GP-IB Beta, platelet glycoprotein 1bβ chain (Human; A31929); Pg1, proteoglycan-1 (mouse; 520811); Biglycan (Human; A40757); Trk (Human; A25184) and LH-CF, lutropinchoriogonadotrophin receptor (Rat; A41343).

FIG. 16(c). The carboxy flanking region of the LRR repeat from the PKD1 protein (126–180 aa) compared to similar regions in other proteins and a consensus accepted from [Rothberg, 1990 #1126]. The shading and amino acid types are as above. The proteins not described above are: Toll (Drosophila; A29943) and GP IX, platelet glycoprotein IX (Human; A46606).

FIG. 17 is a sequence comparison of the C-type lectin domain. The PKD1 lectin domain (403–532aa) is compared to those of: BRA3, acorn barnacle lectin (JC1503); Kupffer cell carbohydrate-binding receptor (Rat; A28166), CSP, cartilage specific protoglycan (Bovine; A27752); Agp; asialoglycoprotein receptor (Human; 55283), E-Selectin (Mouse; B42755) and glycoprotein gp120 (Human; A46274). Black squares show identify with the consensus and shaded boxes conserved residues. Amino acid types are: Very highly conserved residues are shown in bold in the consensus which is adapted from Drickamer 1987, Drickamer 1988.

Figure 18A:
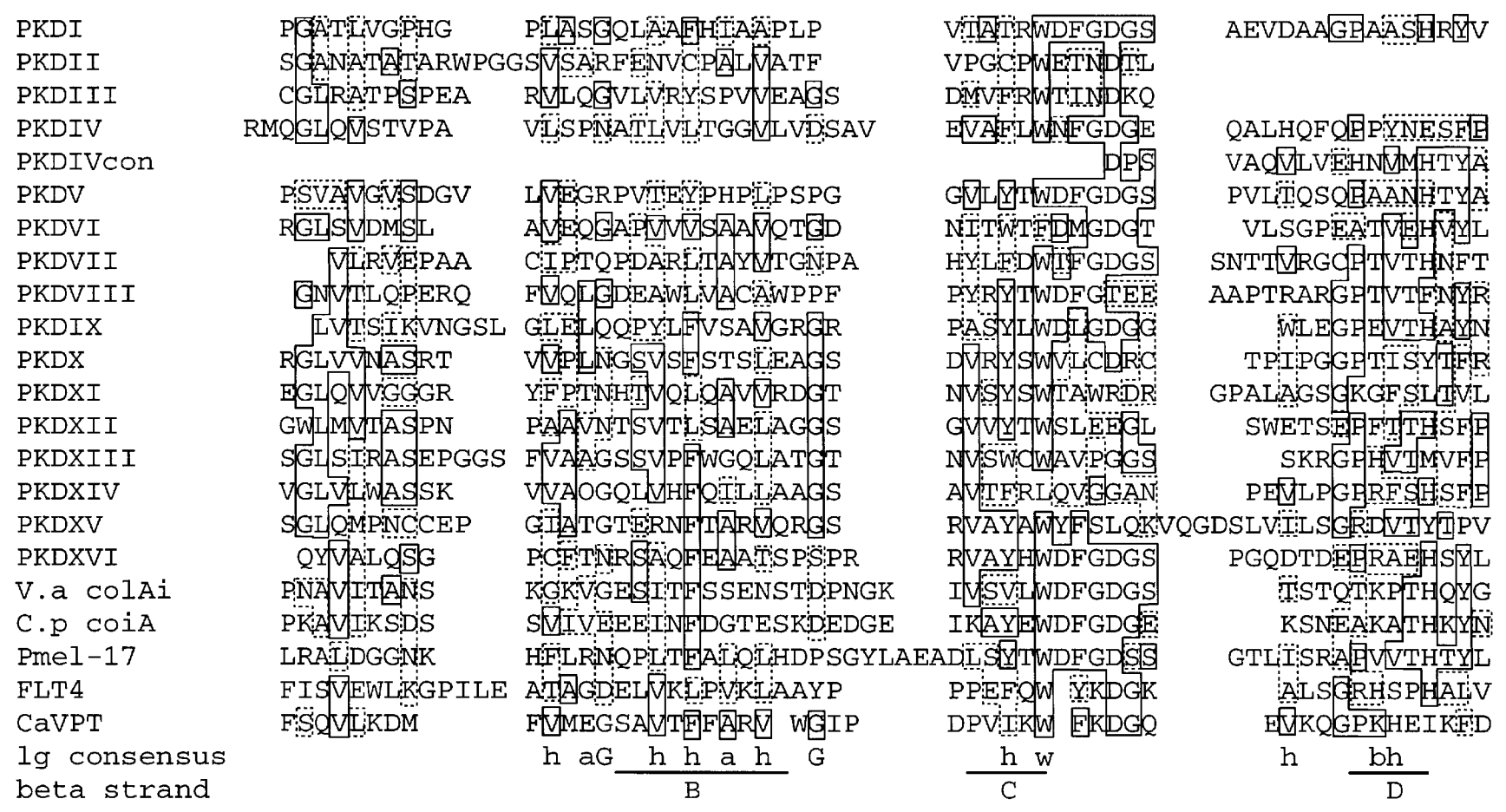
Figure 18B:
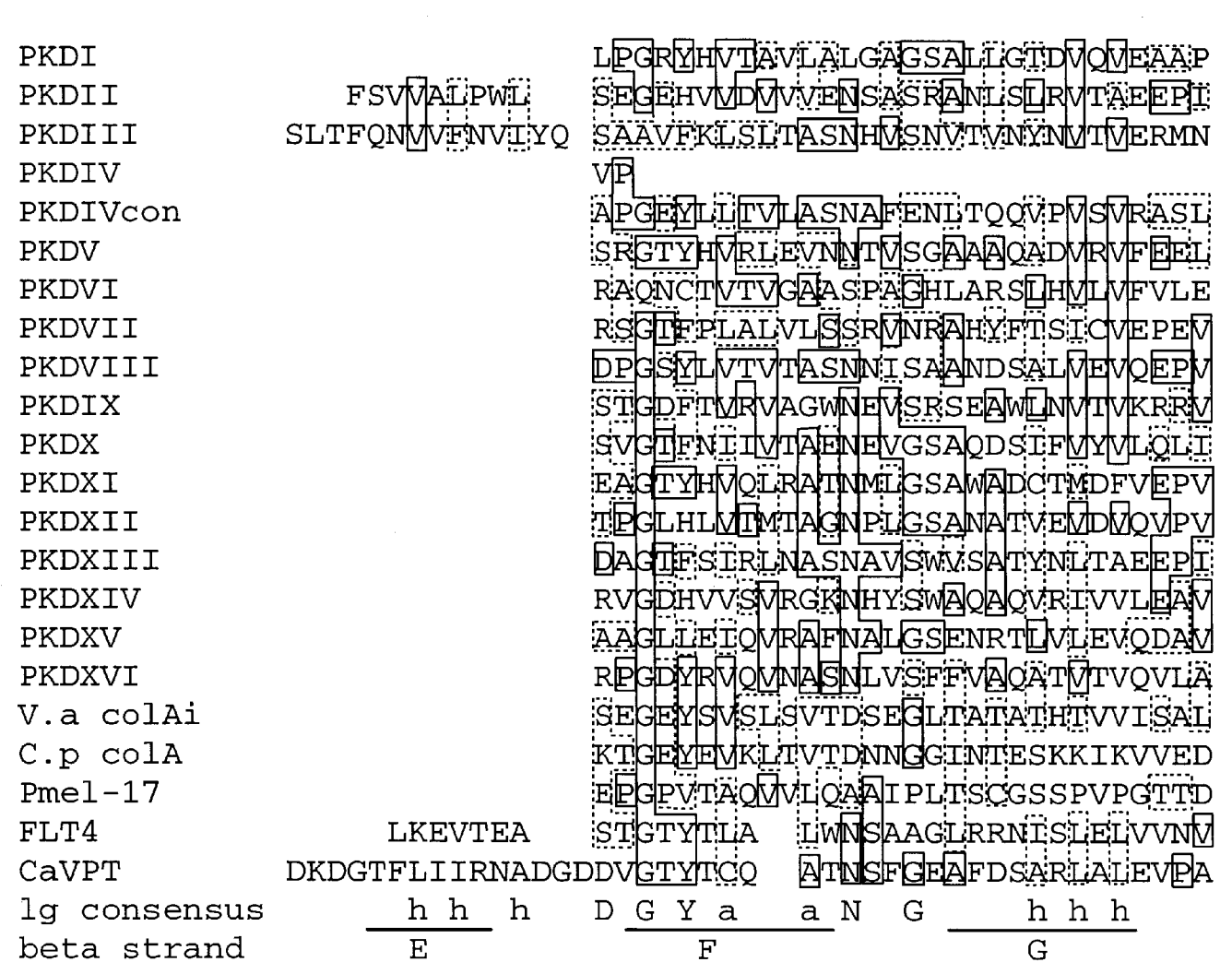

FIG. 18 is a sequence analysis of the Ig-like repeat. The 16 copies of the PKD1 Ig-like repeat (PKDI 273–356 aa; PKDII-XVI, 851–2145aa) are compared to each other and to: V.a. colAi, and C.p. colA collagenases of Vibrio alginolyticus (S19658) and Clostridium perfringens (D13791), respectively; Pmel17, melanocyte specific glycoprotein (Human; A41234), FLT4, Ig repeat IV of fms-like tyrosine kinase 4 (Human; X68203), CaVPT, Ig repeat I of target protein of the calcium vector protein (CAVP) (amphioxius; P05548). black boxes shown amino acids identical in more than 5 repeats and shaded boxes related residues. An Ig consensus determined from Harpaz et al. 1994 and Takagi et al. 1990 is shown in the symbols: a, aliphatic; h, hydrophobic; s, small and b, base with the predicted positions of the β-strands indicated below. The PKD repeat IV has an extra repetition of 20 aa in the centre of the repeat while all of the others are between 84–87 aa.

Figure 19B:
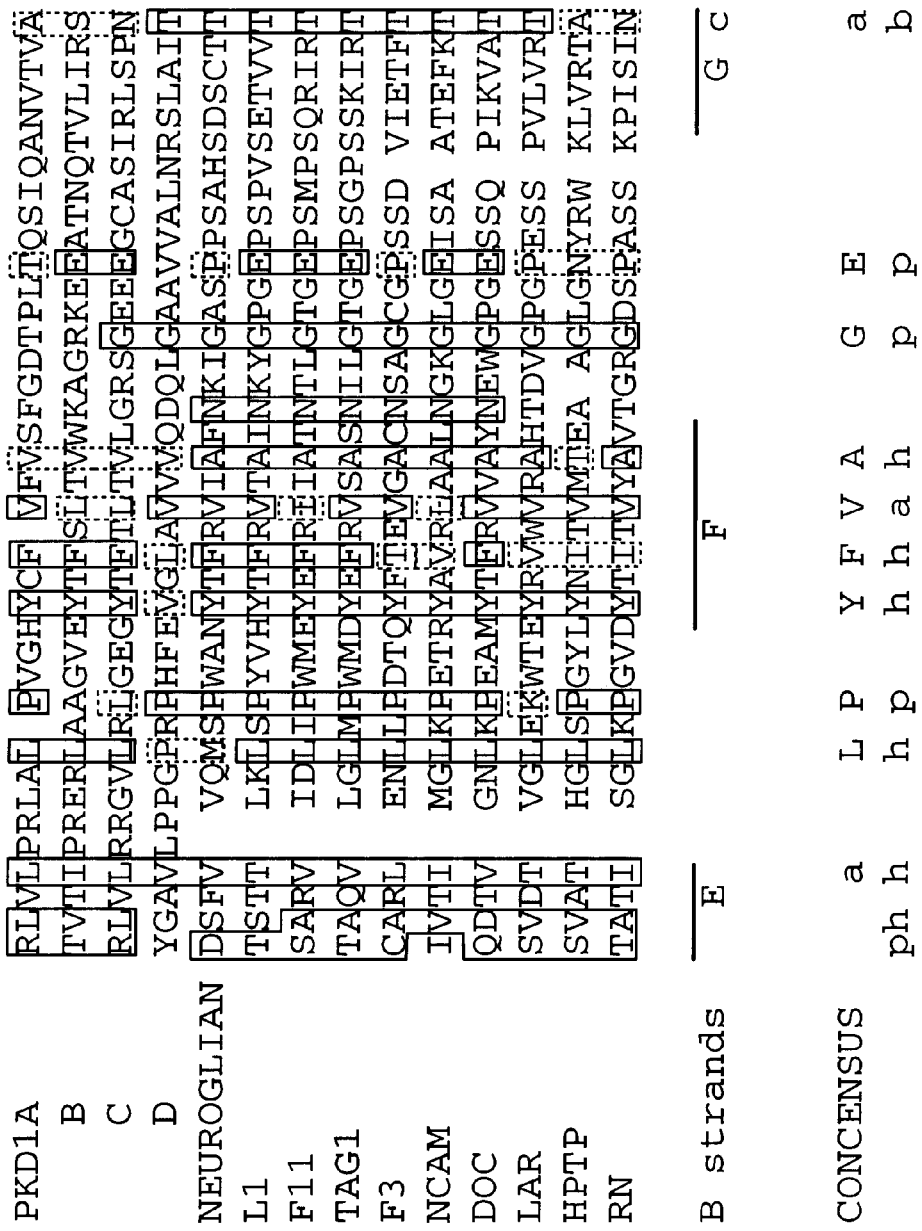

FIG. 19 reveals type III-related fibronectin domains. The four fibronectin-related domains from the PKD1 protein (2169–2573aa) are compared to similar domains in: Neuroglian (Drosophila; A32579); L1, neural recognition molecule L1 (X59847); F11, neural cell recognition molecule F11 (X14877); TAG 1, transiently expressed axonal surface glycoprotein-1 (Human; S28830); F3, Neuro-1 antigen (mouse; SO5944); NCAM, neural cell adhesion molecule (Rat; X06564); DCC, deleted in colorectal cancer (Human; X76132); LAR, Leukocyte-common antigen related molecule (Human; YOO815); HPTP, β protein tyrosine phosphate beta (Human; X54131) and FN, fibronectin (Human; X02761). The consensus sequence is compiled from Borh and Doolittle (1993), Kuma et al. (1993), Baron et al. (1992) and Borh and Doolittle (1992). Black boxes show identity to highly conserved residues and shaded boxes conserved changes or similarity in less highly conserved positions. The approximate positions of the β strands are illustrated. The fibronectin repeats in the PKD1 protein are linked by sequences of 27aa (A–B), 22aa (B–C) and 7aa (C–D) which are not shown.

Figure 20:
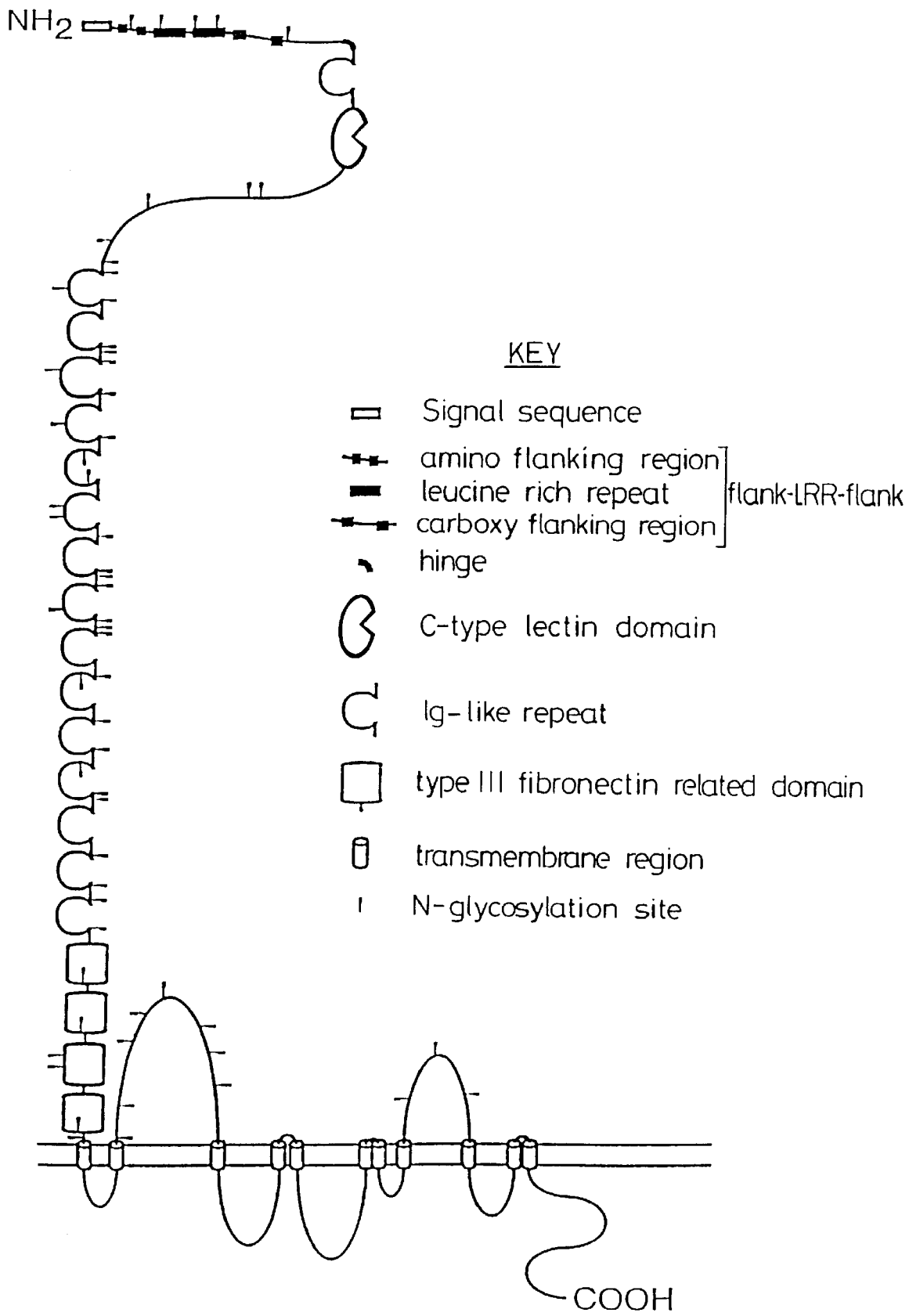

FIG. 20 presents a proposed model of the PKD1 protein, polycystin. The predicted structure of the PKD1 protein is shown.

DETAILED DESCRIPTION

All references mentioned herein are listed in full at the end of the description which are herein incorporated by reference in their entirety. Except where the context clearly indicates otherwise, references to the PBP gene, transcript, sequence, protein or the like can be read as referring to the PKD1 gene, transcript, sequence, protein or the like, respectively.

A Translocation Associated with ADPKD

A major pointer to the identity of the PKD1 gene was provided by a Portuguese pedigree (family 77) with both ADPKD and TSC (FIG. 1b). Cytogenetic analysis showed that the mother, 77-2, has a balanced translocation, 46XX t(16;22) (p13.3;q11.21) which was inherited by her daughter, 77-3. The son, 77-4, has the unbalanced karyotype, 45XY-16-22+der(16) (16qter-->16p13.3:22q11.21-->2qter) and consequently is monosomic for 16p13.3-->16pter as well as for 22q11.21-->22pter. This individual has the clinical phenotype of TSC (see Experimental Procedures); the most likely explanation is that the TSC2 locus located within 16p13.3 is deleted in the unbalanced karyotype.

Further analysis revealed that the mother (77-2), and the daughter (77-3) with the balanced translocation, have the clinical features of ADPKD (see Experimental Procedures), while the parents of 77-2 were cytogenetically normal, with no clinical features of TSC and no renal cysts on ultrasound examination (aged 67 and 82 years). Although kidney cysts can be a feature of TSC, no other clinical signs of TSC were identified in 77-2 or 77-3, making it unlikely that the polycystic kidneys were due to TSC. We therefore investigated the possibility that the translocation disrupted the PKD1 locus in 16p13.3 and proceeded to identify and clone the region containing the breakpoint.

The 77 family was analyzed with polymorphic markers from 16p13.3. Individual 77-4 was hemizygous for MS205.2 and GGG1, but heterozygous for SM6 and more proximal markers, locating the translocation breakpoint between GGG1 and SM6 (see FIG. 1a). Fluorescence in situ hybridization (FISH) of a cosmid from the TSC2 region, CW9D (cosmid 1 in FIG. 1a), to metaphase spreads showed that it hybridized to the der(22) chromosome of 77-2; placing the breakpoint proximal to CW9D and indicating that 77-4 was hemizygous for this region consistent with his TSC phenotype. DNA from members of the 77 family was digested with Cla I, separated by PFGE and hybridized with SM6; revealing a breakpoint fragment of about 100 kb in individuals with the der(16) chromosome (FIG. 1c). The small size of this novel fragment enabled the breakpoint to be localized distal to SM6 in a region of just 60 kb (FIG. 1a). A cosmid contig covering this region was therefore constructed (see Experimental Procedures for details).

The Translocation Breakpoint Lies within a Region Duplicated Elsewhere on Chromosome 16p (16p13.1)

It is noted hereabove that the region between CW21 and N54 (FIG. 1a) was duplicated at a more proximal site on the short arm of chromosome 16 (Germino, et al., 1992; European Chromosome 16 Tuberous Sclerosis Consortium, 1993). FIG. 2 shows that a cosmid, CW10III, from the duplicated region hybridized to two points on 16p; the distal, PKD1 region and a proximal site positioned in 16p13.1. The structure of the duplicated area is complex with each fragment present once in 16p13.3 re-iterated two-four times in 16p13.1 (see FIG. 2). Cosmids spanning the duplicated area in 16p13.3 were subcloned (see FIG. 3a and Experimental Procedures for details) and a restriction map was generated. A genomic map of the PKD1 region was constructed using a radiation hybrid, Hy145.19 which contains the distal portion of 16p but not the duplicate site in 16p13.1.

To localize the 77 translocation breakpoint, subclones from the target region were hybridized to 77-2 DNA, digested with Cla I and separated by PFGE. Once probes mapping across the breakpoint were identified they were hybridized to conventional Southern blots of 77 family DNA. FIG. 3b shows that novel BamH I fragments were detected from the centromeric and telomeric side of the breakpoint, which was localized to the distal part of the probe 8S1 (FIG. 3a). Hence, the balanced translocation was not associated with a substantial deletion, and the breakpoint was located more than 20 kb proximal to the TSC2 locus (FIG. 3a). These results supported the hypothesis that polycystic kidney disease in individuals with the balanced translocation (77-2 and 77-3) was not due to disruption of the TSC2 gene, but indicated that a separate gene mapping just proximal to TSC2, was likely to be the PKD1 gene.

The Polycystic Breakpoint (PBP) Gene is Disrupted By the Translocation

Localization of the 77 breakpoint identified a precise region in which to look for a candidate or the PKD1 gene. During the search for the TSC2 gene we identified other transcripts not associated with TSC including a large transcript (about 14 kb) partially represented in the cDNAs 3A3 and AH4 which mapped to the genomic fragments CW23 and CW21 (FIG. 3a). The orientation of the gene encoding this transcript had been determined by the identification of a polyA tract in the cDNA, AH4: the 3' end of this gene lies very close to the TSC gene, in a tail to tail orientation (European Chromosome 16 Tuberous Sclerosis Consortium, 1993). To determine whether this gene crossed the translocation breakpoint genomic probes from within the duplicated area and flanking the breakpoint were hybridized to Northern blots. Probes from both sides of the breakpoint, between JH5 and JH13 identified the 14 kb transcript (FIG. 3a and see below for details). Therefore, this gene, called 3A3, but not designated the PBP gene extended over the 77 breakpoint and consequently was a candidate for the PKD1 gene. A walk was initiated to increase the extent of the PBP cDNA contig and several new cDNAs were identified using probes from the single copy (non-duplicated) region (see Experimental Procedures for details). A cDNA contig was constructed which extended about 5.7 kb, including about 2 kb into the area that is duplicated (FIG. 3a).

Expression of the PBP Gene

Initial studies of the expression pattern of the PBP gene were undertaken with cDNAs that map entirely within the single copy region (e.g. AH4 and 3A3). FIG. 4a shows that the about 14 kb transcript was identified by 3A3 in various tissue-specific cell lines. From this and other Northern blots we concluded that the PBP gene was expressed in all of the cell lines tested, although often at a low level. The two cell lines which showed the highest level of expression were fibroblasts and a cell line derived from an astrocytoma, G-CCM. Significant levels of expression were also obtained in cell lines derived from kidney (G401) and liver (Hep3B). Measuring the expression of the PBP gene in tissue samples by Northern blotting proved difficult because such a large transcript is susceptible to minor RNA degradation. However, initial results with an RNAse protection assay, using a region of the gene located in the single copy area (see Experimental Procedures), showed a moderate level of expression of the PBP gene in tissue obtained from normal and polycystic kidney (data not shown). The widespread expression of the PBP is consistent with the systemic nature of ADPKD.

Identification of Transcripts that are Partially Homologous to the PBP Transcript New cDNAs were identified with the genomic fragments, JH4 and JH8, that map to the duplicated region (FIG. 3a and see Experimental Procedures). However, when these cDNAs were hybridized to Northern blots a more complex pattern than that seen with 3A3 was observed. As well as the ~14 kb PBP transcript, three other, partially homologous transcripts were identified designated homologous gene-A (HG-A; ~21 kb), HG-B (~17 kb) and HG-C (8.5 kb) FIG. 4b). There were two possible explanations for these results, either the HG. transcripts were alternatively spliced forms of the PBP gene, or the HG transcripts were encoded by gene located in 16p13.1. To determine the genomic location of the HG loci a fragment from the 3' end of one HG cDNA (HG-4/1.1) was isolated. HG-4/1.1 hybridized to all three HG transcripts, but not to the PBP transcript and on a hybrid panel it mapped to 16p13.1 (not the PKD1 area). These results show that all the HG transcripts are related to each other outside the region of homology with the PBP transcript and that the HG loci map to the proximal site (16p13.1).

An Abnormal Transcript Associated with the 77 Translocation

As the PBP gene was transcribed across the region disrupted by the 77 translocation breakpoint, in a proximal to distal direction on the chromosome (see FIG. 3a) it was possible that a novel transcript originating from the PBP promotor would be found in this family. FIG. 4c shows that using a probe to the PBP transcript that mapped mainly proximal to the breakpoint, a novel transcript of approximately 9 kb (PBP-77) derived from the der(16) product of the translocation was detected. Interestingly, the PBP-77 transcript appears to be expressed at a higher level than the normal PBP product. These results confirmed that the 77 translocation disrupts the PBP gene and supports the hypothesis that this is the PKD1 gene.

Mutations of the PBP Gene in Other ADPKD Patients

To prove that the PBP gene is the defective gene at the PKD1 locus, we analyzed this region for mutations in patients with typical ADPKD. The 3' end of the PBP gene was most accessible to study as it maps outside the duplicated area. To screen this region BamH I digests of DNA from 282 apparently unrelated ADPKD patients were hybridized with the probe 1A1H.6 [Seq. I.D. No. 3], (see FIG. 3a). In addition, a large EcoR I fragment (41 kb) which contains a significant proportion of the PBP gene was assayed by field inversion gel electrophoresis (FIGE) in 167 ADPKD patients, using the probe CW10 [Seq. I.D. No. 4]. Two genomic rearrangements were identified in ADPKD patients by these procedures; each identified by both methods.

The first rearrangement was identified in patient OX875 (see Experimental Procedures for clinical details) who was shown to have a 5.5 kb genomic deletion without the 3' end of the PBP gene, producing a smaller transcript (PBP-875) (see FIGS. 5a, b and 3a for details). This genomic deletion results in a ~3 kb internal deletion of the transcript with the ~500 bp adjacent to the polyA tail intact. In this family linkage of ADPKD to chromosome 16 could not be proven because although OX875 has a positive family history of ADPKD there were no living, affected relatives. However, paraffin-embedded tissue from her affected father (now deceased) was available. We demonstrated that this individual has the same rearrangement as OX875 by PCR amplification of a 220 bp fragment spanning the deletion (data not shown). This result and analysis of two unaffected sibs of OX875, that did not have the deletion, showed that this mutation was transmitted with ADPKD.

The second rearrangement detected by hybridization was a 2 kb genomic deletion within the PBP gene, in ADPKD patient OX114 (see Experimental Procedures for clinical details and FIGS. 5c and 3a). No abnormal PBP transcript was identified by Northern blot analysis, but using primers flanking the deletion (see Experimental Procedures) a shortened product was detected by RT-PCR (FIG. 5c). This was cloned and sequenced and shown to have a frame-shift deletion of 446 bp (between base pair 1746 and 2192 of the sequence shown in FIG. 7 [Seq. I.D. No. 1]). OX114 is the only member of the family with ADPKD (she has no children) and ultrasound analysis of her parents at age 78 (father) and 73 years old (mother) showed no evidence of renal cysts. Somatic cell hybrids were produced from OX114 and the deleted chromosome was found to be of paternal origin by haplotype analysis. The father of OX114 (OX984) with seven microsatellite markers from the PKD1 region, as OX114. Renal ultrasound revealed no cysts in OX984 at age 53 and no deletion was detected by DNA analysis (FIG. 5c). Hence, the deletion in OX114 is a de novo event associated with the development of ADPKD. Although it is not possible to show that the ADPKD in chromosome 16-linked, the location of the PBP gene indicated that this is a de novo PKD1 mutation.

To identify more PKD1 associated mutations, single copy regions of the PBP gene were analyzed by RT-PCR using RNA isolated from lymphoblastoid cell lines established from ADPKD patients. cDNA from 48 unrelated patients was amplified with the primer pair 3A3 C [Seq. I.D. Nos. 11 and 12] (see Experimental Procedures) and the product of 260 bp was analyzed on an agarose gel. In one patient, OX32, an additional smaller product (125 bp) was identified, consistent with a deletion or splicing mutation. OX32 comes from a large family in which the disease can be traced through three generations. Analysis of RNA from two affected sibs of OX32 and his parents showed that the abnormal transcript segregates with PKD1 (FIG. 5d).

Amplification of normal genomic DNA with the 3A3 C primers (Seq. I.D. Nos. 11 and 12) generates a product of 418 bp; sequencing showed that this region contains two small introns (5', 75 bp and 3', 83 bp) flanking a 135 bp exon. The product amplified from OX32 genomic DNA was normal in size, excluding a genomic deletion. However, heteroduplex analysis of that DNA revealed larger heteroduplex bands, consistent with a mutation within that genomic interval. The abnormal OX32, RT-PCR product was cloned and sequenced: this demonstrated that, although present in genomic DNA, the 135 bp exon was missing from the abnormal transcript. Sequencing of OX32 genomic DNA demonstrated a G-->C transition at +1 of the splice donor site following the 135 bp exon. This mutation was confirmed in all available affected family members by digesting amplified genomic DNA with the enzyme Bst NI: a site is destroyed by the base substitution. The splicing defect results in an in-frame deletion of 135 bp from the PBP transcript (3696 bp to 3831 bp of the sequence shown in FIG. 7 [Seq. I.D. No. 1]). Together, the three intragenic mutations confirm that the PBP gene is the defective gene at the PKD1 locus.

Deletions that Disrupt the TSC2 and the PKD1 Gene

The deletion called WS-53 disrupts both the TSC2 gene and the PKD1 gene (European Chromosome 16 Tuberous Sclerosis Consortium, 1993), although the full proximal extent of the deletion was not determined. Further study has shown that the deletion extends ~100 kb (see FIG. 6 for details) and deletes most if not all of the PKD1 gene. This patient has TSC but also has unusually severe polycystic disease of,the kidneys. Other patients with a similar phenotype have also been under investigation. Deletions involving both TSC2 and PKD1 were identified and characterized in six patients in whom TSC was associated with infantile polycystic kidney disease. As well as the deletion in WS-53, those in WS-215 and WS-250 also extended proximally well beyond the known distribution of PKD1 and probably delete the entire gene. The deletion in WS-194 extended over the known extent of PKD1, but not much further proximally, while the proximal breakpoints in WS-219 and WS-227 lay within PKD1 itself. Northern analysis of case WS-227 lay within PKD1 itself. Northern analysis of case WS-219 with probe JH8, which lies outside the deletion, showed a reduced level of the PKD1 transcript but no evidence of an abnormally sized transcript (data not shown). Analysis of samples from the clinically unaffected parents of patients WS-53, WS-215, WS-219, WS-227 and WS-250 showed the deletions in these patients to be de novo. The father of WS-194 was unavailable for study.

In a further case (WS-212), renal ultrasound shoed no cysts at four years of age but a deletion was identified which removed the entire TSC2 gene and deleted an XbaI site which is located 42 bp 5' to the polyadenylation signal of PKD1. To determine the precise position of the proximal breakpoint in PKD1, a 587 bp probe from the 3' untranslated region (3'UTR) was hybridized to XbaI digested DNA. A 15 kb XbaI breakpoint fragment was detected with an approximately equal intensity to the normal fragment of 6 kb, indicating that most of the PKD13'VTR was preserved on the mutant chromosome. Evidence that a PKD1 transcript is produced from the deleted chromosome in WS-212 was obtained by 3' rapid identification of cDNA ends (RACE) with a novel, smaller product generated from WS-212 cDNA. Characterization of this product showed that polyadenylation occurs 546 bp 5' to the normal position, within the 3'UTR of PKD1 (231 bp 3' to the stop codon at 5073 bp of the described PKD1 sequence[14] [Seq. I.D. No. 1]). A transcript with an intact open reading frame is thus produced from the deleted WS-212 chromosome. It is likely that a functional PKD1 protein in produced from this transcript, explaining the lack of cystic disease in this patient. The sequence preceding the novel site of polyA addition is: AGTCAGTAATTTATATGGTGTTAAAATGTG(A)n [Seq. I.D. No. 22]. Although not conforming precisely to the consensus of AATAAA, it is likely that part of this AT rich region acts as an alternative polyadenylation signal if, as in this case, the normal signal is deleted (a possible sequence is underlined).

The WS-212 deletion is 75 kb between SM9-CW9 distally and the PKD1 3'UTR proximally. The WS-215 deletion is 160 kb between CW15 and SM6-JH17. WS-194 has 65 kb deleted between CW20 and CW10-CW36. WS-227 has a 50 kb deletion between CW20 and JH11 and WS-219 has a 27 kb deletion between JH1 and JH6. The distal end of the WS-250 deletion is in CW20 but the precise location of the proximal end is not known. However, the same breakpoint fragment of 320 kb is seen with Pvul-digested DNA using probes on adjacent Pvul fragments, CE18 (which normally detects a 245 kb fragment) and Blu24 (235 kb). Hence this deletion can be estimated ~160 kb. b. PFGE analysis of the deletion in WS-219. Mlul digested DNA from a normal control (N) and WS-219 probed with the clones H2, JH1, CW21 and CW10 [Seq. I.D. No. 4] which detect an ~130 kb fragment in normal individuals. CW10 [Seq. I.D. No. 4] also detects a much smaller fragment from the duplicated region situated more proximally on 16p. A novel fragment of 100 kb is seen in WS-219 with probes H2 and CW10 [Seq. I.D. No. 4] which flank the deletion in this patient. JH1 is partially deleted but detects the novel band weakly. The aberrant fragment is not detected by CW-21, which is deleted on the mutant chromosome. BamHl digested DNA of normal control (N) and WS-219 separated by conventional gel electrophoresis and hybridized to probes JH1 and JH6 which flank the deletion. The same breakpoint fragment of ~3 kb is seen with both probes, consistent with a deletion of ~27 kb ending within the BamHl fragments seen by these probes.

Two Further Deletions

In addition we have characterized two further mutations of this gene which were identified in typical PKD1 families. In both cases the mutation is a deletion in the 75 bp intron amplified by the primer pair 3A3C [Seq. I.D. Nos. 11 and 12] (European Polycystic Kidney Disease Consortium, 1994). The deletions are of 18 bp and 20 bp, respectively, in the patients 461 and OX1054. Although these deletions do not disrupt the highly conserved sequences flanking the exon/intron boundaries, they do result in aberrant splicing of the transcript. In both cases, two abnormal mRNAs are produced, one larger and one smaller than normal. Sequencing of these cDNAs showed that the larger transcript includes the deleted intron, and so has an in-frame insertion of 57 bp in 461, while OX1054 has a frameshift insertion of 55 bp. The smaller transcript is due to activation of a cryptic splice site in the exon preceding the deleted intron and results in an in-frame deletion of 66 bp in both patients. The demonstration of two additional mutations of this gene in PKD1 patients further confirms that this is the PKD1 gene.

Partial Characterization of the PKD1 Gene

To characterize the PKD1 gene further, evolutionary conservation was analyzed by 'zoo blotting'. Using probes from the single copy, 3' region (3A3) and from the duplicated area (JH4, JH8) the PKD1 gene was conserved in other mammalian species, including horse, dog, pig and rodents (data not shown). No evidence of related sequences were seen in chicken, frog or drosophila by hybridization at normal stringency. The degree of conservation was similar when probes from the single copy of the duplicated region were employed.

Although the full genomic extent of the PKD1 gene was not yet known, results obtained by hybridization to Northern blots showed that it extended from at least as far as JH13. Several CpG islands were localized 5' of the known extent of the PKD1 gene (FIG. 6), although there was no direct evidence that any of these are associated with this gene.

The cDNA contig extending 5631 bp to the 3' end of the PKD1 transcript was sequenced; where possible more than one cDNA was analyzed and in all regions both strands were sequenced (FIG. 7 [Seq. I.D. No. 1]). We estimated that this accounts for ~40% of the PKD1 transcript. An open reading frame was detected which runs from the 5' end of the region sequenced and spans 4842 bp, leaving a 3' untranslated region of 789 bp which contains the previously described microsatellite, KG8 (Peral, et al., 1994; Snarey, et al., 1994). A polyadenylation signal is present at nucleotides 5598–5603 and a polyA tail was detected in two independent cDNAs (AH4 and AH6) at position, 5620. Comparison with the cDNAs HG-4 and 11BHS21, which are encoded by genes in the duplicate, 16p13.1 region, show that 1866 bp at the 5' end of the partial PKD1 sequence shown in FIG. 7 [Seq. I.D. No. 1] lies within the duplicated area. The predicted amino acid sequence from the available open reading frame extends 1614 residues, and is shown in FIG. 7 [Seq. I.D. No. 1]. A search of the swissprot and NBRF data bases with the available protein sequence, using the Blast program (Altschul, et al., 1990) identified only short regions of similarity (notably, between amino-acids 690–770 and 1390–1530) to a diverse group of proteins; no highly significant areas of homology were recognized. The importance of the short regions of similarity. is unclear as the search for protein motifs with the ProSite Program did not identify any recognized functional protein domains within the PKD1 gene.

The test of identifying and characterizing the PKD1 gene has been more difficult than for other disorders because more than three quarters of the gene is embedded in a region of DNA that is duplicated elsewhere on chromosome 16. This segment of 40–50 kb of DNA, present as a single copy in the PKD1 area (16p13.3), is reiterated as several divergent copies in the more proximal region, 16p13.1. This proximal site contains three gene loci (HG-A, -B and -C) that each produce polyadenylated mRNAs and share substantial homology to the PKD1 gene; it is not known whether these partially homologous transcripts are translated into functional proteins.

Although gene amplification is known as a major mechanism for creating protein diversity during evolution, the discovery of a human disease locus embedded within an area duplicated relatively recently is a new observation. In this case because of the recent nature of the reiteration the whole duplicated genomic region retains a high level of homology, not just the exons. The sequence of events leading to the duplication and which sequence represents the original gene locus are not yet clear. However, early evidence of homology of the 3' ends of the three HG transcripts which are different from the 3' end of the PKD1 gene indicated that the loci in 16p13.1 have probably arisen by further reiteration of sequences at this site, after it separated from the distal locus.

To try to overcome the duplication problem we employed an exon linking approach using RNA isolated from a radiation hybrid, HY145.19, that contains just the PKD1 part of chromosome 16, and not the duplicate site in 16p13.1. Hence, this hybrid produces transcripts from the PKD1 gene but not from the homologous genes (HG-A, HG-B and HG-C). We have also sequenced much of the genomic region containing the PKD1 gene, from the cosmid JH2A, and have sequenced a number of cDNAs from the HG locus. To determine the likely position of PKD1 exons in the genomic DNA we compared HG cDNAs, (HG-4 and HG-7) to the genomic sequence. We then designed primers with sequences corresponding to the genomic DNA, to regions identified by the HG exons and employing DNA generated from the hybrid HY145.19, we amplified sections of the PKD1 transcript. The polymerase Pfu was used to minimise incorporation errors. These amplified fragments were then cloned and sequenced. The PKD1 cDNA contig whose sequence is shown in FIG. 10 is made up of (3'–5') the original 5.7 kb of sequence shown in FIG. 7, and the cDNAs: gap α 22 (890 bp), gap gamma (872 bp), a section of genomic DNA from the clone JH8 (2,724 bp) which corresponds to a large exon, S1–S3 (733 bp), S3–S4 (1,589 bp) and S4–S13 (1,372 bp). Together these make a cDNA of 13,807 nt. When these cDNAs from the PKD1 contig were sequenced an open reading frame was found to run from the start of the contig to the stop codon, a region of 13,018 bp (SEQ ID NO. 5). The predicted protein encoded by the PKD1 transcript is also shown in FIG. 10 (SEQ ID NO. 6) and has 4,339 amino acid residues.

Cloning a Full Length PKD1 cDNA cDNAs known to originate from the PKD1 or HG transcripts show on average a sequence divergence of less than 3%. Consequently, although many cDNAs were identified by hybridisation of various PKD1 genomic probes to cDNA libraries, it proved difficult to differentiate genuine PKD1 clones from those of the HG transcripts. For this reason a novel strategy was employed to clone the PKD1 transcript.

To obtain a template of genomic sequence of the PKD1 gene, clones which contain the transcribed region, JH6 and JH8–JH13, were sequentially truncated and sequenced. These clones were isolated from the cosmid JH2A, which extends into the single copy area containing the 3' portion of the PKD1 gene (FIG. 13) and hence represents the PKD1 and not the HG loci. As a result of this analysis a contig of about 18 kb of genomic sequence was generated, which was ultimately found to encode >95% of the unsequenced portion of the PKD1 transcript.

A number of HG cDNA clones identified by the DNA probes JH8 or JH13 (including HG-4, HG-7C and 13A1) were sequenced. Clones identified by JH8 were chosen because this genomic area is duplicated fewer times than the surrounding DNA, with only the HG-A and HG-B transcripts (not HG-C) homologous to this region. The comparison of these cDNA and genomic sequences showed a characteristic intron/exon pattern and we concluded that the exons highlighted in the genomic sequence were likely to be exons of the PKD1 gene. To prove this, pairs of primers matching the sequence of the putative PKD1 exons and spaced 0.7–2 kb apart in the proposed transcript, were synthesised. Employing RNA from a radiation hybrid, HY145.19, that contains the PKD1 but not the HG loci, PKD1 specific cDNAs were amplified by RT-PCR and cloned (see Experimental Procedures for details). In this way, a number of overlapping cDNAs spanning the PKD1 transcript, for the cDNAs at the 3' end to those homologous to JH13 were cloned (FIG. 13).

Analysis of a further cDNA, HG-6 showed that a short region (~100 bp) of HG-6 lay 5' to the sequenced genomic region and this was located by hybridisation to the genomic clone SM3 (FIG. 13); SM3 was subsequently sequenced. The position of the cDNA in SM3 was identified and the possible 5' extent of this exon was determined in the genomic sequence; and in-frame stop codon was identified hear the 3' end of the exon. This exon lay at a CpG island (described hereinafter) suggesting, along with the presence of the stop codon, that this may be the first exon of the PKD1 gene. to determine the likely transcriptional start site the method of primer extension from three different oligos within the first exon was employed (see Experimental Procedures). In all cases, a transcriptional start was identified at the same G nucleotide and showed the first exon to be 426 bp. The structure of the PKD1 transcript was confirmed by a final exon link, rev1 which starts 3 bp 3' to the proposed transcriptional start (see FIG. 13 and Experimental Procedures for details).

The Intron/exon Structure of the PKD1 Gene

Sequencing the cDNA contig revealed a total sequence of 14, 148 bp which extends over approximately 52 bp of genomic sequence from SM3 to BFS5 (FIG. 13). We were able to determine the intron/exon structure of much of the gene by direct comparison between the cDNA and genomic sequence. In the 3' region of the gene (JH5-BFS5), a partial genomic sequence was obtained at intron/exon borders by sequencing the corresponding genomic clone from exonic primer.

The PKD1 CpG Island

The 5' end of the gene lies at CpG island SM3. SM3 is located entirely within the duplicated region, but this clone was isolated from the cosmid SMll which extends through the duplicated area into the proximal flanking single copy region and therefore is known to originate from this area. FIG. 14 shows a map of the PKD1 CpG island including genomic sites for several methylation sensitive enzymes, the location of the first exon and the GC content across the island. Evidence that the enzyme sites in the PKD1 region (and not just the HG area) digest, was obtained by pulsed field gel electrophoresis with the enzymes Mlul, Notl and BssHll using probes outside the duplicated area. Digestion of the Sacll sites and confirmation of the Notl site was made with a panel of somatic cell hybrids which either contain just the HG (P-MWH2A) or just the PKD1 locus (Hy145.19). These results showed that the Sacll and Notl sites digest in both sets of hybrids (data not shown), indicating that this region is a CpG island in the HG as well as the PKD1 area. Further proof that this is the likely position of a functional promoter was obtained by analysis for DNAase 1 hypersensitivity. A DNAase hypersensitive site in the region 5' to the transcription start site in SM3 was detected (FIGS. 14a and b).

Analysis of the PKD1 Transcript

Analysis of the sequence shows an open reading frame running from the start of the sequence to position 13,117 bp (FIG. 15 [SEQ ID NO. 7]). Detailed sequencing of the genomic region containing the 3' portion of the gene revealed two extra Cs at positions 13,081–2 (FIG. 15 (SEQ ID NO. 7)). An in-frame start codon which is consistent with the Kozak consensus was detected at position 212 bp; just 3' to the stop codon in the 5'UTR. Analysis for a signal sequence cleavage site using the von Hinge (von Hinge 1986) algorithm showed a high probability of a hydrophobic signal sequence with cleavage at amino acid 23 (see FIG. 15 (SEQ ID NO. 8)). The total length of the predicted protein is 4302 aa with a calculated molecular mass after excision of the signal peptide of 460 kD and an estimated isoelectric point of 6.26. However, this may be an underestimate of the total mass of the protein as many potential sites for N-linked glycosylation are present (FIG. 15 (SEQ ID NO.8)).

Homologies with the PKD1 Protein

The predicted PKD1 protein was analysed for homologies with know proteins in the SwissProt and NBRF databases using the BLAST Altschul et al 1990) and FASTA algorithms. This analysis revealed two clear homologies and also a number of other potential similarities which were studied on detail.

Leucine Rich Repeat

Near the 5' end of the PKD1 protein is a region of leucine rich-repeats (LRRs). LRRs are a highly conserved motif usually of 24 residues with precisely spaced leucines (or other aliphatic amino acids) and an asparagine at position 19 (FIG. 16a and reviewed in Kobe and Reisenhofer (1994)).

Two complete LRRs plus a partial repeat unit are found in the PKD1 protein, which have complete homology with the LRR consensus.

Surrounding the LRRs are distinctive cysteine-rich amino and carboxy flanking regions (FIGS. 16b and c). This flank-LRR-flank structure is exclusively found on proteins in extracellular locations and is thought to be involved in protein-protein interactions such as adhesion to other cells or to components of the extracellular matrix or as a receptor concerned with binding or signal transduction. The structure found in the PKD1 protein is similar to that found in the Drosophila protein, slit, which is important for normal central nervous system development (Rothberg, 1990). Although slit contains far more LRRs than the PKD1 protein, with four blocks each consisting of 4 or 5 repeat units, the structure of each block is similar as they finish on the amino and carboxy side with shortened LRRs which are immediately flanked by the cysteine rich regions. In the PKD1 protein two shortened LRRs surround one complete repeat unit and immediately abut the amino and carboxy flanking regions.

The amino flanking region consists of four invariant cysteines and a number of other highly conserved residues in an area of 30–40 amino acids; comparison of the PKD1 region to amino flanking motifs of other proteins is shown in FIG. 4b. The carboxy flanking region extends over an area of between 50–60 residues and consists of an invariant proline and four cysteines plus several other highly conserved amino acids. The similarity of the PKD1 region to carboxy flanking regions from other proteins is shown in FIG. 4c.

Some LRR proteins, such as slit (Rothberg 1990) and small proteoglycans are wholly extracellular but others including Toll (Hashimoto et al, 1990) and trkc (Lamballe 1991) have a single transmembrane sequence, while the LH-CRG receptor and related proteins have seven transmembrane segments and are involved in signal transduction.

C Type Lectin Domain

Analysis of the sequence from exons 6 and 7 showed a high level of homology with a C type lectin domain. C type lectins are found in a variety of proteins in extracellular locations where they bind specific carbohydrates in the presence of $Ca^{2+}$ ion (Drickamer 1987, 1988; Weiss 1992) FIG. 17 illustrates the similarity of the PKD1 lectin domain to those found in a number of proteins including: proteogylcans, which interact with collagens and other components of the extracellular matrix; endocytic receptors, and selectins which are involved in cell adhesion and recognition. Three different selectins have been identified: E-selectin (endothelium), P-selectin (platelets) and L-selectin (lymphocytes) and these work with other cell adhesion molecules to promote binding of the cell carrying the selectin to various other target cells.

Immunoglobulin-like Repeat Motif

Significant homologies were detected between a region of exon 5 and three regions of exon 15, with the same conserved sequence, WDFGDGS (SEQ ID NO. 8), which is also found in a melanocyte-specific secreted glycoprotein, Pmel17 (Kwon et al, 1991) and three prokaryotic collagenases or proteinases (Ohara et al, 1989, Takeuchi et al, 1992 and Matsushita et al, 1994). Further analysis of the amino acid sequence of the PKD1 protein showed that a conserved region of approximately 85 bp could be discerned around this central sequence and that 16 copies of this repeat were present in the PKD1 protein; 1 in exon 5 and the other 15 as a tandem array in exons 11 to 15. FIG. 18 shows that a highly conserved structure is maintained between the repeats although in some cases less similarity is noted with the WDFGDGS (SEQ ID NO. 8) sequence. Further analysis of the most conserved residues found in the repeat units showed similarity to various immunoglobulin (Ig) domains; two Ig repeats which show particular homology to the PKD1 protein are shown (FIG. 18). The repeat unit is most similar to that found in a number of cell adhesion and surface receptors which have recently been defined as the I set of Ig domains (Harpaz 1994). Ig repeats consist of 7–9 β strands of 5–10 residues linked by turns which are packed into two β sheets. The B, C, F and G β-strands of the I set are particularly similar to the PKD1 repeat, although the highly conserved cystine residues which stabilise the two β sheets through a disulphide bond are absent. The D and E β strands, however, seem less similar and in some cases are significantly shortened or apparently absent. Further evidence that this PKD1 repeat has an Ig-like structure is found by analysis of the secondary structure with the predominant configuration found of β strands linked by turns. The WDFGDS (SEQ ID NO. 23) area of the Ig molecule is one that often has a specific binding function (Jones et al., 1995) and this sequence may have a specific binding role in polycystin.

Type III Fibronectin-related Domains

Analysis of the secondary structure of the PKD1 protein beyond the carboxy end of the region of Ig-like repeats showed a continuation of the β stand and turn structure. No evidence of further Ig-like repeats could be found in this area but three pairs of evenly spaced (38–40aa) tryptophan and tyrosine residues was noted which are the most highly conserved positions of the type III fibronectin repeat which has a similar secondary structure to Ig domains. Further analysis and comparison with other type III fibronectin domains showed that in total four fibronectin repeats (one with leucine replacing the conserved tyrosine) could be recognised in this area with many of the most highly conserved residues of this domain found in the PKD1 repeat (FIG. 20).

A large number of proteins with Ig-like repeats have now been described which are involved in cell-cell interactions and cell adhesion (reviewed in: Brummendork and Rathjen, 1994), while type III fibronectin (FNIII) domains are found on extracellular matrix molecules and adhesion proteins. A number of cell adhesion proteins which are located mainly on neural cells, have both Ig-like and FNIII-related domains. In these cases the FNIII repeats are always positioned C-terminal of the Ig-like units and close to a transmembrane domain; a similar pattern is seen in the proposed structure of polycystin. These Ig/FNIII containing proteins such as neuroglican and NrCAM are thought to be involved in neuron-neuron interactions and the patterning of the axonal network.

Many cell adhesion proteins of the Ig superfamily are also involved in communication and signal transduction mediated through their cytoplasmic tails. These cytoplasmic regions are known to bind to cytoskeletal proteins and other intracellular components, and phosphorylation of this part of the molecule is also thought to affect adhesive properties of the protein; potential phosphorylation sites are found in the cytoplasmic tail and one intracellular loop of polycystin (FIG. 20).

Transmembrane Regions

Analysis of hydrophobicity predicted that the deduced protein is an integral membrane protein with a signal peotide and multiple transmembrane (TM) domains located in the C-terminal region. From this analysis 11 regions (including the signal peptide) had a mean hydrophobicity indice higher than 1.4 and therefore were considered as certain membrane spanning domains (see Experimental Procedures for details). Three others with a mean hydrophobicity indice between 0.75–1.0 were considered as putative TM domains. The most likely topology of the protein was predicted using TopPed II programme (see Experimental Procedures for details) and the resulting model included one putative segment plus the 10 certain transmembrane domains and the signal peptide. According to this model the N-terminal end is extracellular and the (highly hydrophobic) carboxy-terminal region is anchored to the membrane by 11 membrane-spanning segments, with the highly charged carboxy end located in the cytoplasm. This topology is supported by the study of N-glycosylation sites with all but one site, out of a total of 61 predicted, in an extracellular location according to the model, including 11 in the two large extracellular loops between TM regions.

However, if degree of hydrophobicity required to define a certain putative transmembrane region is altered within the model, the predicted number of such domains can change to 9 (excluding the most N-terminal pair) or 13 (with two new domains defined between TM7 and TM8). This can be ascertained by studies with specific antibodies.

Most transmembrane proteins containing the types of cell adhesion domain found on polycystin have a single transmembrane domain. The role of the multiple membrane spanning domains found in polycystin is not yet clear.

Proposed Structure of the PKD1 Protein

From the detailed analysis of the predicted PKD1 protein sequence a model of the likely structure of the protein can be formulated (FIG. 20). This model predicts an extracellular N-terminal region of approximately 2550 aa containing several distinctive extracellular domains and an intracellular C-terminus of approximately 225 aa. The intervening region of nearly 1500 aa is associated with the membrane with 11 transmembrane regions predicted and 10 variously sized extracellular and cytoplasmic loops (see FIG. 20). A proline rich hinge is found between the flank-LRR-flank region and the first Ig-like repeat. Two phosphorylation sites for tyrosine kinase and protein kinase C are found in cytoplasmic locations (FIGS. 15 (SEQ ID NO. 8) and 20).

Therefore, the PKD1 protein, named polycystin, has highlighted several clear domains, plus a reiterated motif that occupies over 30% of the protein.

Characterisation of the PKD1 gene has proven to be a uniquely difficult problem because most of the gene lies in a region which is reiterated elsewhere on the chromosome. The high degree of similarity between the two areas (>97%) both in exons and introns has meant that a novel approach has been required to clone the full length transcript; involving extensive genomic sequencing and generating cDNAs from a cell line with the PKD1 but not the HG loci. In this way a contig containing the entire PKD1 transcript has now been cloned.

Preliminary analysis shows that the HG genes are very similar to PKD1 both in terms of genomic structure and sequence over most of their length (apart from the novel 3' regions). The 5' end of the PKD1 gene is at a CpG island which lies within the duplicated area. Homologous areas to this island, in the HG region, also have cleavable sites for methylation sensitive enzymes; these duplicate islands probably lie at the 5' ends of the various HG genes. Analysis for DNAase hypersensitivity also indicates that the HG, CpG islands probably contain active promoters. These results are consistent with the observation of polyadenylated mRNA from the HG genes on Northern blots and the similarity of the expression pattern of the HG and PKD1 genes in different tissue specific cell lines. The HG genes may have complete open reading frames and may encode functional proteins. Antibodies to their 'unique' 3' regions will be required to determine this. Although the PKD1 transcript is large, the overall size of the gene, at 52 kb, is not (the Duchenne muscular dystrophy (DMD) gene which encodes a slightly smaller transcript has a genomic size of over 2 Mb). Indeed, if the first intron of PKD1 is excluded from the analysis, 40.3% of the remainder of the gene is found in the mature mRNA. In the compact structure of the PKD1 gene, some of the introns are close to or smaller than the minimal size of 80 bp thought to be required for efficient splicing, although they are presumably excised effectively. We have shown that deletion of 18 or 10 bp from one small intron (intron 43), resulting in an intron of 55 or 57 bp, leads to aberrant splicing (Peral, 1995). Similar mutations may be found in the other small introns of this gene. The compact nature of the PKD1 gene probably reflects the GC rich area of the genome in which it is found (the PKD1 transcript has a total GC content of about 65%); a similar organisation is seen in other genes from the area of chromosome 16 (Vyas, 1992) is in an AT rich genomic region.

It is clear that polycystin has many features of a cell adhesion or recognition molecule with multiple different extracellular domains. These various binding domains are likely to have different specificities so that it can be envisaged that it will bind to a variety of different proteins (and carbohydrates) both on other cells and possibly in the extracellular matrix. Although provisional evidence indicates a wide range of expression of polycystin in tissue specific cell lines, detailed analysis by in situ of the mRNA and with antibodies to determine the cells expressing this protein both in adult tissue and during development will provide further evidence.

Initial analysis has revealed little clear evidence of alternate splicing, although one cDNA (out of 6 studied) had an extra exon of 255 bp positioned in intron 16. This exon contains an in-frame stop codon and it is not known at this stage if this represents an incompletely spliced mRNA or a splice form of polycystin which terminates at this point. Truncation of the protein here would leave a secreted protein lacking all of the transmembrane and cytoplasmic regions. Interestingly, a similar secreted form of the neural adhesion protein, NCAM, which is normally attached to the cell membrane, is produced by alternate splicing by insertion of an exon containing a stop codon (Gower et al., 1988).

The initial changes that have been noted in ADPKD kidneys are abnormal thickening and splitting of the basement membrane (BM) and simultaneous de-differentiation of associated epithelial cells at the point of tubular dilation. Similar results have been noted in the heterozygote Han:SPRD rat (Schafer et al., 1994) which is a dominant model of PKD, although it is not known if it is a rat model of PKD1. Concurrent changes in cellular characteristics and the BM suggests that a disruption or alteration of communication between the cell and the BM may be the primary change in this disease. Polycystin could play an important role in interaction and communication between epithelial cells and the BM. It is known that signals are required from cells to the extracellular matrix (ECM) for normal BM development and also that communication from the ECM to cells is required for control of cellular differentiation. Communication between the ECM and cells occurs by several different means including through integrins and so polycystin may bind to integrins, although it may interact directly with components of the ECM. Although ADPKD is generally a disease of adulthood, there is plenty of evidence that the cystic changes in the kidney may start much earlier (Milutinovic et al., 1970), even in utero (Reeders, 1986). Expression of polycystin during renal development may be when its major role occurs, perhaps in assembly of the BM and it is then that the errors, which later lead to cyst development, occur.

The plethora of connective tissue abnormalities associated with ADPKD indicate that the adhesion/communication roles of polycystin may be important for assembly and/or maintenance of the BM in many tissues, as well as the kidney. Hence, it is possible that disruption of normal cell adhesion and communication mediated by polycystin may explain the primary defects seen in the kidney and other organs in ADPKD. Clearly molecules that interact with polycystin or have a similar role are candidates for the other renal polycystic diseases of man.

A study of the mutations of the PKD1 gene highlight important functional regions of the protein. All of the mutations described so far in typical PKD1 families involve deletion or other disruption in the 3' end of gene. Two large deletions detected on Southern blots remove a large part of the protein (or make an out of frame product) including the last 6 transmembrane domains and the C-terminal end. The in-frame splicing change described in the same paper would remove most of TM10 and part of the preceding cytoplasmic loop. Two recently described splicing mutations (Peral, 1995) create three different products which either delete part of the cytoplasmic loop between TM7 and TM8 or a larger region of this loop including part of TM7 or insert an extra region into that loop. These mutated genes may make functional protein (they all produce abnormal mRNA) and it is interesting to note that, in each case, these proteins would have an intact extracellular region with disrupted cytoplasmic and transmembrane areas. Such proteins may bind to extracellular targets but are unable to communicate in a normal way.

A group of mutations of PKD1 which completely delete the gene and hence are clearly inactivating have been described (Brook-Carter, 1994). However, in each of these cases the deletions also disrupt the adjacent TSC2 gene making interpretation of these cases difficult (TSC2 mutations alone can cause the development of renal cysts). Nevertheless, the severity of the polycystic disease in these patients indicate that inactivation of one PKD1 allele does promote cyst development. Further more, all these children are often severely affected at birth, cyst formation must occur in utero in these cases and hence polycystin has an important developmental role. A second somatic hit in the target tissue may also be required in these cases (and normal PKD1 patients) before cyst development can occur.

PKD1 Gene and Polycystic Kidney Disease

We have therefore compelling evidence that mutations of the PKD1 gene give rise to the typical phenotype of ADPKD. The location of this gene within the PKD1 candidate region and the available genetic evidence from the families with mutations show that this is the PKD1 gene. The present invention therefore includes the complete PKD1 gene itself and the six PKD1—associated mutations which have been described: a de novo translocation, which was subsequently transmitted with the phenotype; two intragenic deletions (one a de novo event); two further deletions; and a splicing defect.

It has been argued that PKD1 could be recessive at the cellular level, with a second somatic mutation required to give rise to cystic epithelium (Reeders, 1992). This "two hit" process is thought to be the mutational mechanism giving rise to several dominant diseases, such as neurofibromatosis (Legius, et al., 1993) and tuberous sclerosis (Green, et al., 1994) which result from a defect in the control of cellular growth. If this were the case, however, we might expect that a proportion of constitutional PKD1 mutations would be inactivating deletions as seen in these other disorders.

The location of the PKD1 mutations may, however, reflect some ascertainment bias as it is this single copy area which has been screened most intensively for mutations. Nevertheless, no additional deletions were detected when a large part of the gene was screened by FIGE, and studies by PFGE showed no large deletions of this area in 75 PKD1 patients. It is possible that the mutations detected so far result in the production of an abnormal protein which causes disease through a gain of function. However, it is also possible that these mutations eliminate the production of functional protein from this chromosome and result in the PKD1 phenotype by haploinsufficiency, or only after loss of the second PKD1 homologue by somatic mutation.

At least one mutation which seems to delete the entire PKD1 gene has been identified (WS-53) but in this case it also disrupts the adjacent TSC2 gene and the resulting phenotype is of TSC with severe cystic kidney disease. Renal cysts are common in TSC so that the phenotypic significance of deletion of the PKD1 gene in this case is difficult to assess. It is clear that not all cases of renal cystic disease in TSC are due to disruption of the PKD1 gene; chromosome 9 linked TSC (TSC1) families also manifest cystic kidneys and we have analysed many TSC2 patients with kidney cysts who do not have deletion of the PKD1 gene.

Preliminary analysis of the PKD1 protein sequence (SEQ ID NO. 8) has highlighted two regions which provide some clues to the possible function of the PKD1 gene. At the extreme 5' end of the characterised region are two leucine-rich repeats (LRRs) (amino acids 29–74) flanked by characteristic amino flanking (amino acids 6–28) and carboxy flanking sequences (amino acids 76–133) (Rothberg et al., 1990). LRRs are thought to be involved in protein-protein interations (Kobe and Deisenhofer, 1994) and the flanking sequences are only found in extracellular proteins. Other proteins with LRRs flanked on the amino and carboxy sides are receptors or are involved in adhesion or cellular signalling. Further 3' on the protein (amino acids 350–515) is a C-type lectin domain (Curtis et al., 1992). This indicates that this region binds carbohydrates and is also likely to be extracellular. These two regions of homology indicate that the 5' part of the PKD1 protein is extracellular and involved in protein-protein interactions. It is possible that this protein is a constituent of, or plays a role in assembling, the extracellular matrix (ECM) and may act as an adhesive protein in the ECM. It is also possible that the extracellular portion of this protein is important in signalling to other cells. The function of much of the PKD1 protein is still not fully known but the presence of several hydrophobic regions indicates that the protein may be threaded through the cell membrane.

Familial studies indicate that de novo mutations probably account for only a small minority of all ADPKD cases; a recent study detected 5 possible new mutations in 209 families (Davies, et al., 1991). However in our study one of three intragenic muttions detected was a new mutation and the PKD1 associated translocation was also a de novo event. Furthermore, the mutations detected in the two familial cases do not account for a significant proportion of the local PKD1. The OX875 deletion was only detected in 1 of 282 unrelated cases, and the splicing defect was seen in only 1 of 48 unrelated cases. Nevertheless, studies of linkage disequilibrium have found evidence of common haplotypes associated with PKD1 in a proportion of some populations (Peral, et al., 1994; Snarey, et al., 1994) suggesting that common mutations will be identified.

Once a larger range of mutations have been characterised it will be possible to evaluate whether the type and location of mutation determines disease severity, and if there is a correlation between mutation and extra-renal manifestations. Previous studies have provided some evidence that the risk of cerebral aneurysms 'runs true' in families (Huston, et al., 1993) and that some PKD1 families exhibit a consistently mild phenotype (Ryynanen, et al., 1987). A recent study has concluded that there is evidence of anticipation in ADPKD families, especially if the disease is transmitted through the mother (Fink, et al., 1994). Furthermore, analysis of families with early manifestations of ADPKD show that there is a significant intra-familial recurrence risk and that childhood cases are most often transmitted maternally (Rink, et al., 1993; Zerres, et al., 1993). This pattern of inheritance is reminiscent of that seen in diseases in which an expanded trinucleotide repeat was found to be the mutational mechanism (reviewed in Mandel, 1993). However, no evidence for an expanding repeat correlating with PKD1 has been found in this region although such a sequence cannot be excluded.

There is ample evidence that early presymptomatic diagnosis of PKD1 is helpful because it allows complications such as hypertension and urinary tract infections to be monitored and treated quickly (Ravine, et al., 1991). The identification of mutations within a family allow rapid screening of that and other families with the same mutation. However, genetic linkage analysis is likely to remain important for presymptomatic diagnosis. The accuracy and ease of linkage based diagnosis will be improved by the identification of the PKD1 gene as a microsatellite lies in the 3' untranslated region of this gene (KG-8) and several CA repeats are located 5' of the gene (see FIGS. 1a and 6; Peral, et al., 1994; Snarey, et al., 1994).

Experimental Procedures
Clinical Details of Patients
Family 77

77-2 and 77-3 are 48 and 17 years old, respectively and have typical ADPKD. Both have bilateral polycystic kidneys and 77-2 has impaired renal function. Neither patient manifests any signs of TSC (apart from cystic kidneys) on clinical and ophthalmological examination or by CT scan of the brain.

77-4 is 13 years old, severely mentally retarded and has multiple signs of tSC including adenoma sebaceum, depigmented macules and periventricular calcification on CT scan. Renal ultrasound reveals a small number of bilateral renal cysts.
ADPKD Patients OX875 developed ESRD from ADPKD, aged 46. Progressive decline in renal function had been observed over 17 years; ultrasound examinations documented enlarging polycystic kidneys with less extensive hepatic cystic disease. Both kidneys were removed after renal transplantation and pathological examination showed typical advanced cystic disease in kidneys weighing 1920 g and 340 g (normal average 120 g).

OX114 developed ESRD from ADPKD aged 54: diagnosis was made by radiological investigation during an episode of abdominal pain aged 25. A progressive decline in renal function and the development of hypertension was subsequently observed. Ultrasonic examination demonstrated enlarged kidneys with typical cystic disease, with less severe hepatic involvement.

OX32 is a member of a large kindred affected by typical ADPKD in which several members have developed ESRD. The patient himself has been observed for 12 years with progressive renal failure and hypertension following ultrasonic demonstration of polycystic kidneys.

No signs of TSC were observed on clinical examination of any of the ADPKD patients.
DNA Electrophoresis and Hybridisation DNA extraction, restriction digests, electrophoresis, Southern blotting, hybridisation and washing were performed by standard methods or as previously described (Harris, et al., 1990). FIGE was performed with the Biorad FIGE Mapper using programme 5 to separate fragments from 25–50 kb. High molecular weight DNA for PFGE was isolated in agarose blocks and separated on the Biorad CHEF DRII apparatus using appropriate conditions.
Genomic DNA Probes and Somatic Cell Hybrids Many of the DNA probes used in this study have been described previously: MS205.2 (D16S309; Royle, et al., 1992); GGG1 (D16S259; Germino, et al., 1990); N54 (D16S139; Himmelbauer, et al., 1991); SM6 (D16S665), CW23, CW21, and JH1 (European Chromosome 16 Tuberous Sclerosis Consortium, 1993). Microsatellite probes for haplotype analysis were KG8 and W5.2 (Snarey, et al., 1994) SM6, CW3 and CW2, (Peral, et al., 1994), 16AC2.5 (Thompson, et al., 1992); SM7 (Harris, et al., 1991), VK5AC (Aksentijevich, et al., 1993).

New probes isolated during this study were: JH4, JH5, JH6, 11 kb, 6 kb and 6 kb BamH I fragments, respectively, and JH13 and JH14, 4 kb and 2.8 kb BamH I-EcoR I fragments, respectively, all from the cosmid JH2A; JH8 and JH10 are 4.5 kb and 2 kb Sac I fragments, respectively and JH12 a 0.6 Sac I-BamH I fragment, all from JH4; 8S1 and 8S3 are 2.4 kb and 0.6 kb Sac II fragments, respectively, from JH8; CW10 (SEQ ID NO. 4) is a 0.5 kb Not I-Mlu I fragment of SM25A; JH17 is a 2 kb EcoR I fragment of NM17.

The somatic cell hybrids N-OH1 (Germino, et al., 1990), P-MWH2A (European Chromosome 16 Tuberous Sclerosis Consortium, 1993) and Hy145.19 (Himmelbauer, et al., 1991) have previously been described. Somatic cell hybrids containing the paternally derived (BP2-10) and maternally derived (BP2-9) chromosomes from OX114 were produced by the method of Deisseroth and Hendrick (1979).
Constructing a Cosmid Contig Cosmids were isolated from chromosome 16 specific and total genomic libraries, and a contig was constructed using the methods and libraries previously described (European Chromosome 16 Tuberous Sclerosis Consortium, 1993). To ensure that cosmids were derived from the 16p13.3 region (not the duplicate 16p13.1 area) initially, probes from the single copy area were used to screen libraries (e.g. CW21 and N54). Two cosmids mapped entirely within the area duplicated, CW10III and JC10.2B. To establish that these were from the PKD1 area, they were restriction mapped and hybridised with the probe CW10. The fragment sizes detected were compared to results obtained with hybrids containing only the 16p13.3. are (Hy145.19) or only the 16p13.1 region (P-MWH2A).
FISH FISH was performed essentially as previously described (Buckle and Rack, 1993). The hybridisation mixture contained 100 ng of biotin-II-dUTP labelled cosmid DNA and 2.5 mg human Cot-1 DNA (BRL), which was denatured and annealled at 37° C. for 15 min prior to hybridisation at 42° C. overnight. After stringent washes the site of hybridisation was detected with successive layers of fluorescein-conjugated avidin (5 mg/ml) and biotinylated ani-avidin (5 mg/ML) Vector Laboratories). Slides were mounted in Vectashield (Vector Laboratories) containing 1 mg/ml propidium iodide and 1 mg/ml 4', 6-diamidino-2-phenylindole (DAPI), to allow concurrent G-banded analysis under UV light. Results were analysed and images captured using a Bio-Rad MRC 600 confocal laser scanning microscope.

cDNA Screening and Characterisation

Foetal brain cDNAs libraries in 7 phage (Clonetech and Stratagene) were screened by standard methods with genomic fragments in the single copy area (equivalent to CW23 and CW21) or with a 0.8 kb Pvu II-Eco RI single copy fragment of AH3. Six PBP cDNAs were characterised; AH4 (1.7 kb) and 3A3 (2.0 kb) are described in European Chromosome 16 Tuberous Sclerosis Consortium, 1993, and four novel cDNAs AH3 (2.2 kb), AH6(2.0 kb), A1C (2.2 kb) and B1E (2.9 kb). A Striatum library (Stratagene) was screened with JH4 and a HG-C cDNA, 11BHS21 (3.8 KB) WAS ISOLATED, 21p.9 is a 0.9 kb Pvu II-EcoR I subclone of this cDNA. A HG-A or HG-B cDNA, HG-4 (7 kb) was also isolated by screening the foetal brain library (Stratagene) with JH8. HG-4/1.1 is a 1.1 kb Pvu II-EcoR I fragment from the 3' end of HG-4. 1A1H.6 (SEQ ID NO. 3) is a 0.6 kb Hind III-EcoR I subclone of a TSC2 CDNA, 1A-1 (1.7 kb), which was isolated from the Clonetech library. Each cDNA was subcloned into Bluescript and sequenced utilising a combination of sequential truncation and liigonucleotide primers using DyeDeoxy Terminators (Applied Biosystems) and an ABI 373A DNA Sequencer (Applied Biosystems) or by hand with 'Sequenase' T7 DNA polymerase OUSB).

RNA Procedures

Total RNA was isolated from cell lines and tissues by the method of Chomczynskiand Sacchi (1987) and enrichment for mRNA made using the PolyAT tract mRNA Isolation System (Promega). For RNA electrophoresis 0.5% agarose denaturing formaldehyde gels were used which were Northern blotted, hybridised and washed by standard procedures. The 0.24–9.5 kb RNA (Gibco BRL) size standard was used and hybridisation of the probe (1-9B3) to the 13 kb Utrophin transcript (Love, et al., 1989) in total fibroblast RNA was used as a size marker for the large transcripts.

RT-PCR was performed with 2.5 mg of total RNA by the method of Brown et al. (1990) with random hexamer primers, except that AMV-reverse transcriptase (Life Sciences) was employed. To characterise the deletion of the PBP transcript in OX114 we used the primers:

AH# F9 5' TTT GAC AAG CAC ATC TGG CTC TC 3' (SEQ ID NO.9)

AH3 B7 5' TAC ACC AGG AGG CTC CGC AG 3' (SEQ ID NO.10)

in a DMSO containing PCR buffer (Dode, et al., 1990) with 0.5 mM MgCl$_2$ and 36 cycles of: 94° C., 1 min; 61° C., 1 min; 72° C., 2 min plus a final extension of 10 min. The 3A3 C primers used to amplify the OX32 CDNA and DNA were:

3A3 C1 5' CGC CGC TTC ACT AGC TTC GAC 3' (SEQ ID NO. 11)

3A3 C2 5' ACG CTC CAG AGG GAG TCC AC 3' (SEQ ID NO. 12)

These were employed in a PCR buffer and cycle previously described (Harris, et al., 1991) with 1 mM MgCl$_2$ and an annealing temperature of 61° C.

PCR products for sequencing were amplified with Pfu-1 (Stratagene) and ligated into the Srf-1 site in PCR-Script (Stratagene) in the presence of Srf-1.

RNAse Protection

Tissues from normal and end-stage polycystic kidneys were immediately homogenised in guanidinium thiocyanate. RNA was purified on a cesium chloride gradient and 30 mg total RNA was assayed by RNAse protection by the method of Melton, et al., (1984) using a genomic template generated with the 3A3, C primers (SEQ ID NOS. 11 and 12).

Heteroduplex Analysis

Heteroduplex analysis was performed essentially as described by Keen et al. (1991). Samples were amplified from genomic DNA with the 3A3, C primers (SEQ ID NOS. 11 and 12), heated at 95° C. for 5 minutes and incubated at room temperature for at least 30 minutes before loading on a Hydrolink gel (AT Biochem). Hydrolink gels were run for 12–18 hours at 250V and fragments observed after staining with ethidium bromide.

Extraction and Amplification of Paraffin-embedded DNA

DNA from formalin fixed, paraffin wax embedded kidney tissue was prepared by the method of Wright and Manos (1990), except that after proteinase K digestion overnight at 55° C., the DNA was extracted with phenol plus chloroform before ethanol precipitation. Approximately 50 ng of DNA was used for PCR with 1.5 mM MgCl$_2$ and 40 cycles of 94° C. for 1 min, 50° C. for 1 min and 72° C. for 40 s, plus a 10 min extension at 72° C.

The oligonucleotide primers designed to amplify across the genomic deletion of OX875 were:

AHF42: 5'-GGG CAA GGG AGG ATG ACA AG-3' (SEQ ID NO. 13)

JH14B3 : 5'-GGG TTT ATC AGC AGC AAG CGG-3' which produced a product of about 220 bp in individuals with the OX875 deletion.

3' RACE Analysis of WS-212

3' RACE was completed essentially as described (European Polycystic Kidney Disease Consortium (1994)). Reverse transcription was performed with 5 µg total RNA with 0.5 µg of the hybrid dT$_7$ adapter primer using conditions previously described (Fronman et al., (1988)). A specific 3' RACE product was amplified with the primer F5 and adapter primer in 0.5 mM MgCl$_2$ with the program: 57° C., 60 s; 72° C., 15 minutes and 30 cycles of 95° C., 40 s; 57° C., 60 s; 72° C., 60 s plus 72° C., 10 minutes. The amplified product was cloned using the TA cloning system (Invitrogen) and sequenced by conventional methods.

Genomic and cDNA Probes and Somatic Cell Hybrids

The genomic clones CW21, JH5, JH6, JH8, JH10, JH12, JH13 and JH14 and the cDNAs A1C, AH3, 3A3 and AH4 are described herein. Newly described probes are: SM3 a 2.0 kb BamH 1 subclone of the cosmid SM11, JH9, 2.4 kb Sac 1 fragment and JH11, 1.2 kn Sac 1—BamH1 fragment, both from JH4. See Eur. Polycystic Kidney Disease. Consortium, 1994 and Eur. Chromosome 16 Tuberous sclerosis Consortium 1993 for all above clones. DFS5 is a 4.2 kb Not 1-Hind lll fragment of CW23 (Eur. Chromosome 16 Tuberous Sclerosis Consortium, 1993). The cDNAs; BPG4, BPG6, BPG7C and 13-A were isolated from a fetal brain cDNA library in X phage (Stratagene) and are 7 kb, 2 kb, 4.5 kb and 1.2 kb respectively.

The somatic cell hybrids have previously been described, P-MWH2A (Eur. Chromosome 16 Tuberous Sclerosis Consortium, 1993) and Hy145.19 (Himmelbauer et al., 1991).

Exon Linking

Total cellular RNA from the radiation hybrid Hy145.19 was reverse transcribed using random hexamers (Eur. Polycystic Kidney Disease Consortium, 1994). This material was used as a template for PCR using the proof reading polymerase Pfu-1 with the primer pairs described in Table 2 (SEQ ID NO.7). The resultant products were cloned into the Srf-1 site of pPCRscript (SK+) plasmid.

Sequencing

Full length sequence was obtained from the genomic clones, HG cDNAs and exon link clones using the progressive unidirectional deletion technique of Henikoff, (1984). Both strands were then sequenced using DyeDeoxy Terminator Cycle Sequencing and an Applied Biosystems Sequencer 373A. Contig assembly was done using the programmes Assembly line (vs 1.0.7), SeqEd (vs 1.03) and MacVector (4.1.4).

Primer Extension

Primer extension was performed on total cellular fibroblast RNA. 25 µg of RNA was annealed at 60° C. in the presence of 400 mM NaCl to 0.01 pM of HPLC pure oligonucleotide which had been end labelled to a specific activity of $3\times10^7$ cpm/pM with $^{32}$P. Primer extension was then performed in the presence of 50 mM Tris pH8.2, 10 mM DTT, 6 mM $MgCl_2$, 25 mg/ml Actinomycin D, 0.5 mM dNTPs, and 8 units of AMV reverse transcriptase. The extension reaction was continued for 60 min at 42° C. The extension products were compared to a sequencing ladder generated using the same primer on the genomic clone SM3. The primers used were:

N2765:5'-GGCGCGGCGGGCGGCATCGTTA-
    GGGCAGCG-3' (SEQ ID NO.15)

N5496:5'-GGCGGGCGGCATCGTTAGGGCA-
    GCGCGCGC-3' (SEQ ID NO.16)

N5495:5'-ACCTGCTGCTGAGCGACGCCCG-
    CTCGGGGC-3' (SEQ ID NO.17)

Analysis of Sequence Homology

The predicted PKD1 protein was analyzed for homologies with known proteins in the SwissProt and NBRF database using the BLAST (Altschul et al., 1990) and FASTA (Pearson et al., 1988) algorithms. Layouts were prepared by hand and using the programme Pileup.

Transmembrane Regions

Potential transmembrane segments were identified by the method of Sipos and von Heljne (Sipos et al., 1993), using the GES hydrophobicity scale (Engelmen et al., 1986) and a trapezoid sliding window (a full window of 21 residues and a core window of 11 residues), as recommended. Candidate transmembrane domains were selected on the basis of their average hydrophobicity <H>, and were classified as certain (<H>≧1.0) or putative (0.6, <H><1).

The best topology for the protein was predicted on the basis of three different criteria: a) the net charge difference between the 15 N-terminal and the 15 C-terminal residues flanking the most N-terminal transmembrane segment (Hartmann et al., 1989); b) the difference in positively charged residues between the two sides of the membrane in loops smaller than 60 residues, and c) the analysis of the overall amino acid composition of loops longer than 60 residues by the compositional distance method (Nakashima et al., 1992). Using the above criteria the TopPred II program (Sipos wt al., 1993) calculated all the possible topologies of the proteins including the certain transmembrane segments and either included or excluded each of the putative segments to determine the most likely structure.

PKD1 Protein Purification

The PKD1 protein may be purified according to conventional protein purification procedures well known in the art. Alternatively, the protein may be purified from cells harboring a plasmid containing an expressible PKD1 gene. For example, the protein may be expressed in an *E.coli* expression system and purified as follows.

Cells are grown in a 10 liter volume in a Chemap Fermentor (Chemapec, Woodbury, N.Y.) in 2% medium. Fermentation temperature may be 37° C., pH 6.8, and air as provided at 1 vvm. Plasmid selection may be provided using ampicillin for a plasmid containing an ampicillin resistance gene. Typical yield (wet weight) is 30 g/l.

For cell lysis, 50 g wet cell weight of *E.coli* containing the recombinant PKD1 plasmid may be resuspended in a final volume of 100 ml in 50 mM Tris-HCl pH 8.0, 5 mM EDTA, 5 mM DTT, 15 mM mercaptoethanol, 0.5% triton X-100, and 5 mM PMSF. 300 mg lysozyme is added to the suspension, and incubated for 30 min at room temperature. The material is then lyzed using a BEAD BEATER (R) (Biospec Products, Bartlesville, Okla.) containing an equal volume of 0.1–0.15 um glass beads. The liquid is separated from the beads and the supernatant removed, the pellet dissolved in 20 mM Tris-Cl pH 8.0.

The protein may. be purified from the supernatant using DEAE chromatography, as is well known in the art.

Preparation of Antibodies

Antibodies specific for PDK1 protein or a fragment thereof are prepared as follows. A peptide corresponding to at least 8 amino acid residues of the PKD1 sequence of FIG. 15 (SEQ ID NO.8), are synthesized. Coupling of the peptide to carrier protein and immunizations is performed as described (Dymecki, S. M., J. Biol. Chem 267:4815–4823, 1992). Rabbit antibodies against this peptide are raised and sera are titered against peptide antigen by ELISA. The sera exhibiting the highest titer (1:27,000) are most useful.

Techniques for preparing monoclonal antibodies are well known, and monoclonal antibodies of this invention may be prepared by using the synthetic: polypeptides of this invention, preferably bound to a carrier, as the immunogen as was done by Arnheiter et al., Nature, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" the synthetic polypeptides of this invention or their conjugates with a carrier.

Antibodies are utilized along with an "indicating group" also sometimes referred to as a "label". The indicating group or label is utilized in conjunction with the antibody as a means for determining whether an immune reaction has taken place, and in some instances for determining the extent of such a reaction.

The indicating group may be a single atom as in the case of radioactive elements such as iodine 125 or 131, hydrogen 3 or sulfur 35, or NMR-active elements such as fluorine 19 or nitrogen 15. The indicating group may also be a molecule such as a fluorescent dye like fluorescein, or an enzyme, such as horseradish peroxidase (HRP), or the like.

The terms "indicating group" or "label" are used herein to include single atoms and molecules that are linked to the antibody or used separately, and whether those atoms or molecules are used alone or in conjunction with additional reagents. Such indicating groups or labels are themselves well-known in immunochemistry and constitute a part of this invention only insofar as they are utilized with otherwise novel antibodies, methods and/or systems.

Detection of PKD1 and Subcellular Localization

Another embodiment of this invention relates to an assay for the presence of PKD1 protein in cells. Here, an above-described antibody is raised and harvested. The antibody or idiotype-containing polyamide portion thereof is then admixed with candidate tissue and an indicating group. The presence of the naturally occurring amino acid sequence is ascertained by the formation of an immune reaction as signaled by the indicating group. Candidate tissues include any tissue or cell line or bodily fluid to be tested for the presence of PKD1.

Metabolic labeling immunoprecipitation, and immunolocalization assays are performed in cells as described previously (Furth, M. E., et al., Oncogene 1:47–58, 1987; Laemmli, U. K., Nature 227:680–685, 1970; Yarden, Y., et al., EMBO J. 6:3341–3351, 1987; Konopka, J. B., et al., Mol. Cell. Biol. 5:3116–3123, 1985). For immunoblot analysis, total lysates are prepared (using Fruth's lysis buffer) (Fruth, M. E., et al., Oncogene, 1:47–58, 1987). Relative protein concentrations are determined with a colorimetric assay kit (Bio-Rad) with bovine serum albumin as the standard. A protein of lysate containing approximately 0.05 mg of protein is mixed with an equal volume of 2×SDS sample buffer containing 2 mercaptoethanol, boiled for 5 min., fractioned on 10% polyacrylamide-SDS gels (Konopka, J. B., et al., J.Virol., 51:223–232, 1984) and transferred to immunobilon polyvinyldine difluoride (Millipore Corp., Bedford, Mass.) filters. Protein blots are treated with specific antipeptide antibodies (see below). Primary binding of the PKD1-specific antibodies is detected using anti-IgG second antibodies conjugated to horseradish peroxidase and subsequent chemiluminescence development ECL Western blotting system (Amersham International).

For metabolic labeling, $10^6$ cells are labeled with 100 μCi of $^{35}$S-methionine in 1 ml of Dulbecco's modified Eagles medium minus methionine (Amersham Corp.) for 16 h. Immunoprecipitation of PKD1 protein from labeled cells with antipeptide antiserum is performed as described (Dymecki, S. M., et al., supra). Portions of lysates containing $10^7$ cpm of acid-insoluble $^{35}$S-methionine are incubated with 1 μg of the antiserum in 0.5 ml of reaction mixture. Immunoprecipitation samples are analyzed by SDS-polylarcylamide gel electrophoresis and autoradiography.

For immunolocalization studies, $10^7$ CMK cells are resuspended in 1 ml of sonication buffer (60 mM Tris-HCl, pH 7.5, 6mM EDTA, 15 mM EGTA, 0.75M sucrose, 0.03% leupeptin 12 mM phenylmethylsulfonyl fluoride, 30 mM 2-mercaptoethanol). Cells are sonicated 6 times for 10 seconds each and centrifuged at 25,000×g for 10 min at 4° C. The pellet is dissolved in 1 ml of sonication buffer and centrifuged at 25,000×g for 10 min at 4° C.

The pellet (nucleus fraction) is resuspended in 1 ml of sonication buffer and added to an equal volume of 2×SDS sample buffer. The supernatant obtained above (after the first sonication) is again centrifuged at 100,000×g for 40 min at 4° C. The supernatant (cytosolic fraction) is removed and added to an equal volume of 2×concentrated SDS sample buffer. The remaining pellet (membrane fraction) is washed and dissolved in sonication buffer and SDS sample buffer as described above. Protein samples are analyzed by electrophoresis on 10% polyacrylamide gels, according to the Laemmli method (Konopka, J. B., supra) The proteins are transferred from the gels on a 0.45-μm polyvinylidine difluoride membrane for subsequent immunoblot analysis. Primary binding of the PKD1 specific antibodies is detected using anti-IgG second antibodies conjugated to horseradish peroxidase.

For immunohistochemical localization of PKD1 protein, CMK cells or U3T3 are grown on cover slips to approximately 50% confluence and are washed with PBS (pH 7.4) after removing the medium. The cells are prefixed for 1 min at 37° C. in 1% paraformaldehyde containing 0.075% Triton X-100, rinsed with PBS and then fixed for 10 min with 4% paraformaldehyde. After the fixation step, cells are rinsed in PBS, quenched in PBS with o.1 and finally rinsed again in PBS. For antibody staining, the cells are first blocked with a blocking solution (3% bovine serum albumin in PBS) and incubated for 1 h at 37° C. The cells are then incubated for 1 h at 37° C. with antiserum (1:100 dilution or with preimmune rabbit serum (1:100). After the incubation with the primary antibody, the cells are washed in PBS containing 3% bovine and serum albumin and 0.1% Tween 20 and incubated for 1 h at 37° C. in fluorescein-conjugated donkey anti-rabbit IgGs (Jackson Immunoresearch, Maine) diluted 1:100 in blocking solution.

The coverslips are washed in PBS (pH 8.0), and glycerol is added to each coverslip before mounting on glass slides and sealing with clear nail polish. All glass slides are examined with a Zeiss Axiophot microscope.

An indicating group or label is preferably supplied along with the antibody and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

Pharmaceutical Compositions of the Invention; Dosage and Administration

Pharmaceutical formulations comprising PKD1 nucleic acid or protein, or mutants thereof, can be prepared by procedures well known in the art. For example, as injectables, e.g., liquid solutions or suspensions. Solid forms for solution in, or suspension in, a liquid prior to injection also can be prepared. Optionally, the preparation also can be emulsified. The active ingredient can be mixed with excipients which are pharmaceutically acceptable and compatible with the active ingredient. For example, water, saline, dextrose, glycerol, ethanol, etc. or combinations thereof. Also useful are wetting or emulsifying agents, pH buffering agents or adjuvants. PKD1 protein or DNA can be administered parenterally, by injection, for example, either subcutaneously or intramuscularly. Additional formulations which are suitable for other modes of administration include suppositories and, in some cases, oral formulations. In each case, the active protein or the nucleic acid will be present in the range of about 0.05% to about 10%, preferably in the range of about 1–2% by weight. Alternatively, the active protein or the nucleic acid will be administered at a dosage of about 10 mg-2 kg/kg body weight, preferably 50 mg–400 mg/kg/body weight. Administration may be daily, weekly, or in a single dosage, as determined by the physician.

TABLE 1

Details of the exons and introns of the PKD1 gene

| Exons | | | | Introns | |
| --- | --- | --- | --- | --- | --- |
| Exon No. | position (bp) | Size (nt) bp | positions (aa) | Intron No. | Size (bp) |
| 1 | 1–426 | 426 | 1–72 | 1 | ~17 kb |
| 2 | 427–498 | 72 | 73–96 | 2 | 121 |
| 3 | 499–570 | 72 | 97–120 | 3 | 268 |
| 4 | 571–740 | 170 | 121–177 | 4 | 213 |
| 5 | 741–1412 | 672 | 177–401 | 5 | 117 |
| 6 | 1413–1596 | 184 | 401–462 | 6 | 435 |
| 7 | 1597–1817 | 221 | 463–536 | 7 | 188 |
| 8 | 1818–1933 | 118 | 536–575 | 8 | 410 |
| 9 | 1934–2060 | 127 | 525–617 | 9 | 363 |
| 10 | 2061–2308 | 248 | 617–700 | 10 | 452 |
| 11 | 2309–3064 | 756 | 700–952 | 11 | 877 |
| 12 | 3065–3196 | 132 | 952–996 | 12 | 196 |
| 13 | 3197–3372 | 176 | 996–1054 | 13 | 314 |
| 14 | 3373–3506 | 134 | 1055–1099 | 14 | 468 |
| 15 | 3507–7126 | 3,620 | 1099–2306 | 15 | 219 |
| 16 | 7127–7276 | 150 | 2306–2356 | 16 | ? |
| 17 | 7277–7420 | 144 | 2356–2404 | 17 | 127 |
| 18 | 7421–7700 | 280 | 2404–2497 | 18 | 93 |
| 19 | 7701–7914 | 214 | 2497–2568 | 19 | 66 |

TABLE 1-continued

Details of the exons and introns of the PKD1 gene

| Exons | | | | Introns | |
|---|---|---|---|---|---|
| Exon No. | position (bp) | Size (nt) bp | positions (aa) | Intron No. | Size (bp) |
| 20 | 7915–8074 | 160 | 2569–2622 | 20 | ~400 bp |
| 21 | 8075–8227 | 153 | 2622–2673 | 21 | 3.1 kb |
| 22 | 8228–8372 | 145 | 2673–2721 | 22 | 650 |
| 23 | 8373–9002 | 630 | 2721–2931 | 23 | 295 |
| 24 | 9003–9159 | 158 | 2931–2983 | 24 | 180 |
| 25 | 9160–9412 | 254 | 2984–3068 | 25 | 123 |
| 26 | 9413–9608 | 196 | 3068–3133 | 26 | ~1.7 kb |
| 27 | 9609–9779 | 171 | 3133–3190 | 27 | 86 |
| 28 | 9780–9923 | 144 | 3190–3238 | 28 | 93 |
| 29 | 9924–10134 | 211 | 3238–3308 | 29 | 90 |
| 30 | 10135–10261 | 127 | 3309–3351 | 30 | ~1.8 kb |
| 31 | 10262–10378 | 117 | 3351–3390 | 31 | 88 |
| 32 | 10379–10428 | 50 | 3390–3406 | 32 | 224 |
| 33 | 10429–10613 | 185 | 3407–3468 | 33 | 77 |
| 34 | 10614–10707 | 94 | 3468–3499 | 34 | ~3 kb |
| 35 | 10708–10826 | 119 | 3500–3539 | 35 | 78 |
| 36 | 10827–11029 | 203 | 3539–3607 | 36 | 72 |
| 37 | 11030–11224 | 195 | 3607–3672 | 37 | 450 |
| 38 | 11225–11364 | 140 | 3672–3718 | 38 | 361 |
| 39 | 11365–11477 | 113 | 3719–3756 | 39 | 290 |
| 40 | 11478–11619 | 142 | 3756–3803 | 40 | 139 |
| 41 | 11620–11745 | 126 | 3804–3845 | 41 | 183 |
| 42 | 11746–11920 | 175 | 3846–3904 | 42 | ~320 |
| 43 | 11921–12211 | 291 | 3904–4001 | 43 | 75 |
| 44 | 12212–12346 | 135 | 4001–4046 | 44 | 83 |
| 45 | 12347–12652 | 306 | 4046–4148 | 45 | 88 |
| 46 | 12653–14148 | 1,496 | 4148–4302 | | |

TABLE 2

Details of the exon link cDNAs

| Product Name | Product Size (bp) | Oligonucleotide Sequences | Position in cDNA | Exon Position |
|---|---|---|---|---|
| rev1 | 652 | AGCGCCAGCGTCCGAGCGG CTGCACCACCCGCACCTGC | 8–658 200–658 | 1–4 |
| S13 | 1285 | CCGGGCGCTGGACGTTGGGCT AGTGCTCGGCTGTGGCTGGGT | 448–1733 | 2–7 |
| S3/4 | 1608 | CACCCAGCCACAGCCGAGCACT GTGTGGCATTGGGGGACAGCAC | 1712–3320 | 7–13 |
| S1/3 | 732 | TGCTGTCCCCCAATGCCAC ACGGTCACTGTGCAGTTC | 3300–4032 | 13–15 |
| GAP e | 1983 | CCAATGCCACACTGGTACTGACG TGGTAGGTGCCGGCCTCGAG | 3309–5292 | 13–15 |
| GAP d | 2036 | CCGGCACCTACCATGTGCAGC CCAAGGACACAATGGGCACC | 5280–7316 | 15–17 |
| GAP g | 884 | GAGGTGTATCGCACCGCCAG GCCCAGTGGGAAGAGGCGGC | 6773–7657 | 15–18 |
| GAP a | 1211 | TCTTGCCGCCTCTTCCCA GCAGCCCAGTCCGAGTTG | 7634–8862 | 18–23 |

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

REFERENCES

Aksentijevich et al., Am. J. Hum. Genet. 53:451–461, (1993).
Altschul et al., J. Mol. Biol. 215:403–410, (1990).
Bevilacqua, M. P., et al., Science 243:1160–1165, (1989).
Bork et al., Protein Science 2:1185–1187, (1993).
Breuning et al., Lancet ii, 1359–1361, (1987).
Breuning et al., J. Med. Genet. 27:603–613, (1990).
Brook-Carter et al., Nature Genetics 8:328–332, (1994).
Brown et al., Nucl. Acids Res. 18:4191–4195, (1990).
Brümmendorf, T., et al., Protein Profile 1:951–1058, (1994).
Buckle et al., Human Genetic Disease Analysis; IRL Press (K. E. Davies, Ed.) 2:59–82, Oxford, (1993).
Carone, F. A., et al., Laboratory Investigations 70:437–448, (1994).
Carone, F. A., et al., Kidney International 47:861–868, (1995).
Calvet, J. P., Kidney International 43:101–108, (1993).
Chapman et al., N. Eng. J. Med. 327:916–920, (1992).
Chao, M. V., Neuron 9:583–593, (1992).
Chomczynski et al., Anal. Biochem. 162:156–159, (1987).
Curtis et al., Proc. of the Nat'l. Acad. of Sci., USA 89:8356–8360, (1992).
Dalgaard, O. Z., Acta Medica Scandinavica 158:1–251, (1957).
Daoust, M. C., et al., Genomics 25:733–736, (1995).
Davies et al., Q.J. Med. 79:477–485, (1991).
Deisseroth et al., Proc. Natl. Acad. Sci. USA 76:2185–2189, (1979).
Dode et al., Brit. J. Haemat. 76:275–281, (1990).
Drickamer, K., Kidney Int'l. 32:167–180, (1987).
Drickamer, K., J. Biol. Chem. 263:9557–9560, (1988).
Ekblom, P., FASEB Journal 3:2141–2150, (1989).
Engelman et al., Ann. Rev. Bioph. Chem. 15:321–353, (1986).
European Polycystic Kidney Disease Consortium, Cell 77:881–894, (1994).
European Chromosome 16 Tuberous Sclerosis Consortium, Cell 75:1305–1315, (1993).
Fink et al., J. Amer. Soc. Nephrology 3:1863–1870, (1993).
Fink et al., Kidney Int. 45:1153–1162, (1994).
Fronman et al., Biochemistry 85:8998–9002, (1988).
Gabow, P. A., Kidney Int. 40:989–996, (1991).
Gabow, P. A., N.E. J. of Medicine 329:332–342, (1993).
Gabow, P. A., Amer. J. of Kidney Diseases 16:403–413, (1990).
Germino et al., Am. J. Hum. Genet. 46:925–933, (1990).
Germino et al., Genomics 13:144–151, (1992).
Gower, H. J., et al., Cell 55:955–964, (1988).
Green et al., Nature Genet. 6:193–196, (1994).

Harpaz, Y., et al., J. of the Mol. Biol. 238:528–539 (1994).
Harris et al., Genomics 7:195–206, (1990).
Harris et al., Lancet 338:1484–1487, (1991).
Hartmann et al., Proc. Nat'l. Acad. Sci. USA 86:5786–5790, (1989).
Henikoff, S., Gene 28:351–359, (1984).
Himmelbauer et al., Amer. J. Human Genetics. 48:325–334, (1991).
Hossack et al., N. Eng. J. Med. 319:907–912, (1988).
Huston et al., J. Amer. Soc. of Nephrology 3:1871–1877, (1993).
Hyland et al., Hum. Genet. 84:286–288, (1990).
Jia, R., et al., J. of Biol. Chem. 269:1839–1844 (1994).
Jones, E. Y., et al., Nature 373:539–544, (1995).
Keen et al., Trend Genet. 7:5, (1991).
Kimberly, W. J., et al., Genomics 18:467–472, (1993).
Kimberling et al., N. Eng. J. Med. 319:913–918, (1988).
Kobe et al., Trends in Bioch. Sci. 19:415–421, (1994).
Kornblihtt, A. R., et al., EMBO Journal 4:1755–1759, (1985).
Kozak, M., Nucleic Acids Res. 15:8125–8148, (1987).
Kuma et al., Mol. Biol. and Evolution 10:539–551, (1993).
Kwon, B. S., et al., Proc. of the Nat'l. Acad. of Sci., USA 88:9228–9232, (1991).
Lamballe et al., Cell 66:967–979, (1991).
Legius et al., Nature Genet. 3:122–126, (1993).
Love et al., Nature 339:55–58, (1989).
Mandel, J-L, Nature Genetics 4:8–9.
Matsushita, O., et al., Journal of Bacteriology 176:149–156, (1994).
McFarland, K. C., et al., Science 245:494–499, (1989).
Melton et al., Nuc. Acid Res. 12:7035–7056.
Milutinovic, J., et al., Amer. J. of Med. 68:741–744, (1980).
Milutinovic, J., et al., Amer. J. of Clin. Path. 73:740–747, (1979).
Nakashima et al., FEBS Letters 303:141–146, (1992).
Oldberg, et al., EMBO J. 8:2601–2604, (1989).
Oldberg et al., Biochemical J. 243:255–259, (1987).
Parfrey et al., N. Eng. J. Med. 323:1085–1090, (1990).
Pearson et al., Proc. Nat'l Acad. Sci. USA 85:2444–2448, (1988).
Peral et al., Am. J. Hum. Genet. 54:899–908.
Peral et al., Human Molecular Genetics (in press), (1995).
Peters, D. J. M., et al., Nature Genetics 5:359–362, (1993).
Peters, D. J. M., et al., Contributions to Nephrology: Polychystic Kidney Disease (eds. Breuning, M. H., Devoto, M. & Romeo, G), p. 128–139 (1992).
Pound et al., J. Med. Genet. 29:247–248, (1992).
Ravine et al., Lancet 337:127–129, (1991).
Ravine D., et al., Lancet 340:1330–1333, (1992).
Reeders, S. T., Nature Genet. 1:235–237, (1992).
Reeders et al., Lancet i, 6–8, (1986).
Reeders et al., Nature 317:542–544, (1985).
Reeders et al., Genomics 3:150–155, (1988).
Romeo et al., Lancet ii, 8–10, (1988).
Roth, G. J., Blood 77:5–19, (1991).
Rothberg et al., Genes and Development 4:2169–2187, (1990).
Royle et al., Nucl. Acids Res. 20:1164, (1992).
Ryynanen et al., J. Med. Genet. 24:462–465, (1987).
Schäfer, K., et al., Kidney International 46:134–152, (1994).
Scheff et al., Ann. Intern. Med. 92:202–204, (1980).
Sipos et al., European J. Biochemistry 213:1333–1340, (1993).
Snarey et al., Am. J. Hum. Genet. (in press), (1994).
Somlo et al., Genomics 13:152–158, (1992).
Somlo, S., et al., J. of the Amer. Soc. of Nephrology 4: 1371–1378, (1993).
Streuli, M., et al., Journal of Experimental Medicine 168:1523–1530, (1988).
Takagi et al., J. Bioch. Chem. 265:19721–19727, (1990).
Taylor, M. E., et al., J. of Biol. Chem. 265:12156–12162, (1990).
Thompson et al., Genomics 13:402–408, (1992).
Volkmer H., et al., Journal of Cell Biology 118:149–161, (1992).
von Heijne, G., Nuc. Acids Res. 14:4683–4691, (1986).
Wieringa, B., et al., Cell 37:915–925, (1984).
Weis et al., Nature 360:127–134, (1992).
Williams, A. F., et al., Annual Review of Immunology 6:381–405 (1988).
Wilson, P. D., et al., Kidney International 39:450–463, (1991).
Wright et al., PCR Protocols: A Guide to Methods and Applications, 153–166, (1990).
Zerres et al., J. Med. Genet. 30:583–588, (1993).

What is claimed is:

1. An isolated polycystic kidney disease 1 (PKD1) gene having the nucleic acid sequence presented in SEQ ID NO: 7 or a nucleic acid molecule having a sequence complementary to the entire nucleic acid sequence of SEQ ID NO:7.

2. An isolated polycystic kidney disease 1 (PKD1) gene having the nucleic acid sequence presented in SEQ ID NO: 1 or a nucleic acid molecule having a sequence complementary to the entire nucleic acid sequence of SEQ ID NO:1.

3. An isolated polycystic kidney disease 1 (PKD1) gene having the nucleic acid sequence presented in SEQ ID NO: 5 or a nucleic acid molecule having a sequence complementary to the entire nucleic acid sequence of SEQ ID NO:5.

4. An isolated nucleic acid molecule wherein the molecule is an RNA transcript comprising a length of about 14 kB;
    said RNA transcript having a nucleic acid sequence corresponding to the coding region of the nucleic acid sequence of SEQ ID NO: 7,
    or a sequence that is complementary to the entire coding region of the nucleic acid sequence of SEQ ID NO: 7.

5. A recombinant expression vector comprising the isolated nucleic acid of claim 1, 2 or 3.

6. A host cell comprising the vector of claim 5.

7. A recombinant expression vector comprising the isolated nucleic acid complementary to the RNA transcript of claim 4.

8. An isolated nucleic acid isolated from a patient clinically diagnosed with autosomal polycystic kidney disease, which encodes a polycystic kidney disease (PKD1) gene product, and wherein said nucleic acid comprises a mutant PKD1 gene comprising a deletion of at least 18 contiguous nucleotides as compared to the PKD1 sequence presented in SEQ ID NO: 7.

9. A recombinant expression vector containing a polynucleotide consisting of SEQ ID NO: 1, SEQ ID NO: 5 or SEQ ID NO: 7.

10. A host cell comprising the vector of claim 9.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 5631 base pairs
      (B) TYPE: nucleic acid
      (C) STRANDEDNESS: unknown
      (D) TOPOLOGY: unknown (ii) MOLECULE TYPE: cDNA (vi) ORIGINAL SOURCE:
      (A) ORGANISM: Homo sapiens (ix) FEATURE:
      (A) NAME/KEY: CDS
      (B) LOCATION:1..4842

(ix) FEATURE:
    (A) NAME/KEY: misc_feature
    (B) LOCATION:1..5631
    (D) OTHER INFORMATION:/function= "Original 3' end of the
        PKD1 gene"

(xi) SEQUENCE DESCRIPTION: SEQ ID NO: 1:

```
CTC AAC GAG GAG CCC CTG ACG CTG GCG GGC GAG GAG ATC GTG GCC CAG         48
Leu Asn Glu Glu Pro Leu Thr Leu Ala Gly Glu Glu Ile Val Ala Gln
 1               5                  10                  15

GGC AAG CGC TCG GAC CCG CGG AGC CTG CTG TGC TAT GGC GGC GCC CCA         96
Gly Lys Arg Ser Asp Pro Arg Ser Leu Leu Cys Tyr Gly Gly Ala Pro
             20                  25                  30

GGG CCT GGC TGC CAC TTC TCC ATC CCC GAG GCT TTC AGC GGG GCC CTG        144
Gly Pro Gly Cys His Phe Ser Ile Pro Glu Ala Phe Ser Gly Ala Leu
         35                  40                  45

GCC AAC CTC AGT GAC GTG GTG CAG CTC ATC TTT CTG GTG GAC TCC AAT        192
Ala Asn Leu Ser Asp Val Val Gln Leu Ile Phe Leu Val Asp Ser Asn
     50                  55                  60

CCC TTT CCC TTT GGC TAT ATC AGC AAC TAC ACC GTC TCC ACC AAG GTG        240
Pro Phe Pro Phe Gly Tyr Ile Ser Asn Tyr Thr Val Ser Thr Lys Val
 65                  70                  75                  80

GCC TCG ATG GCA TTC CAG ACA CAG GCC GGC GCC CAG ATC CCC ATC GAG        288
Ala Ser Met Ala Phe Gln Thr Gln Ala Gly Ala Gln Ile Pro Ile Glu
                 85                  90                  95

CGG CTG GCC TCA GAG CGC GCC ATC ACC GTG AAG GTG CCC AAC AAC TCG        336
Arg Leu Ala Ser Glu Arg Ala Ile Thr Val Lys Val Pro Asn Asn Ser
            100                 105                 110

GAC TGG GCT GCC CGG GGC CAC CGC AGC TCC GCC AAC TCC GCC AAC TCC        384
Asp Trp Ala Ala Arg Gly His Arg Ser Ser Ala Asn Ser Ala Asn Ser
        115                 120                 125

GTT GTG GTC CAG CCC CAG GCC TCC GTC GGT GCT GTG GTC ACC CTG GAC        432
Val Val Val Gln Pro Gln Ala Ser Val Gly Ala Val Val Thr Leu Asp
    130                 135                 140

AGC AGC AAC CCT GCG GCC GGG CTG CAT CTG CAG CTC AAC TAT ACG CTG        480
Ser Ser Asn Pro Ala Ala Gly Leu His Leu Gln Leu Asn Tyr Thr Leu
145                 150                 155                 160

CTG GAC GGC CAC TAC CTG TCT GAG GAA CCT GAG CCC TAC CTG GCA GTC        528
Leu Asp Gly His Tyr Leu Ser Glu Glu Pro Glu Pro Tyr Leu Ala Val
                165                 170                 175

TAC CTA CAC TCG GAG CCC CGG CCC AAT GAG CAC AAC TGC TCG GCT AGC        576
Tyr Leu His Ser Glu Pro Arg Pro Asn Glu His Asn Cys Ser Ala Ser
            180                 185                 190

AGG AGG ATC CGC CCA GAG TCA CTC CAG GGT GCT GAC CAC CGG CCC TAC        624
Arg Arg Ile Arg Pro Glu Ser Leu Gln Gly Ala Asp His Arg Pro Tyr
        195                 200                 205

ACC TTC TTC ATT TCC CCG GGG AGC AGA GAC CCA GCG GGG AGT TAC CAT        672
Thr Phe Phe Ile Ser Pro Gly Ser Arg Asp Pro Ala Gly Ser Tyr His
    210                 215                 220

CTG AAC CTC TCC AGC CAC TTC CGC TGG TCG GCG CTG CAG GTG TCC GTG        720
Leu Asn Leu Ser Ser His Phe Arg Trp Ser Ala Leu Gln Val Ser Val
225                 230                 235                 240

GGC CTG TAC ACG TCC CTG TGC CAG TAC TTC AGC GAG GAG GAC ATG GTG        768
Gly Leu Tyr Thr Ser Leu Cys Gln Tyr Phe Ser Glu Glu Asp Met Val
                245                 250                 255

TGG CGG ACA GAG GGG CTG CTG CCC CTG GAG GAG ACC TCG CCC CGC CAG        816
Trp Arg Thr Glu Gly Leu Leu Pro Leu Glu Glu Thr Ser Pro Arg Gln
            260                 265                 270

GCC GTC TGC CTC ACC CGC CAC CTC ACC GCC TTC GGC GCC AGC CTC TTC        864
Ala Val Cys Leu Thr Arg His Leu Thr Ala Phe Gly Ala Ser Leu Phe
```

-continued

|     | 275 |     |     |     | 280 |     |     |     |     | 285 |     |     |     |     |      |
|-----|-----|-----|-----|-----|-----|-----|-----|-----|-----|-----|-----|-----|-----|-----|------|
| GTG | CCC | CCA | AGC | CAT | GTC | CGC | TTT | GTG | TTT | CCT | GAG | CCG | ACA | GCG | GAT  | 912 |
| Val | Pro | Pro | Ser | His | Val | Arg | Phe | Val | Phe | Pro | Glu | Pro | Thr | Ala | Asp  |
|     | 290 |     |     |     | 295 |     |     |     |     | 300 |     |     |     |     |      |

```
GTA AAC TAC ATC GTC ATG CTG ACA TGT GCT GTG TGC CTG GTG ACC TAC      960
Val Asn Tyr Ile Val Met Leu Thr Cys Ala Val Cys Leu Val Thr Tyr
305             310                 315                 320

ATG GTC ATG GCC GCC ATC CTG CAC AAG CTG GAC CAG TTG GAT GCC AGC     1008
Met Val Met Ala Ala Ile Leu His Lys Leu Asp Gln Leu Asp Ala Ser
                325                 330                 335

CGG GGC CGC GCC ATC CCT TTC TGT GGG CAG CGG GGC CGC TTC AAG TAC     1056
Arg Gly Arg Ala Ile Pro Phe Cys Gly Gln Arg Gly Arg Phe Lys Tyr
                340                 345                 350

GAG ATC CTC GTC AAG ACA GGC TGG GGC CGG GGC TCA GGT ACC ACG GCC     1104
Glu Ile Leu Val Lys Thr Gly Trp Gly Arg Gly Ser Gly Thr Thr Ala
                355                 360                 365

CAC GTG GGC ATC ATG CTG TAT GGG GTG GAC AGC CGG AGC GGC CAC CGG     1152
His Val Gly Ile Met Leu Tyr Gly Val Asp Ser Arg Ser Gly His Arg
370                 375                 380

CAC CTG GAC GGC GAC AGA GCC TTC CAC CGC AAC AGC CTG GAC ATC TTC     1200
His Leu Asp Gly Asp Arg Ala Phe His Arg Asn Ser Leu Asp Ile Phe
385                 390                 395                 400

CGG ATC GCC ACC CCG CAC AGC CTG GGT AGC GTG TGG AAG ATC CGA GTG     1248
Arg Ile Ala Thr Pro His Ser Leu Gly Ser Val Trp Lys Ile Arg Val
                405                 410                 415

TGG CAC GAC AAC AAA GGG CTC AGC CCT GCC TGG TTC CTG CAG CAC GTC     1296
Trp His Asp Asn Lys Gly Leu Ser Pro Ala Trp Phe Leu Gln His Val
                420                 425                 430

ATC GTC AGG GAC CTG CAG ACG GCA CGC AGC GCC TTC TTC CTG GTC AAT     1344
Ile Val Arg Asp Leu Gln Thr Ala Arg Ser Ala Phe Phe Leu Val Asn
                435                 440                 445

GAC TGG CTT TCG GTG GAG ACG GAG GCC AAC GGG GGC CTG GTG GAG AAG     1392
Asp Trp Leu Ser Val Glu Thr Glu Ala Asn Gly Gly Leu Val Glu Lys
                450                 455                 460

GAG GTG CTG GCC GCG AGC GAC GCA GCC CTT TTG CGC TTC CGG CGC CTG     1440
Glu Val Leu Ala Ala Ser Asp Ala Ala Leu Leu Arg Phe Arg Arg Leu
465                 470                 475                 480

CTG GTG GCT GAG CTG CAG CGT GGC TTC TTT GAC AAG CAC ATC TGG CTC     1488
Leu Val Ala Glu Leu Gln Arg Gly Phe Phe Asp Lys His Ile Trp Leu
                485                 490                 495

TCC ATA TGG GAC CGG CCG CCT CGT AGC CGT TTC ACT CGC ATC CAG AGG     1536
Ser Ile Trp Asp Arg Pro Pro Arg Ser Arg Phe Thr Arg Ile Gln Arg
                500                 505                 510

GCC ACC TGC TGC GTT CTC CTC ATC TGC CTC TTC CTG GGC GCC AAC GCC     1584
Ala Thr Cys Cys Val Leu Leu Ile Cys Leu Phe Leu Gly Ala Asn Ala
                515                 520                 525

GTG TGG TAC GGG GCT GTT GGC GAC TCT GCC TAC AGC ACG GGG CAT GTG     1632
Val Trp Tyr Gly Ala Val Gly Asp Ser Ala Tyr Ser Thr Gly His Val
530                 535                 540

TCC AGG CTG AGC CCG CTG AGC GTC GAC ACA GTC GCT GTT GGC CTG GTG     1680
Ser Arg Leu Ser Pro Leu Ser Val Asp Thr Val Ala Val Gly Leu Val
545                 550                 555                 560

TCC AGC GTG GTT GTC TAT CCC GTC TAC CTG GCC ATC CTT TTT CTC TTC     1728
Ser Ser Val Val Val Tyr Pro Val Tyr Leu Ala Ile Leu Phe Leu Phe
                565                 570                 575

CGG ATG TCC CGG AGC AAG GTG GCT GGG AGC CCG AGC CCC ACA CCT GCC     1776
Arg Met Ser Arg Ser Lys Val Ala Gly Ser Pro Ser Pro Thr Pro Ala
                580                 585                 590

GGG CAG CAG GTG CTG GAC ATC GAC AGC TGC CTG GAC TCG TCC GTG CTG     1824
```

```
                                                                              -continued Gly Gln Gln Val Leu Asp Ile Asp Ser Cys Leu Asp Ser Ser Val Leu
            595                 600                 605

GAC AGC TCC TTC CTC ACG TTC TCA GGC CTC CAC GCT GAG GCC TTT GTT      1872
Asp Ser Ser Phe Leu Thr Phe Ser Gly Leu His Ala Glu Ala Phe Val
610                 615                 620

GGA CAG ATG AAG AGT GAC TTG TTT CTG GAT GAT TCT AAG AGT CTG GTG      1920
Gly Gln Met Lys Ser Asp Leu Phe Leu Asp Asp Ser Lys Ser Leu Val
625                 630                 635                 640

TGC TGG CCC TCC GGC GAG GGA ACG CTC AGT TGG CCG GAC CTG CTC AGT      1968
Cys Trp Pro Ser Gly Glu Gly Thr Leu Ser Trp Pro Asp Leu Leu Ser
            645                 650                 655

GAC CCG TCC ATT GTG GGT AGC AAT CTG CGG CAG CTG GCA CGG GGC CAG      2016
Asp Pro Ser Ile Val Gly Ser Asn Leu Arg Gln Leu Ala Arg Gly Gln
            660                 665                 670

GCG GGC CAT GGG CTG GGC CCA GAG GAG GAC GGC TTC TCC CTG GCC AGC      2064
Ala Gly His Gly Leu Gly Pro Glu Glu Asp Gly Phe Ser Leu Ala Ser
            675                 680                 685

CCC TAC TCG CCT GCC AAA TCC TTC TCA GCA TCA GAT GAA GAC CTG ATC      2112
Pro Tyr Ser Pro Ala Lys Ser Phe Ser Ala Ser Asp Glu Asp Leu Ile
            690                 695                 700

CAG CAG GTC CTT GCC GAG GGG GTC AGC AGC CCA GCC CCT ACC CAA GAC      2160
Gln Gln Val Leu Ala Glu Gly Val Ser Ser Pro Ala Pro Thr Gln Asp
705                 710                 715                 720

ACC CAC ATG GAA ACG GAC CTG CTC AGC AGC CTG TCC AGC ACT CCT GGG      2208
Thr His Met Glu Thr Asp Leu Leu Ser Ser Leu Ser Ser Thr Pro Gly
                725                 730                 735

GAG AAG ACA GAG ACG CTG GCG CTG CAG AGG CTG GGG GAG CTG GGG CCA      2256
Glu Lys Thr Glu Thr Leu Ala Leu Gln Arg Leu Gly Glu Leu Gly Pro
            740                 745                 750

CCC AGC CCA GGC CTG AAC TGG GAA CAG CCC CAG GCA GCG AGG CTG TCC      2304
Pro Ser Pro Gly Leu Asn Trp Glu Gln Pro Gln Ala Ala Arg Leu Ser
            755                 760                 765

AGG ACA GGA CTG GTG GAG GGT CTG CGG AAG CGC CTG CTG CCG GCC TGG      2352
Arg Thr Gly Leu Val Glu Gly Leu Arg Lys Arg Leu Leu Pro Ala Trp
770                 775                 780

TGT GCC TCC CTG GCC CAC GGG CTC AGC CTG CTC CTG GTG GCT GTG GCT      2400
Cys Ala Ser Leu Ala His Gly Leu Ser Leu Leu Leu Val Ala Val Ala
785                 790                 795                 800

GTG GCT GTC TCA GGG TGG GTG GGT GCG AGC TTC CCC CCG GGC GTG AGT      2448
Val Ala Val Ser Gly Trp Val Gly Ala Ser Phe Pro Pro Gly Val Ser
            805                 810                 815

GTT GCG TGG CTC CTG TCC AGC AGC GCC AGC TTC CTG GCC TCA TTC CTC      2496
Val Ala Trp Leu Leu Ser Ser Ser Ala Ser Phe Leu Ala Ser Phe Leu
            820                 825                 830

GGC TGG GAG CCA CTG AAG GTC TTG CTG GAA GCC CTG TAC TTC TCA CTG      2544
Gly Trp Glu Pro Leu Lys Val Leu Leu Glu Ala Leu Tyr Phe Ser Leu
            835                 840                 845

GTG GCC AAG CGG CTG CAC CCG GAT GAA GAT GAC ACC CTG GTA GAG AGC      2592
Val Ala Lys Arg Leu His Pro Asp Glu Asp Asp Thr Leu Val Glu Ser
850                 855                 860

CCG GCT GTG ACG CCT GTG AGC GCA CGT GTG CCC CGC GTA CGG CCA CCC      2640
Pro Ala Val Thr Pro Val Ser Ala Arg Val Pro Arg Val Arg Pro Pro
865                 870                 875                 880

CAC GGC TTT GCA CTC TTC CTG GCC AAG GAA GAA GCC CGC AAG GTC AAG      2688
His Gly Phe Ala Leu Phe Leu Ala Lys Glu Glu Ala Arg Lys Val Lys
            885                 890                 895

AGG CTA CAT GGC ATG CTG CGG AGC CTC CTG GTG TAC ATG CTT TTT CTG      2736
Arg Leu His Gly Met Leu Arg Ser Leu Leu Val Tyr Met Leu Phe Leu
            900                 905                 910
```

```
CTG GTG ACC CTG CTG GCC AGC TAT GGG GAT GCC TCA TGC CAT GGG CAC    2784
Leu Val Thr Leu Leu Ala Ser Tyr Gly Asp Ala Ser Cys His Gly His
        915                 920                 925

GCC TAC CGT CTG CAA AGC GCC ATC AAG CAG GAG CTG CAC AGC CGG GCC    2832
Ala Tyr Arg Leu Gln Ser Ala Ile Lys Gln Glu Leu His Ser Arg Ala
        930                 935                 940

TTC CTG GCC ATC ACG CGG TCT GAG GAG CTC TGG CCA TGG ATG GCC CAC    2880
Phe Leu Ala Ile Thr Arg Ser Glu Glu Leu Trp Pro Trp Met Ala His
945                 950                 955                 960

GTG CTG CTG CCC TAC GTC CAC GGG AAC CAG TCC AGC CCA GAG CTG GGG    2928
Val Leu Leu Pro Tyr Val His Gly Asn Gln Ser Ser Pro Glu Leu Gly
            965                 970                 975

CCC CCA CGG CTG CGG CAG GTG CGG CTG CAG GAA GCA CTC TAC CCA GAC    2976
Pro Pro Arg Leu Arg Gln Val Arg Leu Gln Glu Ala Leu Tyr Pro Asp
        980                 985                 990

CCT CCC GGC CCC AGG GTC CAC ACG TGC TCG GCC GCA GGA GGC TTC AGC    3024
Pro Pro Gly Pro Arg Val His Thr Cys Ser Ala Ala Gly Gly Phe Ser
        995                 1000                1005

ACC AGC GAT TAC GAC GTT GGC TGG GAG AGT CCT CAC AAT GGC TCG GGG    3072
Thr Ser Asp Tyr Asp Val Gly Trp Glu Ser Pro His Asn Gly Ser Gly
    1010                1015                1020

ACG TGG GCC TAT TCA GCG CCG GAT CTG CTG GGG GCA TGG TCC TGG GGC    3120
Thr Trp Ala Tyr Ser Ala Pro Asp Leu Leu Gly Ala Trp Ser Trp Gly
1025                1030                1035                1040

TCC TGT GCC GTG TAT GAC AGC GGG GGC TAC GTG CAG GAG CTG GGC CTG    3168
Ser Cys Ala Val Tyr Asp Ser Gly Gly Tyr Val Gln Glu Leu Gly Leu
                1045                1050                1055

AGC CTG GAG GAG AGC CGC GAC CGG CTG CGC TTC CTG CAG CTG CAC AAC    3216
Ser Leu Glu Glu Ser Arg Asp Arg Leu Arg Phe Leu Gln Leu His Asn
            1060                1065                1070

TGG CTG GAC AAC AGG AGC CGC GCT GTG TTC CTG GAG CTC ACG CGC TAC    3264
Trp Leu Asp Asn Arg Ser Arg Ala Val Phe Leu Glu Leu Thr Arg Tyr
        1075                1080                1085

AGC CCG GCC GTG GGG CTG CAC GCC GCC GTC ACG CTG CGC CTC GAG TTC    3312
Ser Pro Ala Val Gly Leu His Ala Ala Val Thr Leu Arg Leu Glu Phe
        1090                1095                1100

CCG GCG GCC GGC CGC GCC CTG GCC GCC CTC AGC GTC CGC CCC TTT GCG    3360
Pro Ala Ala Gly Arg Ala Leu Ala Ala Leu Ser Val Arg Pro Phe Ala
1105                1110                1115                1120

CTG CGC CGC CTC AGC GCG GGC CTC TCG CTG CCT CTG CTC ACC TCG GTG    3408
Leu Arg Arg Leu Ser Ala Gly Leu Ser Leu Pro Leu Leu Thr Ser Val
            1125                1130                1135

TGC CTG CTG CTG TTC GCC GTG CAC TTC GCC GTG GCC GAG GCC CGT ACT    3456
Cys Leu Leu Leu Phe Ala Val His Phe Ala Val Ala Glu Ala Arg Thr
        1140                1145                1150

TGG CAC AGG GAA GGG CGC TGG CGC GTG CTG CGG CTC GGA GCC TGG GCG    3504
Trp His Arg Glu Gly Arg Trp Arg Val Leu Arg Leu Gly Ala Trp Ala
        1155                1160                1165

CGG TGG CTG CTG GTG GCG CTG ACG GCG GCC ACG GCA CTG GTA CGC CTC    3552
Arg Trp Leu Leu Val Ala Leu Thr Ala Ala Thr Ala Leu Val Arg Leu
    1170                1175                1180

GCC CAG CTG GGT GCC GCT GAC CGC CAG TGG ACC CGT TTC GTG CGC GGC    3600
Ala Gln Leu Gly Ala Ala Asp Arg Gln Trp Thr Arg Phe Val Arg Gly
1185                1190                1195                1200

CGC CCG CGC CGC TTC ACT AGC TTC GAC CAG GTG GCG CAC GTG AGC TCC    3648
Arg Pro Arg Arg Phe Thr Ser Phe Asp Gln Val Ala His Val Ser Ser
                1205                1210                1215

GCA GCC CGT GGC CTG GCG GCC TCG CTG CTC TTC CTG CTT TTG GTC AAG    3696
Ala Ala Arg Gly Leu Ala Ala Ser Leu Leu Phe Leu Leu Leu Val Lys
            1220                1225                1230
```

```
GCT GCC CAG CAC GTA CGC TTC GTG CGC CAG TGG TCC GTC TTT GGC AAG      3744
Ala Ala Gln His Val Arg Phe Val Arg Gln Trp Ser Val Phe Gly Lys
            1235                1240                1245

ACA TTA TGC CGA GCT CTG CCA GAG CTC CTG GGG GTC ACC TTG GGC CTG      3792
Thr Leu Cys Arg Ala Leu Pro Glu Leu Leu Gly Val Thr Leu Gly Leu
        1250                1255                1260

GTG GTG CTC GGG GTA GCC TAC GCC CAG CTG GCC ATC CTG CTC GTG TCT      3840
Val Leu Gly Val Ala Tyr Ala Gln Leu Ala Ile Leu Leu Val Ser
1265                1270                1275                1280

TCC TGT GTG GAC TCC CTC TGG AGC GTG GCC CAG GCC CTG TTG GTG CTG      3888
Ser Cys Val Asp Ser Leu Trp Ser Val Ala Gln Ala Leu Leu Val Leu
                1285                1290                1295

TGC CCT GGG ACT GGG CTC TCT ACC CTG TGT CCT GCC GAG TCC TGG CAC      3936
Cys Pro Gly Thr Gly Leu Ser Thr Leu Cys Pro Ala Glu Ser Trp His
            1300                1305                1310

CTG TCA CCC CTG CTG TGT GTG GGG CTC TGG GCA CTG CGG CTG TGG GGC      3984
Leu Ser Pro Leu Leu Cys Val Gly Leu Trp Ala Leu Arg Leu Trp Gly
        1315                1320                1325

GCC CTA CGG CTG GGG GCT GTT ATT CTC CGC TGG CGC TAC CAC GCC TTG      4032
Ala Leu Arg Leu Gly Ala Val Ile Leu Arg Trp Arg Tyr His Ala Leu
    1330                1335                1340

CGT GGA GAG CTG TAC CGG CCG GCC TGG GAG CCC CAG GAC TAC GAG ATG      4080
Arg Gly Glu Leu Tyr Arg Pro Ala Trp Glu Pro Gln Asp Tyr Glu Met
1345                1350                1355                1360

GTG GAG TTG TTC CTG CGC AGG CTG CGC CTC TGG ATG GGC CTC AGC AAG      4128
Val Glu Leu Phe Leu Arg Arg Leu Arg Leu Trp Met Gly Leu Ser Lys
                1365                1370                1375

GTC AAG GAG TTC CGC CAC AAA GTC CGC TTT GAA GGG ATG GAG CCG CTG      4176
Val Lys Glu Phe Arg His Lys Val Arg Phe Glu Gly Met Glu Pro Leu
            1380                1385                1390

CCC TCT CGC TCC TCC AGG GGC TCC AAG GTA TCC CCG GAT GTG CCC CCA      4224
Pro Ser Arg Ser Ser Arg Gly Ser Lys Val Ser Pro Asp Val Pro Pro
        1395                1400                1405

CCC AGC GCT GGC TCC GAT GCC TCG CAC CCC TCC ACC TCC TCC AGC CAG      4272
Pro Ser Ala Gly Ser Asp Ala Ser His Pro Ser Thr Ser Ser Ser Gln
    1410                1415                1420

CTG GAT GGG CTG AGC GTG AGC CTG GGC CGG CTG GGA ACA AGG TGT GAG      4320
Leu Asp Gly Leu Ser Val Ser Leu Gly Arg Leu Gly Thr Arg Cys Glu
1425                1430                1435                1440

CCT GAG CCC TCC CGC CTC CAA GCC GTG TTC GAG GCC CTG CTC ACC CAG      4368
Pro Glu Pro Ser Arg Leu Gln Ala Val Phe Glu Ala Leu Leu Thr Gln
                1445                1450                1455

TTT GAC CGA CTC AAC CAG GCC ACA GAG GAC GTC TAC CAG CTG GAG CAG      4416
Phe Asp Arg Leu Asn Gln Ala Thr Glu Asp Val Tyr Gln Leu Glu Gln
            1460                1465                1470

CAG CTG CAC AGC CTG CAA GGC CGC AGG AGC AGC CGG GCG CCC GCC GGA      4464
Gln Leu His Ser Leu Gln Gly Arg Arg Ser Ser Arg Ala Pro Ala Gly
        1475                1480                1485

TCT TCC CGT GGC CCA TCC CCG GGC CTG CGG CCA GCA CTG CCC AGC CGC      4512
Ser Ser Arg Gly Pro Ser Pro Gly Leu Arg Pro Ala Leu Pro Ser Arg
    1490                1495                1500

CTT GCC CGG GCC AGT CGG GGT GTG GAC CTG GCC ACT GGC CCC AGC AGG      4560
Leu Ala Arg Ala Ser Arg Gly Val Asp Leu Ala Thr Gly Pro Ser Arg
1505                1510                1515                1520

ACA CCT TCG GGC CAA GAA CAA GGT CCA CCC CAG CAG CAC TTA GTC CTC      4608
Thr Pro Ser Gly Gln Glu Gln Gly Pro Pro Gln Gln His Leu Val Leu
                1525                1530                1535

CTT CCT GGC GGG GGT GGG CCG TGG AGT CGG AGT GGA CAC CGC TCA GTA      4656
Leu Pro Gly Gly Gly Gly Pro Trp Ser Arg Ser Gly His Arg Ser Val
```

|  | 1540 | | | | 1545 | | | | 1550 | | | | |
|---|---|---|---|---|---|---|---|---|---|---|---|---|---|
| TTA | CTT | TCT | GCC | GCT | GTC | AAG | GCC | GAG | GGC | CAG | GCA | GAA TGG CTG CAC | 4704 |
| Leu | Leu | Ser | Ala | Ala | Val | Lys | Ala | Glu | Gly | Gln | Ala | Glu Trp Leu His | |
| | | 1555 | | | | 1560 | | | | 1565 | | | |

```
               1555                1560                1565

GTA GGT TCC CCA GAG AGC AGG CAG GGG CAT CTG TCT GTC TGT GGG CTT      4752
Val Gly Ser Pro Glu Ser Arg Gln Gly His Leu Ser Val Cys Gly Leu
    1570                1575                1580

CAG CAC TTT AAA GAG GCT GTG TGG CCA ACC AGG ACC CAG GGT CCC CTC      4800
Gln His Phe Lys Glu Ala Val Trp Pro Thr Arg Thr Gln Gly Pro Leu
1585                1590                1595                1600

CCC AGC TCC CTT GGG AAG GAC ACA GCA GTA TTG GAC GGT TTC              4842
Pro Ser Ser Leu Gly Lys Asp Thr Ala Val Leu Asp Gly Phe
                1605                1610

TAGCCTCTGA GATGCTAATT TATTTCCCCG AGTCCTCAGG TACAGCGGGC TGTGCCCGGC    4902

CCCACCCCCT GGGCAGATGT CCCCCACTGC TAAGGCTGCT GGCTTCAGGG AGGGTTAGCC    4962

TGCACCGCCG CCACCCTGCC CCTAAGTTAT TACCTCTCCA GTTCCTACCG TACTCCCTGC    5022

ACCGTCTCAC TGTGTGTCTC GTGTCAGTAA TTTATATGGT GTTAAAATGT GTATATTTTT    5082

GTATGTCACT ATTTTCACTA GGGCTGAGGG GCCTGCGCCC AGAGCTGGCC TCCCCCAACA    5142

CCTGCTGCGC TTGGTAGGTG TGGTGGCGTT ATGGCAGCCC GGCTGCTGCT TGGATGCGAG    5202

CTTGGCCTTG GGCCGGTGCT GGGGGCACAG CTGTCTGCCA GGCACTCTCA TCACCCCAGA    5262

GGCCTTGTCA TCCTCCCTTG CCCCAGGCCA GGTAGCAAGA GAGCAGCGCC CAGGCCTGCT    5322

GGCATCAGGT CTGGGCAAGT AGCAGGACTA GGCATGTCAG AGGACCCCAG GGTGGTTAGA    5382

GGAAAAGACT CCTCCTGGGG GCTGGCTCCC AGGGTGGAGG AAGGTGACTG TGTGTGTGTG    5442

TGTGTGCGCG CGCGACGCGC GAGTGTGCTG TATGGCCCAG GCAGCCTCAA GGCCCTCGGA    5502

GCTGGCTGTG CCTGCTTCTG TGTACCACTT CTGTGGGCAT GGCCGCTTCT AGAGCCTCGA    5562

CACCCCCCCA ACCCCCGCAC CAAGCAGACA AAGTCAATAA AAGAGCTGTC TGACTGCAAA    5622

AAAAAAAAA                                                            5631
```

(2) INFORMATION FOR SEQ ID NO: 2:

(i) SEQUENCE CHARACTERISTICS:
        (A) LENGTH: 1614 amino acids
        (B) TYPE: amino acid
        (D) TOPOLOGY: linear (ii) MOLECULE TYPE: protein (xi) SEQUENCE DESCRIPTION: SEQ ID NO: 2:

```
Leu Asn Glu Glu Pro Leu Thr Leu Ala Gly Glu Glu Ile Val Ala Gln
 1               5                  10                  15

Gly Lys Arg Ser Asp Pro Arg Ser Leu Leu Cys Tyr Gly Gly Ala Pro
            20                  25                  30

Gly Pro Gly Cys His Phe Ser Ile Pro Glu Ala Phe Ser Gly Ala Leu
        35                  40                  45

Ala Asn Leu Ser Asp Val Val Gln Leu Ile Phe Leu Val Asp Ser Asn
    50                  55                  60

Pro Phe Pro Phe Gly Tyr Ile Ser Asn Tyr Thr Val Ser Thr Lys Val
65                  70                  75                  80

Ala Ser Met Ala Phe Gln Thr Gln Ala Gly Ala Gln Ile Pro Ile Glu
                85                  90                  95

Arg Leu Ala Ser Glu Arg Ala Ile Thr Val Lys Val Pro Asn Asn Ser
            100                 105                 110
```

```
Asp Trp Ala Ala Arg Gly His Arg Ser Ser Ala Asn Ser Ala Asn Ser
    115                 120                 125

Val Val Val Gln Pro Gln Ala Ser Val Gly Ala Val Val Thr Leu Asp
130                 135                 140

Ser Ser Asn Pro Ala Ala Gly Leu His Leu Gln Leu Asn Tyr Thr Leu
145                 150                 155                 160

Leu Asp Gly His Tyr Leu Ser Glu Glu Pro Glu Pro Tyr Leu Ala Val
                165                 170                 175

Tyr Leu His Ser Glu Pro Arg Pro Asn Glu His Asn Cys Ser Ala Ser
            180                 185                 190

Arg Arg Ile Arg Pro Glu Ser Leu Gln Gly Ala Asp His Arg Pro Tyr
        195                 200                 205

Thr Phe Phe Ile Ser Pro Gly Ser Arg Asp Pro Ala Gly Ser Tyr His
    210                 215                 220

Leu Asn Leu Ser Ser His Phe Arg Trp Ser Ala Leu Gln Val Ser Val
225                 230                 235                 240

Gly Leu Tyr Thr Ser Leu Cys Gln Tyr Phe Ser Glu Glu Asp Met Val
                245                 250                 255

Trp Arg Thr Glu Gly Leu Leu Pro Leu Glu Glu Thr Ser Pro Arg Gln
            260                 265                 270

Ala Val Cys Leu Thr Arg His Leu Thr Ala Phe Gly Ala Ser Leu Phe
        275                 280                 285

Val Pro Pro Ser His Val Arg Phe Val Phe Pro Glu Pro Thr Ala Asp
    290                 295                 300

Val Asn Tyr Ile Val Met Leu Thr Cys Ala Val Cys Leu Val Thr Tyr
305                 310                 315                 320

Met Val Met Ala Ala Ile Leu His Lys Leu Asp Gln Leu Asp Ala Ser
                325                 330                 335

Arg Gly Arg Ala Ile Pro Phe Cys Gly Gln Arg Gly Arg Phe Lys Tyr
            340                 345                 350

Glu Ile Leu Val Lys Thr Gly Trp Gly Arg Gly Ser Gly Thr Thr Ala
        355                 360                 365

His Val Gly Ile Met Leu Tyr Gly Val Asp Ser Arg Ser Gly His Arg
    370                 375                 380

His Leu Asp Gly Asp Arg Ala Phe His Arg Asn Ser Leu Asp Ile Phe
385                 390                 395                 400

Arg Ile Ala Thr Pro His Ser Leu Gly Ser Val Trp Lys Ile Arg Val
                405                 410                 415

Trp His Asp Asn Lys Gly Leu Ser Pro Ala Trp Phe Leu Gln His Val
            420                 425                 430

Ile Val Arg Asp Leu Gln Thr Ala Arg Ser Ala Phe Phe Leu Val Asn
        435                 440                 445

Asp Trp Leu Ser Val Glu Thr Glu Ala Asn Gly Gly Leu Val Glu Lys
    450                 455                 460

Glu Val Leu Ala Ala Ser Asp Ala Ala Leu Leu Arg Phe Arg Arg Leu
465                 470                 475                 480

Leu Val Ala Glu Leu Gln Arg Gly Phe Phe Asp Lys His Ile Trp Leu
                485                 490                 495

Ser Ile Trp Asp Arg Pro Pro Arg Ser Arg Phe Thr Arg Ile Gln Arg
            500                 505                 510

Ala Thr Cys Cys Val Leu Leu Ile Cys Leu Phe Leu Gly Ala Asn Ala
        515                 520                 525

Val Trp Tyr Gly Ala Val Gly Asp Ser Ala Tyr Ser Thr Gly His Val
```

-continued

```
        530                 535                 540
Ser Arg Leu Ser Pro Leu Ser Val Asp Thr Val Ala Val Gly Leu Val
545                 550                 555                 560

Ser Ser Val Val Val Tyr Pro Val Tyr Leu Ala Ile Leu Phe Leu Phe
                565                 570                 575

Arg Met Ser Arg Ser Lys Val Ala Gly Ser Pro Ser Pro Thr Pro Ala
                580                 585                 590

Gly Gln Gln Val Leu Asp Ile Asp Ser Cys Leu Asp Ser Ser Val Leu
                595                 600                 605

Asp Ser Ser Phe Leu Thr Phe Ser Gly Leu His Ala Glu Ala Phe Val
                610                 615                 620

Gly Gln Met Lys Ser Asp Leu Phe Leu Asp Asp Ser Lys Ser Leu Val
625                 630                 635                 640

Cys Trp Pro Ser Gly Glu Gly Thr Leu Ser Trp Pro Asp Leu Leu Ser
                645                 650                 655

Asp Pro Ser Ile Val Gly Ser Asn Leu Arg Gln Leu Ala Arg Gly Gln
                660                 665                 670

Ala Gly His Gly Leu Gly Pro Glu Glu Asp Gly Phe Ser Leu Ala Ser
                675                 680                 685

Pro Tyr Ser Pro Ala Lys Ser Phe Ser Ala Ser Asp Glu Asp Leu Ile
                690                 695                 700

Gln Gln Val Leu Ala Glu Gly Val Ser Ser Pro Ala Pro Thr Gln Asp
705                 710                 715                 720

Thr His Met Glu Thr Asp Leu Leu Ser Ser Leu Ser Ser Thr Pro Gly
                725                 730                 735

Glu Lys Thr Glu Thr Leu Ala Leu Gln Arg Leu Gly Glu Leu Gly Pro
                740                 745                 750

Pro Ser Pro Gly Leu Asn Trp Glu Gln Pro Gln Ala Ala Arg Leu Ser
                755                 760                 765

Arg Thr Gly Leu Val Glu Gly Leu Arg Lys Arg Leu Leu Pro Ala Trp
                770                 775                 780

Cys Ala Ser Leu Ala His Gly Leu Ser Leu Leu Val Ala Val Ala
785                 790                 795                 800

Val Ala Val Ser Gly Trp Val Gly Ala Ser Phe Pro Pro Gly Val Ser
                805                 810                 815

Val Ala Trp Leu Leu Ser Ser Ser Ala Ser Phe Leu Ala Ser Phe Leu
                820                 825                 830

Gly Trp Glu Pro Leu Lys Val Leu Leu Glu Ala Leu Tyr Phe Ser Leu
                835                 840                 845

Val Ala Lys Arg Leu His Pro Asp Glu Asp Thr Leu Val Glu Ser
850                 855                 860

Pro Ala Val Thr Pro Val Ser Ala Arg Val Pro Arg Val Arg Pro Pro
865                 870                 875                 880

His Gly Phe Ala Leu Phe Leu Ala Lys Glu Glu Ala Arg Lys Val Lys
                885                 890                 895

Arg Leu His Gly Met Leu Arg Ser Leu Leu Val Tyr Met Leu Phe Leu
                900                 905                 910

Leu Val Thr Leu Leu Ala Ser Tyr Gly Asp Ala Ser Cys His Gly His
                915                 920                 925

Ala Tyr Arg Leu Gln Ser Ala Ile Lys Gln Glu Leu His Ser Arg Ala
                930                 935                 940

Phe Leu Ala Ile Thr Arg Ser Glu Glu Leu Trp Pro Trp Met Ala His
945                 950                 955                 960
```

-continued

Val Leu Leu Pro Tyr Val His Gly Asn Gln Ser Ser Pro Glu Leu Gly
                965                 970                 975

Pro Pro Arg Leu Arg Gln Val Arg Leu Gln Glu Ala Leu Tyr Pro Asp
            980                 985                 990

Pro Pro Gly Pro Arg Val His Thr Cys Ser Ala Ala Gly Gly Phe Ser
            995                 1000                1005

Thr Ser Asp Tyr Asp Val Gly Trp Glu Ser Pro His Asn Gly Ser Gly
            1010                1015                1020

Thr Trp Ala Tyr Ser Ala Pro Asp Leu Leu Gly Ala Trp Ser Trp Gly
1025                1030                1035                1040

Ser Cys Ala Val Tyr Asp Ser Gly Gly Tyr Val Gln Glu Leu Gly Leu
                1045                1050                1055

Ser Leu Glu Glu Ser Arg Asp Arg Leu Arg Phe Leu Gln Leu His Asn
                1060                1065                1070

Trp Leu Asp Asn Arg Ser Arg Ala Val Phe Leu Glu Leu Thr Arg Tyr
                1075                1080                1085

Ser Pro Ala Val Gly Leu His Ala Ala Val Thr Leu Arg Leu Glu Phe
                1090                1095                1100

Pro Ala Ala Gly Arg Ala Leu Ala Ala Leu Ser Val Arg Pro Phe Ala
1105                1110                1115                1120

Leu Arg Arg Leu Ser Ala Gly Leu Ser Leu Pro Leu Leu Thr Ser Val
                1125                1130                1135

Cys Leu Leu Leu Phe Ala Val His Phe Ala Val Ala Glu Ala Arg Thr
                1140                1145                1150

Trp His Arg Glu Gly Arg Trp Arg Val Leu Arg Leu Gly Ala Trp Ala
                1155                1160                1165

Arg Trp Leu Leu Val Ala Leu Thr Ala Ala Thr Ala Leu Val Arg Leu
                1170                1175                1180

Ala Gln Leu Gly Ala Ala Asp Arg Gln Trp Thr Arg Phe Val Arg Gly
1185                1190                1195                1200

Arg Pro Arg Arg Phe Thr Ser Phe Asp Gln Val Ala His Val Ser Ser
                1205                1210                1215

Ala Ala Arg Gly Leu Ala Ala Ser Leu Leu Phe Leu Leu Leu Val Lys
                1220                1225                1230

Ala Ala Gln His Val Arg Phe Val Arg Gln Trp Ser Val Phe Gly Lys
                1235                1240                1245

Thr Leu Cys Arg Ala Leu Pro Glu Leu Leu Gly Val Thr Leu Gly Leu
                1250                1255                1260

Val Val Leu Gly Val Ala Tyr Ala Gln Leu Ala Ile Leu Leu Val Ser
1265                1270                1275                1280

Ser Cys Val Asp Ser Leu Trp Ser Val Ala Gln Ala Leu Leu Val Leu
                1285                1290                1295

Cys Pro Gly Thr Gly Leu Ser Thr Leu Cys Pro Ala Glu Ser Trp His
                1300                1305                1310

Leu Ser Pro Leu Leu Cys Val Gly Leu Trp Ala Leu Arg Leu Trp Gly
                1315                1320                1325

Ala Leu Arg Leu Gly Ala Val Ile Leu Arg Trp Arg Tyr His Ala Leu
                1330                1335                1340

Arg Gly Glu Leu Tyr Arg Pro Ala Trp Glu Pro Gln Asp Tyr Glu Met
1345                1350                1355                1360

Val Glu Leu Phe Leu Arg Arg Leu Arg Leu Trp Met Gly Leu Ser Lys
                1365                1370                1375

-continued

```
Val Lys Glu Phe Arg His Lys Val Arg Phe Glu Gly Met Glu Pro Leu
        1380                1385                1390

Pro Ser Arg Ser Ser Arg Gly Ser Lys Val Ser Pro Asp Val Pro Pro
        1395                1400                1405

Pro Ser Ala Gly Ser Asp Ala Ser His Pro Ser Thr Ser Ser Ser Gln
        1410                1415                1420

Leu Asp Gly Leu Ser Val Ser Leu Gly Arg Leu Gly Thr Arg Cys Glu
1425                1430                1435                1440

Pro Glu Pro Ser Arg Leu Gln Ala Val Phe Glu Ala Leu Leu Thr Gln
            1445                1450                1455

Phe Asp Arg Leu Asn Gln Ala Thr Glu Asp Val Tyr Gln Leu Glu Gln
            1460                1465                1470

Gln Leu His Ser Leu Gln Gly Arg Arg Ser Ser Arg Ala Pro Ala Gly
        1475                1480                1485

Ser Ser Arg Gly Pro Ser Pro Gly Leu Arg Pro Ala Leu Pro Ser Arg
        1490                1495                1500

Leu Ala Arg Ala Ser Arg Gly Val Asp Leu Ala Thr Gly Pro Ser Arg
1505                1510                1515                1520

Thr Pro Ser Gly Gln Glu Gln Gly Pro Pro Gln His Leu Val Leu
            1525                1530                1535

Leu Pro Gly Gly Gly Gly Pro Trp Ser Arg Ser Gly His Arg Ser Val
        1540                1545                1550

Leu Leu Ser Ala Ala Val Lys Ala Glu Gly Gln Ala Glu Trp Leu His
        1555                1560                1565

Val Gly Ser Pro Glu Ser Arg Gln Gly His Leu Ser Val Cys Gly Leu
    1570                1575                1580

Gln His Phe Lys Glu Ala Val Trp Pro Thr Arg Thr Gln Gly Pro Leu
1585                1590                1595                1600

Pro Ser Ser Leu Gly Lys Asp Thr Ala Val Leu Asp Gly Phe
                1605                1610
```

(2) INFORMATION FOR SEQ ID NO: 3:

(i) SEQUENCE CHARACTERISTICS:
        (A) LENGTH: 553 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..533
        (D) OTHER INFORMATION:/function= "1A1 H.6 probe"

(xi) SEQUENCE DESCRIPTION: SEQ ID NO: 3:

```
AGCTTGGCAC CATCAAGGGC CAGTTCAACT TTGTCCACGT GATCGTCACC CCGCTGGACT    60

ACGAGTGCAA CCTGGTGTCC CTGCAGTGCA GGAAAGACAT GGAGGGCCTT GTGGACACCA   120

GCGTGGCCAA GATCGTGTCT GACCGCAACC TGCCCTTCGT GGCCCGCCAG ATGGCCCTGC   180

ACGCAAATAT GGCCTCACAG GTGCATCATA GCCGCTCCAA CCCCACCGAT ATCTACCCCT   240

CCAAGTGGAT TGCCCGGCTC CGCCACATCA AGCGGCTCCG CCAGCGGATC TGCGAGGAAG   300

CCGCCTACTC CAACCCCAGC CTACCTCTGG TGCACCCTCC GTCCCATAGC AAAGCCCCTG   360

CACAGACTCC AGCCGAGCCC ACACCTGGCT ATGAGGTGGG CCAGCGGAAG CGCCTCATCT   420
```

```
CCTCGGTGGA GGACTTCACC GAGTTTGTGT GAGGCCGGGG CCCTCCCTCC TGCACTGGCC      480

TTGGACGGTA TTGCCTGTCA GTGAAATAAA TAAAGTCCTG ACCCCAGTGC ACAGACATAG      540

AGGCACAGAT TGC                                                        553

(2) INFORMATION FOR SEQ ID NO: 4:

(i) SEQUENCE CHARACTERISTICS:
        (A) LENGTH: 517 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION:1..517
        (D) OTHER INFORMATION:/function= "CW10 probe"

(xi) SEQUENCE DESCRIPTION: SEQ ID NO: 4:

CTGGTGTGTG TGAGACGTGC GGGGCTGGGA AGTGTTGGCA GAGCCGCGAG TACCGTCCTC       60

ACTCCTTTTG TTCTTTTGAC GTAAGCTGGC GAGTGGCACT GCCTGAGTTC CGCTCAGTGC      120

CCGCCCTGAT GTGCGGACCC CGCTGCATTC TTGCTGTTAG GTGGTGGCGG TGTGCGCTGT      180

CGCTGGTGGG CACCGAGAGT CTTTGGGAGC TTTGGGGAGG TTGTGCCAAG CCTGAGCCTC      240

GACGTCCCCC TTCCCGGCTT TCTGTTGGCT CTTCTGAGGC CAGGGCATCT CTATGAGGGC      300

CTCCTGCTGG AGCCGTCTCT GTGGATCTCC TCTGCCATCC TGGCCCATGA GTGGGTGATG      360

CGCTGGCCAC CATCTGGTGA CAGTGGCCGG GCACCGCTGC CAAATGTGGG TCCCGCATCT      420

GCAAGCCCCT CCCTGGGTCC CCTAGGGTAT GGGGTGGTTC TGCCACTGCC CTCGCTCCCC      480

CACCTTGGGG TGCCTCTCCC CCTGCTCGTG GGGGAGA                              517

(2) INFORMATION FOR SEQ ID NO: 5:

(i) SEQUENCE CHARACTERISTICS:
        (A) LENGTH: 13807 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION:2..13018

(ix) FEATURE:
        (A) NAME/KEY: misc_feature
        (B) LOCATION:7295..8184
        (D) OTHER INFORMATION:/function= "g alpha 22 fragment"

(ix) FEATURE:
        (A) NAME/KEY: misc_feature
        (B) LOCATION:6422..7294
        (D) OTHER INFORMATION:/function= "GAP GAMMA PETER
            fragment"

(ix) FEATURE:
        (A) NAME/KEY: misc_feature
        (B) LOCATION:3697..6421
        (D) OTHER INFORMATION:/function= "JH8 fragment"
```

(ix) FEATURE:
            (A) NAME/KEY: misc_feature
            (B) LOCATION:1373..1701
            (D) OTHER INFORMATION:/function= "S3/S4 PETER fragment"

(ix) FEATURE:
            (A) NAME/KEY: misc_feature
            (B) LOCATION:2176..2962
            (D) OTHER INFORMATION:/function= "S3/S4 CON2 PETER
                fragment"

(ix) FEATURE:
            (A) NAME/KEY: misc_feature
            (B) LOCATION:2963..3696
            (D) OTHER INFORMATION:/function= "S1/S3 PETER fragment"

(ix) FEATURE:
            (A) NAME/KEY: misc_feature
            (B) LOCATION:118..1372
            (D) OTHER INFORMATION:/function= "S4/JH13 fragment"

(ix) FEATURE:
            (A) NAME/KEY: misc_feature
            (B) LOCATION:1..85
            (D) OTHER INFORMATION:/function= "5' COMPLETE [Split]
                fragment"

(ix) FEATURE:
            (A) NAME/KEY: misc_feature
            (B) LOCATION:87..3696
            (D) OTHER INFORMATION:/function= "5' COMPLETE [Split]
                fragment"

(ix) FEATURE:
            (A) NAME/KEY: misc_feature
            (B) LOCATION:1..85
            (D) OTHER INFORMATION:/function= "6 (5) R cDNA [Split]
                fragment"

(ix) FEATURE:
            (A) NAME/KEY: misc_feature
            (B) LOCATION:87..117
            (D) OTHER INFORMATION:/product= "6 (5) R cDNA [Split]
                fragment"

(xi) SEQUENCE DESCRIPTION: SEQ ID NO: 5:

```
C GGC GCC GCC TGC CGC GTC AAC TGC TCG GGC CGC GGG CTG CGG ACG         46
  Gly Ala Ala Cys Arg Val Asn Cys Ser Gly Arg Gly Leu Arg Thr
  1615                1620                1625

CTC GGT CCC GCG CTG CGC ATC CCC GCG GAC GCC ACA GCG CTA GAC GTC       94
Leu Gly Pro Ala Leu Arg Ile Pro Ala Asp Ala Thr Ala Leu Asp Val
1630                1635                1640                1645

TCC CAC AAC CTG CTC CGG GCG CTG GAC GTT GGG CTC CTG GCG AAC CTC      142
Ser His Asn Leu Leu Arg Ala Leu Asp Val Gly Leu Leu Ala Asn Leu
                1650                1655                1660

TCG GCG CTG GCA GAG CTG GAT ATA AGC AAC AAC AAG ATT TCT ACG TTA      190
Ser Ala Leu Ala Glu Leu Asp Ile Ser Asn Asn Lys Ile Ser Thr Leu
            1665                1670                1675

GAA GAA GGA ATA TTT GCT AAT TTA TTT AAT TTA AGT GAA ATA AAC CTG      238
Glu Glu Gly Ile Phe Ala Asn Leu Phe Asn Leu Ser Glu Ile Asn Leu
        1680                1685                1690

AGT GGG AAC CCG TTT GAG TGT GAC TGT GGC CTG GCG TGG CTG CCG CGA      286
Ser Gly Asn Pro Phe Glu Cys Asp Cys Gly Leu Ala Trp Leu Pro Arg
    1695                1700                1705

TGG GCG GAG GAG CAG CAG GTG CGG GTG GTG CAG CCC GAG GCA GCC ACG      334
Trp Ala Glu Glu Gln Gln Val Arg Val Val Gln Pro Glu Ala Ala Thr
1710                1715                1720                1725

TGT GCT GGG CCT GGC TCC CTG GCT GGC CAG CCT CTG CTT GGC ATC CCC      382
Cys Ala Gly Pro Gly Ser Leu Ala Gly Gln Pro Leu Leu Gly Ile Pro
                1730                1735                1740
```

-continued

```
TTG CTG GAC AGT GGC TGT GGT GAG GAG TAT GTC GCC TGC CTC CCT GAC       430
Leu Leu Asp Ser Gly Cys Gly Glu Glu Tyr Val Ala Cys Leu Pro Asp
            1745                1750                1755

AAC AGC TCA GGC ACC GTG GCA GCA GTG TCC TTT TCA GCT GCC CAC GAA       478
Asn Ser Ser Gly Thr Val Ala Ala Val Ser Phe Ser Ala Ala His Glu
            1760                1765                1770

GGC CTG CTT CAG CCA GAG GCC TGC AGC GCC TTC TGC TTC TCC ACC GGC       526
Gly Leu Leu Gln Pro Glu Ala Cys Ser Ala Phe Cys Phe Ser Thr Gly
            1775                1780                1785

CAG GGC CTC GCA GCC CTC TCG GAG CAG GGC TGG TGC CTG TGT GGG GCG       574
Gln Gly Leu Ala Ala Leu Ser Glu Gln Gly Trp Cys Leu Cys Gly Ala
1790                1795                1800                1805

GCC CAG CCC TCC AGT GCC TCC TTT GCC TGC CTG TCC CTC TGC TCC GGC       622
Ala Gln Pro Ser Ser Ala Ser Phe Ala Cys Leu Ser Leu Cys Ser Gly
            1810                1815                1820

CCC CCG CCA CCT CCT GCC CCC ACC TGT AGG GGC CCC ACC CTC CTC CAG       670
Pro Pro Pro Pro Pro Ala Pro Thr Cys Arg Gly Pro Thr Leu Leu Gln
            1825                1830                1835

CAC GTC TTC CCT GCC TCC CCA GGG GCC ACC CTG GTG GGG CCC CAC GGA       718
His Val Phe Pro Ala Ser Pro Gly Ala Thr Leu Val Gly Pro His Gly
            1840                1845                1850

CCT CTG GCC TCT GGC CAG CTA GCA GCC TTC CAC ATC GCT GCC CCG CTC       766
Pro Leu Ala Ser Gly Gln Leu Ala Ala Phe His Ile Ala Ala Pro Leu
            1855                1860                1865

CCT GTC ACT GCC ACA CGC TGG GAC TTC GGA GAC GGC TCC GCC GAG GTG       814
Pro Val Thr Ala Thr Arg Trp Asp Phe Gly Asp Gly Ser Ala Glu Val
1870                1875                1880                1885

GAT GCC GCT GGG CCG GCT GCC TCG CAT CGC TAT GTG CTG CCT GGG CGC       862
Asp Ala Ala Gly Pro Ala Ala Ser His Arg Tyr Val Leu Pro Gly Arg
            1890                1895                1900

TAT CAC GTG ACG GCC GTG CTG GCC CTG GGG GCC GGC TCA GCC CTG CTG       910
Tyr His Val Thr Ala Val Leu Ala Leu Gly Ala Gly Ser Ala Leu Leu
            1905                1910                1915

GGG ACA GAC GTG CAG GTG GAA GCG GCA CCT GCC GCC CTG GAG CTC GTG       958
Gly Thr Asp Val Gln Val Glu Ala Ala Pro Ala Ala Leu Glu Leu Val
            1920                1925                1930

TGC CCG TCC TCG GTG CAG AGT GAC GAG AGC CTT GAC CTC AGC ATC CAG      1006
Cys Pro Ser Ser Val Gln Ser Asp Glu Ser Leu Asp Leu Ser Ile Gln
            1935                1940                1945

AAC CGC GGT GGT TCA GGC CTG GAG GCC GCC TAC AGC ATC GTG GCC CTG      1054
Asn Arg Gly Gly Ser Gly Leu Glu Ala Ala Tyr Ser Ile Val Ala Leu
1950                1955                1960                1965

GGC GAG GAG CCG GCC CGA GCG GTG CAC CCG CTC TGC CCC TCG GAC ACG      1102
Gly Glu Glu Pro Ala Arg Ala Val His Pro Leu Cys Pro Ser Asp Thr
            1970                1975                1980

GAG ATC TTC CCT GGC AAC GGG CAC TGC TAC CGC CTG GTG GTG GAG AAG      1150
Glu Ile Phe Pro Gly Asn Gly His Cys Tyr Arg Leu Val Val Glu Lys
            1985                1990                1995

GCG GCC TGG CTG CAG GCG CAG GAG CAG TGT CAG GCC TGG GCC GGG GCC      1198
Ala Ala Trp Leu Gln Ala Gln Glu Gln Cys Gln Ala Trp Ala Gly Ala
            2000                2005                2010

GCC CTG GCA ATG GTG GAC AGT CCC GCC GTG CAG CGC TTC CTG GTC TCC      1246
Ala Leu Ala Met Val Asp Ser Pro Ala Val Gln Arg Phe Leu Val Ser
            2015                2020                2025

CGG GTC ACC AGG AGC CTA GAC GTG TGG ATC GGC TTC TCG ACT GTG CAG      1294
Arg Val Thr Arg Ser Leu Asp Val Trp Ile Gly Phe Ser Thr Val Gln
2030                2035                2040                2045

GGG GTG GAG GTG GGC CCA GCG CCG CAG GGC GAG GCC TTC AGC CTG GAG      1342
Gly Val Glu Val Gly Pro Ala Pro Gln Gly Glu Ala Phe Ser Leu Glu
```

-continued

```
                    2050                2055                2060

AGC TGC CAG AAC TGG CTG CCC GGG GAG CCA CAC CCA GCC ACA GCC GAG    1390
Ser Cys Gln Asn Trp Leu Pro Gly Glu Pro His Pro Ala Thr Ala Glu
            2065                2070                2075

CAC TGC GTC CGG CTC GGG CCC ACC GGG TGG TGT AAC ACC GAC CTG TGC    1438
His Cys Val Arg Leu Gly Pro Thr Gly Trp Cys Asn Thr Asp Leu Cys
            2080                2085                2090

TCA GCG CCG CAC AGC TAC GTC TGC GAG CTG CAG CCC GGA GGC CCA GTG    1486
Ser Ala Pro His Ser Tyr Val Cys Glu Leu Gln Pro Gly Gly Pro Val
            2095                2100                2105

CAG GAT GCC GAG AAC CTC CTC GTG GGA GCG CCC AGT GGG GAC CTG CAG    1534
Gln Asp Ala Glu Asn Leu Leu Val Gly Ala Pro Ser Gly Asp Leu Gln
2110                2115                2120                2125

GGA CCC CTG ACG CCT CTG GCA CAG CAG GAC GGC CTC TCA GCC CCG CAC    1582
Gly Pro Leu Thr Pro Leu Ala Gln Gln Asp Gly Leu Ser Ala Pro His
            2130                2135                2140

GAG CCC GTG GAG GTC ATG GTA TTC CCG GGC CTG CGT CTG AGC CGT GAA    1630
Glu Pro Val Glu Val Met Val Phe Pro Gly Leu Arg Leu Ser Arg Glu
            2145                2150                2155

GCC TTC CTC ACC ACG GCC GAA TTT GGG ACC CAG GAG CTC CGG CGG CCC    1678
Ala Phe Leu Thr Thr Ala Glu Phe Gly Thr Gln Glu Leu Arg Arg Pro
            2160                2165                2170

GCC CAG CTG CGG CTG CAG GTG TAC CGG CTC CTC AGC ACA GCA GGG ACC    1726
Ala Gln Leu Arg Leu Gln Val Tyr Arg Leu Leu Ser Thr Ala Gly Thr
            2175                2180                2185

CCG GAG AAC GGC AGC GAG CCT GAG AGC AGG TCC CCG GAC AAC AGG ACC    1774
Pro Glu Asn Gly Ser Glu Pro Glu Ser Arg Ser Pro Asp Asn Arg Thr
2190                2195                2200                2205

CAG CTG GCC CCC GCG TGC ATG CCA GGG GGA CGC TGG TGC CCT GGA GCC    1822
Gln Leu Ala Pro Ala Cys Met Pro Gly Gly Arg Trp Cys Pro Gly Ala
            2210                2215                2220

AAC ATC TGC TTG CCG CTG GAC GCC TCT TGC CAC CCC CAG GCC TGC GCC    1870
Asn Ile Cys Leu Pro Leu Asp Ala Ser Cys His Pro Gln Ala Cys Ala
            2225                2230                2235

AAT GGC TGC ACG TCA GGG CCA GGG CTA CCC GGG GCC CCC TAT GCG CTA    1918
Asn Gly Cys Thr Ser Gly Pro Gly Leu Pro Gly Ala Pro Tyr Ala Leu
            2240                2245                2250

TGG AGA GAG TTC CTC TTC TCC GTT GCC GCG GGG CCC CCC GCG CAG TAC    1966
Trp Arg Glu Phe Leu Phe Ser Val Ala Ala Gly Pro Pro Ala Gln Tyr
            2255                2260                2265

TCG GTC ACC CTC CAC GGC CAG GAT GTC CTC ATG CTC CCT GGT GAC CTC    2014
Ser Val Thr Leu His Gly Gln Asp Val Leu Met Leu Pro Gly Asp Leu
2270                2275                2280                2285

GTT GGC TTG CAG CAC GAC GCT GGC CCT GGC GCC CTC CTG CAC TGC TCG    2062
Val Gly Leu Gln His Asp Ala Gly Pro Gly Ala Leu Leu His Cys Ser
            2290                2295                2300

CCG GCT CCC GGC CAC CCT GGT CCC CAG GCC CCG TAC CTC TCC GCC AAC    2110
Pro Ala Pro Gly His Pro Gly Pro Gln Ala Pro Tyr Leu Ser Ala Asn
            2305                2310                2315

GCC TCG TCA TGG CTG CCC CAC TTG CCA GCC CAG CTG GAG GGC ACT TGG    2158
Ala Ser Ser Trp Leu Pro His Leu Pro Ala Gln Leu Glu Gly Thr Trp
            2320                2325                2330

GCC TGC CCT GCC TGT GCC CTG CGG CTG CTT GCA GCC ACG GAA CAG CTC    2206
Ala Cys Pro Ala Cys Ala Leu Arg Leu Leu Ala Ala Thr Glu Gln Leu
            2335                2340                2345

ACC GTG CTG CTG GGC TTG AGG CCC AAC CCT GGA CTG CGG ATG CCT GGG    2254
Thr Val Leu Leu Gly Leu Arg Pro Asn Pro Gly Leu Arg Met Pro Gly
2350                2355                2360                2365

CGC TAT GAG GTC CGG GCA GAG GTG GGC AAT GGC GTG TCC AGG CAC AAC    2302
```

```
                    -continued

Arg Tyr Glu Val Arg Ala Glu Val Gly Asn Gly Val Ser Arg His Asn
            2370                2375                2380

CTC TCC TGC AGC TTT GAC GTG GTC TCC CCA GTG GCT GGG CTG CGG GTC      2350
Leu Ser Cys Ser Phe Asp Val Val Ser Pro Val Ala Gly Leu Arg Val
            2385                2390                2395

ATC TAC CCT GCC CCC CGC GAC GGC CGC CTC TAC GTG CCC ACC AAC GGC      2398
Ile Tyr Pro Ala Pro Arg Asp Gly Arg Leu Tyr Val Pro Thr Asn Gly
    2400                2405                2410

TCA GCC TTG GTG CTC CAG GTG GAC TCT GGT GCC AAC GCC ACG GCC ACG      2446
Ser Ala Leu Val Leu Gln Val Asp Ser Gly Ala Asn Ala Thr Ala Thr
        2415                2420                2425

GCT CGC TGG CCT GGG GGC AGT GTC AGC GCC CGC TTT GAG AAT GTC TGC      2494
Ala Arg Trp Pro Gly Gly Ser Val Ser Ala Arg Phe Glu Asn Val Cys
2430                2435                2440                2445

CCT GCC CTG GTG GCC ACC TTC GTG CCC GGC TGC CCC TGG GAG ACC AAC      2542
Pro Ala Leu Val Ala Thr Phe Val Pro Gly Cys Pro Trp Glu Thr Asn
            2450                2455                2460

GAT ACC CTG TTC TCA GTG GTA GCA CTG CCG TGG CTC AGT GAG GGG GAG      2590
Asp Thr Leu Phe Ser Val Val Ala Leu Pro Trp Leu Ser Glu Gly Glu
            2465                2470                2475

CAC GTG GTG GAC GTG GTG GTG GAA AAC AGC GCC AGC CGG GCC AAC CTC      2638
His Val Val Asp Val Val Val Glu Asn Ser Ala Ser Arg Ala Asn Leu
            2480                2485                2490

AGC CTG CGG GTG ACG GCG GAG GAG CCC ATC TGT GGC CTC CGC GCC ACG      2686
Ser Leu Arg Val Thr Ala Glu Glu Pro Ile Cys Gly Leu Arg Ala Thr
        2495                2500                2505

CCC AGC CCC GAG GCC CGT GTA CTG CAG GGA GTC CTA GTG AGG TAC AGC      2734
Pro Ser Pro Glu Ala Arg Val Leu Gln Gly Val Leu Val Arg Tyr Ser
2510                2515                2520                2525

CCC GTG GTG GAG GCC GGC TCG GAC ATG GTC TTC CGG TGG ACC ATC AAC      2782
Pro Val Val Glu Ala Gly Ser Asp Met Val Phe Arg Trp Thr Ile Asn
            2530                2535                2540

GAC AAG CAG TCC CTG ACC TTC CAG AAC GTG GTC TTC AAT GTC ATT TAT      2830
Asp Lys Gln Ser Leu Thr Phe Gln Asn Val Val Phe Asn Val Ile Tyr
            2545                2550                2555

CAG AGC GCG GCG GTC TTC AAG CTC TCA CTG ACG GCC TCC AAC CAC GTG      2878
Gln Ser Ala Ala Val Phe Lys Leu Ser Leu Thr Ala Ser Asn His Val
        2560                2565                2570

AGC AAC GTC ACC GTG AAC TAC AAC GTA ACC GTG GAG CGG ATG AAC AGG      2926
Ser Asn Val Thr Val Asn Tyr Asn Val Thr Val Glu Arg Met Asn Arg
    2575                2580                2585

ATG CAG GGT CTG CAG GTC TCC ACA GTG CCG GCC GTG CTG TCC CCC AAT      2974
Met Gln Gly Leu Gln Val Ser Thr Val Pro Ala Val Leu Ser Pro Asn
2590                2595                2600                2605

GCC ACA CTG GTA CTG ACG GGT GGT GTG CTG GTG GAC TCA GCT GTG GAG      3022
Ala Thr Leu Val Leu Thr Gly Gly Val Leu Val Asp Ser Ala Val Glu
            2610                2615                2620

GTG GCC TTC CTG TGG AAC TTT GGG GAT GGG GAG CAG GCC CTC CAC CAG      3070
Val Ala Phe Leu Trp Asn Phe Gly Asp Gly Glu Gln Ala Leu His Gln
            2625                2630                2635

TTC CAG CCT CCG TAC AAC GAG TCC TTC CCG GTT CCA GAC CCC TCG GTG      3118
Phe Gln Pro Pro Tyr Asn Glu Ser Phe Pro Val Pro Asp Pro Ser Val
            2640                2645                2650

GCC CAG GTG CTG GTG GAG CAC AAT GTC ATG CAC ACC TAC GCT GCC CCA      3166
Ala Gln Val Leu Val Glu His Asn Val Met His Thr Tyr Ala Ala Pro
        2655                2660                2665

GGT GAG TAC CTC CTG ACC GTG CTG GCA TCT AAT GCC TTC GAG AAC CTG      3214
Gly Glu Tyr Leu Leu Thr Val Leu Ala Ser Asn Ala Phe Glu Asn Leu
2670                2675                2680                2685
```

```
ACG CAG CAG GTG CCT GTG AGC GTG CGC GCC TCC CTG CCC TCC GTG GCT    3262
Thr Gln Gln Val Pro Val Ser Val Arg Ala Ser Leu Pro Ser Val Ala
            2690                2695                2700

GTG GGT GTG AGT GAC GGC GTC CTG GTG GCC GGC CGG CCC GTC ACC TTC    3310
Val Gly Val Ser Asp Gly Val Leu Val Ala Gly Arg Pro Val Thr Phe
            2705                2710                2715

TAC CCG CAC CCG CTG CCC TCG CCT GGG GGT GTT CTT TAC ACG TGG GAC    3358
Tyr Pro His Pro Leu Pro Ser Pro Gly Gly Val Leu Tyr Thr Trp Asp
            2720                2725                2730

TTC GGG GAC GGC TCC CCT GTC CTG ACC CAG AGC CAG CCG GCT GCC AAC    3406
Phe Gly Asp Gly Ser Pro Val Leu Thr Gln Ser Gln Pro Ala Ala Asn
            2735                2740                2745

CAC ACC TAT GCC TCG AGG GGC ACC TAC CAC GTG CGC CTG GAG GTC AAC    3454
His Thr Tyr Ala Ser Arg Gly Thr Tyr His Val Arg Leu Glu Val Asn
2750                2755                2760                2765

AAC ACG GTG AGC GGT GCG GCG GCC CAG GCG GAT GTG CGC GTC TTT GAG    3502
Asn Thr Val Ser Gly Ala Ala Ala Gln Ala Asp Val Arg Val Phe Glu
            2770                2775                2780

GAG CTC CGC GGA CTC AGC GTG GAC ATG AGC CTG GCC GTG GAG CAG GGC    3550
Glu Leu Arg Gly Leu Ser Val Asp Met Ser Leu Ala Val Glu Gln Gly
            2785                2790                2795

GCC CCC GTG GTG GTC AGC GCC GCG GTG CAG ACG GGC GAC AAC ATC ACG    3598
Ala Pro Val Val Val Ser Ala Ala Val Gln Thr Gly Asp Asn Ile Thr
            2800                2805                2810

TGG ACC TTC GAC ATG GGG GAC GGC ACC GTG CTG TCG GGC CCG GAG GCA    3646
Trp Thr Phe Asp Met Gly Asp Gly Thr Val Leu Ser Gly Pro Glu Ala
            2815                2820                2825

ACA GTG GAG CAT GTG TAC CTG CGG GCA CAG AAC TGC ACA GTG ACC GTG    3694
Thr Val Glu His Val Tyr Leu Arg Ala Gln Asn Cys Thr Val Thr Val
2830                2835                2840                2845

GGT GCG GCC AGC CCC GCC GGC CAC CTG GCC CGG AGC CTG CAC GTG CTG    3742
Gly Ala Ala Ser Pro Ala Gly His Leu Ala Arg Ser Leu His Val Leu
            2850                2855                2860

GTC TTC GTC CTG GAG GTG CTG CGC GTT GAA CCC GCC GCC TGC ATC CCC    3790
Val Phe Val Leu Glu Val Leu Arg Val Glu Pro Ala Ala Cys Ile Pro
            2865                2870                2875

ACG CAG CCT GAC GCG CGG CTC ACG GCC TAC GTC ACC GGG AAC CCG GCC    3838
Thr Gln Pro Asp Ala Arg Leu Thr Ala Tyr Val Thr Gly Asn Pro Ala
            2880                2885                2890

CAC TAC CTC TTC GAC TGG ACC TTC GGG GAT GGC TCC TCC AAC ACG ACC    3886
His Tyr Leu Phe Asp Trp Thr Phe Gly Asp Gly Ser Ser Asn Thr Thr
            2895                2900                2905

GTG CGG GGG TGC CCG ACG GTG ACA CAC AAC TTC ACG CGG AGC GGC ACG    3934
Val Arg Gly Cys Pro Thr Val Thr His Asn Phe Thr Arg Ser Gly Thr
2910                2915                2920                2925

TTC CCC CTG GCG CTG GTG CTG TCC AGC CGC GTG AAC AGG GCG CAT TAC    3982
Phe Pro Leu Ala Leu Val Leu Ser Ser Arg Val Asn Arg Ala His Tyr
            2930                2935                2940

TTC ACC AGC ATC TGC GTG GAG CCA GAG GTG GGC AAC GTC ACC CTG CAG    4030
Phe Thr Ser Ile Cys Val Glu Pro Glu Val Gly Asn Val Thr Leu Gln
            2945                2950                2955

CCA GAG AGG CAG TTT GTG CAG CTC GGG GAC GAG GCC TGG CTG GTG GCA    4078
Pro Glu Arg Gln Phe Val Gln Leu Gly Asp Glu Ala Trp Leu Val Ala
            2960                2965                2970

TGT GCC TGG CCC CCG TTC CCC TAC CGC TAC ACC TGG GAC TTT GGC ACC    4126
Cys Ala Trp Pro Pro Phe Pro Tyr Arg Tyr Thr Trp Asp Phe Gly Thr
            2975                2980                2985

GAG GAA GCC GCC CCC ACC CGT GCC AGG GGC CCT GAG GTG ACG TTC ATC    4174
Glu Glu Ala Ala Pro Thr Arg Ala Arg Gly Pro Glu Val Thr Phe Ile
2990                2995                3000                3005
```

```
TAC CGA GAC CCA GGC TCC TAT CTT GTG ACA GTC ACC GCG TCC AAC AAC     4222
Tyr Arg Asp Pro Gly Ser Tyr Leu Val Thr Val Thr Ala Ser Asn Asn
                3010                3015                3020

ATC TCT GCT GCC AAT GAC TCA GCC CTG GTG GAG GTG CAG GAG CCC GTG     4270
Ile Ser Ala Ala Asn Asp Ser Ala Leu Val Glu Val Gln Glu Pro Val
            3025                3030                3035

CTG GTC ACC AGC ATC AAG GTC AAT GGC TCC CTT GGG CTG GAG CTG CAG     4318
Leu Val Thr Ser Ile Lys Val Asn Gly Ser Leu Gly Leu Glu Leu Gln
            3040                3045                3050

CAG CCG TAC CTG TTC TCT GCT GTG GGC CGT GGG CGC CCC GCC AGC TAC     4366
Gln Pro Tyr Leu Phe Ser Ala Val Gly Arg Gly Arg Pro Ala Ser Tyr
            3055                3060                3065

CTG TGG GAT CTG GGG GAC GGT GGG TGG CTC GAG GGT CCG GAG GTC ACC     4414
Leu Trp Asp Leu Gly Asp Gly Gly Trp Leu Glu Gly Pro Glu Val Thr
3070                3075                3080                3085

CAC GCT TAC AAC AGC ACA GGT GAC TTC ACC GTT AGG GTG GCC GGC TGG     4462
His Ala Tyr Asn Ser Thr Gly Asp Phe Thr Val Arg Val Ala Gly Trp
                3090                3095                3100

AAT GAG GTG AGC CGC AGC GAG GCC TGG CTC AAT GTG ACG GTG AAG CGG     4510
Asn Glu Val Ser Arg Ser Glu Ala Trp Leu Asn Val Thr Val Lys Arg
            3105                3110                3115

CGC GTG CGG GGG CTC GTC GTC AAT GCA AGC CGC ACG GTG GTG CCC CTG     4558
Arg Val Arg Gly Leu Val Val Asn Ala Ser Arg Thr Val Val Pro Leu
            3120                3125                3130

AAT GGG AGC GTG AGC TTC AGC ACG TCG CTG GAG GCC GGC AGT GAT GTG     4606
Asn Gly Ser Val Ser Phe Ser Thr Ser Leu Glu Ala Gly Ser Asp Val
            3135                3140                3145

CGC TAT TCC TGG GTG CTC TGT GAC CGC TGC ACG CCC ATC CCT GGG GGT     4654
Arg Tyr Ser Trp Val Leu Cys Asp Arg Cys Thr Pro Ile Pro Gly Gly
3150                3155                3160                3165

CCT ACC ATC TCT TAC ACC TTC CGC TCC GTG GGC ACC TTC AAT ATC ATC     4702
Pro Thr Ile Ser Tyr Thr Phe Arg Ser Val Gly Thr Phe Asn Ile Ile
                3170                3175                3180

GTC ACG GCT GAG AAC GAG GTG GGC TCC GCC CAG GAC AGC ATC TTC GTC     4750
Val Thr Ala Glu Asn Glu Val Gly Ser Ala Gln Asp Ser Ile Phe Val
            3185                3190                3195

TAT GTC CTG CAG CTC ATA GAG GGG CTG CAG GTG GTG GGC GGT GGC CGC     4798
Tyr Val Leu Gln Leu Ile Glu Gly Leu Gln Val Val Gly Gly Gly Arg
            3200                3205                3210

TAC TTC CCC ACC AAC CAC ACG GTA CAG CTG CAG GCC GTG GTT AGG GAT     4846
Tyr Phe Pro Thr Asn His Thr Val Gln Leu Gln Ala Val Val Arg Asp
            3215                3220                3225

GGC ACC AAC GTC TCC TAC AGC TGG ACT GCC TGG AGG GAC AGG GGC CCG     4894
Gly Thr Asn Val Ser Tyr Ser Trp Thr Ala Trp Arg Asp Arg Gly Pro
3230                3235                3240                3245

GCC CTG GCC GGC AGC GGC AAA GGC TTC TCG CTC ACC GTG CTC GAG GCC     4942
Ala Leu Ala Gly Ser Gly Lys Gly Phe Ser Leu Thr Val Leu Glu Ala
            3250                3255                3260

GGC ACC TAC CAT GTG CAG CTG CGG GCC ACC AAC ATG CTG GGC AGC GCC     4990
Gly Thr Tyr His Val Gln Leu Arg Ala Thr Asn Met Leu Gly Ser Ala
            3265                3270                3275

TGG GCC GAC TGC ACC ATG GAC TTC GTG GAG CCT GTG GGG TGG CTG ATG     5038
Trp Ala Asp Cys Thr Met Asp Phe Val Glu Pro Val Gly Trp Leu Met
            3280                3285                3290

GTG ACC GCC TCC CCG AAC CCA GCT GCC GTC AAC ACA AGC GTC ACC CTC     5086
Val Thr Ala Ser Pro Asn Pro Ala Ala Val Asn Thr Ser Val Thr Leu
            3295                3300                3305

AGT GCC GAG CTG GCT GGT GGC AGT GGT GTC GTA TAC ACT TGG TCC TTG     5134
Ser Ala Glu Leu Ala Gly Gly Ser Gly Val Val Tyr Thr Trp Ser Leu
```

-continued

| | | | |
|---|---|---|---|
| 3310 | 3315 | 3320 | 3325 |

GAG GAG GGG CTG AGC TGG GAG ACC TCC GAG CCA TTT ACC ACC CAT AGC   5182
Glu Glu Gly Leu Ser Trp Glu Thr Ser Glu Pro Phe Thr Thr His Ser
            3330                3335                3340

TTC CCC ACA CCC GGC CTG CAC TTG GTC ACC ATG ACG GCA GGG AAC CCG   5230
Phe Pro Thr Pro Gly Leu His Leu Val Thr Met Thr Ala Gly Asn Pro
            3345                3350                3355

CTG GGC TCA GCC AAC GCC ACC GTG GAA GTG GAT GTG CAG GTG CCT GTG   5278
Leu Gly Ser Ala Asn Ala Thr Val Glu Val Asp Val Gln Val Pro Val
            3360                3365                3370

AGT GGC CTC AGC ATC AGG GCC AGC GAG CCC GGA GGC AGC TTC GTG GCG   5326
Ser Gly Leu Ser Ile Arg Ala Ser Glu Pro Gly Gly Ser Phe Val Ala
            3375                3380                3385

GCC GGG TCC TCT GTG CCC TTT TGG GGG CAG CTG GCC ACG GGC ACC AAT   5374
Ala Gly Ser Ser Val Pro Phe Trp Gly Gln Leu Ala Thr Gly Thr Asn
3390                3395                3400                3405

GTG AGC TGG TGC TGG GCT GTG CCC GGC GGC AGC AGC AAG CGT GGC CCT   5422
Val Ser Trp Cys Trp Ala Val Pro Gly Gly Ser Ser Lys Arg Gly Pro
            3410                3415                3420

CAT GTC ACC ATG GTC TTC CCG GAT GCT GGC ACC TTC TCC ATC CGG CTC   5470
His Val Thr Met Val Phe Pro Asp Ala Gly Thr Phe Ser Ile Arg Leu
            3425                3430                3435

AAT GCC TCC AAC GCA GTC AGC TGG GTC TCA GCC ACG TAC AAC CTC ACG   5518
Asn Ala Ser Asn Ala Val Ser Trp Val Ser Ala Thr Tyr Asn Leu Thr
            3440                3445                3450

GCG GAG GAG CCC ATC GTG GGC CTG GTG CTG TGG GCC AGC AGC AAG GTG   5566
Ala Glu Glu Pro Ile Val Gly Leu Val Leu Trp Ala Ser Ser Lys Val
            3455                3460                3465

GTG GCG CCC GGG CAG CTG GTC CAT TTT CAG ATC CTG CTG GCT GCC GGC   5614
Val Ala Pro Gly Gln Leu Val His Phe Gln Ile Leu Leu Ala Ala Gly
3470                3475                3480                3485

TCA GCT GTC ACC TTC CGC CTG CAG GTC GGC GGG GCC AAC CCC GAG GTG   5662
Ser Ala Val Thr Phe Arg Leu Gln Val Gly Gly Ala Asn Pro Glu Val
            3490                3495                3500

CTC CCC GGG CCC CGT TTC TCC CAC AGC TTC CCC CGC GTC GGA GAC CAC   5710
Leu Pro Gly Pro Arg Phe Ser His Ser Phe Pro Arg Val Gly Asp His
            3505                3510                3515

GTG GTG AGC GTG CGG GGC AAA AAC CAC GTG AGC TGG GCC CAG GCG CAG   5758
Val Val Ser Val Arg Gly Lys Asn His Val Ser Trp Ala Gln Ala Gln
            3520                3525                3530

GTG CGC ATC GTG GTG CTG GAG GCC GTG AGT GGG CTG CAG ATG CCC AAC   5806
Val Arg Ile Val Val Leu Glu Ala Val Ser Gly Leu Gln Met Pro Asn
            3535                3540                3545

TGC TGC GAG CCT GGC ATC GCC ACG GGC ACT GAG AGG AAC TTC ACA GCC   5854
Cys Cys Glu Pro Gly Ile Ala Thr Gly Thr Glu Arg Asn Phe Thr Ala
3550                3555                3560                3565

CGC GTG CAG CGC GGC TCT CGG GTC GCC TAC GCC TGG TAC TTC TCG CTG   5902
Arg Val Gln Arg Gly Ser Arg Val Ala Tyr Ala Trp Tyr Phe Ser Leu
            3570                3575                3580

CAG AAG GTC CAG GGC GAC TCG CTG GTC ATC CTG TCG GGC CGC GAC GTC   5950
Gln Lys Val Gln Gly Asp Ser Leu Val Ile Leu Ser Gly Arg Asp Val
            3585                3590                3595

ACC TAC ACG CCC GTG GCC GCG GGG CTG TTG GAG ATC CAG GTG CGC GCC   5998
Thr Tyr Thr Pro Val Ala Ala Gly Leu Leu Glu Ile Gln Val Arg Ala
            3600                3605                3610

TTC AAC GCC CTG GGC AGT GAG AAC CGC ACG CTG GTG CTG GAG GTT CAG   6046
Phe Asn Ala Leu Gly Ser Glu Asn Arg Thr Leu Val Leu Glu Val Gln
            3615                3620                3625

GAC GCC GTC CAG TAT GTG GCC CTG CAG AGC GGC CCC TGC TTC ACC AAC   6094

-continued

```
Asp Ala Val Gln Tyr Val Ala Leu Gln Ser Gly Pro Cys Phe Thr Asn
3630                3635                3640                3645

CGC TCG GCG CAG TTT GAG GCC GCC ACC AGC CCC AGC CCC CGG CGT GTG        6142
Arg Ser Ala Gln Phe Glu Ala Ala Thr Ser Pro Ser Pro Arg Arg Val
                3650                3655                3660

GCC TAC CAC TGG GAC TTT GGG GAT GGG TCG CCA GGG CAG GAC ACA GAT        6190
Ala Tyr His Trp Asp Phe Gly Asp Gly Ser Pro Gly Gln Asp Thr Asp
3665                3670                3675

GAG CCC AGG GCC GAG CAC TCC TAC CTG AGG CCT GGG GAC TAC CGC GTG        6238
Glu Pro Arg Ala Glu His Ser Tyr Leu Arg Pro Gly Asp Tyr Arg Val
        3680                3685                3690

CAG GTG AAC GCC TCC AAC CTG GTG AGC TTC TTC GTG GCG CAG GCC ACG        6286
Gln Val Asn Ala Ser Asn Leu Val Ser Phe Phe Val Ala Gln Ala Thr
            3695                3700                3705

GTG ACC GTC CAG GTG CTG GCC TGC CGG GAG CCG GAG GTG GAC GTG GTC        6334
Val Thr Val Gln Val Leu Ala Cys Arg Glu Pro Glu Val Asp Val Val
3710                3715                3720                3725

CTG CCC CTG CAG GTG CTG ATG CGG CGA TCA CAG CGC AAC TAC TTG GAG        6382
Leu Pro Leu Gln Val Leu Met Arg Arg Ser Gln Arg Asn Tyr Leu Glu
                3730                3735                3740

GCC CAC GTT GAC CTG CGC GAC TGC GTC ACC TAC CAG ACT GAG TAC CGC        6430
Ala His Val Asp Leu Arg Asp Cys Val Thr Tyr Gln Thr Glu Tyr Arg
            3745                3750                3755

TGG GAG GTG TAT CGC ACC GCC AGC TGC CAG CGG CCG GGG CGC CCA GCG        6478
Trp Glu Val Tyr Arg Thr Ala Ser Cys Gln Arg Pro Gly Arg Pro Ala
        3760                3765                3770

CGT GTG GCC CTG CCC GGC GTG GAC GTG AGC CGG CCT CGG CTG GTG CTG        6526
Arg Val Ala Leu Pro Gly Val Asp Val Ser Arg Pro Arg Leu Val Leu
    3775                3780                3785

CCG CGG CTG GCG CTG CCT GTG GGG CAC TAC TGC TTT GTG TTT GTC GTG        6574
Pro Arg Leu Ala Leu Pro Val Gly His Tyr Cys Phe Val Phe Val Val
3790                3795                3800                3805

TCA TTT GGG GAC ACG CCA CTG ACA CAG AGC ATC CAG GCC AAT GTG ACG        6622
Ser Phe Gly Asp Thr Pro Leu Thr Gln Ser Ile Gln Ala Asn Val Thr
                3810                3815                3820

GTG GCC CCC GAG CGC CTG GTG CCC ATC ATT GAG GGT GGC TCA TAC CGC        6670
Val Ala Pro Glu Arg Leu Val Pro Ile Ile Glu Gly Gly Ser Tyr Arg
            3825                3830                3835

GTG TGG TCA GAC ACA CGG GAC CTG GTG CTG GAT GGG AGC GAG TCC TAC        6718
Val Trp Ser Asp Thr Arg Asp Leu Val Leu Asp Gly Ser Glu Ser Tyr
        3840                3845                3850

GAC CCC AAC CTG GAG GAC GGC GAC CAG ACG CCG CTC AGT TTC CAC TGG        6766
Asp Pro Asn Leu Glu Asp Gly Asp Gln Thr Pro Leu Ser Phe His Trp
    3855                3860                3865

GCC TGT GTG GCT TCG ACA CAG AGG GAG GCT GGC GGG TGT GCG CTG AAC        6814
Ala Cys Val Ala Ser Thr Gln Arg Glu Ala Gly Gly Cys Ala Leu Asn
3870                3875                3880                3885

TTT GGG CCC CGC GGG AGC AGC ACG GTC ACC ATT CCA CGG GAG CGG CTG        6862
Phe Gly Pro Arg Gly Ser Ser Thr Val Thr Ile Pro Arg Glu Arg Leu
                3890                3895                3900

GCG GCT GGC GTG GAG TAC ACC TTC AGC CTG ACC GTG TGG AAG GCC GGC        6910
Ala Ala Gly Val Glu Tyr Thr Phe Ser Leu Thr Val Trp Lys Ala Gly
            3905                3910                3915

CGC AAG GAG GAG GCC ACC AAC CAG ACG GTG CTG ATC CGG AGT GGC CGG        6958
Arg Lys Glu Glu Ala Thr Asn Gln Thr Val Leu Ile Arg Ser Gly Arg
        3920                3925                3930

GTG CCC ATT GTG TCC TTG GAG TGT GTG TCC TGC AAG GCA CAG GCC GTG        7006
Val Pro Ile Val Ser Leu Glu Cys Val Ser Cys Lys Ala Gln Ala Val
    3935                3940                3945
```

```
TAC GAA GTG AGC CGC AGC TCC TAC GTG TAC TTG GAG GGC CGC TGC CTC      7054
Tyr Glu Val Ser Arg Ser Ser Tyr Val Tyr Leu Glu Gly Arg Cys Leu
3950            3955                3960                3965

AAT TGC AGC AGC GGC TCC AAG CGA GGG CGG TGG GCT GCA CGT ACG TTC      7102
Asn Cys Ser Ser Gly Ser Lys Arg Gly Arg Trp Ala Ala Arg Thr Phe
                3970                3975                3980

AGC AAC AAG ACG CTG GTG CTG GAT GAG ACC ACC ACA TCC ACG GGC AGT      7150
Ser Asn Lys Thr Leu Val Leu Asp Glu Thr Thr Thr Ser Thr Gly Ser
            3985                3990                3995

GCA GGC ATG CGA CTG GTG CTG CGG CGG GGC GTG CTG CGG GAC GGC GAG      7198
Ala Gly Met Arg Leu Val Leu Arg Arg Gly Val Leu Arg Asp Gly Glu
        4000                4005                4010

GGA TAC ACC TTC ACG CTC ACG GTG CTG GGC CGC TCT GGC GAG GAG GAG      7246
Gly Tyr Thr Phe Thr Leu Thr Val Leu Gly Arg Ser Gly Glu Glu Glu
        4015                4020                4025

GGC TGC GCC TCC ATC CGC CTG TCC CCC AAC CGC CCG CCG CTG GGG GGC      7294
Gly Cys Ala Ser Ile Arg Leu Ser Pro Asn Arg Pro Pro Leu Gly Gly
4030            4035                4040                4045

TCT TGC CGC CTC TTC CCA CTG GGC GCT GTG CAC GCC CTC ACC ACC AAG      7342
Ser Cys Arg Leu Phe Pro Leu Gly Ala Val His Ala Leu Thr Thr Lys
                4050                4055                4060

GTG CAC TTC GAA TGC ACG GGC TGG CAT GAC GCG GAG GAT GCT GGC GCC      7390
Val His Phe Glu Cys Thr Gly Trp His Asp Ala Glu Asp Ala Gly Ala
            4065                4070                4075

CCG CTG GTG TAC GCC CTG CTG CTG CGG CGC TGT CGC CAG GGC CAC TGC      7438
Pro Leu Val Tyr Ala Leu Leu Leu Arg Arg Cys Arg Gln Gly His Cys
        4080                4085                4090

GAG GAG TTC TGT GTC TAC AAG GGC AGC CTC TCC AGC TAC GGA GCC GTG      7486
Glu Glu Phe Cys Val Tyr Lys Gly Ser Leu Ser Ser Tyr Gly Ala Val
        4095                4100                4105

CTG CCC CCG GGT TTC AGG CCA CAC TTC GAG GTG GGC CTG GCC GTG GTG      7534
Leu Pro Pro Gly Phe Arg Pro His Phe Glu Val Gly Leu Ala Val Val
4110            4115                4120                4125

GTG CAG GAC CAG CTG GGA GCC GCT GTG GTC GCC CTC AAC AGG TCT TTG      7582
Val Gln Asp Gln Leu Gly Ala Ala Val Val Ala Leu Asn Arg Ser Leu
                4130                4135                4140

GCC ATC ACC CTC CCA GAG CCC AAC GGC AGC GCA ACG GGG CTC ACA GTC      7630
Ala Ile Thr Leu Pro Glu Pro Asn Gly Ser Ala Thr Gly Leu Thr Val
            4145                4150                4155

TGG CTG CAC GGG CTC ACC GCT AGT GTG CTC CCA GGG CTG CTG CGG CAG      7678
Trp Leu His Gly Leu Thr Ala Ser Val Leu Pro Gly Leu Leu Arg Gln
        4160                4165                4170

GCC GAT CCC CAG CAC GTC ATC GAG TAC TCG TTG GCC CTG GTC ACC GTG      7726
Ala Asp Pro Gln His Val Ile Glu Tyr Ser Leu Ala Leu Val Thr Val
        4175                4180                4185

CTG AAC GAG TAC GAG CGG GCC CTG GAC GTG GCG GCA GAG CCC AAG CAC      7774
Leu Asn Glu Tyr Glu Arg Ala Leu Asp Val Ala Ala Glu Pro Lys His
4190            4195                4200                4205

GAG CGG CAG CAC CGA GCC CAG ATA CGC AAG AAC ATC ACG GAG ACT CTG      7822
Glu Arg Gln His Arg Ala Gln Ile Arg Lys Asn Ile Thr Glu Thr Leu
                4210                4215                4220

GTG TCC CTG AGG GTC CAC ACT GTG GAT GAC ATC CAG CAG ATC GCT GCT      7870
Val Ser Leu Arg Val His Thr Val Asp Asp Ile Gln Gln Ile Ala Ala
            4225                4230                4235

GCG CTG GCC CAG TGC ATG GGG CCC AGC AGG GAG CTC GTA TGC CGC TCG      7918
Ala Leu Ala Gln Cys Met Gly Pro Ser Arg Glu Leu Val Cys Arg Ser
        4240                4245                4250

TGC CTG AAG CAG ACG CTG CAC AAG CTG GAG GCC ATG ATG CTC ATC CTG      7966
Cys Leu Lys Gln Thr Leu His Lys Leu Glu Ala Met Met Leu Ile Leu
        4255                4260                4265
```

-continued

| | | |
|---|---|---|
| CAG GCA GAG ACC ACC GCG GGC ACC GTG ACG CCC ACC GCC ATC GGA GAC<br>Gln Ala Glu Thr Thr Ala Gly Thr Val Thr Pro Thr Ala Ile Gly Asp<br>4270                    4275                    4280                    4285 | 8014 |
| AGC ATC CTC AAC ATC ACA GGA GAC CTC ATC CAC CTG GCC AGC TCG GAC<br>Ser Ile Leu Asn Ile Thr Gly Asp Leu Ile His Leu Ala Ser Ser Asp<br>                    4290                    4295                    4300 | 8062 |
| GTG CGG GCA CCA CAG CCC TCA GAG CTG GGA GCC GAG TCA CCA TCT CGG<br>Val Arg Ala Pro Gln Pro Ser Glu Leu Gly Ala Glu Ser Pro Ser Arg<br>                    4305                    4310                    4315 | 8110 |
| ATG GTG GCG TCC CAG GCC TAC AAC CTG ACC TCT GCC CTC ATG CGC ATC<br>Met Val Ala Ser Gln Ala Tyr Asn Leu Thr Ser Ala Leu Met Arg Ile<br>4320                    4325                    4330 | 8158 |
| CTC ATG CGC TCC CGC GTG CTC AAC GAG GAG CCC CTG ACG CTG GCG GGC<br>Leu Met Arg Ser Arg Val Leu Asn Glu Glu Pro Leu Thr Leu Ala Gly<br>                    4335                    4340                    4345 | 8206 |
| GAG GAG ATC GTG GCC CAG GGC AAG CGC TCG GAC CCG CGG AGC CTG CTG<br>Glu Glu Ile Val Ala Gln Gly Lys Arg Ser Asp Pro Arg Ser Leu Leu<br>4350                    4355                    4360                    4365 | 8254 |
| TGC TAT GGC GGC GCC CCA GGG CCT GGC TGC CAC TTC TCC ATC CCC GAG<br>Cys Tyr Gly Gly Ala Pro Gly Pro Gly Cys His Phe Ser Ile Pro Glu<br>                    4370                    4375                    4380 | 8302 |
| GCT TTC AGC GGG GCC CTG GCC AAC CTC AGT GAC GTG GTG CAG CTC ATC<br>Ala Phe Ser Gly Ala Leu Ala Asn Leu Ser Asp Val Val Gln Leu Ile<br>                    4385                    4390                    4395 | 8350 |
| TTT CTG GTG GAC TCC AAT CCC TTT CCC TTT GGC TAT ATC AGC AAC TAC<br>Phe Leu Val Asp Ser Asn Pro Phe Pro Phe Gly Tyr Ile Ser Asn Tyr<br>                    4400                    4405                    4410 | 8398 |
| ACC GTC TCC ACC AAG GTG GCC TCG ATG GCA TTC CAG ACA CAG GCC GGC<br>Thr Val Ser Thr Lys Val Ala Ser Met Ala Phe Gln Thr Gln Ala Gly<br>                    4415                    4420                    4425 | 8446 |
| GCC CAG ATC CCC ATC GAG CGG CTG GCC TCA GAG CGC GCC ATC ACC GTG<br>Ala Gln Ile Pro Ile Glu Arg Leu Ala Ser Glu Arg Ala Ile Thr Val<br>4430                    4435                    4440                    4445 | 8494 |
| AAG GTG CCC AAC AAC TCG GAC TGG GCT GCC CGG GGC CAC CGC AGC TCC<br>Lys Val Pro Asn Asn Ser Asp Trp Ala Ala Arg Gly His Arg Ser Ser<br>                    4450                    4455                    4460 | 8542 |
| GCC AAC TCC GCC AAC TCC GTT GTG GTC CAG CCC CAG GCC TCC GTC GGT<br>Ala Asn Ser Ala Asn Ser Val Val Val Gln Pro Gln Ala Ser Val Gly<br>                    4465                    4470                    4475 | 8590 |
| GCT GTG GTC ACC CTG GAC AGC AGC AAC CCT GCG GCC GGG CTG CAT CTG<br>Ala Val Val Thr Leu Asp Ser Ser Asn Pro Ala Ala Gly Leu His Leu<br>                    4480                    4485                    4490 | 8638 |
| CAG CTC AAC TAT ACG CTG CTG GAC GGC CAC TAC CTG TCT GAG GAA CCT<br>Gln Leu Asn Tyr Thr Leu Leu Asp Gly His Tyr Leu Ser Glu Glu Pro<br>                    4495                    4500                    4505 | 8686 |
| GAG CCC TAC CTG GCA GTC TAC CTA CAC TCG GAG CCC CGG CCC AAT GAG<br>Glu Pro Tyr Leu Ala Val Tyr Leu His Ser Glu Pro Arg Pro Asn Glu<br>4510                    4515                    4520                    4525 | 8734 |
| CAC AAC TGC TCG GCT AGC AGG AGG ATC CGC CCA GAG TCA CTC CAG GGT<br>His Asn Cys Ser Ala Ser Arg Arg Ile Arg Pro Glu Ser Leu Gln Gly<br>                    4530                    4535                    4540 | 8782 |
| GCT GAC CAC CGG CCC TAC ACC TTC TTC ATT TCC CCG GGG AGC AGA GAC<br>Ala Asp His Arg Pro Tyr Thr Phe Phe Ile Ser Pro Gly Ser Arg Asp<br>                    4545                    4550                    4555 | 8830 |
| CCA GCG GGG AGT TAC CAT CTG AAC CTC TCC AGC CAC TTC CGC TGG TCG<br>Pro Ala Gly Ser Tyr His Leu Asn Leu Ser Ser His Phe Arg Trp Ser<br>                    4560                    4565                    4570 | 8878 |
| GCG CTG CAG GTG TCC GTG GGC CTG TAC ACG TCC CTG TGC CAG TAC TTC<br>Ala Leu Gln Val Ser Val Gly Leu Tyr Thr Ser Leu Cys Gln Tyr Phe | 8926 |

```
                4575                 4580                 4585
AGC GAG GAG GAC ATG GTG TGG CGG ACA GAG GGG CTG CTG CCC CTG GAG        8974
Ser Glu Glu Asp Met Val Trp Arg Thr Glu Gly Leu Leu Pro Leu Glu
4590                 4595                 4600                 4605

GAG ACC TCG CCC CGC CAG GCC GTC TGC CTC ACC CGC CAC CTC ACC GCC        9022
Glu Thr Ser Pro Arg Gln Ala Val Cys Leu Thr Arg His Leu Thr Ala
            4610                 4615                 4620

TTC GGC GCC AGC CTC TTC GTG CCC CCA AGC CAT GTC CGC TTT GTG TTT        9070
Phe Gly Ala Ser Leu Phe Val Pro Pro Ser His Val Arg Phe Val Phe
        4625                 4630                 4635

CCT GAG CCG ACA GCG GAT GTA AAC TAC ATC GTC ATG CTG ACA TGT GCT        9118
Pro Glu Pro Thr Ala Asp Val Asn Tyr Ile Val Met Leu Thr Cys Ala
            4640                 4645                 4650

GTG TGC CTG GTG ACC TAC ATG GTC ATG GCC GCC ATC CTG CAC AAG CTG        9166
Val Cys Leu Val Thr Tyr Met Val Met Ala Ala Ile Leu His Lys Leu
            4655                 4660                 4665

GAC CAG TTG GAT GCC AGC CGG GGC CGC GCC ATC CCT TTC TGT GGG CAG        9214
Asp Gln Leu Asp Ala Ser Arg Gly Arg Ala Ile Pro Phe Cys Gly Gln
4670                 4675                 4680                 4685

CGG GGC CGC TTC AAG TAC GAG ATC CTC GTC AAG ACA GGC TGG GGC CGG        9262
Arg Gly Arg Phe Lys Tyr Glu Ile Leu Val Lys Thr Gly Trp Gly Arg
            4690                 4695                 4700

GGC TCA GGT ACC ACG GCC CAC GTG GGC ATC ATG CTG TAT GGG GTG GAC        9310
Gly Ser Gly Thr Thr Ala His Val Gly Ile Met Leu Tyr Gly Val Asp
            4705                 4710                 4715

AGC CGG AGC GGC CAC CGG CAC CTG GAC GGC GAC AGA GCC TTC CAC CGC        9358
Ser Arg Ser Gly His Arg His Leu Asp Gly Asp Arg Ala Phe His Arg
        4720                 4725                 4730

AAC AGC CTG GAC ATC TTC CGG ATC GCC ACC CCG CAC AGC CTG GGT AGC        9406
Asn Ser Leu Asp Ile Phe Arg Ile Ala Thr Pro His Ser Leu Gly Ser
        4735                 4740                 4745

GTG TGG AAG ATC CGA GTG TGG CAC GAC AAC AAA GGG CTC AGC CCT GCC        9454
Val Trp Lys Ile Arg Val Trp His Asp Asn Lys Gly Leu Ser Pro Ala
4750                 4755                 4760                 4765

TGG TTC CTG CAG CAC GTC ATC GTC AGG GAC CTG CAG ACG GCA CGC AGC        9502
Trp Phe Leu Gln His Val Ile Val Arg Asp Leu Gln Thr Ala Arg Ser
            4770                 4775                 4780

GCC TTC TTC CTG GTC AAT GAC TGG CTT TCG GTG GAG ACG GAG GCC AAC        9550
Ala Phe Phe Leu Val Asn Asp Trp Leu Ser Val Glu Thr Glu Ala Asn
            4785                 4790                 4795

GGG GGC CTG GTG GAG AAG GAG GTG CTG GCC GCG AGC GAC GCA GCC CTT        9598
Gly Gly Leu Val Glu Lys Glu Val Leu Ala Ala Ser Asp Ala Ala Leu
            4800                 4805                 4810

TTG CGC TTC CGG CGC CTG CTG GTG GCT GAG CTG CAG CGT GGC TTC TTT        9646
Leu Arg Phe Arg Arg Leu Leu Val Ala Glu Leu Gln Arg Gly Phe Phe
        4815                 4820                 4825

GAC AAG CAC ATC TGG CTC TCC ATA TGG GAC CGG CCG CCT CGT AGC CGT        9694
Asp Lys His Ile Trp Leu Ser Ile Trp Asp Arg Pro Pro Arg Ser Arg
4830                 4835                 4840                 4845

TTC ACT CGC ATC CAG AGG GCC ACC TGC TGC GTT CTC CTC ATC TGC CTC        9742
Phe Thr Arg Ile Gln Arg Ala Thr Cys Cys Val Leu Leu Ile Cys Leu
            4850                 4855                 4860

TTC CTG GGC GCC AAC GCC GTG TGG TAC GGG GCT GTT GGC GAC TCT GCC        9790
Phe Leu Gly Ala Asn Ala Val Trp Tyr Gly Ala Val Gly Asp Ser Ala
        4865                 4870                 4875

TAC AGC ACG GGG CAT GTG TCC AGG CTG AGC CCG CTG AGC GTC GAC ACA        9838
Tyr Ser Thr Gly His Val Ser Arg Leu Ser Pro Leu Ser Val Asp Thr
        4880                 4885                 4890

GTC GCT GTT GGC CTG GTG TCC AGC GTG GTT GTC TAT CCC GTC TAC CTG        9886
```

```
Val Ala Val Gly Leu Val Ser Ser Val Val Tyr Pro Val Tyr Leu
    4895                4900                4905

GCC ATC CTT TTT CTC TTC CGG ATG TCC CGG AGC AAG GTG GCT GGG AGC           9934
Ala Ile Leu Phe Leu Phe Arg Met Ser Arg Ser Lys Val Ala Gly Ser
4910                4915                4920                4925

CCG AGC CCC ACA CCT GCC GGG CAG CAG GTG CTG GAC ATC GAC AGC TGC           9982
Pro Ser Pro Thr Pro Ala Gly Gln Gln Val Leu Asp Ile Asp Ser Cys
        4930                4935                4940

CTG GAC TCG TCC GTG CTG GAC AGC TCC TTC CTC ACG TTC TCA GGC CTC          10030
Leu Asp Ser Ser Val Leu Asp Ser Ser Phe Leu Thr Phe Ser Gly Leu
    4945                4950                4955

CAC GCT GAG GCC TTT GTT GGA CAG ATG AAG AGT GAC TTG TTT CTG GAT          10078
His Ala Glu Ala Phe Val Gly Gln Met Lys Ser Asp Leu Phe Leu Asp
        4960                4965                4970

GAT TCT AAG AGT CTG GTG TGC TGG CCC TCC GGC GAG GGA ACG CTC AGT          10126
Asp Ser Lys Ser Leu Val Cys Trp Pro Ser Gly Glu Gly Thr Leu Ser
    4975                4980                4985

TGG CCG GAC CTG CTC AGT GAC CCG TCC ATT GTG GGT AGC AAT CTG CGG          10174
Trp Pro Asp Leu Leu Ser Asp Pro Ser Ile Val Gly Ser Asn Leu Arg
4990                4995                5000                5005

CAG CTG GCA CGG GGC CAG GCG GGC CAT GGG CTG GGC CCA GAG GAG GAC          10222
Gln Leu Ala Arg Gly Gln Ala Gly His Gly Leu Gly Pro Glu Glu Asp
        5010                5015                5020

GGC TTC TCC CTG GCC AGC CCC TAC TCG CCT GCC AAA TCC TTC TCA GCA          10270
Gly Phe Ser Leu Ala Ser Pro Tyr Ser Pro Ala Lys Ser Phe Ser Ala
    5025                5030                5035

TCA GAT GAA GAC CTG ATC CAG CAG GTC CTT GCC GAG GGG GTC AGC AGC          10318
Ser Asp Glu Asp Leu Ile Gln Gln Val Leu Ala Glu Gly Val Ser Ser
        5040                5045                5050

CCA GCC CCT ACC CAA GAC ACC CAC ATG GAA ACG GAC CTG CTC AGC AGC          10366
Pro Ala Pro Thr Gln Asp Thr His Met Glu Thr Asp Leu Leu Ser Ser
    5055                5060                5065

CTG TCC AGC ACT CCT GGG GAG AAG ACA GAG ACG CTG GCG CTG CAG AGG          10414
Leu Ser Ser Thr Pro Gly Glu Lys Thr Glu Thr Leu Ala Leu Gln Arg
5070                5075                5080                5085

CTG GGG GAG CTG GGG CCA CCC AGC CCA GGC CTG AAC TGG GAA CAG CCC          10462
Leu Gly Glu Leu Gly Pro Pro Ser Pro Gly Leu Asn Trp Glu Gln Pro
        5090                5095                5100

CAG GCA GCG AGG CTG TCC AGG ACA GGA CTG GTG GAG GGT CTG CGG AAG          10510
Gln Ala Ala Arg Leu Ser Arg Thr Gly Leu Val Glu Gly Leu Arg Lys
    5105                5110                5115

CGC CTG CTG CCG GCC TGG TGT GCC TCC CTG GCC CAC GGG CTC AGC CTG          10558
Arg Leu Leu Pro Ala Trp Cys Ala Ser Leu Ala His Gly Leu Ser Leu
        5120                5125                5130

CTC CTG GTG GCT GTG GCT GTG GCT GTC TCA GGG TGG GTG GGT GCG AGC          10606
Leu Leu Val Ala Val Ala Val Ala Val Ser Gly Trp Val Gly Ala Ser
    5135                5140                5145

TTC CCC CCG GGC GTG AGT GTT GCG TGG CTC CTG TCC AGC AGC GCC AGC          10654
Phe Pro Pro Gly Val Ser Val Ala Trp Leu Leu Ser Ser Ser Ala Ser
5150                5155                5160                5165

TTC CTG GCC TCA TTC CTC GGC TGG GAG CCA CTG AAG GTC TTG CTG GAA          10702
Phe Leu Ala Ser Phe Leu Gly Trp Glu Pro Leu Lys Val Leu Leu Glu
        5170                5175                5180

GCC CTG TAC TTC TCA CTG GTG GCC AAG CGG CTG CAC CCG GAT GAA GAT          10750
Ala Leu Tyr Phe Ser Leu Val Ala Lys Arg Leu His Pro Asp Glu Asp
    5185                5190                5195

GAC ACC CTG GTA GAG AGC CCG GCT GTG ACG CCT GTG AGC GCA CGT GTG          10798
Asp Thr Leu Val Glu Ser Pro Ala Val Thr Pro Val Ser Ala Arg Val
        5200                5205                5210
```

```
                                     -continued

CCC CGC GTA CGG CCA CCC CAC GGC TTT GCA CTC TTC CTG GCC AAG GAA    10846
Pro Arg Val Arg Pro Pro His Gly Phe Ala Leu Phe Leu Ala Lys Glu
5215                 5220                 5225

GAA GCC CGC AAG GTC AAG AGG CTA CAT GGC ATG CTG CGG AGC CTC CTG    10894
Glu Ala Arg Lys Val Lys Arg Leu His Gly Met Leu Arg Ser Leu Leu
5230                 5235                 5240                 5245

GTG TAC ATG CTT TTT CTG CTG GTG ACC CTG CTG GCC AGC TAT GGG GAT    10942
Val Tyr Met Leu Phe Leu Leu Val Thr Leu Leu Ala Ser Tyr Gly Asp
                5250                 5255                 5260

GCC TCA TGC CAT GGG CAC GCC TAC CGT CTG CAA AGC GCC ATC AAG CAG    10990
Ala Ser Cys His Gly His Ala Tyr Arg Leu Gln Ser Ala Ile Lys Gln
            5265                 5270                 5275

GAG CTG CAC AGC CGG GCC TTC CTG GCC ATC ACG CGG TCT GAG GAG CTC    11038
Glu Leu His Ser Arg Ala Phe Leu Ala Ile Thr Arg Ser Glu Glu Leu
        5280                 5285                 5290

TGG CCA TGG ATG GCC CAC GTG CTG CTG CCC TAC GTC CAC GGG AAC CAG    11086
Trp Pro Trp Met Ala His Val Leu Leu Pro Tyr Val His Gly Asn Gln
    5295                 5300                 5305

TCC AGC CCA GAG CTG GGG CCC CCA CGG CTG CGG CAG GTG CGG CTG CAG    11134
Ser Ser Pro Glu Leu Gly Pro Pro Arg Leu Arg Gln Val Arg Leu Gln
5310                 5315                 5320                 5325

GAA GCA CTC TAC CCA GAC CCT CCC GGC CCC AGG GTC CAC ACG TGC TCG    11182
Glu Ala Leu Tyr Pro Asp Pro Pro Gly Pro Arg Val His Thr Cys Ser
                5330                 5335                 5340

GCC GCA GGA GGC TTC AGC ACC AGC GAT TAC GAC GTT GGC TGG GAG AGT    11230
Ala Ala Gly Gly Phe Ser Thr Ser Asp Tyr Asp Val Gly Trp Glu Ser
            5345                 5350                 5355

CCT CAC AAT GGC TCG GGG ACG TGG GCC TAT TCA GCG CCG GAT CTG CTG    11278
Pro His Asn Gly Ser Gly Thr Trp Ala Tyr Ser Ala Pro Asp Leu Leu
        5360                 5365                 5370

GGG GCA TGG TCC TGG GGC TCC TGT GCC GTG TAT GAC AGC GGG GGC TAC    11326
Gly Ala Trp Ser Trp Gly Ser Cys Ala Val Tyr Asp Ser Gly Gly Tyr
    5375                 5380                 5385

GTG CAG GAG CTG GGC CTG AGC CTG GAG GAG AGC CGC GAC CGG CTG CGC    11374
Val Gln Glu Leu Gly Leu Ser Leu Glu Glu Ser Arg Asp Arg Leu Arg
5390                 5395                 5400                 5405

TTC CTG CAG CTG CAC AAC TGG CTG GAC AAC AGG AGC CGC GCT GTG TTC    11422
Phe Leu Gln Leu His Asn Trp Leu Asp Asn Arg Ser Arg Ala Val Phe
                5410                 5415                 5420

CTG GAG CTC ACG CGC TAC AGC CCG GCC GTG GGG CTG CAC GCC GCC GTC    11470
Leu Glu Leu Thr Arg Tyr Ser Pro Ala Val Gly Leu His Ala Ala Val
            5425                 5430                 5435

ACG CTG CGC CTC GAG TTC CCG GCG GCC GGC CGC GCC CTG GCC GCC CTC    11518
Thr Leu Arg Leu Glu Phe Pro Ala Ala Gly Arg Ala Leu Ala Ala Leu
        5440                 5445                 5450

AGC GTC CGC CCC TTT GCG CTG CGC CGC CTC AGC GCG GGC CTC TCG CTG    11566
Ser Val Arg Pro Phe Ala Leu Arg Arg Leu Ser Ala Gly Leu Ser Leu
    5455                 5460                 5465

CCT CTG CTC ACC TCG GTG TGC CTG CTG CTG TTC GCC GTG CAC TTC GCC    11614
Pro Leu Leu Thr Ser Val Cys Leu Leu Leu Phe Ala Val His Phe Ala
5470                 5475                 5480                 5485

GTG GCC GAG GCC CGT ACT TGG CAC AGG GAA GGG CGC TGG CGC GTG CTG    11662
Val Ala Glu Ala Arg Thr Trp His Arg Glu Gly Arg Trp Arg Val Leu
                5490                 5495                 5500

CGG CTC GGA GCC TGG GCG CGG TGG CTG CTG GTG GCG CTG ACG GCG GCC    11710
Arg Leu Gly Ala Trp Ala Arg Trp Leu Leu Val Ala Leu Thr Ala Ala
            5505                 5510                 5515

ACG GCA CTG GTA CGC CTC GCC CAG CTG GGT GCG GCT GAC CGC CAG TGG    11758
Thr Ala Leu Val Arg Leu Ala Gln Leu Gly Ala Ala Asp Arg Gln Trp
        5520                 5525                 5530
```

```
ACC CGT TTC GTG CGC GGC CGC CCG CGC CGC TTC ACT AGC TTC GAC CAG        11806
Thr Arg Phe Val Arg Gly Arg Pro Arg Arg Phe Thr Ser Phe Asp Gln
        5535                5540                5545

GTG GCG CAC GTG AGC TCC GCA GCC CGT GGC CTG GCG GCC TCG CTG CTC        11854
Val Ala His Val Ser Ser Ala Ala Arg Gly Leu Ala Ala Ser Leu Leu
5550            5555                5560                5565

TTC CTG CTT TTG GTC AAG GCT GCC CAG CAC GTA CGC TTC GTG CGC CAG        11902
Phe Leu Leu Leu Val Lys Ala Ala Gln His Val Arg Phe Val Arg Gln
            5570                5575                5580

TGG TCC GTC TTT GGC AAG ACA TTA TGC CGA GCT CTG CCA GAG CTC CTG        11950
Trp Ser Val Phe Gly Lys Thr Leu Cys Arg Ala Leu Pro Glu Leu Leu
        5585                5590                5595

GGG GTC ACC TTG GGC CTG GTG GTG CTC GGG GTA GCC TAC GCC CAG CTG        11998
Gly Val Thr Leu Gly Leu Val Val Leu Gly Val Ala Tyr Ala Gln Leu
    5600                5605                5610

GCC ATC CTG CTC GTG TCT TCC TGT GTG GAC TCC CTC TGG AGC GTG GCC        12046
Ala Ile Leu Leu Val Ser Ser Cys Val Asp Ser Leu Trp Ser Val Ala
        5615                5620                5625

CAG GCC CTG TTG GTG CTG TGC CCT GGG ACT GGG CTC TCT ACC CTG TGT        12094
Gln Ala Leu Leu Val Leu Cys Pro Gly Thr Gly Leu Ser Thr Leu Cys
5630            5635                5640                5645

CCT GCC GAG TCC TGG CAC CTG TCA CCC CTG CTG TGT GTG GGG CTC TGG        12142
Pro Ala Glu Ser Trp His Leu Ser Pro Leu Leu Cys Val Gly Leu Trp
            5650                5655                5660

GCA CTG CGG CTG TGG GGC GCC CTA CGG CTG GGG GCT GTT ATT CTC CGC        12190
Ala Leu Arg Leu Trp Gly Ala Leu Arg Leu Gly Ala Val Ile Leu Arg
        5665                5670                5675

TGG CGC TAC CAC GCC TTG CGT GGA GAG CTG TAC CGG CCG GCC TGG GAG        12238
Trp Arg Tyr His Ala Leu Arg Gly Glu Leu Tyr Arg Pro Ala Trp Glu
    5680                5685                5690

CCC CAG GAC TAC GAG ATG GTG GAG TTG TTC CTG CGC AGG CTG CGC CTC        12286
Pro Gln Asp Tyr Glu Met Val Glu Leu Phe Leu Arg Arg Leu Arg Leu
        5695                5700                5705

TGG ATG GGC CTC AGC AAG GTC AAG GAG TTC CGC CAC AAA GTC CGC TTT        12334
Trp Met Gly Leu Ser Lys Val Lys Glu Phe Arg His Lys Val Arg Phe
5710            5715                5720                5725

GAA GGG ATG GAG CCG CTG CCC TCT CGC TCC TCC AGG GGC TCC AAG GTA        12382
Glu Gly Met Glu Pro Leu Pro Ser Arg Ser Ser Arg Gly Ser Lys Val
            5730                5735                5740

TCC CCG GAT GTG CCC CCA CCC AGC GCT GGC TCC GAT GCC TCG CAC CCC        12430
Ser Pro Asp Val Pro Pro Pro Ser Ala Gly Ser Asp Ala Ser His Pro
        5745                5750                5755

TCC ACC TCC TCC AGC CAG CTG GAT GGG CTG AGC GTG AGC CTG GGC CGG        12478
Ser Thr Ser Ser Ser Gln Leu Asp Gly Leu Ser Val Ser Leu Gly Arg
    5760                5765                5770

CTG GGG ACA AGG TGT GAG CCT GAG CCC TCC CGC CTC CAA GCC GTG TTC        12526
Leu Gly Thr Arg Cys Glu Pro Glu Pro Ser Arg Leu Gln Ala Val Phe
        5775                5780                5785

GAG GCC CTG CTC ACC CAG TTT GAC CGA CTC AAC CAG GCC ACA GAG GAC        12574
Glu Ala Leu Leu Thr Gln Phe Asp Arg Leu Asn Gln Ala Thr Glu Asp
5790            5795                5800                5805

GTC TAC CAG CTG GAG CAG CAG CTG CAC AGC CTG CAA GGC CGC AGG AGC        12622
Val Tyr Gln Leu Glu Gln Gln Leu His Ser Leu Gln Gly Arg Arg Ser
            5810                5815                5820

AGC CGG GCG CCC GCC GGA TCT TCC CGT GGC CCA TCC CCG GGC CTG CGG        12670
Ser Arg Ala Pro Ala Gly Ser Ser Arg Gly Pro Ser Pro Gly Leu Arg
        5825                5830                5835

CCA GCA CTG CCC AGC CGC CTT GCC CGG GCC AGT CGG GGT GTG GAC CTG        12718
Pro Ala Leu Pro Ser Arg Leu Ala Arg Ala Ser Arg Gly Val Asp Leu
```

```
                5840              5845                5850
GCC ACT GGC CCC AGC AGG ACA CCT TCG GGC CAA GAA CAA GGT CCA CCC    12766
Ala Thr Gly Pro Ser Arg Thr Pro Ser Gly Gln Glu Gln Gly Pro Pro
        5855                5860                5865

CAG CAG CAC TTA GTC CTC CTT CCT GGC GGG GGT GGG CCG TGG AGT CGG    12814
Gln Gln His Leu Val Leu Leu Pro Gly Gly Gly Gly Pro Trp Ser Arg
5870            5875                5880                5885

AGT GGA CAC CGC TCA GTA TTA CTT TCT GCC GCT GTC AAG GCC GAG GGC    12862
Ser Gly His Arg Ser Val Leu Leu Ser Ala Ala Val Lys Ala Glu Gly
            5890                5895                5900

CAG GCA GAA TGG CTG CAC GTA GGT TCC CCA GAG AGC AGG CAG GGG CAT    12910
Gln Ala Glu Trp Leu His Val Gly Ser Pro Glu Ser Arg Gln Gly His
                5905                5910                5915

CTG TCT GTC TGT GGG CTT CAG CAC TTT AAA GAG GCT GTG TGG CCA ACC    12958
Leu Ser Val Cys Gly Leu Gln His Phe Lys Glu Ala Val Trp Pro Thr
        5920                5925                5930

AGG ACC CAG GGT CCC CTC CCC AGC TCC CTT GGG AAG GAC ACA GCA GTA    13006
Arg Thr Gln Gly Pro Leu Pro Ser Ser Leu Gly Lys Asp Thr Ala Val
            5935                5940                5945

TTG GAC GGT TTC TAGCCTCTGA GATGCTAATT TATTTCCCCG AGTCCTCAGG        13058
Leu Asp Gly Phe
5950

TACAGCGGGC TGTGCCCGGC CCCACCCCCT GGGCAGATGT CCCCCACTGC TAAGGCTGCT  13118

GGCTTCAGGG AGGGTTAGCC TGCACCGCCG CCACCCTGCC CCTAAGTTAT ACCTCTCCA   13178

GTTCCTACCG TACTCCCTGC ACCGTCTCAC TGTGTGTCTC GTGTCAGTAA TTTATATGGT  13238

GTTAAAATGT GTATATTTTT GTATGTCACT ATTTTCACTA GGGCTGAGGG GCCTGCGCCC  13298

AGAGCTGGCC TCCCCCAACA CCTGCTGCGC TTGGTAGGTG TGGTGGCGTT ATGGCAGCCC  13358

GGCTGCTGCT TGGATGCGAG CTTGGCCTTG GGCCGGTGCT GGGGGCACAG CTGTCTGCCA  13418

GGCACTCTCA TCACCCCAGA GGCCTTGTCA TCCTCCCTTG CCCCAGGCCA GGTAGCAAGA  13478

GAGCAGCGCC CAGGCCTGCT GGCATCAGGT CTGGGCAAGT AGCAGGACTA GGCATGTCAG  13538

AGGACCCCAG GGTGGTTAGA GGAAAAGACT CCTCCTGGGG GCTGGCTCCC AGGGTGGAGG  13598

AAGGTGACTG TGTGTGTGTG TGTGTGCGCG CGCGACGCGC GAGTGTGCTG TATGGCCCAG  13658

GCAGCCTCAA GGCCCTCGGA GCTGGCTGTG CCTGCTTCTG TGTACCACTT CTGTGGGCAT  13718

GGCCGCTTCT AGAGCCTCGA CACCCCCCCA ACCCCCGCAC CAAGCAGACA AAGTCAATAA  13778

AAGAGCTGTC TGACTGCAAA AAAAAAAA                                    13807
```

(2) INFORMATION FOR SEQ ID NO: 6:

(i) SEQUENCE CHARACTERISTICS:
        (A) LENGTH: 4339 amino acids
        (B) TYPE: amino acid
        (D) TOPOLOGY: linear (ii) MOLECULE TYPE: protein (xi) SEQUENCE DESCRIPTION: SEQ ID NO: 6:

```
Gly Ala Ala Cys Arg Val Asn Cys Ser Gly Arg Gly Leu Arg Thr Leu
1               5                   10                  15

Gly Pro Ala Leu Arg Ile Pro Ala Asp Ala Thr Ala Leu Asp Val Ser
            20                  25                  30

His Asn Leu Leu Arg Ala Leu Asp Val Gly Leu Leu Ala Asn Leu Ser
        35                  40                  45

Ala Leu Ala Glu Leu Asp Ile Ser Asn Asn Lys Ile Ser Thr Leu Glu
50                  55                  60
```

-continued

```
Glu Gly Ile Phe Ala Asn Leu Phe Asn Leu Ser Glu Ile Asn Leu Ser
 65                  70                  75                  80

Gly Asn Pro Phe Glu Cys Asp Cys Gly Leu Ala Trp Leu Pro Arg Trp
                 85                  90                  95

Ala Glu Glu Gln Gln Val Arg Val Val Gln Pro Glu Ala Ala Thr Cys
            100                 105                 110

Ala Gly Pro Gly Ser Leu Ala Gly Gln Pro Leu Leu Gly Ile Pro Leu
            115                 120                 125

Leu Asp Ser Gly Cys Gly Glu Glu Tyr Val Ala Cys Leu Pro Asp Asn
130                 135                 140

Ser Ser Gly Thr Val Ala Ala Val Ser Phe Ser Ala Ala His Glu Gly
145                 150                 155                 160

Leu Leu Gln Pro Glu Ala Cys Ser Ala Phe Cys Phe Ser Thr Gly Gln
                165                 170                 175

Gly Leu Ala Ala Leu Ser Glu Gln Gly Trp Cys Leu Cys Gly Ala Ala
            180                 185                 190

Gln Pro Ser Ser Ala Ser Phe Ala Cys Leu Ser Leu Cys Ser Gly Pro
            195                 200                 205

Pro Pro Pro Ala Pro Thr Cys Arg Gly Pro Thr Leu Leu Gln His
210                 215                 220

Val Phe Pro Ala Ser Pro Gly Ala Thr Leu Val Gly Pro His Gly Pro
225                 230                 235                 240

Leu Ala Ser Gly Gln Leu Ala Ala Phe His Ile Ala Ala Pro Leu Pro
                245                 250                 255

Val Thr Ala Thr Arg Trp Asp Phe Gly Asp Gly Ser Ala Glu Val Asp
            260                 265                 270

Ala Ala Gly Pro Ala Ala Ser His Arg Tyr Val Leu Pro Gly Arg Tyr
            275                 280                 285

His Val Thr Ala Val Leu Ala Leu Gly Ala Gly Ser Ala Leu Leu Gly
            290                 295                 300

Thr Asp Val Gln Val Glu Ala Ala Pro Ala Ala Leu Glu Leu Val Cys
305                 310                 315                 320

Pro Ser Ser Val Gln Ser Asp Glu Ser Leu Asp Leu Ser Ile Gln Asn
                325                 330                 335

Arg Gly Gly Ser Gly Leu Glu Ala Ala Tyr Ser Ile Val Ala Leu Gly
            340                 345                 350

Glu Glu Pro Ala Arg Ala Val His Pro Leu Cys Pro Ser Asp Thr Glu
            355                 360                 365

Ile Phe Pro Gly Asn Gly His Cys Tyr Arg Leu Val Val Glu Lys Ala
370                 375                 380

Ala Trp Leu Gln Ala Gln Glu Gln Cys Gln Ala Trp Ala Gly Ala Ala
385                 390                 395                 400

Leu Ala Met Val Asp Ser Pro Ala Val Gln Arg Phe Leu Val Ser Arg
                405                 410                 415

Val Thr Arg Ser Leu Asp Val Trp Ile Gly Phe Ser Thr Val Gln Gly
            420                 425                 430

Val Glu Val Gly Pro Ala Pro Gln Gly Glu Ala Phe Ser Leu Glu Ser
            435                 440                 445

Cys Gln Asn Trp Leu Pro Gly Glu Pro His Pro Ala Thr Ala Glu His
            450                 455                 460

Cys Val Arg Leu Gly Pro Thr Gly Trp Cys Asn Thr Asp Leu Cys Ser
465                 470                 475                 480
```

```
Ala Pro His Ser Tyr Val Cys Glu Leu Gln Pro Gly Gly Pro Val Gln
                485                 490                 495

Asp Ala Glu Asn Leu Leu Val Gly Ala Pro Ser Gly Asp Leu Gln Gly
            500                 505                 510

Pro Leu Thr Pro Leu Ala Gln Gln Asp Gly Leu Ser Ala Pro His Glu
        515                 520                 525

Pro Val Glu Val Met Val Phe Pro Gly Leu Arg Leu Ser Arg Glu Ala
    530                 535                 540

Phe Leu Thr Thr Ala Glu Phe Gly Thr Gln Glu Leu Arg Arg Pro Ala
545                 550                 555                 560

Gln Leu Arg Leu Gln Val Tyr Arg Leu Leu Ser Thr Ala Gly Thr Pro
                565                 570                 575

Glu Asn Gly Ser Glu Pro Glu Ser Arg Ser Pro Asp Asn Arg Thr Gln
            580                 585                 590

Leu Ala Pro Ala Cys Met Pro Gly Gly Arg Trp Cys Pro Gly Ala Asn
        595                 600                 605

Ile Cys Leu Pro Leu Asp Ala Ser Cys His Pro Gln Ala Cys Ala Asn
    610                 615                 620

Gly Cys Thr Ser Gly Pro Gly Leu Pro Gly Ala Pro Tyr Ala Leu Trp
625                 630                 635                 640

Arg Glu Phe Leu Phe Ser Val Ala Ala Gly Pro Pro Ala Gln Tyr Ser
                645                 650                 655

Val Thr Leu His Gly Gln Asp Val Leu Met Leu Pro Gly Asp Leu Val
            660                 665                 670

Gly Leu Gln His Asp Ala Gly Pro Gly Ala Leu Leu His Cys Ser Pro
        675                 680                 685

Ala Pro Gly His Pro Gly Pro Gln Ala Pro Tyr Leu Ser Ala Asn Ala
    690                 695                 700

Ser Ser Trp Leu Pro His Leu Pro Ala Gln Leu Glu Gly Thr Trp Ala
705                 710                 715                 720

Cys Pro Ala Cys Ala Leu Arg Leu Leu Ala Ala Thr Glu Gln Leu Thr
                725                 730                 735

Val Leu Leu Gly Leu Arg Pro Asn Pro Gly Leu Arg Met Pro Gly Arg
            740                 745                 750

Tyr Glu Val Arg Ala Glu Val Gly Asn Gly Val Ser Arg His Asn Leu
        755                 760                 765

Ser Cys Ser Phe Asp Val Val Ser Pro Val Ala Gly Leu Arg Val Ile
    770                 775                 780

Tyr Pro Ala Pro Arg Asp Gly Arg Leu Tyr Val Pro Thr Asn Gly Ser
785                 790                 795                 800

Ala Leu Val Leu Gln Val Asp Ser Gly Ala Asn Ala Thr Ala Thr Ala
                805                 810                 815

Arg Trp Pro Gly Gly Ser Val Ser Ala Arg Phe Glu Asn Val Cys Pro
            820                 825                 830

Ala Leu Val Ala Thr Phe Val Pro Gly Cys Pro Trp Glu Thr Asn Asp
        835                 840                 845

Thr Leu Phe Ser Val Val Ala Leu Pro Trp Leu Ser Glu Gly Glu His
    850                 855                 860

Val Val Asp Val Val Glu Asn Ser Ala Ser Arg Ala Asn Leu Ser
865                 870                 875                 880

Leu Arg Val Thr Ala Glu Glu Pro Ile Cys Gly Leu Arg Ala Thr Pro
                885                 890                 895

Ser Pro Glu Ala Arg Val Leu Gln Gly Val Leu Val Arg Tyr Ser Pro
```

-continued

```
                900                 905                 910
Val Val Glu Ala Gly Ser Asp Met Val Phe Arg Trp Thr Ile Asn Asp
            915                 920                 925
Lys Gln Ser Leu Thr Phe Gln Asn Val Val Phe Asn Val Ile Tyr Gln
            930                 935                 940
Ser Ala Ala Val Phe Lys Leu Ser Leu Thr Ala Ser Asn His Val Ser
945                 950                 955                 960
Asn Val Thr Val Asn Tyr Asn Val Thr Val Glu Arg Met Asn Arg Met
                965                 970                 975
Gln Gly Leu Gln Val Ser Thr Val Pro Ala Val Leu Ser Pro Asn Ala
            980                 985                 990
Thr Leu Val Leu Thr Gly Gly Val Leu Val Asp Ser Ala Val Glu Val
            995                 1000                1005
Ala Phe Leu Trp Asn Phe Gly Asp Gly Glu Gln Ala Leu His Gln Phe
            1010                1015                1020
Gln Pro Pro Tyr Asn Glu Ser Phe Pro Val Pro Asp Pro Ser Val Ala
1025                1030                1035                1040
Gln Val Leu Val Glu His Asn Val Met His Thr Tyr Ala Ala Pro Gly
            1045                1050                1055
Glu Tyr Leu Leu Thr Val Leu Ala Ser Asn Ala Phe Glu Asn Leu Thr
            1060                1065                1070
Gln Gln Val Pro Val Ser Val Arg Ala Ser Leu Pro Ser Val Ala Val
            1075                1080                1085
Gly Val Ser Asp Gly Val Leu Val Ala Gly Arg Pro Val Thr Phe Tyr
            1090                1095                1100
Pro His Pro Leu Pro Ser Pro Gly Gly Val Leu Tyr Thr Trp Asp Phe
1105                1110                1115                1120
Gly Asp Gly Ser Pro Val Leu Thr Gln Ser Gln Pro Ala Ala Asn His
            1125                1130                1135
Thr Tyr Ala Ser Arg Gly Thr Tyr His Val Arg Leu Glu Val Asn Asn
            1140                1145                1150
Thr Val Ser Gly Ala Ala Ala Gln Ala Asp Val Arg Val Phe Glu Glu
            1155                1160                1165
Leu Arg Gly Leu Ser Val Asp Met Ser Leu Ala Val Glu Gln Gly Ala
            1170                1175                1180
Pro Val Val Ser Ala Ala Val Gln Thr Gly Asp Asn Ile Thr Trp
1185                1190                1195                1200
Thr Phe Asp Met Gly Asp Gly Thr Val Leu Ser Gly Pro Glu Ala Thr
            1205                1210                1215
Val Glu His Val Tyr Leu Arg Ala Gln Asn Cys Thr Val Thr Val Gly
            1220                1225                1230
Ala Ala Ser Pro Ala Gly His Leu Ala Arg Ser Leu His Val Leu Val
            1235                1240                1245
Phe Val Leu Glu Val Leu Arg Val Glu Pro Ala Ala Cys Ile Pro Thr
            1250                1255                1260
Gln Pro Asp Ala Arg Leu Thr Ala Tyr Val Thr Gly Asn Pro Ala His
1265                1270                1275                1280
Tyr Leu Phe Asp Trp Thr Phe Gly Asp Gly Ser Ser Asn Thr Thr Val
            1285                1290                1295
Arg Gly Cys Pro Thr Val Thr His Asn Phe Thr Arg Ser Gly Thr Phe
            1300                1305                1310
Pro Leu Ala Leu Val Leu Ser Ser Arg Val Asn Arg Ala His Tyr Phe
            1315                1320                1325
```

```
Thr Ser Ile Cys Val Glu Pro Glu Val Gly Asn Val Thr Leu Gln Pro
    1330                1335                1340
Glu Arg Gln Phe Val Gln Leu Gly Asp Glu Ala Trp Leu Val Ala Cys
1345                1350                1355                1360
Ala Trp Pro Pro Phe Pro Tyr Arg Tyr Thr Trp Asp Phe Gly Thr Glu
                1365                1370                1375
Glu Ala Ala Pro Thr Arg Ala Arg Gly Pro Glu Val Thr Phe Ile Tyr
                1380                1385                1390
Arg Asp Pro Gly Ser Tyr Leu Val Thr Val Thr Ala Ser Asn Asn Ile
                1395                1400                1405
Ser Ala Ala Asn Asp Ser Ala Leu Val Glu Val Gln Glu Pro Val Leu
    1410                1415                1420
Val Thr Ser Ile Lys Val Asn Gly Ser Leu Gly Leu Glu Leu Gln Gln
1425                1430                1435                1440
Pro Tyr Leu Phe Ser Ala Val Gly Arg Gly Arg Pro Ala Ser Tyr Leu
                1445                1450                1455
Trp Asp Leu Gly Asp Gly Gly Trp Leu Glu Gly Pro Glu Val Thr His
                1460                1465                1470
Ala Tyr Asn Ser Thr Gly Asp Phe Thr Val Arg Val Ala Gly Trp Asn
                1475                1480                1485
Glu Val Ser Arg Ser Glu Ala Trp Leu Asn Val Thr Val Lys Arg Arg
    1490                1495                1500
Val Arg Gly Leu Val Val Asn Ala Ser Arg Thr Val Val Pro Leu Asn
1505                1510                1515                1520
Gly Ser Val Ser Phe Ser Thr Ser Leu Glu Ala Gly Ser Asp Val Arg
                1525                1530                1535
Tyr Ser Trp Val Leu Cys Asp Arg Cys Thr Pro Ile Pro Gly Gly Pro
                1540                1545                1550
Thr Ile Ser Tyr Thr Phe Arg Ser Val Gly Thr Phe Asn Ile Ile Val
                1555                1560                1565
Thr Ala Glu Asn Glu Val Gly Ser Ala Gln Asp Ser Ile Phe Val Tyr
    1570                1575                1580
Val Leu Gln Leu Ile Glu Gly Leu Gln Val Gly Gly Gly Arg Tyr
1585                1590                1595                1600
Phe Pro Thr Asn His Thr Val Gln Leu Gln Ala Val Val Arg Asp Gly
                1605                1610                1615
Thr Asn Val Ser Tyr Ser Trp Thr Ala Trp Arg Asp Arg Gly Pro Ala
                1620                1625                1630
Leu Ala Gly Ser Gly Lys Gly Phe Ser Leu Thr Val Leu Glu Ala Gly
                1635                1640                1645
Thr Tyr His Val Gln Leu Arg Ala Thr Asn Met Leu Gly Ser Ala Trp
    1650                1655                1660
Ala Asp Cys Thr Met Asp Phe Val Glu Pro Val Gly Trp Leu Met Val
1665                1670                1675                1680
Thr Ala Ser Pro Asn Pro Ala Val Asn Thr Ser Val Thr Leu Ser
                1685                1690                1695
Ala Glu Leu Ala Gly Gly Ser Gly Val Val Tyr Thr Trp Ser Leu Glu
                1700                1705                1710
Glu Gly Leu Ser Trp Glu Thr Ser Glu Pro Phe Thr Thr His Ser Phe
                1715                1720                1725
Pro Thr Pro Gly Leu His Leu Val Thr Met Thr Ala Gly Asn Pro Leu
                1730                1735                1740
```

```
Gly Ser Ala Asn Ala Thr Val Glu Val Asp Val Gln Val Pro Val Ser
1745                1750                1755                1760

Gly Leu Ser Ile Arg Ala Ser Glu Pro Gly Gly Ser Phe Val Ala Ala
            1765                1770                1775

Gly Ser Ser Val Pro Phe Trp Gly Gln Leu Ala Thr Gly Thr Asn Val
            1780                1785                1790

Ser Trp Cys Trp Ala Val Pro Gly Gly Ser Lys Arg Gly Pro His
        1795                1800                1805

Val Thr Met Val Phe Pro Asp Ala Gly Thr Phe Ser Ile Arg Leu Asn
    1810                1815                1820

Ala Ser Asn Ala Val Ser Trp Val Ser Ala Thr Tyr Asn Leu Thr Ala
1825                1830                1835                1840

Glu Glu Pro Ile Val Gly Leu Val Leu Trp Ala Ser Ser Lys Val Val
            1845                1850                1855

Ala Pro Gly Gln Leu Val His Phe Gln Ile Leu Leu Ala Ala Gly Ser
            1860                1865                1870

Ala Val Thr Phe Arg Leu Gln Val Gly Gly Ala Asn Pro Glu Val Leu
            1875                1880                1885

Pro Gly Pro Arg Phe Ser His Ser Phe Pro Arg Val Gly Asp His Val
            1890                1895                1900

Val Ser Val Arg Gly Lys Asn His Val Ser Trp Ala Gln Ala Gln Val
1905                1910                1915                1920

Arg Ile Val Val Leu Glu Ala Val Ser Gly Leu Gln Met Pro Asn Cys
            1925                1930                1935

Cys Glu Pro Gly Ile Ala Thr Gly Thr Glu Arg Asn Phe Thr Ala Arg
            1940                1945                1950

Val Gln Arg Gly Ser Arg Val Ala Tyr Ala Trp Tyr Phe Ser Leu Gln
            1955                1960                1965

Lys Val Gln Gly Asp Ser Leu Val Ile Leu Ser Gly Arg Asp Val Thr
            1970                1975                1980

Tyr Thr Pro Val Ala Ala Gly Leu Leu Glu Ile Gln Val Arg Ala Phe
1985                1990                1995                2000

Asn Ala Leu Gly Ser Glu Asn Arg Thr Leu Val Leu Glu Val Gln Asp
            2005                2010                2015

Ala Val Gln Tyr Val Ala Leu Gln Ser Gly Pro Cys Phe Thr Asn Arg
            2020                2025                2030

Ser Ala Gln Phe Glu Ala Ala Thr Ser Pro Ser Pro Arg Arg Val Ala
            2035                2040                2045

Tyr His Trp Asp Phe Gly Asp Gly Ser Pro Gly Gln Asp Thr Asp Glu
            2050                2055                2060

Pro Arg Ala Glu His Ser Tyr Leu Arg Pro Gly Asp Tyr Arg Val Gln
2065                2070                2075                2080

Val Asn Ala Ser Asn Leu Val Ser Phe Phe Val Ala Gln Ala Thr Val
            2085                2090                2095

Thr Val Gln Val Leu Ala Cys Arg Glu Pro Glu Val Asp Val Val Leu
            2100                2105                2110

Pro Leu Gln Val Leu Met Arg Arg Ser Gln Arg Asn Tyr Leu Glu Ala
            2115                2120                2125

His Val Asp Leu Arg Asp Cys Val Thr Tyr Gln Thr Glu Tyr Arg Trp
        2130                2135                2140

Glu Val Tyr Arg Thr Ala Ser Cys Gln Arg Pro Gly Arg Pro Ala Arg
2145                2150                2155                2160

Val Ala Leu Pro Gly Val Asp Val Ser Arg Pro Arg Leu Val Leu Pro
```

-continued

```
                2165                2170                2175
Arg Leu Ala Leu Pro Val Gly His Tyr Cys Phe Val Phe Val Ser
                2180                2185                2190
Phe Gly Asp Thr Pro Leu Thr Gln Ser Ile Gln Ala Asn Val Thr Val
        2195                2200                2205
Ala Pro Glu Arg Leu Val Pro Ile Ile Glu Gly Gly Ser Tyr Arg Val
        2210                2215                2220
Trp Ser Asp Thr Arg Asp Leu Val Leu Asp Gly Ser Glu Ser Tyr Asp
2225                2230                2235                2240
Pro Asn Leu Glu Asp Gly Asp Gln Thr Pro Leu Ser Phe His Trp Ala
                2245                2250                2255
Cys Val Ala Ser Thr Gln Arg Glu Ala Gly Gly Cys Ala Leu Asn Phe
                2260                2265                2270
Gly Pro Arg Gly Ser Ser Thr Val Thr Ile Pro Arg Glu Arg Leu Ala
                2275                2280                2285
Ala Gly Val Glu Tyr Thr Phe Ser Leu Thr Val Trp Lys Ala Gly Arg
                2290                2295                2300
Lys Glu Glu Ala Thr Asn Gln Thr Val Leu Ile Arg Ser Gly Arg Val
2305                2310                2315                2320
Pro Ile Val Ser Leu Glu Cys Val Ser Cys Lys Ala Gln Ala Val Tyr
                2325                2330                2335
Glu Val Ser Arg Ser Ser Tyr Val Tyr Leu Glu Gly Arg Cys Leu Asn
                2340                2345                2350
Cys Ser Ser Gly Ser Lys Arg Gly Arg Trp Ala Ala Arg Thr Phe Ser
                2355                2360                2365
Asn Lys Thr Leu Val Leu Asp Glu Thr Thr Thr Ser Thr Gly Ser Ala
                2370                2375                2380
Gly Met Arg Leu Val Leu Arg Arg Gly Val Leu Arg Asp Gly Glu Gly
2385                2390                2395                2400
Tyr Thr Phe Thr Leu Thr Val Leu Gly Arg Ser Gly Glu Glu Glu Gly
                2405                2410                2415
Cys Ala Ser Ile Arg Leu Ser Pro Asn Arg Pro Pro Leu Gly Gly Ser
                2420                2425                2430
Cys Arg Leu Phe Pro Leu Gly Ala Val His Ala Leu Thr Thr Lys Val
                2435                2440                2445
His Phe Glu Cys Thr Gly Trp His Asp Ala Glu Asp Ala Gly Ala Pro
                2450                2455                2460
Leu Val Tyr Ala Leu Leu Leu Arg Arg Cys Arg Gln Gly His Cys Glu
2465                2470                2475                2480
Glu Phe Cys Val Tyr Lys Gly Ser Leu Ser Ser Tyr Gly Ala Val Leu
                2485                2490                2495
Pro Pro Gly Phe Arg Pro His Phe Glu Val Gly Leu Ala Val Val Val
                2500                2505                2510
Gln Asp Gln Leu Gly Ala Ala Val Val Ala Leu Asn Arg Ser Leu Ala
        2515                2520                2525
Ile Thr Leu Pro Glu Pro Asn Gly Ser Ala Thr Gly Leu Thr Val Trp
        2530                2535                2540
Leu His Gly Leu Thr Ala Ser Val Leu Pro Gly Leu Leu Arg Gln Ala
2545                2550                2555                2560
Asp Pro Gln His Val Ile Glu Tyr Ser Leu Ala Leu Val Thr Val Leu
                2565                2570                2575
Asn Glu Tyr Glu Arg Ala Leu Asp Val Ala Ala Glu Pro Lys His Glu
                2580                2585                2590
```

```
Arg Gln His Arg Ala Gln Ile Arg Lys Asn Ile Thr Glu Thr Leu Val
        2595                2600                2605
Ser Leu Arg Val His Thr Val Asp Asp Ile Gln Gln Ile Ala Ala Ala
        2610                2615                2620
Leu Ala Gln Cys Met Gly Pro Ser Arg Glu Leu Val Cys Arg Ser Cys
2625            2630                2635                2640
Leu Lys Gln Thr Leu His Lys Leu Glu Ala Met Met Leu Ile Leu Gln
            2645                2650                2655
Ala Glu Thr Thr Ala Gly Thr Val Thr Pro Thr Ala Ile Gly Asp Ser
        2660                2665                2670
Ile Leu Asn Ile Thr Gly Asp Leu Ile His Leu Ala Ser Ser Asp Val
        2675                2680                2685
Arg Ala Pro Gln Pro Ser Glu Leu Gly Ala Glu Ser Pro Ser Arg Met
    2690                2695                2700
Val Ala Ser Gln Ala Tyr Asn Leu Thr Ser Ala Leu Met Arg Ile Leu
2705            2710                2715                2720
Met Arg Ser Arg Val Leu Asn Glu Glu Pro Leu Thr Leu Ala Gly Glu
            2725                2730                2735
Glu Ile Val Ala Gln Gly Lys Arg Ser Asp Pro Arg Ser Leu Leu Cys
        2740                2745                2750
Tyr Gly Gly Ala Pro Gly Pro Gly Cys His Phe Ser Ile Pro Glu Ala
        2755                2760                2765
Phe Ser Gly Ala Leu Ala Asn Leu Ser Asp Val Val Gln Leu Ile Phe
        2770                2775                2780
Leu Val Asp Ser Asn Pro Phe Pro Phe Gly Tyr Ile Ser Asn Tyr Thr
2785            2790                2795                2800
Val Ser Thr Lys Val Ala Ser Met Ala Phe Gln Thr Gln Ala Gly Ala
            2805                2810                2815
Gln Ile Pro Ile Glu Arg Leu Ala Ser Glu Arg Ala Ile Thr Val Lys
        2820                2825                2830
Val Pro Asn Asn Ser Asp Trp Ala Ala Arg Gly His Arg Ser Ser Ala
        2835                2840                2845
Asn Ser Ala Asn Ser Val Val Val Gln Pro Gln Ala Ser Val Gly Ala
    2850                2855                2860
Val Val Thr Leu Asp Ser Ser Asn Pro Ala Ala Gly Leu His Leu Gln
2865            2870                2875                2880
Leu Asn Tyr Thr Leu Leu Asp Gly His Tyr Leu Ser Glu Glu Pro Glu
            2885                2890                2895
Pro Tyr Leu Ala Val Tyr Leu His Ser Glu Pro Arg Pro Asn Glu His
        2900                2905                2910
Asn Cys Ser Ala Ser Arg Arg Ile Arg Pro Glu Ser Leu Gln Gly Ala
        2915                2920                2925
Asp His Arg Pro Tyr Thr Phe Phe Ile Ser Pro Gly Ser Arg Asp Pro
    2930                2935                2940
Ala Gly Ser Tyr His Leu Asn Leu Ser Ser His Phe Arg Trp Ser Ala
2945            2950                2955                2960
Leu Gln Val Ser Val Gly Leu Tyr Thr Ser Leu Cys Gln Tyr Phe Ser
            2965                2970                2975
Glu Glu Asp Met Val Trp Arg Thr Glu Gly Leu Leu Pro Leu Glu Glu
        2980                2985                2990
Thr Ser Pro Arg Gln Ala Val Cys Leu Thr Arg His Leu Thr Ala Phe
        2995                3000                3005
```

-continued

```
Gly Ala Ser Leu Phe Val Pro Pro Ser His Val Arg Phe Val Phe Pro
    3010                3015                3020

Glu Pro Thr Ala Asp Val Asn Tyr Ile Val Met Leu Thr Cys Ala Val
3025            3030                3035                3040

Cys Leu Val Thr Tyr Met Val Met Ala Ala Ile Leu His Lys Leu Asp
                3045                3050                3055

Gln Leu Asp Ala Ser Arg Gly Arg Ala Ile Pro Phe Cys Gly Gln Arg
            3060                3065                3070

Gly Arg Phe Lys Tyr Glu Ile Leu Val Lys Thr Gly Trp Gly Arg Gly
        3075                3080                3085

Ser Gly Thr Thr Ala His Val Gly Ile Met Leu Tyr Gly Val Asp Ser
    3090                3095                3100

Arg Ser Gly His Arg His Leu Asp Gly Asp Arg Ala Phe His Arg Asn
3105                3110                3115                3120

Ser Leu Asp Ile Phe Arg Ile Ala Thr Pro His Ser Leu Gly Ser Val
                3125                3130                3135

Trp Lys Ile Arg Val Trp His Asp Asn Lys Gly Leu Ser Pro Ala Trp
            3140                3145                3150

Phe Leu Gln His Val Ile Val Arg Asp Leu Gln Thr Ala Arg Ser Ala
        3155                3160                3165

Phe Phe Leu Val Asn Asp Trp Leu Ser Val Glu Thr Glu Ala Asn Gly
    3170                3175                3180

Gly Leu Val Glu Lys Glu Val Leu Ala Ala Ser Asp Ala Ala Leu Leu
3185                3190                3195                3200

Arg Phe Arg Arg Leu Leu Val Ala Glu Leu Gln Arg Gly Phe Phe Asp
                3205                3210                3215

Lys His Ile Trp Leu Ser Ile Trp Asp Arg Pro Arg Ser Arg Phe
            3220                3225                3230

Thr Arg Ile Gln Arg Ala Thr Cys Cys Val Leu Leu Ile Cys Leu Phe
        3235                3240                3245

Leu Gly Ala Asn Ala Val Trp Tyr Gly Ala Val Gly Asp Ser Ala Tyr
    3250                3255                3260

Ser Thr Gly His Val Ser Arg Leu Ser Pro Leu Ser Val Asp Thr Val
3265                3270                3275                3280

Ala Val Gly Leu Val Ser Val Val Tyr Pro Val Tyr Leu Ala
                3285                3290                3295

Ile Leu Phe Leu Phe Arg Met Ser Arg Ser Lys Val Ala Gly Ser Pro
            3300                3305                3310

Ser Pro Thr Pro Ala Gly Gln Gln Val Leu Asp Ile Asp Ser Cys Leu
        3315                3320                3325

Asp Ser Ser Val Leu Asp Ser Ser Phe Leu Thr Phe Ser Gly Leu His
    3330                3335                3340

Ala Glu Ala Phe Val Gly Gln Met Lys Ser Asp Leu Phe Leu Asp Asp
3345                3350                3355                3360

Ser Lys Ser Leu Val Cys Trp Pro Ser Gly Glu Gly Thr Leu Ser Trp
                3365                3370                3375

Pro Asp Leu Leu Ser Asp Pro Ser Ile Val Gly Ser Asn Leu Arg Gln
            3380                3385                3390

Leu Ala Arg Gly Gln Ala Gly His Gly Leu Gly Pro Glu Glu Asp Gly
        3395                3400                3405

Phe Ser Leu Ala Ser Pro Tyr Ser Pro Ala Lys Ser Phe Ser Ala Ser
    3410                3415                3420

Asp Glu Asp Leu Ile Gln Gln Val Leu Ala Glu Gly Val Ser Ser Pro
```

```
                    -continued
3425              3430              3435              3440

Ala Pro Thr Gln Asp Thr His Met Glu Thr Asp Leu Leu Ser Ser Leu
                3445              3450              3455

Ser Ser Thr Pro Gly Glu Lys Thr Glu Thr Leu Ala Leu Gln Arg Leu
                3460              3465              3470

Gly Glu Leu Gly Pro Pro Ser Pro Gly Leu Asn Trp Glu Gln Pro Gln
                3475              3480              3485

Ala Ala Arg Leu Ser Arg Thr Gly Leu Val Glu Gly Leu Arg Lys Arg
                3490              3495              3500

Leu Leu Pro Ala Trp Cys Ala Ser Leu Ala His Gly Leu Ser Leu Leu
3505              3510              3515              3520

Leu Val Ala Val Ala Val Ala Val Ser Gly Trp Val Gly Ala Ser Phe
                3525              3530              3535

Pro Pro Gly Val Ser Val Ala Trp Leu Leu Ser Ser Ser Ala Ser Phe
                3540              3545              3550

Leu Ala Ser Phe Leu Gly Trp Glu Pro Leu Lys Val Leu Leu Glu Ala
                3555              3560              3565

Leu Tyr Phe Ser Leu Val Ala Lys Arg Leu His Pro Asp Glu Asp Asp
                3570              3575              3580

Thr Leu Val Glu Ser Pro Ala Val Thr Pro Val Ser Ala Arg Val Pro
3585              3590              3595              3600

Arg Val Arg Pro Pro His Gly Phe Ala Leu Phe Leu Ala Lys Glu Glu
                3605              3610              3615

Ala Arg Lys Val Lys Arg Leu His Gly Met Leu Arg Ser Leu Leu Val
                3620              3625              3630

Tyr Met Leu Phe Leu Leu Val Thr Leu Leu Ala Ser Tyr Gly Asp Ala
                3635              3640              3645

Ser Cys His Gly His Ala Tyr Arg Leu Gln Ser Ala Ile Lys Gln Glu
3650              3655              3660

Leu His Ser Arg Ala Phe Leu Ala Ile Thr Arg Ser Glu Glu Leu Trp
3665              3670              3675              3680

Pro Trp Met Ala His Val Leu Leu Pro Tyr Val His Gly Asn Gln Ser
                3685              3690              3695

Ser Pro Glu Leu Gly Pro Pro Arg Leu Arg Gln Val Arg Leu Gln Glu
                3700              3705              3710

Ala Leu Tyr Pro Asp Pro Pro Gly Pro Arg Val His Thr Cys Ser Ala
                3715              3720              3725

Ala Gly Gly Phe Ser Thr Ser Asp Tyr Asp Val Gly Trp Glu Ser Pro
                3730              3735              3740

His Asn Gly Ser Gly Thr Trp Ala Tyr Ser Ala Pro Asp Leu Leu Gly
3745              3750              3755              3760

Ala Trp Ser Trp Gly Ser Cys Ala Val Tyr Asp Ser Gly Gly Tyr Val
                3765              3770              3775

Gln Glu Leu Gly Leu Ser Leu Glu Glu Ser Arg Asp Arg Leu Arg Phe
                3780              3785              3790

Leu Gln Leu His Asn Trp Leu Asp Asn Arg Ser Arg Ala Val Phe Leu
                3795              3800              3805

Glu Leu Thr Arg Tyr Ser Pro Ala Val Gly Leu His Ala Ala Val Thr
                3810              3815              3820

Leu Arg Leu Glu Phe Pro Ala Ala Gly Arg Ala Leu Ala Ala Leu Ser
3825              3830              3835              3840

Val Arg Pro Phe Ala Leu Arg Arg Leu Ser Ala Gly Leu Ser Leu Pro
                3845              3850              3855
```

-continued

```
Leu Leu Thr Ser Val Cys Leu Leu Phe Ala Val His Phe Ala Val
            3860                3865                3870
Ala Glu Ala Arg Thr Trp His Arg Glu Gly Arg Trp Arg Val Leu Arg
            3875                3880                3885
Leu Gly Ala Trp Ala Arg Trp Leu Leu Val Ala Leu Thr Ala Ala Thr
            3890                3895                3900
Ala Leu Val Arg Leu Ala Gln Leu Gly Ala Ala Asp Arg Gln Trp Thr
3905                3910                3915                3920
Arg Phe Val Arg Gly Arg Pro Arg Arg Phe Thr Ser Phe Asp Gln Val
            3925                3930                3935
Ala His Val Ser Ser Ala Ala Arg Gly Leu Ala Ala Ser Leu Leu Phe
            3940                3945                3950
Leu Leu Leu Val Lys Ala Ala Gln His Val Arg Phe Val Arg Gln Trp
            3955                3960                3965
Ser Val Phe Gly Lys Thr Leu Cys Arg Ala Leu Pro Glu Leu Leu Gly
            3970                3975                3980
Val Thr Leu Gly Leu Val Val Leu Gly Val Ala Tyr Ala Gln Leu Ala
3985                3990                3995                4000
Ile Leu Leu Val Ser Ser Cys Val Asp Ser Leu Trp Ser Val Ala Gln
            4005                4010                4015
Ala Leu Leu Val Leu Cys Pro Gly Thr Gly Leu Ser Thr Leu Cys Pro
            4020                4025                4030
Ala Glu Ser Trp His Leu Ser Pro Leu Leu Cys Val Gly Leu Trp Ala
            4035                4040                4045
Leu Arg Leu Trp Gly Ala Leu Arg Leu Gly Ala Val Ile Leu Arg Trp
            4050                4055                4060
Arg Tyr His Ala Leu Arg Gly Glu Leu Tyr Arg Pro Ala Trp Glu Pro
4065                4070                4075                4080
Gln Asp Tyr Glu Met Val Glu Leu Phe Leu Arg Arg Leu Arg Leu Trp
            4085                4090                4095
Met Gly Leu Ser Lys Val Lys Glu Phe Arg His Lys Val Arg Phe Glu
            4100                4105                4110
Gly Met Glu Pro Leu Pro Ser Arg Ser Ser Arg Gly Ser Lys Val Ser
            4115                4120                4125
Pro Asp Val Pro Pro Ser Ala Gly Ser Asp Ala Ser His Pro Ser
            4130                4135                4140
Thr Ser Ser Ser Gln Leu Asp Gly Leu Ser Val Ser Leu Gly Arg Leu
4145                4150                4155                4160
Gly Thr Arg Cys Glu Pro Glu Pro Ser Arg Leu Gln Ala Val Phe Glu
            4165                4170                4175
Ala Leu Leu Thr Gln Phe Asp Arg Leu Asn Gln Ala Thr Glu Asp Val
            4180                4185                4190
Tyr Gln Leu Glu Gln Gln Leu His Ser Leu Gln Gly Arg Arg Ser Ser
            4195                4200                4205
Arg Ala Pro Ala Gly Ser Ser Arg Gly Pro Ser Pro Gly Leu Arg Pro
            4210                4215                4220
Ala Leu Pro Ser Arg Leu Ala Arg Ala Ser Arg Gly Val Asp Leu Ala
4225                4230                4235                4240
Thr Gly Pro Ser Arg Thr Pro Ser Gly Gln Glu Gln Gly Pro Pro Gln
            4245                4250                4255
Gln His Leu Val Leu Leu Pro Gly Gly Gly Pro Trp Ser Arg Ser
            4260                4265                4270
```

```
Gly His Arg Ser Val Leu Leu Ser Ala Ala Val Lys Ala Glu Gly Gln
            4275                4280                4285

Ala Glu Trp Leu His Val Gly Ser Pro Glu Ser Arg Gln Gly His Leu
        4290                4295                4300

Ser Val Cys Gly Leu Gln His Phe Lys Glu Ala Val Trp Pro Thr Arg
4305                4310                4315                4320

Thr Gln Gly Pro Leu Pro Ser Ser Leu Gly Lys Asp Thr Ala Val Leu
                4325                4330                4335

Asp Gly Phe (2) INFORMATION FOR SEQ ID NO: 7:

(i) SEQUENCE CHARACTERISTICS:
        (A) LENGTH: 14148 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION:212..13117

(ix) FEATURE:
        (A) NAME/KEY: misc_feature
        (B) LOCATION:212..278
        (D) OTHER INFORMATION:/note= "Probable signal sequence"

(ix) FEATURE:
        (A) NAME/KEY: misc_feature
        (B) LOCATION:359..4574
        (D) OTHER INFORMATION:/note= "N-linked glycosylation
            sites at the following positions: 359, 476, 557, 572, 770

(ix) FEATURE:
        (A) NAME/KEY: misc_feature
        (B) LOCATION:4574..8144
        (D) OTHER INFORMATION:/note= "N-linked glycosylation
            sites at following locations: 4559, 4574, 4631, 4763,
            4832

(ix) FEATURE:
        (A) NAME/KEY: misc_feature
        (B) LOCATION:8363..11741
        (D) OTHER INFORMATION:/note= "N-linked glycosylation
            sites at following locations: 8471, 8663, 8732, 8843,
            8984

(ix) FEATURE:
        (A) NAME/KEY: misc_feature
        (B) LOCATION:7949..8009
        (D) OTHER INFORMATION:/note= "Predicted transmembrane
            domain"

(ix) FEATURE:
        (A) NAME/KEY: misc_feature
        (B) LOCATION:8288..8348
        (D) OTHER INFORMATION:/note= "Predicted transmembrane
            domain"

(ix) FEATURE:
        (A) NAME/KEY: misc_feature
        (B) LOCATION:9434..9494
        (D) OTHER INFORMATION:/note= "Predicted transmembrane
            domain"

(ix) FEATURE:
        (A) NAME/KEY: misc_feature
        (B) LOCATION:10052..10112
        (D) OTHER INFORMATION:/note= "Predicted transmembrane
```

```
        (ix) FEATURE:
              (A) NAME/KEY: misc_feature
              (B) LOCATION:10178..10238
              (D) OTHER INFORMATION:/note= "Predicted transmembrane
                  domain"

(ix) FEATURE:
              (A) NAME/KEY: misc_feature
              (B) LOCATION:10886..10946
              (D) OTHER INFORMATION:/note= "Predicted transmembrane
                  domain"

(ix) FEATURE:
              (A) NAME/KEY: misc_feature
              (B) LOCATION:10955..11015
              (D) OTHER INFORMATION:/note= "Predicted transmembrane
                  domain"

(ix) FEATURE:
              (A) NAME/KEY: misc_feature
              (B) LOCATION:11216..11276
              (D) OTHER INFORMATION:/note= "Predicted transmembrane
                  domain"

(ix) FEATURE:
              (A) NAME/KEY: misc_feature
              (B) LOCATION:11894..11954
              (D) OTHER INFORMATION:/note= "Predicted transmembrane
                  domain"

(ix) FEATURE:
              (A) NAME/KEY: misc_feature
              (B) LOCATION:12293..12353
              (D) OTHER INFORMATION:/note= "Predicted transmembrane
                  domain"

(ix) FEATURE:
              (A) NAME/KEY: misc_feature
              (B) LOCATION:12377..12437
              (D) OTHER INFORMATION:/note= "Predicted transmembrane
                  domain"

(ix) FEATURE:
              (A) NAME/KEY: misc_feature
              (B) LOCATION:212..278
              (D) OTHER INFORMATION:/note= "Possible hinge sequence"

(ix) FEATURE:
              (A) NAME/KEY: misc_feature
              (B) LOCATION:279
              (D) OTHER INFORMATION:/note= "Cleavage site"

(xi) SEQUENCE DESCRIPTION: SEQ ID NO: 7:

GCACTGCAGC GCCAGCGTCC GAGCGGGCGG CCGAGCTCCC GGAGCGGCCT GGCCCCGAGC      60

CCCGAGCGGG CGTCGCTCAG CAGCAGGTCG CGGCCGCGCA GCCCCATCCA GCCCCGCGCC     120

CGCCATGCCG TCCGCGGGCC CCGCCTGAGC TGCGGTCTCC GCGCGCGGGC GGGCCTGGGG     180

ACGGCGGGGC CATGCGCGCG CTGCCCTAAC G ATG CCG CCC GCC GCG CCC GCC        232
                                  Met Pro Pro Ala Ala Pro Ala
                                                4340        4345

CGC CTG GCG CTG GCC CTG GGC CTG GGC CTG TGG CTC GGG GCG CTG GCG      280
Arg Leu Ala Leu Ala Leu Gly Leu Gly Leu Trp Leu Gly Ala Leu Ala
        4350                4355                4360

GGG GGC CCC GGG CGC GGC TGC GGG CCC TGC GAG CCC CCC TGC CTC TGC      328
Gly Gly Pro Gly Arg Gly Cys Gly Pro Cys Glu Pro Pro Cys Leu Cys
    4365                4370                4375

GGC CCA GCG CCC GGC GCC GCC TGC CGC GTC AAC TGC TCG GGC CGC GGG      376
Gly Pro Ala Pro Gly Ala Ala Cys Arg Val Asn Cys Ser Gly Arg Gly
    4380                4385                4390

CTG CGG ACG CTC GGT CCC GCG CTG CGC ATC CCC GCG GAC GCC ACA GCG      424
```

```
Leu Arg Thr Leu Gly Pro Ala Leu Arg Ile Pro Ala Asp Ala Thr Ala
4395                4400                4405                4410

CTA GAC GTC TCC CAC AAC CTG CTC CGG GCG CTG GAC GTT GGG CTC CTG         472
Leu Asp Val Ser His Asn Leu Leu Arg Ala Leu Asp Val Gly Leu Leu
                4415                4420                4425

GCG AAC CTC TCG GCG CTG GCA GAG CTG GAT ATA AGC AAC AAC AAG ATT         520
Ala Asn Leu Ser Ala Leu Ala Glu Leu Asp Ile Ser Asn Asn Lys Ile
                4430                4435                4440

TCT ACG TTA GAA GAA GGA ATA TTT GCT AAT TTA TTT AAT TTA AGT GAA         568
Ser Thr Leu Glu Glu Gly Ile Phe Ala Asn Leu Phe Asn Leu Ser Glu
                4445                4450                4455

ATA AAC CTG AGT GGG AAC CCG TTT GAG TGT GAC TGT GGC CTG GCG TGG         616
Ile Asn Leu Ser Gly Asn Pro Phe Glu Cys Asp Cys Gly Leu Ala Trp
                4460                4465                4470

CTG CCG CGA TGG GCG GAG GAG CAG CAG GTG CGG GTG GTG CAG CCC GAG         664
Leu Pro Arg Trp Ala Glu Glu Gln Gln Val Arg Val Val Gln Pro Glu
4475                4480                4485                4490

GCA GCC ACG TGT GCT GGG CCT GGC TCC CTG GCT GGC CAG CCT CTG CTT         712
Ala Ala Thr Cys Ala Gly Pro Gly Ser Leu Ala Gly Gln Pro Leu Leu
                4495                4500                4505

GGC ATC CCC TTG CTG GAC AGT GGC TGT GGT GAG GAG TAT GTC GCC TGC         760
Gly Ile Pro Leu Leu Asp Ser Gly Cys Gly Glu Glu Tyr Val Ala Cys
                4510                4515                4520

CTC CCT GAC AAC AGC TCA GGC ACC GTG GCA GCA GTG TCC TTT TCA GCT         808
Leu Pro Asp Asn Ser Ser Gly Thr Val Ala Ala Val Ser Phe Ser Ala
                4525                4530                4535

GCC CAC GAA GGC CTG CTT CAG CCA GAG GCC TGC AGC GCC TTC TGC TTC         856
Ala His Glu Gly Leu Leu Gln Pro Glu Ala Cys Ser Ala Phe Cys Phe
                4540                4545                4550

TCC ACC GGC CAG GGC CTC GCA GCC CTC TCG GAG CAG GGC TGG TGC CTG         904
Ser Thr Gly Gln Gly Leu Ala Ala Leu Ser Glu Gln Gly Trp Cys Leu
4555                4560                4565                4570

TGT GGG GCG GCC CAG CCC TCC AGT GCC TCC TTT GCC TGC CTG TCC CTC         952
Cys Gly Ala Ala Gln Pro Ser Ser Ala Ser Phe Ala Cys Leu Ser Leu
                4575                4580                4585

TGC TCC GGC CCC CCG CCA CCT CCT GCC CCC ACC TGT AGG GGC CCC ACC        1000
Cys Ser Gly Pro Pro Pro Pro Ala Pro Thr Cys Arg Gly Pro Thr
                4590                4595                4600

CTC CTC CAG CAC GTC TTC CCT GCC TCC CCA GGG GCC ACC CTG GTG GGG        1048
Leu Leu Gln His Val Phe Pro Ala Ser Pro Gly Ala Thr Leu Val Gly
                4605                4610                4615

CCC CAC GGA CCT CTG GCC TCT GGC CAG CTA GCA GCC TTC CAC ATC GCT        1096
Pro His Gly Pro Leu Ala Ser Gly Gln Leu Ala Ala Phe His Ile Ala
                4620                4625                4630

GCC CCG CTC CCT GTC ACT GCC ACA CGC TGG GAC TTC GGA GAC GGC TCC        1144
Ala Pro Leu Pro Val Thr Ala Thr Arg Trp Asp Phe Gly Asp Gly Ser
4635                4640                4645                4650

GCC GAG GTG GAT GCC GCT GGG CCG GCT GCC TCG CAT CGC TAT GTG CTG        1192
Ala Glu Val Asp Ala Ala Gly Pro Ala Ala Ser His Arg Tyr Val Leu
                4655                4660                4665

CCT GGG CGC TAT CAC GTG ACG GCC GTG CTG GCC CTG GGG GCC GGC TCA        1240
Pro Gly Arg Tyr His Val Thr Ala Val Leu Ala Leu Gly Ala Gly Ser
                4670                4675                4680

GCC CTG CTG GGG ACA GAC GTG CAG GTG GAA GCG GCA CCT GCC GCC CTG        1288
Ala Leu Leu Gly Thr Asp Val Gln Val Glu Ala Ala Pro Ala Ala Leu
                4685                4690                4695

GAG CTC GTG TGC CCG TCC TCG GTG CAG AGT GAC GAG AGC CTT GAC CTC        1336
Glu Leu Val Cys Pro Ser Ser Val Gln Ser Asp Glu Ser Leu Asp Leu
                4700                4705                4710
```

| | |
|---|---|
| AGC ATC CAG AAC CGC GGT GGT TCA GGC CTG GAG GCC GCC TAC AGC ATC<br>Ser Ile Gln Asn Arg Gly Gly Ser Gly Leu Glu Ala Ala Tyr Ser Ile<br>4715                4720                4725                4730 | 1384 |
| GTG GCC CTG GGC GAG GAG CCG GCC CGA GCG GTG CAC CCG CTC TGC CCC<br>Val Ala Leu Gly Glu Glu Pro Ala Arg Ala Val His Pro Leu Cys Pro<br>                4735                4740                4745 | 1432 |
| TCG GAC ACG GAG ATC TTC CCT GGC AAC GGG CAC TGC TAC CGC CTG GTG<br>Ser Asp Thr Glu Ile Phe Pro Gly Asn Gly His Cys Tyr Arg Leu Val<br>                4750                4755                4760 | 1480 |
| GTG GAG AAG GCG GCC TGG CTG CAG GCG CAG GAG CAG TGT CAG GCC TGG<br>Val Glu Lys Ala Ala Trp Leu Gln Ala Gln Glu Gln Cys Gln Ala Trp<br>4765                4770                4775 | 1528 |
| GCC GGG GCC GCC CTG GCA ATG GTG GAC AGT CCC GCC GTG CAG CGC TTC<br>Ala Gly Ala Ala Leu Ala Met Val Asp Ser Pro Ala Val Gln Arg Phe<br>                4780                4785                4790 | 1576 |
| CTG GTC TCC CGG GTC ACC AGG AGC CTA GAC GTG TGG ATC GGC TTC TCG<br>Leu Val Ser Arg Val Thr Arg Ser Leu Asp Val Trp Ile Gly Phe Ser<br>4795                4800                4805                4810 | 1624 |
| ACT GTG CAG GGG GTG GAG GTG GGC CCA GCG CCG CAG GGC GAG GCC TTC<br>Thr Val Gln Gly Val Glu Val Gly Pro Ala Pro Gln Gly Glu Ala Phe<br>                4815                4820                4825 | 1672 |
| AGC CTG GAG AGC TGC CAG AAC TGG CTG CCC GGG GAG CCA CAC CCA GCC<br>Ser Leu Glu Ser Cys Gln Asn Trp Leu Pro Gly Glu Pro His Pro Ala<br>                4830                4835                4840 | 1720 |
| ACA GCC GAG CAC TGC GTC CGG CTC GGG CCC ACC GGG TGG TGT AAC ACC<br>Thr Ala Glu His Cys Val Arg Leu Gly Pro Thr Gly Trp Cys Asn Thr<br>                4845                4850                4855 | 1768 |
| GAC CTG TGC TCA GCG CCG CAC AGC TAC GTC TGC GAG CTG CAG CCC GGA<br>Asp Leu Cys Ser Ala Pro His Ser Tyr Val Cys Glu Leu Gln Pro Gly<br>                4860                4865                4870 | 1816 |
| GGC CCA GTG CAG GAT GCC GAG AAC CTC CTC GTG GGA GCG CCC AGT GGG<br>Gly Pro Val Gln Asp Ala Glu Asn Leu Leu Val Gly Ala Pro Ser Gly<br>4875                4880                4885                4890 | 1864 |
| GAC CTG CAG GGA CCC CTG ACG CCT CTG GCA CAG CAG GAC GGC CTC TCA<br>Asp Leu Gln Gly Pro Leu Thr Pro Leu Ala Gln Gln Asp Gly Leu Ser<br>                4895                4900                4905 | 1912 |
| GCC CCG CAC GAG CCC GTG GAG GTC ATG GTA TTC CCG GGC CTG CGT CTG<br>Ala Pro His Glu Pro Val Glu Val Met Val Phe Pro Gly Leu Arg Leu<br>                4910                4915                4920 | 1960 |
| AGC CGT GAA GCC TTC CTC ACC ACG GCC GAA TTT GGG ACC CAG GAG CTC<br>Ser Arg Glu Ala Phe Leu Thr Thr Ala Glu Phe Gly Thr Gln Glu Leu<br>                4925                4930                4935 | 2008 |
| CGG CGG CCC GCC CAG CTG CGG CTG CAG GTG TAC CGG CTC CTC AGC ACA<br>Arg Arg Pro Ala Gln Leu Arg Leu Gln Val Tyr Arg Leu Leu Ser Thr<br>                4940                4945                4950 | 2056 |
| GCA GGG ACC CCG GAG AAC GGC AGC GAG CCT GAG AGC AGG TCC CCG GAC<br>Ala Gly Thr Pro Glu Asn Gly Ser Glu Pro Glu Ser Arg Ser Pro Asp<br>4955                4960                4965                4970 | 2104 |
| AAC AGG ACC CAG CTG GCC CCC GCG TGC ATG CCA GGG GGA CGC TGG TGC<br>Asn Arg Thr Gln Leu Ala Pro Ala Cys Met Pro Gly Gly Arg Trp Cys<br>                4975                4980                4985 | 2152 |
| CCT GGA GCC AAC ATC TGC TTG CCG CTG GAC GCC TCT TGC CAC CCC CAG<br>Pro Gly Ala Asn Ile Cys Leu Pro Leu Asp Ala Ser Cys His Pro Gln<br>                4990                4995                5000 | 2200 |
| GCC TGC GCC AAT GGC TGC ACG TCA GGG CCA GGG CTA CCC GGG GCC CCC<br>Ala Cys Ala Asn Gly Cys Thr Ser Gly Pro Gly Leu Pro Gly Ala Pro<br>                5005                5010                5015 | 2248 |
| TAT GCG CTA TGG AGA GAG TTC CTC TTC TCC GTT GCC GCG GGG CCC CCC<br>Tyr Ala Leu Trp Arg Glu Phe Leu Phe Ser Val Ala Ala Gly Pro Pro<br>                5020                5025                5030 | 2296 |

```
GCG CAG TAC TCG GTC ACC CTC CAC GGC CAG GAT GTC CTC ATG CTC CCT     2344
Ala Gln Tyr Ser Val Thr Leu His Gly Gln Asp Val Leu Met Leu Pro
5035             5040             5045             5050

GGT GAC CTC GTT GGC TTG CAG CAC GAC GCT GGC CCT GGC GCC CTC CTG     2392
Gly Asp Leu Val Gly Leu Gln His Asp Ala Gly Pro Gly Ala Leu Leu
         5055             5060             5065

CAC TGC TCG CCG GCT CCC GGC CAC CCT GGT CCC CAG GCC CCG TAC CTC     2440
His Cys Ser Pro Ala Pro Gly His Pro Gly Pro Gln Ala Pro Tyr Leu
             5070             5075             5080

TCC GCC AAC GCC TCG TCA TGG CTG CCC CAC TTG CCA GCC CAG CTG GAG     2488
Ser Ala Asn Ala Ser Ser Trp Leu Pro His Leu Pro Ala Gln Leu Glu
         5085             5090             5095

GGC ACT TGG GCC TGC CCT GCC TGT GCC CTG CGG CTG CTT GCA GCC ACG     2536
Gly Thr Trp Ala Cys Pro Ala Cys Ala Leu Arg Leu Leu Ala Ala Thr
     5100             5105             5110

GAA CAG CTC ACC GTG CTG CTG GGC TTG AGG CCC AAC CCT GGA CTG CGG     2584
Glu Gln Leu Thr Val Leu Leu Gly Leu Arg Pro Asn Pro Gly Leu Arg
5115             5120             5125             5130

ATG CCT GGG CGC TAT GAG GTC CGG GCA GAG GTG GGC AAT GGC GTG TCC     2632
Met Pro Gly Arg Tyr Glu Val Arg Ala Glu Val Gly Asn Gly Val Ser
             5135             5140             5145

AGG CAC AAC CTC TCC TGC AGC TTT GAC GTG GTC TCC CCA GTG GCT GGG     2680
Arg His Asn Leu Ser Cys Ser Phe Asp Val Val Ser Pro Val Ala Gly
         5150             5155             5160

CTG CGG GTC ATC TAC CCT GCC CCC CGC GAC GGC CGC CTC TAC GTG CCC     2728
Leu Arg Val Ile Tyr Pro Ala Pro Arg Asp Gly Arg Leu Tyr Val Pro
         5165             5170             5175

ACC AAC GGC TCA GCC TTG GTG CTC CAG GTG GAC TCT GGT GCC AAC GCC     2776
Thr Asn Gly Ser Ala Leu Val Leu Gln Val Asp Ser Gly Ala Asn Ala
         5180             5185             5190

ACG GCC ACG GCT CGC TGG CCT GGG GGC AGT GTC AGC GCC CGC TTT GAG     2824
Thr Ala Thr Ala Arg Trp Pro Gly Gly Ser Val Ser Ala Arg Phe Glu
5195             5200             5205             5210

AAT GTC TGC CCT GCC CTG GTG GCC ACC TTC GTG CCC GGC TGC CCC TGG     2872
Asn Val Cys Pro Ala Leu Val Ala Thr Phe Val Pro Gly Cys Pro Trp
             5215             5220             5225

GAG ACC AAC GAT ACC CTG TTC TCA GTG GTA GCA CTG CCG TGG CTC AGT     2920
Glu Thr Asn Asp Thr Leu Phe Ser Val Val Ala Leu Pro Trp Leu Ser
         5230             5235             5240

GAG GGG GAG CAC GTG GTG GAC GTG GTG GTG GAA AAC AGC GCC AGC CGG     2968
Glu Gly Glu His Val Val Asp Val Val Val Glu Asn Ser Ala Ser Arg
         5245             5250             5255

GCC AAC CTC AGC CTG CGG GTG ACG GCG GAG GAG CCC ATC TGT GGC CTC     3016
Ala Asn Leu Ser Leu Arg Val Thr Ala Glu Glu Pro Ile Cys Gly Leu
         5260             5265             5270

CGC GCC ACG CCC AGC CCC GAG GCC CGT GTA CTG CAG GGA GTC CTA GTG     3064
Arg Ala Thr Pro Ser Pro Glu Ala Arg Val Leu Gln Gly Val Leu Val
5275             5280             5285             5290

AGG TAC AGC CCC GTG GTG GAG GCC GGC TCG GAC ATG GTC TTC CGG TGG     3112
Arg Tyr Ser Pro Val Val Glu Ala Gly Ser Asp Met Val Phe Arg Trp
             5295             5300             5305

ACC ATC AAC GAC AAG CAG TCC CTG ACC TTC CAG AAC GTG GTC TTC AAT     3160
Thr Ile Asn Asp Lys Gln Ser Leu Thr Phe Gln Asn Val Val Phe Asn
         5310             5315             5320

GTC ATT TAT CAG AGC GCG GCG GTC TTC AAG CTC TCA CTG ACG GCC TCC     3208
Val Ile Tyr Gln Ser Ala Ala Val Phe Lys Leu Ser Leu Thr Ala Ser
         5325             5330             5335

AAC CAC GTG AGC AAC GTC ACC GTG AAC TAC AAC GTA ACC GTG GAG CGG     3256
Asn His Val Ser Asn Val Thr Val Asn Tyr Asn Val Thr Val Glu Arg
```

```
     5340              5345              5350
ATG AAC AGG ATG CAG GGT CTG CAG GTC TCC ACA GTG CCG GCC GTG CTG        3304
Met Asn Arg Met Gln Gly Leu Gln Val Ser Thr Val Pro Ala Val Leu
5355              5360              5365              5370

TCC CCC AAT GCC ACA CTG GTA CTG ACG GGT GGT GTG CTG GTG GAC TCA        3352
Ser Pro Asn Ala Thr Leu Val Leu Thr Gly Gly Val Leu Val Asp Ser
                  5375              5380              5385

GCT GTG GAG GTG GCC TTC CTG TGG AAC TTT GGG GAT GGG GAG CAG GCC        3400
Ala Val Glu Val Ala Phe Leu Trp Asn Phe Gly Asp Gly Glu Gln Ala
              5390              5395              5400

CTC CAC CAG TTC CAG CCT CCG TAC AAC GAG TCC TTC CCG GTT CCA GAC        3448
Leu His Gln Phe Gln Pro Pro Tyr Asn Glu Ser Phe Pro Val Pro Asp
          5405              5410              5415

CCC TCG GTG GCC CAG GTG CTG GTG GAG CAC AAT GTC ATG CAC ACC TAC        3496
Pro Ser Val Ala Gln Val Leu Val Glu His Asn Val Met His Thr Tyr
      5420              5425              5430

GCT GCC CCA GGT GAG TAC CTC CTG ACC GTG CTG GCA TCT AAT GCC TTC        3544
Ala Ala Pro Gly Glu Tyr Leu Leu Thr Val Leu Ala Ser Asn Ala Phe
5435              5440              5445              5450

GAG AAC CTG ACG CAG CAG GTG CCT GTG AGC GTG CGC GCC TCC CTG CCC        3592
Glu Asn Leu Thr Gln Gln Val Pro Val Ser Val Arg Ala Ser Leu Pro
                  5455              5460              5465

TCC GTG GCT GTG GGT GTG AGT GAC GGC GTC CTG GTG GCC GGC CGG CCC        3640
Ser Val Ala Val Gly Val Ser Asp Gly Val Leu Val Ala Gly Arg Pro
              5470              5475              5480

GTC ACC TTC TAC CCG CAC CCG CTG CCC TCG CCT GGG GGT GTT CTT TAC        3688
Val Thr Phe Tyr Pro His Pro Leu Pro Ser Pro Gly Gly Val Leu Tyr
          5485              5490              5495

ACG TGG GAC TTC GGG GAC GGC TCC CCT GTC CTG ACC CAG AGC CAG CCG        3736
Thr Trp Asp Phe Gly Asp Gly Ser Pro Val Leu Thr Gln Ser Gln Pro
      5500              5505              5510

GCT GCC AAC CAC ACC TAT GCC TCG AGG GGC ACC TAC CAC GTG CGC CTG        3784
Ala Ala Asn His Thr Tyr Ala Ser Arg Gly Thr Tyr His Val Arg Leu
5515              5520              5525              5530

GAG GTC AAC AAC ACG GTG AGC GGT GCG GCG GCC CAG GCG GAT GTG CGC        3832
Glu Val Asn Asn Thr Val Ser Gly Ala Ala Ala Gln Ala Asp Val Arg
                  5535              5540              5545

GTC TTT GAG GAG CTC CGC GGA CTC AGC GTG GAC ATG AGC CTG GCC GTG        3880
Val Phe Glu Glu Leu Arg Gly Leu Ser Val Asp Met Ser Leu Ala Val
              5550              5555              5560

GAG CAG GGC GCC CCC GTG GTG GTC AGC GCC GCG GTG CAG ACG GGC GAC        3928
Glu Gln Gly Ala Pro Val Val Val Ser Ala Ala Val Gln Thr Gly Asp
          5565              5570              5575

AAC ATC ACG TGG ACC TTC GAC ATG GGG GAC GGC ACC GTG CTG TCG GGC        3976
Asn Ile Thr Trp Thr Phe Asp Met Gly Asp Gly Thr Val Leu Ser Gly
      5580              5585              5590

CCG GAG GCA ACA GTG GAG CAT GTG TAC CTG CGG GCA CAG AAC TGC ACA        4024
Pro Glu Ala Thr Val Glu His Val Tyr Leu Arg Ala Gln Asn Cys Thr
5595              5600              5605              5610

GTG ACC GTG GGT GCG GCC AGC CCC GCC GGC CAC CTG GCC CGG AGC CTG        4072
Val Thr Val Gly Ala Ala Ser Pro Ala Gly His Leu Ala Arg Ser Leu
                  5615              5620              5625

CAC GTG CTG GTC TTC GTC CTG GAG GTG CTG CGC GTT GAA CCC GCC GCC        4120
His Val Leu Val Phe Val Leu Glu Val Leu Arg Val Glu Pro Ala Ala
              5630              5635              5640

TGC ATC CCC ACG CAG CCT GAC GCG CGG CTC ACG GCC TAC GTC ACC GGG        4168
Cys Ile Pro Thr Gln Pro Asp Ala Arg Leu Thr Ala Tyr Val Thr Gly
          5645              5650              5655

AAC CCG GCC CAC TAC CTC TTC GAC TGG ACC TTC GGG GAT GGC TCC TCC        4216
```

```
                                                     -continued

Asn Pro Ala His Tyr Leu Phe Asp Trp Thr Phe Gly Asp Gly Ser Ser
    5660                5665                5670

AAC ACG ACC GTG CGG GGG TGC CCG ACG GTG ACA CAC AAC TTC ACG CGG    4264
Asn Thr Thr Val Arg Gly Cys Pro Thr Val Thr His Asn Phe Thr Arg
5675            5680                5685                5690

AGC GGC ACG TTC CCC CTG GCG CTG GTG CTG TCC AGC CGC GTG AAC AGG    4312
Ser Gly Thr Phe Pro Leu Ala Leu Val Leu Ser Ser Arg Val Asn Arg
                5695                5700                5705

GCG CAT TAC TTC ACC AGC ATC TGC GTG GAG CCA GAG GTG GGC AAC GTC    4360
Ala His Tyr Phe Thr Ser Ile Cys Val Glu Pro Glu Val Gly Asn Val
            5710                5715                5720

ACC CTG CAG CCA GAG AGG CAG TTT GTG CAG CTC GGG GAC GAG GCC TGG    4408
Thr Leu Gln Pro Glu Arg Gln Phe Val Gln Leu Gly Asp Glu Ala Trp
        5725                5730                5735

CTG GTG GCA TGT GCC TGG CCC CCG TTC CCC TAC CGC TAC ACC TGG GAC    4456
Leu Val Ala Cys Ala Trp Pro Pro Phe Pro Tyr Arg Tyr Thr Trp Asp
    5740                5745                5750

TTT GGC ACC GAG GAA GCC GCC CCC ACC CGT GCC AGG GGC CCT GAG GTG    4504
Phe Gly Thr Glu Glu Ala Ala Pro Thr Arg Ala Arg Gly Pro Glu Val
5755            5760                5765                5770

ACG TTC ATC TAC CGA GAC CCA GGC TCC TAT CTT GTG ACA GTC ACC GCG    4552
Thr Phe Ile Tyr Arg Asp Pro Gly Ser Tyr Leu Val Thr Val Thr Ala
                5775                5780                5785

TCC AAC AAC ATC TCT GCT GCC AAT GAC TCA GCC CTG GTG GAG GTG CAG    4600
Ser Asn Asn Ile Ser Ala Ala Asn Asp Ser Ala Leu Val Glu Val Gln
            5790                5795                5800

GAG CCC GTG CTG GTC ACC AGC ATC AAG GTC AAT GGC TCC CTT GGG CTG    4648
Glu Pro Val Leu Val Thr Ser Ile Lys Val Asn Gly Ser Leu Gly Leu
        5805                5810                5815

GAG CTG CAG CAG CCG TAC CTG TTC TCT GCT GTG GGC CGT GGG CGC CCC    4696
Glu Leu Gln Gln Pro Tyr Leu Phe Ser Ala Val Gly Arg Gly Arg Pro
    5820                5825                5830

GCC AGC TAC CTG TGG GAT CTG GGG GAC GGT GGG TGG CTC GAG GGT CCG    4744
Ala Ser Tyr Leu Trp Asp Leu Gly Asp Gly Gly Trp Leu Glu Gly Pro
5835            5840                5845                5850

GAG GTC ACC CAC GCT TAC AAC AGC ACA GGT GAC TTC ACC GTT AGG GTG    4792
Glu Val Thr His Ala Tyr Asn Ser Thr Gly Asp Phe Thr Val Arg Val
                5855                5860                5865

GCC GGC TGG AAT GAG GTG AGC CGC AGC GAG GCC TGG CTC AAT GTG ACG    4840
Ala Gly Trp Asn Glu Val Ser Arg Ser Glu Ala Trp Leu Asn Val Thr
            5870                5875                5880

GTG AAG CGG CGC GTG CGG GGG CTC GTC GTC AAT GCA AGC CGC ACG GTG    4888
Val Lys Arg Arg Val Arg Gly Leu Val Val Asn Ala Ser Arg Thr Val
        5885                5890                5895

GTG CCC CTG AAT GGG AGC GTG AGC TTC AGC ACG TCG CTG GAG GCC GGC    4936
Val Pro Leu Asn Gly Ser Val Ser Phe Ser Thr Ser Leu Glu Ala Gly
    5900                5905                5910

AGT GAT GTG CGC TAT TCC TGG GTG CTC TGT GAC CGC TGC ACG CCC ATC    4984
Ser Asp Val Arg Tyr Ser Trp Val Leu Cys Asp Arg Cys Thr Pro Ile
5915            5920                5925                5930

CCT GGG GGT CCT ACC ATC TCT TAC ACC TTC CGC TCC GTG GGC ACC TTC    5032
Pro Gly Gly Pro Thr Ile Ser Tyr Thr Phe Arg Ser Val Gly Thr Phe
                5935                5940                5945

AAT ATC ATC GTC ACG GCT GAG AAC GAG GTG GGC TCC GCC CAG GAC AGC    5080
Asn Ile Ile Val Thr Ala Glu Asn Glu Val Gly Ser Ala Gln Asp Ser
            5950                5955                5960

ATC TTC GTC TAT GTC CTG CAG CTC ATA GAG GGG CTG CAG GTG GTG GGC    5128
Ile Phe Val Tyr Val Leu Gln Leu Ile Glu Gly Leu Gln Val Val Gly
        5965                5970                5975
```

-continued

| | |
|---|---|
| GGT GGC CGC TAC TTC CCC ACC AAC CAC ACG GTA CAG CTG CAG GCC GTG<br>Gly Gly Arg Tyr Phe Pro Thr Asn His Thr Val Gln Leu Gln Ala Val<br>        5980                  5985                  5990 | 5176 |
| GTT AGG GAT GGC ACC AAC GTC TCC TAC AGC TGG ACT GCC TGG AGG GAC<br>Val Arg Asp Gly Thr Asn Val Ser Tyr Ser Trp Thr Ala Trp Arg Asp<br>5995                  6000                  6005                  6010 | 5224 |
| AGG GGC CCG GCC CTG GCC GGC AGC GGC AAA GGC TTC TCG CTC ACC GTG<br>Arg Gly Pro Ala Leu Ala Gly Ser Gly Lys Gly Phe Ser Leu Thr Val<br>                6015                  6020                  6025 | 5272 |
| CTC GAG GCC GGC ACC TAC CAT GTG CAG CTG CGG GCC ACC AAC ATG CTG<br>Leu Glu Ala Gly Thr Tyr His Val Gln Leu Arg Ala Thr Asn Met Leu<br>                6030                  6035                  6040 | 5320 |
| GGC AGC GCC TGG GCC GAC TGC ACC ATG GAC TTC GTG GAG CCT GTG GGG<br>Gly Ser Ala Trp Ala Asp Cys Thr Met Asp Phe Val Glu Pro Val Gly<br>                6045                  6050                  6055 | 5368 |
| TGG CTG ATG GTG ACC GCC TCC CCG AAC CCA GCT GCC GTC AAC ACA AGC<br>Trp Leu Met Val Thr Ala Ser Pro Asn Pro Ala Ala Val Asn Thr Ser<br>                6060                  6065                  6070 | 5416 |
| GTC ACC CTC AGT GCC GAG CTG GCT GGT GGC AGT GGT GTC GTA TAC ACT<br>Val Thr Leu Ser Ala Glu Leu Ala Gly Gly Ser Gly Val Val Tyr Thr<br>6075                  6080                  6085                  6090 | 5464 |
| TGG TCC TTG GAG GAG GGG CTG AGC TGG GAG ACC TCC GAG CCA TTT ACC<br>Trp Ser Leu Glu Glu Gly Leu Ser Trp Glu Thr Ser Glu Pro Phe Thr<br>                6095                  6100                  6105 | 5512 |
| ACC CAT AGC TTC CCC ACA CCC GGC CTG CAC TTG GTC ACC ATG ACG GCA<br>Thr His Ser Phe Pro Thr Pro Gly Leu His Leu Val Thr Met Thr Ala<br>                6110                  6115                  6120 | 5560 |
| GGG AAC CCG CTG GGC TCA GCC AAC GCC ACC GTG GAA GTG GAT GTG CAG<br>Gly Asn Pro Leu Gly Ser Ala Asn Ala Thr Val Glu Val Asp Val Gln<br>                6125                  6130                  6135 | 5608 |
| GTG CCT GTG AGT GGC CTC AGC ATC AGG GCC AGC GAG CCC GGA GGC AGC<br>Val Pro Val Ser Gly Leu Ser Ile Arg Ala Ser Glu Pro Gly Gly Ser<br>                6140                  6145                  6150 | 5656 |
| TTC GTG GCG GCC GGG TCC TCT GTG CCC TTT TGG GGG CAG CTG GCC ACG<br>Phe Val Ala Ala Gly Ser Ser Val Pro Phe Trp Gly Gln Leu Ala Thr<br>6155                6160                  6165                  6170 | 5704 |
| GGC ACC AAT GTG AGC TGG TGC TGG GCT GTG CCC GGC GGC AGC AGC AAG<br>Gly Thr Asn Val Ser Trp Cys Trp Ala Val Pro Gly Gly Ser Ser Lys<br>                6175                  6180                  6185 | 5752 |
| CGT GGC CCT CAT GTC ACC ATG GTC TTC CCG GAT GCT GGC ACC TTC TCC<br>Arg Gly Pro His Val Thr Met Val Phe Pro Asp Ala Gly Thr Phe Ser<br>                6190                  6195                  6200 | 5800 |
| ATC CGG CTC AAT GCC TCC AAC GCA GTC AGC TGG GTC TCA GCC ACG TAC<br>Ile Arg Leu Asn Ala Ser Asn Ala Val Ser Trp Val Ser Ala Thr Tyr<br>                6205                  6210                  6215 | 5848 |
| AAC CTC ACG GCG GAG GAG CCC ATC GTG GGC CTG GTG CTG TGG GCC AGC<br>Asn Leu Thr Ala Glu Glu Pro Ile Val Gly Leu Val Leu Trp Ala Ser<br>                6220                  6225                  6230 | 5896 |
| AGC AAG GTG GTG GCG CCC GGG CAG CTG GTC CAT TTT CAG ATC CTG CTG<br>Ser Lys Val Val Ala Pro Gly Gln Leu Val His Phe Gln Ile Leu Leu<br>6235                  6240                  6245                  6250 | 5944 |
| GCT GCC GGC TCA GCT GTC ACC TTC CGC CTG CAG GTC GGC GGG GCC AAC<br>Ala Ala Gly Ser Ala Val Thr Phe Arg Leu Gln Val Gly Gly Ala Asn<br>                6255                  6260                  6265 | 5992 |
| CCC GAG GTG CTC CCC GGG CCC CGT TTC TCC CAC AGC TTC CCC CGC GTC<br>Pro Glu Val Leu Pro Gly Pro Arg Phe Ser His Ser Phe Pro Arg Val<br>                6270                  6275                  6280 | 6040 |
| GGA GAC CAC GTG GTG AGC GTG CGG GGC AAA AAC CAC GTG AGC TGG GCC<br>Gly Asp His Val Val Ser Val Arg Gly Lys Asn His Val Ser Trp Ala<br>                6285                  6290                  6295 | 6088 |

-continued

```
CAG GCG CAG GTG CGC ATC GTG GTG CTG GAG GCC GTG AGT GGG CTG CAG        6136
Gln Ala Gln Val Arg Ile Val Val Leu Glu Ala Val Ser Gly Leu Gln
        6300            6305            6310

ATG CCC AAC TGC TGC GAG CCT GGC ATC GCC ACG GGC ACT GAG AGG AAC        6184
Met Pro Asn Cys Cys Glu Pro Gly Ile Ala Thr Gly Thr Glu Arg Asn
6315            6320            6325            6330

TTC ACA GCC CGC GTG CAG CGC GGC TCT CGG GTC GCC TAC GCC TGG TAC        6232
Phe Thr Ala Arg Val Gln Arg Gly Ser Arg Val Ala Tyr Ala Trp Tyr
            6335            6340            6345

TTC TCG CTG CAG AAG GTC CAG GGC GAC TCG CTG GTC ATC CTG TCG GGC        6280
Phe Ser Leu Gln Lys Val Gln Gly Asp Ser Leu Val Ile Leu Ser Gly
        6350            6355            6360

CGC GAC GTC ACC TAC ACG CCC GTG GCC GCG GGG CTG TTG GAG ATC CAG        6328
Arg Asp Val Thr Tyr Thr Pro Val Ala Ala Gly Leu Leu Glu Ile Gln
        6365            6370            6375

GTG CGC GCC TTC AAC GCC CTG GGC AGT GAG AAC CGC ACG CTG GTG CTG        6376
Val Arg Ala Phe Asn Ala Leu Gly Ser Glu Asn Arg Thr Leu Val Leu
        6380            6385            6390

GAG GTT CAG GAC GCC GTC CAG TAT GTG GCC CTG CAG AGC GGC CCC TGC        6424
Glu Val Gln Asp Ala Val Gln Tyr Val Ala Leu Gln Ser Gly Pro Cys
6395            6400            6405            6410

TTC ACC AAC CGC TCG GCG CAG TTT GAG GCC GCC ACC AGC CCC AGC CCC        6472
Phe Thr Asn Arg Ser Ala Gln Phe Glu Ala Ala Thr Ser Pro Ser Pro
            6415            6420            6425

CGG CGT GTG GCC TAC CAC TGG GAC TTT GGG GAT GGG TCG CCA GGG CAG        6520
Arg Arg Val Ala Tyr His Trp Asp Phe Gly Asp Gly Ser Pro Gly Gln
        6430            6435            6440

GAC ACA GAT GAG CCC AGG GCC GAG CAC TCC TAC CTG AGG CCT GGG GAC        6568
Asp Thr Asp Glu Pro Arg Ala Glu His Ser Tyr Leu Arg Pro Gly Asp
        6445            6450            6455

TAC CGC GTG CAG GTG AAC GCC TCC AAC CTG GTG AGC TTC TTC GTG GCG        6616
Tyr Arg Val Gln Val Asn Ala Ser Asn Leu Val Ser Phe Phe Val Ala
        6460            6465            6470

CAG GCC ACG GTG ACC GTC CAG GTG CTG GCC TGC CGG GAG CCG GAG GTG        6664
Gln Ala Thr Val Thr Val Gln Val Leu Ala Cys Arg Glu Pro Glu Val
6475            6480            6485            6490

GAC GTG GTC CTG CCC CTG CAG GTG CTG ATG CGG CGA TCA CAG CGC AAC        6712
Asp Val Val Leu Pro Leu Gln Val Leu Met Arg Arg Ser Gln Arg Asn
            6495            6500            6505

TAC TTG GAG GCC CAC GTT GAC CTG CGC GAC TGC GTC ACC TAC CAG ACT        6760
Tyr Leu Glu Ala His Val Asp Leu Arg Asp Cys Val Thr Tyr Gln Thr
        6510            6515            6520

GAG TAC CGC TGG GAG GTG TAT CGC ACC GCC AGC TGC CAG CGG CCG GGG        6808
Glu Tyr Arg Trp Glu Val Tyr Arg Thr Ala Ser Cys Gln Arg Pro Gly
        6525            6530            6535

CGC CCA GCG CGT GTG GCC CTG CCC GGC GTG GAC GTG AGC CGG CCT CGG        6856
Arg Pro Ala Arg Val Ala Leu Pro Gly Val Asp Val Ser Arg Pro Arg
        6540            6545            6550

CTG GTG CTG CCG CGG CTG GCG CTG CCT GTG GGG CAC TAC TGC TTT GTG        6904
Leu Val Leu Pro Arg Leu Ala Leu Pro Val Gly His Tyr Cys Phe Val
6555            6560            6565            6570

TTT GTC GTG TCA TTT GGG GAC ACG CCA CTG ACA CAG AGC ATC CAG GCC        6952
Phe Val Val Ser Phe Gly Asp Thr Pro Leu Thr Gln Ser Ile Gln Ala
            6575            6580            6585

AAT GTG ACG GTG GCC CCC GAG CGC CTG GTG CCC ATC ATT GAG GGT GGC        7000
Asn Val Thr Val Ala Pro Glu Arg Leu Val Pro Ile Ile Glu Gly Gly
        6590            6595            6600

TCA TAC CGC GTG TGG TCA GAC ACA CGG GAC CTG GTG CTG GAT GGG AGC        7048
Ser Tyr Arg Val Trp Ser Asp Thr Arg Asp Leu Val Leu Asp Gly Ser
```

-continued

| | | | | | | | | | | | | | | | |
|---|---|---|---|---|---|---|---|---|---|---|---|---|---|---|---|
| | | 6605 | | | | 6610 | | | | | 6615 | | | | |
| GAG | TCC | TAC | GAC | CCC | AAC | CTG | GAG | GAC | GGC | GAC | CAG | ACG | CCG | CTC | AGT | 7096 |
| Glu | Ser | Tyr | Asp | Pro | Asn | Leu | Glu | Asp | Gly | Asp | Gln | Thr | Pro | Leu | Ser |
| | | | | 6620 | | | | 6625 | | | | 6630 |

```
                   6605                6610                     6615
GAG TCC TAC GAC CCC AAC CTG GAG GAC GGC GAC CAG ACG CCG CTC AGT           7096
Glu Ser Tyr Asp Pro Asn Leu Glu Asp Gly Asp Gln Thr Pro Leu Ser
            6620            6625            6630

TTC CAC TGG GCC TGT GTG GCT TCG ACA CAG AGG GAG GCT GGC GGG TGT           7144
Phe His Trp Ala Cys Val Ala Ser Thr Gln Arg Glu Ala Gly Gly Cys
6635                6640            6645                6650

GCG CTG AAC TTT GGG CCC CGC GGG AGC AGC ACG GTC ACC ATT CCA CGG           7192
Ala Leu Asn Phe Gly Pro Arg Gly Ser Ser Thr Val Thr Ile Pro Arg
                6655            6660                6665

GAG CGG CTG GCG GCT GGC GTG GAG TAC ACC TTC AGC CTG ACC GTG TGG           7240
Glu Arg Leu Ala Ala Gly Val Glu Tyr Thr Phe Ser Leu Thr Val Trp
            6670            6675            6680

AAG GCC GGC CGC AAG GAG GAG GCC ACC AAC CAG ACG GTG CTG ATC CGG           7288
Lys Ala Gly Arg Lys Glu Glu Ala Thr Asn Gln Thr Val Leu Ile Arg
            6685            6690            6695

AGT GGC CGG GTG CCC ATT GTG TCC TTG GAG TGT GTG TCC TGC AAG GCA           7336
Ser Gly Arg Val Pro Ile Val Ser Leu Glu Cys Val Ser Cys Lys Ala
        6700            6705            6710

CAG GCC GTG TAC GAA GTG AGC CGC AGC TCC TAC GTG TAC TTG GAG GGC           7384
Gln Ala Val Tyr Glu Val Ser Arg Ser Ser Tyr Val Tyr Leu Glu Gly
6715            6720            6725                6730

CGC TGC CTC AAT TGC AGC AGC GGC TCC AAG CGA GGG CGG TGG GCT GCA           7432
Arg Cys Leu Asn Cys Ser Ser Gly Ser Lys Arg Gly Arg Trp Ala Ala
                6735            6740            6745

CGT ACG TTC AGC AAC AAG ACG CTG GTG CTG GAT GAG ACC ACC ACA TCC           7480
Arg Thr Phe Ser Asn Lys Thr Leu Val Leu Asp Glu Thr Thr Thr Ser
            6750            6755            6760

ACG GGC AGT GCA GGC ATG CGA CTG GTG CTG CGG CGG GGC GTG CTG CGG           7528
Thr Gly Ser Ala Gly Met Arg Leu Val Leu Arg Arg Gly Val Leu Arg
            6765            6770            6775

GAC GGC GAG GGA TAC ACC TTC ACG CTC ACG GTG CTG GGC CGC TCT GGC           7576
Asp Gly Glu Gly Tyr Thr Phe Thr Leu Thr Val Leu Gly Arg Ser Gly
            6780            6785            6790

GAG GAG GAG GGC TGC GCC TCC ATC CGC CTG TCC CCC AAC CGC CCG CCG           7624
Glu Glu Glu Gly Cys Ala Ser Ile Arg Leu Ser Pro Asn Arg Pro Pro
6795                6800            6805                6810

CTG GGG GGC TCT TGC CGC CTC TTC CCA CTG GGC GCT GTG CAC GCC CTC           7672
Leu Gly Gly Ser Cys Arg Leu Phe Pro Leu Gly Ala Val His Ala Leu
                6815            6820            6825

ACC ACC AAG GTG CAC TTC GAA TGC ACG GGC TGG CAT GAC GCG GAG GAT           7720
Thr Thr Lys Val His Phe Glu Cys Thr Gly Trp His Asp Ala Glu Asp
            6830            6835            6840

GCT GGC GCC CCG CTG GTG TAC GCC CTG CTG CTG CGG CGC TGT CGC CAG           7768
Ala Gly Ala Pro Leu Val Tyr Ala Leu Leu Leu Arg Arg Cys Arg Gln
            6845            6850            6855

GGC CAC TGC GAG GAG TTC TGT GTC TAC AAG GGC AGC CTC TCC AGC TAC           7816
Gly His Cys Glu Glu Phe Cys Val Tyr Lys Gly Ser Leu Ser Ser Tyr
            6860            6865            6870

GGA GCC GTG CTG CCC CCG GGT TTC AGG CCA CAC TTC GAG GTG GGC CTG           7864
Gly Ala Val Leu Pro Pro Gly Phe Arg Pro His Phe Glu Val Gly Leu
6875                6880            6885                6890

GCC GTG GTG GTG CAG GAC CAG CTG GGA GCC GCT GTG GTC GCC CTC AAC           7912
Ala Val Val Val Gln Asp Gln Leu Gly Ala Ala Val Val Ala Leu Asn
                6895            6900            6905

AGG TCT TTG GCC ATC ACC CTC CCA GAG CCC AAC GGC AGC GCA ACG GGG           7960
Arg Ser Leu Ala Ile Thr Leu Pro Glu Pro Asn Gly Ser Ala Thr Gly
                6910            6915            6920

CTC ACA GTC TGG CTG CAC GGG CTC ACC GCT AGT GTG CTC CCA GGG CTG           8008
```

```
                                                        -continued

Leu Thr Val Trp Leu His Gly Leu Thr Ala Ser Val Leu Pro Gly Leu
            6925                6930                6935

CTG CGG CAG GCC GAT CCC CAG CAC GTC ATC GAG TAC TCG TTG GCC CTG         8056
Leu Arg Gln Ala Asp Pro Gln His Val Ile Glu Tyr Ser Leu Ala Leu
    6940                6945                6950

GTC ACC GTG CTG AAC GAG TAC GAG CGG GCC CTG GAC GTG GCG GCA GAG         8104
Val Thr Val Leu Asn Glu Tyr Glu Arg Ala Leu Asp Val Ala Ala Glu
6955                6960                6965                6970

CCC AAG CAC GAG CGG CAG CAC CGA GCC CAG ATA CGC AAG AAC ATC ACG         8152
Pro Lys His Glu Arg Gln His Arg Ala Gln Ile Arg Lys Asn Ile Thr
                6975                6980                6985

GAG ACT CTG GTG TCC CTG AGG GTC CAC ACT GTG GAT GAC ATC CAG CAG         8200
Glu Thr Leu Val Ser Leu Arg Val His Thr Val Asp Asp Ile Gln Gln
            6990                6995                7000

ATC GCT GCT GCG CTG GCC CAG TGC ATG GGG CCC AGC AGG GAG CTC GTA         8248
Ile Ala Ala Ala Leu Ala Gln Cys Met Gly Pro Ser Arg Glu Leu Val
        7005                7010                7015

TGC CGC TCG TGC CTG AAG CAG ACG CTG CAC AAG CTG GAG GCC ATG ATG         8296
Cys Arg Ser Cys Leu Lys Gln Thr Leu His Lys Leu Glu Ala Met Met
    7020                7025                7030

CTC ATC CTG CAG GCA GAG ACC ACC GCG GGC ACC GTG ACG CCC ACC GCC         8344
Leu Ile Leu Gln Ala Glu Thr Thr Ala Gly Thr Val Thr Pro Thr Ala
7035                7040                7045                7050

ATC GGA GAC AGC ATC CTC AAC ATC ACA GGA GAC CTC ATC CAC CTG GCC         8392
Ile Gly Asp Ser Ile Leu Asn Ile Thr Gly Asp Leu Ile His Leu Ala
                7055                7060                7065

AGC TCG GAC GTG CGG GCA CCA CAG CCC TCA GAG CTG GGA GCC GAG TCA         8440
Ser Ser Asp Val Arg Ala Pro Gln Pro Ser Glu Leu Gly Ala Glu Ser
            7070                7075                7080

CCA TCT CGG ATG GTG GCG TCC CAG GCC TAC AAC CTG ACC TCT GCC CTC         8488
Pro Ser Arg Met Val Ala Ser Gln Ala Tyr Asn Leu Thr Ser Ala Leu
        7085                7090                7095

ATG CGC ATC CTC ATG CGC TCC CGC GTG CTC AAC GAG GAG CCC CTG ACG         8536
Met Arg Ile Leu Met Arg Ser Arg Val Leu Asn Glu Glu Pro Leu Thr
    7100                7105                7110

CTG GCG GGC GAG GAG ATC GTG GCC CAG GGC AAG CGC TCG GAC CCG CGG         8584
Leu Ala Gly Glu Glu Ile Val Ala Gln Gly Lys Arg Ser Asp Pro Arg
7115                7120                7125                7130

AGC CTG CTG TGC TAT GGC GGC GCC CCA GGG CCT GGC TGC CAC TTC TCC         8632
Ser Leu Leu Cys Tyr Gly Gly Ala Pro Gly Pro Gly Cys His Phe Ser
                7135                7140                7145

ATC CCC GAG GCT TTC AGC GGG GCC CTG GCC AAC CTC AGT GAC GTG GTG         8680
Ile Pro Glu Ala Phe Ser Gly Ala Leu Ala Asn Leu Ser Asp Val Val
            7150                7155                7160

CAG CTC ATC TTT CTG GTG GAC TCC AAT CCC TTT CCC TTT GGC TAT ATC         8728
Gln Leu Ile Phe Leu Val Asp Ser Asn Pro Phe Pro Phe Gly Tyr Ile
        7165                7170                7175

AGC AAC TAC ACC GTC TCC ACC AAG GTG GCC TCG ATG GCA TTC CAG ACA         8776
Ser Asn Tyr Thr Val Ser Thr Lys Val Ala Ser Met Ala Phe Gln Thr
    7180                7185                7190

CAG GCC GGC GCC CAG ATC CCC ATC GAG CGG CTG GCC TCA GAG CGC GCC         8824
Gln Ala Gly Ala Gln Ile Pro Ile Glu Arg Leu Ala Ser Glu Arg Ala
7195                7200                7205                7210

ATC ACC GTG AAG GTG CCC AAC AAC TCG GAC TGG GCT GCC CGG GGC CAC         8872
Ile Thr Val Lys Val Pro Asn Asn Ser Asp Trp Ala Ala Arg Gly His
                7215                7220                7225

CGC AGC TCC GCC AAC TCC GCC AAC TCC GTT GTG GTC CAG CCC CAG GCC         8920
Arg Ser Ser Ala Asn Ser Ala Asn Ser Val Val Val Gln Pro Gln Ala
            7230                7235                7240
```

-continued

| | |
|---|---|
| TCC GTC GGT GCT GTG GTC ACC CTG GAC AGC AGC AAC CCT GCG GCC GGG<br>Ser Val Gly Ala Val Val Thr Leu Asp Ser Ser Asn Pro Ala Ala Gly<br>              7245                      7250                      7255 | 8968 |
| CTG CAT CTG CAG CTC AAC TAT ACG CTG CTG GAC GGC CAC TAC CTG TCT<br>Leu His Leu Gln Leu Asn Tyr Thr Leu Leu Asp Gly His Tyr Leu Ser<br>        7260                      7265                      7270 | 9016 |
| GAG GAA CCT GAG CCC TAC CTG GCA GTC TAC CTA CAC TCG GAG CCC CGG<br>Glu Glu Pro Glu Pro Tyr Leu Ala Val Tyr Leu His Ser Glu Pro Arg<br>7275                      7280                      7285                      7290 | 9064 |
| CCC AAT GAG CAC AAC TGC TCG GCT AGC AGG AGG ATC CGC CCA GAG TCA<br>Pro Asn Glu His Asn Cys Ser Ala Ser Arg Arg Ile Arg Pro Glu Ser<br>              7295                      7300                      7305 | 9112 |
| CTC CAG GGT GCT GAC CAC CGG CCC TAC ACC TTC TTC ATT TCC CCG GGG<br>Leu Gln Gly Ala Asp His Arg Pro Tyr Thr Phe Phe Ile Ser Pro Gly<br>7310                      7315                                    7320 | 9160 |
| AGC AGA GAC CCA GCG GGG AGT TAC CAT CTG AAC CTC TCC AGC CAC TTC<br>Ser Arg Asp Pro Ala Gly Ser Tyr His Leu Asn Leu Ser Ser His Phe<br>              7325                      7330                      7335 | 9208 |
| CGC TGG TCG GCG CTG CAG GTG TCC GTG GGC CTG TAC ACG TCC CTG TGC<br>Arg Trp Ser Ala Leu Gln Val Ser Val Gly Leu Tyr Thr Ser Leu Cys<br>7340                      7345                      7350 | 9256 |
| CAG TAC TTC AGC GAG GAG GAC ATG GTG TGG CGG ACA GAG GGG CTG CTG<br>Gln Tyr Phe Ser Glu Glu Asp Met Val Trp Arg Thr Glu Gly Leu Leu<br>7355                      7360                      7365                      7370 | 9304 |
| CCC CTG GAG GAG ACC TCG CCC CGC CAG GCC GTC TGC CTC ACC CGC CAC<br>Pro Leu Glu Glu Thr Ser Pro Arg Gln Ala Val Cys Leu Thr Arg His<br>              7375                      7380                      7385 | 9352 |
| CTC ACC GCC TTC GGC GCC AGC CTC TTC GTG CCC CCA AGC CAT GTC CGC<br>Leu Thr Ala Phe Gly Ala Ser Leu Phe Val Pro Pro Ser His Val Arg<br>                      7390                      7395                      7400 | 9400 |
| TTT GTG TTT CCT GAG CCG ACA GCG GAT GTA AAC TAC ATC GTC ATG CTG<br>Phe Val Phe Pro Glu Pro Thr Ala Asp Val Asn Tyr Ile Val Met Leu<br>              7405                      7410                      7415 | 9448 |
| ACA TGT GCT GTG TGC CTG GTG ACC TAC ATG GTC ATG GCC GCC ATC CTG<br>Thr Cys Ala Val Cys Leu Val Thr Tyr Met Val Met Ala Ala Ile Leu<br>        7420                      7425                      7430 | 9496 |
| CAC AAG CTG GAC CAG TTG GAT GCC AGC CGG GGC CGC GCC ATC CCT TTC<br>His Lys Leu Asp Gln Leu Asp Ala Ser Arg Gly Arg Ala Ile Pro Phe<br>7435                      7440                      7445                      7450 | 9544 |
| TGT GGG CAG CGG GGC CGC TTC AAG TAC GAG ATC CTC GTC AAG ACA GGC<br>Cys Gly Gln Arg Gly Arg Phe Lys Tyr Glu Ile Leu Val Lys Thr Gly<br>              7455                      7460                      7465 | 9592 |
| TGG GGC CGG GGC TCA GGT ACC ACG GCC CAC GTG GGC ATC ATG CTG TAT<br>Trp Gly Arg Gly Ser Gly Thr Thr Ala His Val Gly Ile Met Leu Tyr<br>              7470                      7475                      7480 | 9640 |
| GGG GTG GAC AGC CGG AGC GGC CAC CGG CAC CTG GAC GGC GAC AGA GCC<br>Gly Val Asp Ser Arg Ser Gly His Arg His Leu Asp Gly Asp Arg Ala<br>        7485                      7490                      7495 | 9688 |
| TTC CAC CGC AAC AGC CTG GAC ATC TTC CGG ATC GCC ACC CCG CAC AGC<br>Phe His Arg Asn Ser Leu Asp Ile Phe Arg Ile Ala Thr Pro His Ser<br>7500                      7505                      7510 | 9736 |
| CTG GGT AGC GTG TGG AAG ATC CGA GTG TGG CAC GAC AAC AAA GGG CTC<br>Leu Gly Ser Val Trp Lys Ile Arg Val Trp His Asp Asn Lys Gly Leu<br>7515                      7520                      7525                      7530 | 9784 |
| AGC CCT GCC TGG TTC CTG CAG CAC GTC ATC GTC AGG GAC CTG CAG ACG<br>Ser Pro Ala Trp Phe Leu Gln His Val Ile Val Arg Asp Leu Gln Thr<br>                      7535                      7540                      7545 | 9832 |
| GCA CGC AGC GCC TTC TTC CTG GTC AAT GAC TGG CTT TCG GTG GAG ACG<br>Ala Arg Ser Ala Phe Phe Leu Val Asn Asp Trp Leu Ser Val Glu Thr<br>              7550                      7555                      7560 | 9880 |

```
GAG GCC AAC GGG GGC CTG GTG GAG AAG GAG GTG CTG GCC GCG AGC GAC       9928
Glu Ala Asn Gly Gly Leu Val Glu Lys Glu Val Leu Ala Ala Ser Asp
            7565            7570            7575

GCA GCC CTT TTG CGC TTC CGG CGC CTG CTG GTG GCT GAG CTG CAG CGT       9976
Ala Ala Leu Leu Arg Phe Arg Arg Leu Leu Val Ala Glu Leu Gln Arg
            7580            7585            7590

GGC TTC TTT GAC AAG CAC ATC TGG CTC TCC ATA TGG GAC CGG CCG CCT      10024
Gly Phe Phe Asp Lys His Ile Trp Leu Ser Ile Trp Asp Arg Pro Pro
7595            7600            7605            7610

CGT AGC CGT TTC ACT CGC ATC CAG AGG GCC ACC TGC TGC GTT CTC CTC      10072
Arg Ser Arg Phe Thr Arg Ile Gln Arg Ala Thr Cys Cys Val Leu Leu
            7615            7620            7625

ATC TGC CTC TTC CTG GGC GCC AAC GCC GTG TGG TAC GGG GCT GTT GGC      10120
Ile Cys Leu Phe Leu Gly Ala Asn Ala Val Trp Tyr Gly Ala Val Gly
            7630            7635            7640

GAC TCT GCC TAC AGC ACG GGG CAT GTG TCC AGG CTG AGC CCG CTG AGC      10168
Asp Ser Ala Tyr Ser Thr Gly His Val Ser Arg Leu Ser Pro Leu Ser
            7645            7650            7655

GTC GAC ACA GTC GCT GTT GGC CTG GTG TCC AGC GTG GTT GTC TAT CCC      10216
Val Asp Thr Val Ala Val Gly Leu Val Ser Ser Val Val Val Tyr Pro
            7660            7665            7670

GTC TAC CTG GCC ATC CTT TTT CTC TTC CGG ATG TCC CGG AGC AAG GTG      10264
Val Tyr Leu Ala Ile Leu Phe Leu Phe Arg Met Ser Arg Ser Lys Val
7675            7680            7685            7690

GCT GGG AGC CCG AGC CCC ACA CCT GCC GGG CAG CAG GTG CTG GAC ATC      10312
Ala Gly Ser Pro Ser Pro Thr Pro Ala Gly Gln Gln Val Leu Asp Ile
            7695            7700            7705

GAC AGC TGC CTG GAC TCG TCC GTG CTG GAC AGC TCC TTC CTC ACG TTC      10360
Asp Ser Cys Leu Asp Ser Ser Val Leu Asp Ser Ser Phe Leu Thr Phe
            7710            7715            7720

TCA GGC CTC CAC GCT GAG GCC TTT GTT GGA CAG ATG AAG AGT GAC TTG      10408
Ser Gly Leu His Ala Glu Ala Phe Val Gly Gln Met Lys Ser Asp Leu
            7725            7730            7735

TTT CTG GAT GAT TCT AAG AGT CTG GTG TGC TGG CCC TCC GGC GAG GGA      10456
Phe Leu Asp Asp Ser Lys Ser Leu Val Cys Trp Pro Ser Gly Glu Gly
            7740            7745            7750

ACG CTC AGT TGG CCG GAC CTG CTC AGT GAC CCG TCC ATT GTG GGT AGC      10504
Thr Leu Ser Trp Pro Asp Leu Leu Ser Asp Pro Ser Ile Val Gly Ser
7755            7760            7765            7770

AAT CTG CGG CAG CTG GCA CGG GGC CAG GCG GGC CAT GGG CTG GGC CCA      10552
Asn Leu Arg Gln Leu Ala Arg Gly Gln Ala Gly His Gly Leu Gly Pro
            7775            7780            7785

GAG GAG GAC GGC TTC TCC CTG GCC AGC CCC TAC TCG CCT GCC AAA TCC      10600
Glu Glu Asp Gly Phe Ser Leu Ala Ser Pro Tyr Ser Pro Ala Lys Ser
            7790            7795            7800

TTC TCA GCA TCA GAT GAA GAC CTG ATC CAG CAG GTC CTT GCC GAG GGG      10648
Phe Ser Ala Ser Asp Glu Asp Leu Ile Gln Gln Val Leu Ala Glu Gly
            7805            7810            7815

GTC AGC AGC CCA GCC CCT ACC CAA GAC ACC CAC ATG GAA ACG GAC CTG      10696
Val Ser Ser Pro Ala Pro Thr Gln Asp Thr His Met Glu Thr Asp Leu
            7820            7825            7830

CTC AGC AGC CTG TCC AGC ACT CCT GGG GAG AAG ACA GAG ACG CTG GCG      10744
Leu Ser Ser Leu Ser Ser Thr Pro Gly Glu Lys Thr Glu Thr Leu Ala
7835            7840            7845            7850

CTG CAG AGG CTG GGG GAG CTG GGG CCA CCC AGC CCA GGC CTG AAC TGG      10792
Leu Gln Arg Leu Gly Glu Leu Gly Pro Pro Ser Pro Gly Leu Asn Trp
            7855            7860            7865

GAA CAG CCC CAG GCA GCG AGG CTG TCC AGG ACA GGA CTG GTG GAG GGT      10840
Glu Gln Pro Gln Ala Ala Arg Leu Ser Arg Thr Gly Leu Val Glu Gly
```

-continued

```
              7870                7875                7880
CTG CGG AAG CGC CTG CTG CCG GCC TGG TGT GCC TCC CTG GCC CAC GGG      10888
Leu Arg Lys Arg Leu Leu Pro Ala Trp Cys Ala Ser Leu Ala His Gly
            7885                7890                7895

CTC AGC CTG CTC CTG GTG GCT GTG GCT GTG GCT GTC TCA GGG TGG GTG      10936
Leu Ser Leu Leu Leu Val Ala Val Ala Val Ala Val Ser Gly Trp Val
        7900                7905                7910

GGT GCG AGC TTC CCC CCG GGC GTG AGT GTT GCG TGG CTC CTG TCC AGC      10984
Gly Ala Ser Phe Pro Pro Gly Val Ser Val Ala Trp Leu Leu Ser Ser
7915                7920                7925                7930

AGC GCC AGC TTC CTG GCC TCA TTC CTC GGC TGG GAG CCA CTG AAG GTC      11032
Ser Ala Ser Phe Leu Ala Ser Phe Leu Gly Trp Glu Pro Leu Lys Val
            7935                7940                7945

TTG CTG GAA GCC CTG TAC TTC TCA CTG GTG GCC AAG CGG CTG CAC CCG      11080
Leu Leu Glu Ala Leu Tyr Phe Ser Leu Val Ala Lys Arg Leu His Pro
            7950                7955                7960

GAT GAA GAT GAC ACC CTG GTA GAG AGC CCG GCT GTG ACG CCT GTG AGC      11128
Asp Glu Asp Asp Thr Leu Val Glu Ser Pro Ala Val Thr Pro Val Ser
            7965                7970                7975

GCA CGT GTG CCC CGC GTA CGG CCA CCC CAC GGC TTT GCA CTC TTC CTG      11176
Ala Arg Val Pro Arg Val Arg Pro Pro His Gly Phe Ala Leu Phe Leu
        7980                7985                7990

GCC AAG GAA GAA GCC CGC AAG GTC AAG AGG CTA CAT GGC ATG CTG CGG      11224
Ala Lys Glu Glu Ala Arg Lys Val Lys Arg Leu His Gly Met Leu Arg
7995                8000                8005                8010

AGC CTC CTG GTG TAC ATG CTT TTT CTG CTG GTG ACC CTG CTG GCC AGC      11272
Ser Leu Leu Val Tyr Met Leu Phe Leu Leu Val Thr Leu Leu Ala Ser
            8015                8020                8025

TAT GGG GAT GCC TCA TGC CAT GGG CAC GCC TAC CGT CTG CAA AGC GCC      11320
Tyr Gly Asp Ala Ser Cys His Gly His Ala Tyr Arg Leu Gln Ser Ala
            8030                8035                8040

ATC AAG CAG GAG CTG CAC AGC CGG GCC TTC CTG GCC ATC ACG CGG TCT      11368
Ile Lys Gln Glu Leu His Ser Arg Ala Phe Leu Ala Ile Thr Arg Ser
            8045                8050                8055

GAG GAG CTC TGG CCA TGG ATG GCC CAC GTG CTG CTG CCC TAC GTC CAC      11416
Glu Glu Leu Trp Pro Trp Met Ala His Val Leu Leu Pro Tyr Val His
            8060                8065                8070

GGG AAC CAG TCC AGC CCA GAG CTG GGG CCC CCA CGG CTG CGG CAG GTG      11464
Gly Asn Gln Ser Ser Pro Glu Leu Gly Pro Pro Arg Leu Arg Gln Val
8075                8080                8085                8090

CGG CTG CAG GAA GCA CTC TAC CCA GAC CCT CCC GGC CCC AGG GTC CAC      11512
Arg Leu Gln Glu Ala Leu Tyr Pro Asp Pro Pro Gly Pro Arg Val His
            8095                8100                8105

ACG TGC TCG GCC GCA GGA GGC TTC AGC ACC AGC GAT TAC GAC GTT GGC      11560
Thr Cys Ser Ala Ala Gly Gly Phe Ser Thr Ser Asp Tyr Asp Val Gly
            8110                8115                8120

TGG GAG AGT CCT CAC AAT GGC TCG GGG ACG TGG GCC TAT TCA GCG CCG      11608
Trp Glu Ser Pro His Asn Gly Ser Gly Thr Trp Ala Tyr Ser Ala Pro
            8125                8130                8135

GAT CTG CTG GGG GCA TGG TCC TGG GGC TCC TGT GCC GTG TAT GAC AGC      11656
Asp Leu Leu Gly Ala Trp Ser Trp Gly Ser Cys Ala Val Tyr Asp Ser
            8140                8145                8150

GGG GGC TAC GTG CAG GAG CTG GGC CTG AGC CTG GAG GAG AGC CGC GAC      11704
Gly Gly Tyr Val Gln Glu Leu Gly Leu Ser Leu Glu Glu Ser Arg Asp
8155                8160                8165                8170

CGG CTG CGC TTC CTG CAG CTG CAC AAC TGG CTG GAC AAC AGG AGC CGC      11752
Arg Leu Arg Phe Leu Gln Leu His Asn Trp Leu Asp Asn Arg Ser Arg
            8175                8180                8185

GCT GTG TTC CTG GAG CTC ACG CGC TAC AGC CCG GCC GTG GGG CTG CAC      11800
```

```
                                                           -continued

Ala Val Phe Leu Glu Leu Thr Arg Tyr Ser Pro Ala Val Gly Leu His
         8190                8195             8200

GCC GCC GTC ACG CTG CGC CTC GAG TTC CCG GCG GCC GGC CGC GCC CTG     11848
Ala Ala Val Thr Leu Arg Leu Glu Phe Pro Ala Ala Gly Arg Ala Leu
         8205                8210             8215

GCC GCC CTC AGC GTC CGC CCC TTT GCG CTG CGC CGC CTC AGC GCG GGC     11896
Ala Ala Leu Ser Val Arg Pro Phe Ala Leu Arg Arg Leu Ser Ala Gly
         8220                8225             8230

CTC TCG CTG CCT CTG CTC ACC TCG GTG TGC CTG CTG CTG TTC GCC GTG     11944
Leu Ser Leu Pro Leu Leu Thr Ser Val Cys Leu Leu Leu Phe Ala Val
8235             8240                8245             8250

CAC TTC GCC GTG GCC GAG GCC CGT ACT TGG CAC AGG GAA GGG CGC TGG     11992
His Phe Ala Val Ala Glu Ala Arg Thr Trp His Arg Glu Gly Arg Trp
         8255                8260             8265

CGC GTG CTG CGG CTC GGA GCC TGG GCG CGG TGG CTG CTG GTG GCG CTG     12040
Arg Val Leu Arg Leu Gly Ala Trp Ala Arg Trp Leu Leu Val Ala Leu
         8270                8275             8280

ACG GCG GCC ACG GCA CTG GTA CGC CTC GCC CAG CTG GGT GCC GCT GAC     12088
Thr Ala Ala Thr Ala Leu Val Arg Leu Ala Gln Leu Gly Ala Ala Asp
         8285                8290             8295

CGC CAG TGG ACC CGT TTC GTG CGC GGC CGC CCG CGC CGC TTC ACT AGC     12136
Arg Gln Trp Thr Arg Phe Val Arg Gly Arg Pro Arg Arg Phe Thr Ser
         8300                8305             8310

TTC GAC CAG GTG GCG CAC GTG AGC TCC GCA GCC CGT GGC CTG GCG GCC     12184
Phe Asp Gln Val Ala His Val Ser Ser Ala Ala Arg Gly Leu Ala Ala
8315             8320                8325             8330

TCG CTG CTC TTC CTG CTT TTG GTC AAG GCT GCC CAG CAC GTA CGC TTC     12232
Ser Leu Leu Phe Leu Leu Leu Val Lys Ala Ala Gln His Val Arg Phe
         8335                8340             8345

GTG CGC CAG TGG TCC GTC TTT GGC AAG ACA TTA TGC CGA GCT CTG CCA     12280
Val Arg Gln Trp Ser Val Phe Gly Lys Thr Leu Cys Arg Ala Leu Pro
         8350                8355             8360

GAG CTC CTG GGG GTC ACC TTG GGC CTG GTG GTG CTC GGG GTA GCC TAC     12328
Glu Leu Leu Gly Val Thr Leu Gly Leu Val Val Leu Gly Val Ala Tyr
         8365                8370             8375

GCC CAG CTG GCC ATC CTG CTC GTG TCT TCC TGT GTG GAC TCC CTC TGG     12376
Ala Gln Leu Ala Ile Leu Leu Val Ser Ser Cys Val Asp Ser Leu Trp
         8380                8385             8390

AGC GTG GCC CAG GCC CTG TTG GTG CTG TGC CCT GGG ACT GGG CTC TCT     12424
Ser Val Ala Gln Ala Leu Leu Val Leu Cys Pro Gly Thr Gly Leu Ser
8395             8400                8405             8410

ACC CTG TGT CCT GCC GAG TCC TGG CAC CTG TCA CCC CTG CTG TGT GTG     12472
Thr Leu Cys Pro Ala Glu Ser Trp His Leu Ser Pro Leu Leu Cys Val
         8415                8420             8425

GGG CTC TGG GCA CTG CGG CTG TGG GGC GCC CTA CGG CTG GGG GCT GTT     12520
Gly Leu Trp Ala Leu Arg Leu Trp Gly Ala Leu Arg Leu Gly Ala Val
         8430                8435             8440

ATT CTC CGC TGG CGC TAC CAC GCC TTG CGT GGA GAG CTG TAC CGG CCG     12568
Ile Leu Arg Trp Arg Tyr His Ala Leu Arg Gly Glu Leu Tyr Arg Pro
         8445                8450             8455

GCC TGG GAG CCC CAG GAC TAC GAG ATG GTG GAG TTG TTC CTG CGC AGG     12616
Ala Trp Glu Pro Gln Asp Tyr Glu Met Val Glu Leu Phe Leu Arg Arg
         8460                8465             8470

CTG CGC CTC TGG ATG GGC CTC AGC AAG GTC AAG GAG TTC CGC CAC AAA     12664
Leu Arg Leu Trp Met Gly Leu Ser Lys Val Lys Glu Phe Arg His Lys
8475             8480                8485             8490

GTC CGC TTT GAA GGG ATG GAG CCG CTG CCC TCT CGC TCC TCC AGG GGC     12712
Val Arg Phe Glu Gly Met Glu Pro Leu Pro Ser Arg Ser Ser Arg Gly
         8495                8500             8505
```

```
TCC AAG GTA TCC CCG GAT GTG CCC CCA CCC AGC GCT GGC TCC GAT GCC        12760
Ser Lys Val Ser Pro Asp Val Pro Pro Pro Ser Ala Gly Ser Asp Ala
        8510            8515            8520

TCG CAC CCC TCC ACC TCC TCC AGC CAG CTG GAT GGG CTG AGC GTG AGC        12808
Ser His Pro Ser Thr Ser Ser Ser Gln Leu Asp Gly Leu Ser Val Ser
        8525            8530            8535

CTG GGC CGG CTG GGG ACA AGG TGT GAG CCT GAG CCC TCC CGC CTC CAA        12856
Leu Gly Arg Leu Gly Thr Arg Cys Glu Pro Glu Pro Ser Arg Leu Gln
        8540            8545            8550

GCC GTG TTC GAG GCC CTG CTC ACC CAG TTT GAC CGA CTC AAC CAG GCC        12904
Ala Val Phe Glu Ala Leu Leu Thr Gln Phe Asp Arg Leu Asn Gln Ala
8555            8560            8565            8570

ACA GAG GAC GTC TAC CAG CTG GAG CAG CAG CTG CAC AGC CTG CAA GGC        12952
Thr Glu Asp Val Tyr Gln Leu Glu Gln Gln Leu His Ser Leu Gln Gly
            8575            8580            8585

CGC AGG AGC AGC CGG GCG CCC GCC GGA TCT TCC CGT GGC CCA TCC CCG        13000
Arg Arg Ser Ser Arg Ala Pro Ala Gly Ser Ser Arg Gly Pro Ser Pro
        8590            8595            8600

GGC CTG CGG CCA GCA CTG CCC AGC CGC CTT GCC CGG GCC AGT CGG GGT        13048
Gly Leu Arg Pro Ala Leu Pro Ser Arg Leu Ala Arg Ala Ser Arg Gly
        8605            8610            8615

GTG GAC CTG GCC ACT GGC CCC AGC AGG ACA CCC CTT CGG GCC AAG AAC        13096
Val Asp Leu Ala Thr Gly Pro Ser Arg Thr Pro Leu Arg Ala Lys Asn
        8620            8625            8630

AAG GTC CAC CCC AGC AGC ACT TAGTCCTCCT TCCTGGCGGG GGTGGGCCGT           13147
Lys Val His Pro Ser Ser Thr
8635            8640

GGAGTCGGAG TGGACACCGC TCAGTATTAC TTTCTGCCGC TGTCAAGGCC GAGGGCCAGG     13207

CAGAATGGCT GCACGTAGGT TCCCCAGAGA GCAGGCAGGG GCATCTGTCT GTCTGTGGGC     13267

TTCAGCACTT TAAAGAGGCT GTGTGGCCAA CCAGGACCCA GGGTCCCCTC CCCAGCTCCC     13327

TTGGGAAGGA CACAGCAGTA TTGGACGGTT TCTAGCCTCT GAGATGCTAA TTTATTTCCC     13387

CGAGTCCTCA GGTACAGCGG GCTGTGCCCG GCCCCACCCC CTGGGCAGAT GTCCCCCACT     13447

GCTAAGGCTG CTGGCTTCAG GGAGGGTTAG CCTGCACCGC CGCCACCCTG CCCTAAGTT      13507

ATTACCTCTC CAGTTCCTAC CGTACTCCCT GCACCGTCTC ACTGTGTGTC TCGTGTCAGT     13567

AATTTATATG GTGTTAAAAT GTGTATATTT TTGTATGTCA CTATTTTCAC TAGGGCTGAG     13627

GGGCCTGCGC CCAGAGCTGG CCTCCCCCAA CACCTGCTGC GCTTGGTAGG TGTGGTGGCG     13687

TTATGGCAGC CCGGCTGCTG CTTGGATGCG AGCTTGGCCT TGGGCCGGTG CTGGGGGCAC     13747

AGCTGTCTGC CAGGCACTCT CATCACCCCA GAGGCCTTGT CATCCTCCCT TGCCCCAGGC     13807

CAGGTAGCAA GAGAGCAGCG CCCAGGCCTG CTGGCATCAG GTCTGGGCAA GTAGCAGGAC     13867

TAGGCATGTC AGAGGACCCC AGGGTGGTTA GAGGAAAAGA CTCCTCCTGG GGGCTGGCTC     13927

CCAGGGTGGA GGAAGGTGAC TGTGTGTGTG TGTGTGTGCG CGCGCGACGC GCGAGTGTGC     13987

TGTATGGCCC AGGCAGCCTC AAGGCCCTCG GAGCTGGCTG TGCCTGCTTC TGTGTACCAC     14047

TTCTGTGGGC ATGGCCGCTT CTAGAGCCTC GACACCCCCC CAACCCCCGC ACCAAGCAGA     14107

CAAAGTCAAT AAAAGAGCTG TCTGACTGCA AAAAAAAAA A                         14148

(2) INFORMATION FOR SEQ ID NO: 8:

(i) SEQUENCE CHARACTERISTICS:
        (A) LENGTH: 4302 amino acids
        (B) TYPE: amino acid
        (D) TOPOLOGY: linear (ii) MOLECULE TYPE: protein
```

(xi) SEQUENCE DESCRIPTION: SEQ ID NO: 8:

```
Met Pro Pro Ala Ala Pro Ala Arg Leu Ala Leu Ala Leu Gly Leu Gly
 1               5                  10                  15

Leu Trp Leu Gly Ala Leu Ala Gly Gly Pro Gly Arg Gly Cys Gly Pro
             20                  25                  30

Cys Glu Pro Pro Cys Leu Cys Gly Pro Ala Pro Gly Ala Ala Cys Arg
         35                  40                  45

Val Asn Cys Ser Gly Arg Gly Leu Arg Thr Leu Gly Pro Ala Leu Arg
     50                  55                  60

Ile Pro Ala Asp Ala Thr Ala Leu Asp Val Ser His Asn Leu Leu Arg
 65                  70                  75                  80

Ala Leu Asp Val Gly Leu Leu Ala Asn Leu Ser Ala Leu Ala Glu Leu
                 85                  90                  95

Asp Ile Ser Asn Asn Lys Ile Ser Thr Leu Glu Glu Gly Ile Phe Ala
                100                 105                 110

Asn Leu Phe Asn Leu Ser Glu Ile Asn Leu Ser Gly Asn Pro Phe Glu
            115                 120                 125

Cys Asp Cys Gly Leu Ala Trp Leu Pro Arg Trp Ala Glu Glu Gln Gln
        130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Pro Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Ala Thr Arg
    290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
        355                 360                 365

Ser Asp Glu Ser Leu Asp Leu Ser Ile Gln Asn Arg Gly Gly Ser Gly
    370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
```

-continued

```
                405                 410                 415
Gly His Cys Tyr Arg Leu Val Val Glu Lys Ala Ala Trp Leu Gln Ala
                420                 425                 430
Gln Glu Gln Cys Gln Ala Trp Ala Gly Ala Ala Leu Ala Met Val Asp
                435                 440                 445
Ser Pro Ala Val Gln Arg Phe Leu Val Ser Arg Val Thr Arg Ser Leu
            450                 455                 460
Asp Val Trp Ile Gly Phe Ser Thr Val Gln Gly Val Glu Val Gly Pro
465                 470                 475                 480
Ala Pro Gln Gly Glu Ala Phe Ser Leu Glu Ser Cys Gln Asn Trp Leu
                485                 490                 495
Pro Gly Glu Pro His Pro Ala Thr Ala Glu His Cys Val Arg Leu Gly
                500                 505                 510
Pro Thr Gly Trp Cys Asn Thr Asp Leu Cys Ser Ala Pro His Ser Tyr
            515                 520                 525
Val Cys Glu Leu Gln Pro Gly Gly Pro Val Gln Asp Ala Glu Asn Leu
        530                 535                 540
Leu Val Gly Ala Pro Ser Gly Asp Leu Gln Gly Pro Leu Thr Pro Leu
545                 550                 555                 560
Ala Gln Gln Asp Gly Leu Ser Ala Pro His Glu Pro Val Glu Val Met
                565                 570                 575
Val Phe Pro Gly Leu Arg Leu Ser Arg Glu Ala Phe Leu Thr Thr Ala
                580                 585                 590
Glu Phe Gly Thr Gln Glu Leu Arg Arg Pro Ala Gln Leu Arg Leu Gln
                595                 600                 605
Val Tyr Arg Leu Leu Ser Thr Ala Gly Thr Pro Glu Asn Gly Ser Glu
            610                 615                 620
Pro Glu Ser Arg Ser Pro Asp Asn Arg Thr Gln Leu Ala Pro Ala Cys
625                 630                 635                 640
Met Pro Gly Gly Arg Trp Cys Pro Gly Ala Asn Ile Cys Leu Pro Leu
                645                 650                 655
Asp Ala Ser Cys His Pro Gln Ala Cys Ala Asn Gly Cys Thr Ser Gly
                660                 665                 670
Pro Gly Leu Pro Gly Ala Pro Tyr Ala Leu Trp Arg Glu Phe Leu Phe
            675                 680                 685
Ser Val Ala Ala Gly Pro Pro Ala Gln Tyr Ser Val Thr Leu His Gly
        690                 695                 700
Gln Asp Val Leu Met Leu Pro Gly Asp Leu Val Gly Leu Gln His Asp
705                 710                 715                 720
Ala Gly Pro Gly Ala Leu Leu His Cys Ser Pro Ala Pro Gly His Pro
                725                 730                 735
Gly Pro Gln Ala Pro Tyr Leu Ser Ala Asn Ala Ser Ser Trp Leu Pro
            740                 745                 750
His Leu Pro Ala Gln Leu Glu Gly Thr Trp Ala Cys Pro Ala Cys Ala
                755                 760                 765
Leu Arg Leu Leu Ala Ala Thr Glu Gln Leu Thr Val Leu Leu Gly Leu
            770                 775                 780
Arg Pro Asn Pro Gly Leu Arg Met Pro Gly Arg Tyr Glu Val Arg Ala
785                 790                 795                 800
Glu Val Gly Asn Gly Val Ser Arg His Asn Leu Ser Cys Ser Phe Asp
                805                 810                 815
Val Val Ser Pro Val Ala Gly Leu Arg Val Ile Tyr Pro Ala Pro Arg
            820                 825                 830
```

-continued

```
Asp Gly Arg Leu Tyr Val Pro Thr Asn Gly Ser Ala Leu Val Leu Gln
        835                 840                 845
Val Asp Ser Gly Ala Asn Ala Thr Ala Thr Ala Arg Trp Pro Gly Gly
850                 855                 860
Ser Val Ser Ala Arg Phe Glu Asn Val Cys Pro Ala Leu Val Ala Thr
865                 870                 875                 880
Phe Val Pro Gly Cys Pro Trp Glu Thr Asn Asp Thr Leu Phe Ser Val
                885                 890                 895
Val Ala Leu Pro Trp Leu Ser Glu Gly Glu His Val Val Asp Val Val
            900                 905                 910
Val Glu Asn Ser Ala Ser Arg Ala Asn Leu Ser Leu Arg Val Thr Ala
            915                 920                 925
Glu Glu Pro Ile Cys Gly Leu Arg Ala Thr Pro Ser Pro Glu Ala Arg
        930                 935                 940
Val Leu Gln Gly Val Leu Val Arg Tyr Ser Pro Val Glu Ala Gly
945                 950                 955                 960
Ser Asp Met Val Phe Arg Trp Thr Ile Asn Asp Lys Gln Ser Leu Thr
                965                 970                 975
Phe Gln Asn Val Val Phe Asn Val Ile Tyr Gln Ser Ala Ala Val Phe
            980                 985                 990
Lys Leu Ser Leu Thr Ala Ser Asn His Val Ser Asn Val Thr Val Asn
        995                 1000                1005
Tyr Asn Val Thr Val Glu Arg Met Asn Arg Met Gln Gly Leu Gln Val
            1010                1015                1020
Ser Thr Val Pro Ala Val Leu Ser Pro Asn Ala Thr Leu Val Leu Thr
1025                1030                1035                1040
Gly Gly Val Leu Val Asp Ser Ala Val Glu Val Ala Phe Leu Trp Asn
                1045                1050                1055
Phe Gly Asp Gly Glu Gln Ala Leu His Gln Phe Gln Pro Pro Tyr Asn
            1060                1065                1070
Glu Ser Phe Pro Val Pro Asp Pro Ser Val Ala Gln Val Leu Val Glu
        1075                1080                1085
His Asn Val Met His Thr Tyr Ala Ala Pro Gly Glu Tyr Leu Leu Thr
        1090                1095                1100
Val Leu Ala Ser Asn Ala Phe Glu Asn Leu Thr Gln Gln Val Pro Val
1105                1110                1115                1120
Ser Val Arg Ala Ser Leu Pro Ser Val Ala Val Gly Val Ser Asp Gly
                1125                1130                1135
Val Leu Val Ala Gly Arg Pro Val Thr Phe Tyr Pro His Pro Leu Pro
            1140                1145                1150
Ser Pro Gly Gly Val Leu Tyr Thr Trp Asp Phe Gly Asp Gly Ser Pro
            1155                1160                1165
Val Leu Thr Gln Ser Gln Pro Ala Ala Asn His Thr Tyr Ala Ser Arg
        1170                1175                1180
Gly Thr Tyr His Val Arg Leu Gly Val Asn Asn Thr Val Ser Gly Ala
1185                1190                1195                1200
Ala Ala Gln Ala Asp Val Arg Val Phe Glu Glu Leu Arg Gly Leu Ser
                1205                1210                1215
Val Asp Met Ser Leu Ala Val Glu Gln Gly Ala Pro Val Val Val Ser
            1220                1225                1230
Ala Ala Val Gln Thr Gly Asp Asn Ile Thr Trp Thr Phe Asp Met Gly
        1235                1240                1245
```

-continued

```
Asp Gly Thr Val Leu Ser Gly Pro Glu Ala Thr Val Glu His Val Tyr
    1250                1255                1260
Leu Arg Ala Gln Asn Cys Thr Val Thr Val Gly Ala Ala Ser Pro Ala
1265                1270                1275                1280
Gly His Leu Ala Arg Ser Leu His Val Leu Val Phe Val Leu Glu Val
                1285                1290                1295
Leu Arg Val Glu Pro Ala Ala Cys Ile Pro Thr Gln Pro Asp Ala Arg
            1300                1305                1310
Leu Thr Ala Tyr Val Thr Gly Asn Pro Ala His Tyr Leu Phe Asp Trp
        1315                1320                1325
Thr Phe Gly Asp Gly Ser Ser Asn Thr Thr Val Arg Gly Cys Pro Thr
    1330                1335                1340
Val Thr His Asn Phe Thr Arg Ser Gly Thr Phe Pro Leu Ala Leu Val
1345                1350                1355                1360
Leu Ser Ser Arg Val Asn Arg Ala His Tyr Phe Thr Ser Ile Cys Val
                1365                1370                1375
Glu Pro Glu Val Gly Asn Val Thr Leu Gln Pro Glu Arg Gln Phe Val
            1380                1385                1390
Gln Leu Gly Asp Glu Ala Trp Leu Val Ala Cys Ala Trp Pro Pro Phe
        1395                1400                1405
Pro Tyr Arg Tyr Thr Trp Asp Phe Gly Thr Glu Ala Ala Pro Thr
    1410                1415                1420
Arg Ala Arg Gly Pro Glu Val Thr Phe Ile Tyr Arg Asp Pro Gly Ser
1425                1430                1435                1440
Tyr Leu Val Thr Val Thr Ala Ser Asn Asn Ile Ser Ala Ala Asn Asp
                1445                1450                1455
Ser Ala Leu Val Glu Val Gln Glu Pro Val Leu Val Thr Ser Ile Lys
            1460                1465                1470
Val Asn Gly Ser Leu Gly Leu Glu Leu Gln Gln Pro Tyr Leu Phe Ser
        1475                1480                1485
Ala Val Gly Arg Gly Arg Pro Ala Ser Tyr Leu Trp Asp Leu Gly Asp
    1490                1495                1500
Gly Gly Trp Leu Glu Gly Pro Glu Val Thr His Ala Tyr Asn Ser Thr
1505                1510                1515                1520
Gly Asp Phe Thr Val Arg Val Ala Gly Trp Asn Glu Val Ser Arg Ser
                1525                1530                1535
Glu Ala Trp Leu Asn Val Thr Val Lys Arg Arg Val Arg Gly Leu Val
            1540                1545                1550
Val Asn Ala Ser Arg Thr Val Val Pro Leu Asn Gly Ser Val Ser Phe
        1555                1560                1565
Ser Thr Ser Leu Glu Ala Gly Ser Asp Val Arg Tyr Ser Trp Val Leu
    1570                1575                1580
Cys Asp Arg Cys Thr Pro Ile Pro Gly Gly Pro Thr Ile Ser Tyr Thr
1585                1590                1595                1600
Phe Arg Ser Val Gly Thr Phe Asn Ile Ile Val Thr Ala Glu Asn Glu
                1605                1610                1615
Val Gly Ser Ala Gln Asp Ser Ile Phe Val Tyr Val Leu Gln Leu Ile
            1620                1625                1630
Glu Gly Leu Gln Val Val Gly Gly Gly Arg Tyr Phe Pro Thr Asn His
        1635                1640                1645
Thr Val Gln Leu Gln Ala Val Val Arg Asp Gly Thr Asn Val Ser Tyr
    1650                1655                1660
Ser Trp Thr Ala Trp Arg Asp Arg Gly Pro Ala Leu Ala Gly Ser Gly
```

```
             1665                1670                1675                1680

Lys Gly Phe Ser Leu Thr Val Leu Glu Ala Gly Thr Tyr His Val Gln
            1685                1690                1695

Leu Arg Ala Thr Asn Met Leu Gly Ser Ala Trp Ala Asp Cys Thr Met
        1700                1705                1710

Asp Phe Val Glu Pro Val Gly Trp Leu Met Val Thr Ala Ser Pro Asn
        1715                1720                1725

Pro Ala Ala Val Asn Thr Ser Val Thr Leu Ser Ala Glu Leu Ala Gly
        1730                1735                1740

Gly Ser Gly Val Val Tyr Thr Trp Ser Leu Glu Glu Gly Leu Ser Trp
1745                1750                1755                1760

Glu Thr Ser Glu Pro Phe Thr Thr His Ser Phe Pro Thr Pro Gly Leu
            1765                1770                1775

His Leu Val Thr Met Thr Ala Gly Asn Pro Leu Gly Ser Ala Asn Ala
            1780                1785                1790

Thr Val Glu Val Asp Val Gln Val Pro Val Ser Gly Leu Ser Ile Arg
        1795                1800                1805

Ala Ser Glu Pro Gly Gly Ser Phe Val Ala Ala Gly Ser Ser Val Pro
        1810                1815                1820

Phe Trp Gly Gln Leu Ala Thr Gly Thr Asn Val Ser Trp Cys Trp Ala
1825                1830                1835                1840

Val Pro Gly Gly Ser Ser Lys Arg Gly Pro His Val Thr Met Val Phe
            1845                1850                1855

Pro Asp Ala Gly Thr Phe Ser Ile Arg Leu Asn Ala Ser Asn Ala Val
            1860                1865                1870

Ser Trp Val Ser Ala Thr Tyr Asn Leu Thr Ala Glu Glu Pro Ile Val
        1875                1880                1885

Gly Leu Val Leu Trp Ala Ser Ser Lys Val Val Ala Pro Gly Gln Leu
        1890                1895                1900

Val His Phe Gln Ile Leu Leu Ala Ala Gly Ser Ala Val Thr Phe Arg
1905                1910                1915                1920

Leu Gln Val Gly Gly Ala Asn Pro Glu Val Leu Pro Gly Pro Arg Phe
            1925                1930                1935

Ser His Ser Phe Pro Arg Val Gly Asp His Val Val Ser Val Arg Gly
            1940                1945                1950

Lys Asn His Val Ser Trp Ala Gln Ala Gln Val Arg Ile Val Val Leu
            1955                1960                1965

Glu Ala Val Ser Gly Leu Gln Met Pro Asn Cys Cys Glu Pro Gly Ile
        1970                1975                1980

Ala Thr Gly Thr Glu Arg Asn Phe Thr Ala Arg Val Gln Arg Gly Ser
1985                1990                1995                2000

Arg Val Ala Tyr Ala Trp Tyr Phe Ser Leu Gln Lys Val Gln Gly Asp
            2005                2010                2015

Ser Leu Val Ile Leu Ser Gly Arg Asp Val Thr Tyr Thr Pro Val Ala
            2020                2025                2030

Ala Gly Leu Leu Glu Ile Gln Val Arg Ala Phe Asn Ala Leu Gly Ser
            2035                2040                2045

Glu Asn Arg Thr Leu Val Leu Glu Val Gln Asp Ala Val Gln Tyr Val
        2050                2055                2060

Ala Leu Gln Ser Gly Pro Cys Phe Thr Asn Arg Ser Ala Gln Phe Glu
2065                2070                2075                2080

Ala Ala Thr Ser Pro Ser Pro Arg Arg Val Ala Tyr His Trp Asp Phe
            2085                2090                2095
```

-continued

```
Gly Asp Gly Ser Pro Gly Gln Asp Thr Asp Glu Pro Arg Ala Glu His
            2100                2105                2110
Ser Tyr Leu Arg Pro Gly Asp Tyr Arg Val Gln Val Asn Ala Ser Asn
            2115                2120                2125
Leu Val Ser Phe Phe Val Ala Gln Ala Thr Val Thr Val Gln Val Leu
            2130                2135                2140
Ala Cys Arg Glu Pro Glu Val Asp Val Val Leu Pro Leu Gln Val Leu
2145                2150                2155                2160
Met Arg Arg Ser Gln Arg Asn Tyr Leu Glu Ala His Val Asp Leu Arg
            2165                2170                2175
Asp Cys Val Thr Tyr Gln Thr Glu Tyr Arg Trp Glu Val Tyr Arg Thr
            2180                2185                2190
Ala Ser Cys Gln Arg Pro Gly Arg Pro Ala Arg Val Ala Leu Pro Gly
            2195                2200                2205
Val Asp Val Ser Arg Pro Arg Leu Val Leu Pro Arg Leu Ala Leu Pro
            2210                2215                2220
Val Gly His Tyr Cys Phe Val Phe Val Val Ser Phe Gly Asp Thr Pro
2225                2230                2235                2240
Leu Thr Gln Ser Ile Gln Ala Asn Val Thr Val Ala Pro Glu Arg Leu
            2245                2250                2255
Val Pro Ile Ile Glu Gly Gly Ser Tyr Arg Val Trp Ser Asp Thr Arg
            2260                2265                2270
Asp Leu Val Leu Asp Gly Ser Glu Ser Tyr Asp Pro Asn Leu Glu Asp
            2275                2280                2285
Gly Asp Gln Thr Pro Leu Ser Phe His Trp Ala Cys Val Ala Ser Thr
            2290                2295                2300
Gln Arg Glu Ala Gly Gly Cys Ala Leu Asn Phe Gly Pro Arg Gly Ser
2305                2310                2315                2320
Ser Thr Val Thr Ile Pro Arg Glu Arg Leu Ala Ala Gly Val Glu Tyr
            2325                2330                2335
Thr Phe Ser Leu Thr Val Trp Lys Ala Gly Arg Lys Glu Glu Ala Thr
            2340                2345                2350
Asn Gln Thr Val Leu Ile Arg Ser Gly Arg Val Pro Ile Val Ser Leu
            2355                2360                2365
Glu Cys Val Ser Cys Lys Ala Gln Ala Val Tyr Glu Val Ser Arg Ser
            2370                2375                2380
Ser Tyr Val Tyr Leu Glu Gly Arg Cys Leu Asn Cys Ser Ser Gly Ser
2385                2390                2395                2400
Lys Arg Gly Arg Trp Ala Ala Arg Thr Phe Ser Asn Lys Thr Leu Val
            2405                2410                2415
Leu Asp Glu Thr Thr Thr Ser Thr Gly Ser Ala Gly Met Arg Leu Val
            2420                2425                2430
Leu Arg Arg Gly Val Leu Arg Asp Gly Glu Gly Tyr Thr Phe Thr Leu
            2435                2440                2445
Thr Val Leu Gly Arg Ser Gly Glu Glu Gly Cys Ala Ser Ile Arg
            2450                2455                2460
Leu Ser Pro Asn Arg Pro Pro Leu Gly Gly Ser Cys Arg Leu Phe Pro
2465                2470                2475                2480
Leu Gly Ala Val His Ala Leu Thr Thr Lys Val His Phe Glu Cys Thr
            2485                2490                2495
Gly Trp His Asp Ala Glu Asp Ala Gly Ala Pro Leu Val Tyr Ala Leu
            2500                2505                2510
```

-continued

```
Leu Leu Arg Arg Cys Arg Gln Gly His Cys Glu Glu Phe Cys Val Tyr
        2515                2520                2525
Lys Gly Ser Leu Ser Ser Tyr Gly Ala Val Leu Pro Pro Gly Phe Arg
    2530                2535                2540
Pro His Phe Glu Val Gly Leu Ala Val Val Gln Asp Gln Leu Gly
2545                2550                2555                2560
Ala Ala Val Val Ala Leu Asn Arg Ser Leu Ala Ile Thr Leu Pro Glu
            2565                2570                2575
Pro Asn Gly Ser Ala Thr Gly Leu Thr Val Trp Leu His Gly Leu Thr
            2580                2585                2590
Ala Ser Val Leu Pro Gly Leu Leu Arg Gln Ala Asp Pro Gln His Val
        2595                2600                2605
Ile Glu Tyr Ser Leu Ala Leu Val Thr Val Leu Asn Glu Tyr Glu Arg
    2610                2615                2620
Ala Leu Asp Val Ala Ala Glu Pro Lys His Glu Arg Gln His Arg Ala
2625                2630                2635                2640
Gln Ile Arg Lys Asn Ile Thr Glu Thr Leu Val Ser Leu Arg Val His
        2645                2650                2655
Thr Val Asp Asp Ile Gln Gln Ile Ala Ala Ala Leu Ala Gln Cys Met
            2660                2665                2670
Gly Pro Ser Arg Glu Leu Val Cys Arg Ser Cys Leu Lys Gln Thr Leu
        2675                2680                2685
His Lys Leu Glu Ala Met Met Leu Ile Leu Gln Ala Glu Thr Thr Ala
    2690                2695                2700
Gly Thr Val Thr Pro Thr Ala Ile Gly Asp Ser Ile Leu Asn Ile Thr
2705                2710                2715                2720
Gly Asp Leu Ile His Leu Ala Ser Ser Asp Val Arg Ala Pro Gln Pro
            2725                2730                2735
Ser Glu Leu Gly Ala Glu Ser Pro Ser Arg Met Val Ala Ser Gln Ala
        2740                2745                2750
Tyr Asn Leu Thr Ser Ala Leu Met Arg Ile Leu Met Arg Ser Arg Val
    2755                2760                2765
Leu Asn Glu Glu Pro Leu Thr Leu Ala Gly Glu Glu Ile Val Ala Gln
    2770                2775                2780
Gly Lys Arg Ser Asp Pro Arg Ser Leu Leu Cys Tyr Gly Gly Ala Pro
2785                2790                2795                2800
Gly Pro Gly Cys His Phe Ser Ile Pro Glu Ala Phe Ser Gly Ala Leu
            2805                2810                2815
Ala Asn Leu Ser Asp Val Val Gln Leu Ile Phe Leu Val Asp Ser Asn
            2820                2825                2830
Pro Phe Pro Phe Gly Tyr Ile Ser Asn Tyr Thr Val Ser Thr Lys Val
        2835                2840                2845
Ala Ser Met Ala Phe Gln Thr Gln Ala Gly Ala Gln Ile Pro Ile Glu
    2850                2855                2860
Arg Leu Ala Ser Glu Arg Ala Ile Thr Val Lys Val Pro Asn Asn Ser
2865                2870                2875                2880
Asp Trp Ala Ala Arg Gly His Arg Ser Ser Ala Asn Ser Ala Asn Ser
            2885                2890                2895
Val Val Val Gln Pro Gln Ala Ser Val Gly Ala Val Val Thr Leu Asp
        2900                2905                2910
Ser Ser Asn Pro Ala Ala Gly Leu His Leu Gln Leu Asn Tyr Thr Leu
    2915                2920                2925
Leu Asp Gly His Tyr Leu Ser Glu Glu Pro Glu Pro Tyr Leu Ala Val
```

```
                    2930                2935                2940

Tyr Leu His Ser Glu Pro Arg Pro Asn Glu His Asn Cys Ser Ala Ser
2945                2950                2955                2960

Arg Arg Ile Arg Pro Glu Ser Leu Gln Gly Ala Asp His Arg Pro Tyr
                    2965                2970                2975

Thr Phe Phe Ile Ser Pro Gly Ser Arg Asp Pro Ala Gly Ser Tyr His
                    2980                2985                2990

Leu Asn Leu Ser Ser His Phe Arg Trp Ser Ala Leu Gln Val Ser Val
                    2995                3000                3005

Gly Leu Tyr Thr Ser Leu Cys Gln Tyr Phe Ser Glu Glu Asp Met Val
                    3010                3015                3020

Trp Arg Thr Glu Gly Leu Leu Pro Leu Glu Glu Thr Ser Pro Arg Gln
3025                3030                3035                3040

Ala Val Cys Leu Thr Arg His Leu Thr Ala Phe Gly Ala Ser Leu Phe
                    3045                3050                3055

Val Pro Pro Ser His Val Arg Phe Val Phe Pro Glu Pro Thr Ala Asp
                    3060                3065                3070

Val Asn Tyr Ile Val Met Leu Thr Cys Ala Val Cys Leu Val Thr Tyr
                    3075                3080                3085

Met Val Met Ala Ala Ile Leu His Lys Leu Asp Gln Leu Asp Ala Ser
                    3090                3095                3100

Arg Gly Arg Ala Ile Pro Phe Cys Gly Gln Arg Gly Arg Phe Lys Tyr
3105                3110                3115                3120

Glu Ile Leu Val Lys Thr Gly Trp Gly Arg Gly Ser Gly Thr Thr Ala
                    3125                3130                3135

His Val Gly Ile Met Leu Tyr Gly Val Asp Ser Arg Ser Gly His Arg
                    3140                3145                3150

His Leu Asp Gly Asp Arg Ala Phe His Arg Asn Ser Leu Asp Ile Phe
                    3155                3160                3165

Arg Ile Ala Thr Pro His Ser Leu Gly Ser Val Trp Lys Ile Arg Val
                    3170                3175                3180

Trp His Asp Asn Lys Gly Leu Ser Pro Ala Trp Phe Leu Gln His Val
3185                3190                3195                3200

Ile Val Arg Asp Leu Gln Thr Ala Arg Ser Ala Phe Phe Leu Val Asn
                    3205                3210                3215

Asp Trp Leu Ser Val Glu Thr Glu Ala Asn Gly Gly Leu Val Glu Lys
                    3220                3225                3230

Glu Val Leu Ala Ala Ser Asp Ala Ala Leu Leu Arg Phe Arg Arg Leu
                    3235                3240                3245

Leu Val Ala Glu Leu Gln Arg Gly Phe Phe Asp Lys His Ile Trp Leu
                    3250                3255                3260

Ser Ile Trp Asp Arg Pro Pro Arg Ser Arg Phe Thr Arg Ile Gln Arg
3265                3270                3275                3280

Ala Thr Cys Cys Val Leu Leu Ile Cys Leu Phe Leu Gly Ala Asn Ala
                    3285                3290                3295

Val Trp Tyr Gly Ala Val Gly Asp Ser Ala Tyr Ser Thr Gly His Val
                    3300                3305                3310

Ser Arg Leu Ser Pro Leu Ser Val Asp Thr Val Ala Val Gly Leu Val
                    3315                3320                3325

Ser Ser Val Val Val Tyr Pro Val Tyr Leu Ala Ile Leu Phe Leu Phe
                    3330                3335                3340

Arg Met Ser Arg Ser Lys Val Ala Gly Ser Pro Ser Pro Thr Pro Ala
3345                3350                3355                3360
```

-continued

```
Gly Gln Gln Val Leu Asp Ile Asp Ser Cys Leu Asp Ser Ser Val Leu
            3365                3370                3375

Asp Ser Ser Phe Leu Thr Phe Ser Gly Leu His Ala Glu Ala Phe Val
            3380                3385                3390

Gly Gln Met Lys Ser Asp Leu Phe Leu Asp Asp Ser Lys Ser Leu Val
            3395                3400                3405

Cys Trp Pro Ser Gly Glu Gly Thr Leu Ser Trp Pro Asp Leu Leu Ser
            3410                3415                3420

Asp Pro Ser Ile Val Gly Ser Asn Leu Arg Gln Leu Ala Arg Gly Gln
3425                3430                3435                3440

Ala Gly His Gly Leu Gly Pro Glu Glu Asp Gly Phe Ser Leu Ala Ser
            3445                3450                3455

Pro Tyr Ser Pro Ala Lys Ser Phe Ser Ala Ser Asp Glu Asp Leu Ile
            3460                3465                3470

Gln Gln Val Leu Ala Glu Gly Val Ser Ser Pro Ala Pro Thr Gln Asp
            3475                3480                3485

Thr His Met Glu Thr Asp Leu Leu Ser Ser Leu Ser Ser Thr Pro Gly
            3490                3495                3500

Glu Lys Thr Glu Thr Leu Ala Leu Gln Arg Leu Gly Glu Leu Gly Pro
3505                3510                3515                3520

Pro Ser Pro Gly Leu Asn Trp Glu Gln Pro Gln Ala Ala Arg Leu Ser
            3525                3530                3535

Arg Thr Gly Leu Val Glu Gly Leu Arg Lys Arg Leu Leu Pro Ala Trp
            3540                3545                3550

Cys Ala Ser Leu Ala His Gly Leu Ser Leu Leu Leu Val Ala Val Ala
            3555                3560                3565

Val Ala Val Ser Gly Trp Val Gly Ala Ser Phe Pro Pro Gly Val Ser
            3570                3575                3580

Val Ala Trp Leu Leu Ser Ser Ser Ala Ser Phe Leu Ala Ser Phe Leu
3585                3590                3595                3600

Gly Trp Glu Pro Leu Lys Val Leu Leu Glu Ala Leu Tyr Phe Ser Leu
            3605                3610                3615

Val Ala Lys Arg Leu His Pro Asp Glu Asp Thr Leu Val Glu Ser
            3620                3625                3630

Pro Ala Val Thr Pro Val Ser Ala Arg Val Pro Arg Val Arg Pro Pro
            3635                3640                3645

His Gly Phe Ala Leu Phe Leu Ala Lys Glu Glu Ala Arg Lys Val Lys
            3650                3655                3660

Arg Leu His Gly Met Leu Arg Ser Leu Leu Val Tyr Met Leu Phe Leu
3665                3670                3675                3680

Leu Val Thr Leu Leu Ala Ser Tyr Gly Asp Ala Ser Cys His Gly His
            3685                3690                3695

Ala Tyr Arg Leu Gln Ser Ala Ile Lys Gln Glu Leu His Ser Arg Ala
            3700                3705                3710

Phe Leu Ala Ile Thr Arg Ser Glu Glu Leu Trp Pro Trp Met Ala His
            3715                3720                3725

Val Leu Leu Pro Tyr Val His Gly Asn Gln Ser Ser Pro Glu Leu Gly
            3730                3735                3740

Pro Pro Arg Leu Arg Gln Val Arg Leu Gln Glu Ala Leu Tyr Pro Asp
3745                3750                3755                3760

Pro Pro Gly Pro Arg Val His Thr Cys Ser Ala Ala Gly Gly Phe Ser
            3765                3770                3775
```

-continued

```
Thr Ser Asp Tyr Asp Val Gly Trp Glu Ser Pro His Asn Gly Ser Gly
            3780                3785                3790

Thr Trp Ala Tyr Ser Ala Pro Asp Leu Leu Gly Ala Trp Ser Trp Gly
            3795                3800                3805

Ser Cys Ala Val Tyr Asp Ser Gly Gly Tyr Val Gln Glu Leu Gly Leu
            3810                3815                3820

Ser Leu Glu Glu Ser Arg Asp Arg Leu Arg Phe Leu Gln Leu His Asn
3825                3830                3835                3840

Trp Leu Asp Asn Arg Ser Arg Ala Val Phe Leu Glu Leu Thr Arg Tyr
            3845                3850                3855

Ser Pro Ala Val Gly Leu His Ala Ala Val Thr Leu Arg Leu Glu Phe
            3860                3865                3870

Pro Ala Ala Gly Arg Ala Leu Ala Ala Leu Ser Val Arg Pro Phe Ala
            3875                3880                3885

Leu Arg Arg Leu Ser Ala Gly Leu Ser Leu Pro Leu Leu Thr Ser Val
            3890                3895                3900

Cys Leu Leu Leu Phe Ala Val His Phe Ala Val Ala Glu Ala Arg Thr
3905                3910                3915                3920

Trp His Arg Glu Gly Arg Trp Arg Val Leu Arg Leu Gly Ala Trp Ala
            3925                3930                3935

Arg Trp Leu Leu Val Ala Leu Thr Ala Ala Thr Ala Leu Val Arg Leu
            3940                3945                3950

Ala Gln Leu Gly Ala Ala Asp Arg Gln Trp Thr Arg Phe Val Arg Gly
            3955                3960                3965

Arg Pro Arg Arg Phe Thr Ser Phe Asp Gln Val Ala His Val Ser Ser
            3970                3975                3980

Ala Ala Arg Gly Leu Ala Ala Ser Leu Leu Phe Leu Leu Leu Val Lys
3985                3990                3995                4000

Ala Ala Gln His Val Arg Phe Val Arg Gln Trp Ser Val Phe Gly Lys
            4005                4010                4015

Thr Leu Cys Arg Ala Leu Pro Glu Leu Leu Gly Val Thr Leu Gly Leu
            4020                4025                4030

Val Val Leu Gly Val Ala Tyr Ala Gln Leu Ala Ile Leu Leu Val Ser
            4035                4040                4045

Ser Cys Val Asp Ser Leu Trp Ser Val Ala Gln Ala Leu Leu Val Leu
            4050                4055                4060

Cys Pro Gly Thr Gly Leu Ser Thr Leu Cys Pro Ala Glu Ser Trp His
4065                4070                4075                4080

Leu Ser Pro Leu Leu Cys Val Gly Leu Trp Ala Leu Arg Leu Trp Gly
            4085                4090                4095

Ala Leu Arg Leu Gly Ala Val Ile Leu Arg Trp Arg Tyr His Ala Leu
            4100                4105                4110

Arg Gly Glu Leu Tyr Arg Pro Ala Trp Glu Pro Gln Asp Tyr Glu Met
            4115                4120                4125

Val Glu Leu Phe Leu Arg Arg Leu Arg Leu Trp Met Gly Leu Ser Lys
            4130                4135                4140

Val Lys Glu Phe Arg His Lys Val Arg Phe Glu Gly Met Glu Pro Leu
4145                4150                4155                4160

Pro Ser Arg Ser Ser Arg Gly Ser Lys Val Ser Pro Asp Val Pro Pro
            4165                4170                4175

Pro Ser Ala Gly Ser Asp Ala Ser His Pro Ser Thr Ser Ser Ser Gln
            4180                4185                4190

Leu Asp Gly Leu Ser Val Ser Leu Gly Arg Leu Gly Thr Arg Cys Glu
```

```
                     4195              4200              4205
Pro Glu Pro Ser Arg Leu Gln Ala Val Phe Glu Ala Leu Leu Thr Gln
         4210              4215              4220
Phe Asp Arg Leu Asn Gln Ala Thr Glu Asp Val Tyr Gln Leu Glu Gln
4225              4230              4235              4240
Gln Leu His Ser Leu Gln Gly Arg Arg Ser Ser Arg Ala Pro Ala Gly
                 4245              4250              4255
Ser Ser Arg Gly Pro Ser Pro Gly Leu Arg Pro Ala Leu Pro Ser Arg
             4260              4265              4270
Leu Ala Arg Ala Ser Arg Gly Val Asp Leu Ala Thr Gly Pro Ser Arg
         4275              4280              4285
Thr Pro Leu Arg Ala Lys Asn Lys Val His Pro Ser Ser Thr
    4290              4295              4300
```

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..23
        (D) OTHER INFORMATION:/function= "AH3 F9 primer"

(xi) SEQUENCE DESCRIPTION: SEQ ID NO: 9:

TTTGACAAGC ACATCTGGCT CTC                        23

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..20
        (D) OTHER INFORMATION:/function= "AH3 B7 primer"

(xi) SEQUENCE DESCRIPTION: SEQ ID NO: 10:

TACACCAGGA GGCTCCGCAG                           20

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: cDNA (vi) ORIGINAL SOURCE:
        (A) ORGANISM: Homo sapiens (ix) FEATURE:
            (A) NAME/KEY: misc_feature
            (B) LOCATION:1..21
            (D) OTHER INFORMATION:/function= "3A3 C1 primer"

(xi) SEQUENCE DESCRIPTION: SEQ ID NO: 11:

CGCCGCTTCA CTAGCTTCGA C                                              21

(2) INFORMATION FOR SEQ ID NO: 12:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (ii) MOLECULE TYPE: cDNA (vi) ORIGINAL SOURCE:
            (A) ORGANISM: Homo sapiens (ix) FEATURE:
            (A) NAME/KEY: misc_feature
            (B) LOCATION:1..20
            (D) OTHER INFORMATION:/function= "3A3 C2 primer"

(xi) SEQUENCE DESCRIPTION: SEQ ID NO: 12:

ACGCTCCAGA GGGAGTCCAC                                                20

(2) INFORMATION FOR SEQ ID NO: 13:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (ii) MOLECULE TYPE: cDNA (vi) ORIGINAL SOURCE:
            (A) ORGANISM: Homo sapiens (ix) FEATURE:
            (A) NAME/KEY: misc_feature
            (B) LOCATION:1..20
            (D) OTHER INFORMATION:/function= "AH4F2 primer"

(xi) SEQUENCE DESCRIPTION: SEQ ID NO: 13:

GGGCAAGGGA GGATGACAAG                                                20

(2) INFORMATION FOR SEQ ID NO: 14:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: DNA (genomic)

(vi) ORIGINAL SOURCE:
            (A) ORGANISM: Homo sapiens (ix) FEATURE:
            (A) NAME/KEY: misc_feature
            (B) LOCATION:1..21
            (D) OTHER INFORMATION:/function= "JH14B3 primer"

(xi) SEQUENCE DESCRIPTION: SEQ ID NO: 14:

GGGTTTATCA GCAGCAAGCG G                                              21

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..30
        (D) OTHER INFORMATION:/function= "N2765 primer"

(xi) SEQUENCE DESCRIPTION: SEQ ID NO: 15:

GGCGCGGCGG GCGGCATCGT TAGGGCAGCG        30

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..30
        (D) OTHER INFORMATION:/function= "N5496 primer"

(xi) SEQUENCE DESCRIPTION: SEQ ID NO: 16:

GGCGGGCGGC ATCGTTAGGG CAGCGCGCGC        30

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..30
        (D) OTHER INFORMATION:/function= "N5495 primer"

(xi) SEQUENCE DESCRIPTION: SEQ ID NO: 17:

ACCTGCTGCT GAGCGACGCC CGCTCGGGGC        30

(2) INFORMATION FOR SEQ ID NO: 18:

(i) SEQUENCE CHARACTERISTICS:
        (A) LENGTH: 54 base pairs
        (B) TYPE: nucleic acid
        (C) STRANDEDNESS: unknown
        (D) TOPOLOGY: unknown (ii) MOLECULE TYPE: genomic DNA (vi) ORIGINAL SOURCE:
            (A) ORGANISM: Homo sapiens (xi) SEQUENCE DESCRIPTION: SEQ ID NO: 18:

TTTTGGTCAA GGTGAGGGCT GGGCCGGTGG GCGCGGGGCT GGGCGCACAC CCCA                54

(2) INFORMATION FOR SEQ ID NO: 19:

(i) SEQUENCE CHARACTERISTICS:
            (A) LENGTH: 554 base pairs
            (B) TYPE: nucleic acid
            (C) STRANDEDNESS: unknown
            (D) TOPOLOGY: unknown (ii) MOLECULE TYPE: cDNA (vi) ORIGINAL SOURCE:
            (A) ORGANISM: Homo sapiens (ix) FEATURE:
            (A) NAME/KEY: misc_feature
            (D) OTHER INFORMATION:/function= "1A1H0.6 probe"

(xi) SEQUENCE DESCRIPTION: SEQ ID NO: 19:

AAGCTTGGCA CCATCAAGGG CCAGTTCAAC TTTGTCCACG TGATCGTCAC CCCGCTGGAC          60

TACGAGTGCA ACCTGGTGTC CCTGCAGTGC AGGAAAGACA TGGAGGGCCT TGTGGACACC         120

AGCGTGGCCA AGATCGTGTC TGACCGCAAC CTGCCCTTCG TGGCCCGCCA GATGGCCCTG         180

CACGCAAATA TGGCCTCACA GGTGCATCAT AGCCGCTCCA ACCCCACCGA TATCTACCCC         240

TCCAAGTGGA TTGCCCGGCT CCGCCACATC AAGCGGCTCC GCCAGCGGAT CTGCGAGGAA         300

GCCGCCTACT CCAACCCCAG CCTACCTCTG GTGCACCCTC CGTCCCATAG CAAAGCCCCT         360

GCACAGACTC CAGCCGAGCC CACACCTGGC TATGAGGTGG CCAGCGGAA GCGCCTCATC          420

TCCTCGGTGG AGGACTTCAC CGAGTTTGTG TGAGGCCGGG GCCCTCCCTC CTGCACTGGC         480

CTTGGACGGT ATTGCCTGTC AGTGAAATAA ATAAAGTCCT GACCCCAGTG CACAGACATA        540

GAGGCACAGA TTGC                                                           554

(2) INFORMATION FOR SEQ ID NO: 20:

(i) SEQUENCE CHARACTERISTICS:
            (A) LENGTH: 192 base pairs
            (B) TYPE: nucleic acid
            (C) STRANDEDNESS: unknown
            (D) TOPOLOGY: unknown (ii) MOLECULE TYPE: other nucleic acid (vi) ORIGINAL SOURCE:
            (A) ORGANISM: Homo sapiens (ix) FEATURE:
            (A) NAME/KEY: misc_feature
            (D) OTHER INFORMATION:/function= "CW10F probe"

(xi) SEQUENCE DESCRIPTION: SEQ ID NO: 20:

GTCCGCGGTC GCACGTACGC TTCTGGTGTG TGTGAGACGT GCGGGCTGG GAAGTGTTGG          60

CAGACGGCGA GTACGTCCTC ACTCCTTTTG TTCTTTTGAC CTAAGCTGGC GAGTGGCACT        120

GCTGAGTTCC GCTCAGTGCC CGCCCTGATG TGCGACCCCC GTGCATTCTT GCTGTTAGGT       180

GGTGGCGGTG TG                                                            192

(2) INFORMATION FOR SEQ ID NO: 21:

-continued

```
    (i) SEQUENCE CHARACTERISTICS:
        (A) LENGTH: 41 base pairs
        (B) TYPE: nucleic acid
        (C) STRANDEDNESS: unknown
        (D) TOPOLOGY: unknown (ii) MOLECULE TYPE: other nucleic acid (vi) ORIGINAL SOURCE:
        (A) ORGANISM: Homo sapiens (ix) FEATURE:
        (A) NAME/KEY: misc_feature
        (D) OTHER INFORMATION:/function= "CW10R probe"

(xi) SEQUENCE DESCRIPTION: SEQ ID NO: 21:

AGGCAGGTCT CCCCCACGAC CAGGGGAGAG GCACCCAAGG T                              41

(2) INFORMATION FOR SEQ ID NO: 22:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: other nucleic acid (vi) ORIGINAL SOURCE:
        (A) ORGANISM: Homo sapiens (xi) SEQUENCE DESCRIPTION: SEQ ID NO: 22:

AGTCAGTAAT TTATATGGTG TTAAAATGTG A                                         31

(2) INFORMATION FOR SEQ ID NO: 23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 23:

Trp Asp Phe Gly Asp Ser
 1               5
```